US012787639B2

(12) United States Patent
Lee et al.

(10) Patent No.: US 12,787,639 B2
(45) Date of Patent: Nov. 3, 2026

(54) ORGANIC ELECTRONIC ELEMENT COMPRISING COMPOUND FOR ORGANIC ELECTRONIC ELEMENT AND AN ELECTRONIC DEVICE THEREOF

(71) Applicant: DUK SAN NEOLUX CO., LTD., Cheonan-si (KR)

(72) Inventors: Sun Hee Lee, Cheonan-si (KR); Hyung Dong Lee, Cheonan-si (KR); Soung Yun Mun, Cheonan-si (KR); Jung Wook Lee, Cheonan-si (KR)

(73) Assignee: DUK SAN NEOLUX CO., LTD., Cheonan-si (KR)

(*) Notice: Subject to any disclaimer, the term of this patent is extended or adjusted under 35 U.S.C. 154(b) by 994 days.

(21) Appl. No.: 17/595,301

(22) PCT Filed: May 14, 2020

(86) PCT No.: PCT/KR2020/006333

§ 371 (c)(1),
(2) Date: Nov. 12, 2021

(87) PCT Pub. No.: WO2020/231197

PCT Pub. Date: Nov. 19, 2020

(65) Prior Publication Data

US 2022/0199911 A1 Jun. 23, 2022

(30) Foreign Application Priority Data

May 14, 2019 (KR) ........................ 10-2019-0056575

(51) Int. Cl.

| | |
|---|---|
| ***H10K 85/60*** | (2023.01) |
| ***C07D 251/24*** | (2006.01) |
| ***C07D 307/77*** | (2006.01) |
| ***C07D 307/91*** | (2006.01) |
| ***C07D 333/76*** | (2006.01) |
| ***C07D 405/10*** | (2006.01) |
| ***C07D 405/14*** | (2006.01) |
| ***C07D 409/10*** | (2006.01) |
| ***C07D 409/12*** | (2006.01) |
| ***C09K 11/06*** | (2006.01) |
| ***H10K 50/11*** | (2023.01) |
| ***H10K 50/19*** | (2023.01) |
| ***H10K 101/10*** | (2023.01) |
| ***H10K 101/30*** | (2023.01) |

(52) U.S. Cl.

CPC ......... *H10K 85/636* (2023.02); *C07D 251/24* (2013.01); *C07D 307/77* (2013.01); *C07D 307/91* (2013.01); *C07D 333/76* (2013.01); *C07D 405/10* (2013.01); *C07D 405/14* (2013.01); *C07D 409/10* (2013.01); *C07D 409/12* (2013.01); *C09K 11/06* (2013.01); *H10K 85/626* (2023.02); *H10K 85/633* (2023.02); *H10K 85/654* (2023.02); *H10K 85/6574* (2023.02); *H10K 85/6576* (2023.02); *C09K 2211/1018* (2013.01); *H10K 50/11* (2023.02); *H10K 50/19* (2023.02); *H10K 85/622* (2023.02); *H10K 85/624* (2023.02); *H10K 2101/10* (2023.02); *H10K 2101/30* (2023.02)

(58) Field of Classification Search

CPC ............... H10K 50/11; H10K 2101/10; H10K 2101/90; H10K 85/633; H10K 85/636; H10K 85/654; H10K 85/6574; H10K 85/6576; H10K 85/626; H10K 85/624; H10K 85/622; C07D 251/24; C07D 307/77; C07D 307/91; C07D 333/76; C07D 405/10; C07D 405/14; C07D 409/10; C07D 409/12

See application file for complete search history.

(56) References Cited

U.S. PATENT DOCUMENTS

| | | | | |
|---|---|---|---|---|
| 2002/0121860 A1* | 9/2002 | Seo | H10K 50/16 | 313/506 |
| 2003/0170491 A1* | 9/2003 | Liao | H05B 45/60 | 257/88 |
| 2005/0110400 A1* | 5/2005 | Nakamura | H10K 59/8791 | 313/506 |
| 2007/0252516 A1* | 11/2007 | Kondakova | H10K 50/11 | 428/917 |
| 2015/0340618 A1* | 11/2015 | Lee | C07D 213/06 | 544/294 |

(Continued)

FOREIGN PATENT DOCUMENTS

| | | |
|---|---|---|
| JP | 2010215759 A * | 9/2010 |
| JP | 2017-222714 A | 12/2017 |

(Continued)

OTHER PUBLICATIONS

Nishizeki et al., machine translation of JP-2010215759-A (2010) pp. 1-178. (Year: 2010).*
Lee et al., machine translation of KR-20180061074-A (2018) pp. 1-53. (Year: 2018).*
Lee et al., machine translation of KR-20190007789-A (2019) pp. 1-83. (Year: 2019).*
First Office Action for corresponding KR 10-2019-0056575, 58 pages, mailed Mar. 12, 2024, with translation.
Notice of Allowance from corresponding JP Patent Application No. 10-2019-0056575, issued Nov. 7, 2024, 2 pages.

*Primary Examiner* — Dylan C Kershner

(74) *Attorney, Agent, or Firm* — Vorys, Sater, Seymour and Pease LLP; Mih Suhn Koh

(57) ABSTRACT

Provided are an organic electric element including an anode, a cathode, and an organic material layer formed between the anode and the cathode, and electronic device thereof, and by including the compounds of Formulas 1 and 2 in the organic material layer, the driving voltage of the organic electric element can be lowered, and the luminous efficiency and life time of the organic electric element can be improved.

11 Claims, 3 Drawing Sheets

(56) References Cited

U.S. PATENT DOCUMENTS

| | | | | |
|---|---|---|---|---|
| 2020/0266358 | A1* | 8/2020 | Yang | H10K 85/346 |
| 2022/0123233 | A1 | 4/2022 | Lee | |

FOREIGN PATENT DOCUMENTS

| | | | | | |
|---|---|---|---|---|---|
| JP | 2017222714 | A2 | | 12/2017 | |
| KR | 10-1072817 | B1 | | 10/2011 | |
| KR | 10-2016-0074376 | A | | 6/2016 | |
| KR | 10-2016-0149994 | A | | 12/2016 | |
| KR | 10-2017-0122115 | A | | 11/2017 | |
| KR | 10-2018-0022325 | A | | 3/2018 | |
| KR | 20180061074 | A | * | 6/2018 | |
| KR | 10-2018-0090931 | A | | 8/2018 | |
| KR | 20180090931 | A | | 8/2018 | |
| KR | 10-2018-0112962 | A | | 10/2018 | |
| KR | 10-2019-0005522 | A | | 1/2019 | |
| KR | 10-2019-0007789 | A | | 1/2019 | |
| KR | 20190007789 | A | * | 1/2019 | |
| KR | 10-2019-0019251 | A | | 2/2019 | |
| KR | 10-2019-0038254 | A | | 4/2019 | |
| KR | 10-2020-0043269 | A | | 4/2020 | |
| KR | 10-2020-0099933 | A | | 8/2020 | |
| WO | WO-2015084114 | A1 | * | 6/2015 | C07C 211/54 |
| WO | WO-2020009398 | A1 | * | 1/2020 | C09K 11/06 |

* cited by examiner

ORGANIC ELECTRONIC ELEMENT COMPRISING COMPOUND FOR ORGANIC ELECTRONIC ELEMENT AND AN ELECTRONIC DEVICE THEREOF

CROSS-REFERENCE TO RELATED APPLICATION

This patent application claims priority from and the benefit under 35 U.S.C. § 119 to § 121, and § 365 of Korean Patent Application No. 10-2019-0056575, filed on May 14, 2019, and International Patent Application No. PCT/KR2020/006333, filed on May 14, 2020, which is hereby incorporated by reference for all purposes as if fully set forth herein. Further, this application claims the benefit of priority in countries other than U.S., which is hereby incorporated by reference herein.

BACKGROUND

Technical Field

The present invention relates to organic electric element comprising compound for organic electric element and an electronic device thereof.

Background Art

In general, an organic light emitting phenomenon refers to a phenomenon in which electric energy is converted into light energy of an organic material. An organic electric element utilizing the organic light emitting phenomenon usually has a structure including an anode, a cathode, and an organic material layer interposed therebetween. In many cases, the organic material layer has a multi-layered structure having respectively different materials in order to improve efficiency and stability of an organic electric element, and for example, may include a hole injection layer, a hole transport layer, a light emitting layer, an electron transport layer, an electron injection layer, or the like.

Materials used as an organic material layer in an organic electric element may be classified into a light emitting material and a charge transport material, for example, a hole injection material, a hole transport material, an electron transport material, an electron injection material, and the like according to its function. Further, the light emitting material may be divided into a high molecular weight type and a low molecular weight type according to its molecular weight, and may also be divided into a fluorescent material derived from excited singlet states of electron and a phosphorescent material derived from excited triplet states of electron according to its light emitting mechanism. Further, the light emitting material may be divided into blue, green, and red light emitting material and yellow and orange light emitting material required for better natural color reproduction according to its light emitting color.

Meanwhile, when only one material is used as a light emitting material, there occur problems of shift of a maximum luminescence wavelength to a longer wavelength due to intermolecular interactions and lowering of the efficiency of a corresponding element due to a deterioration in color purity or a reduction in luminous efficiency. On account of this, a host/dopant system may be used as the light emitting material in order to enhance the color purity and increase the luminous efficiency through energy transfer. This is based on the principle that if a small amount of dopant having a smaller energy band gap than a host forming a light emitting layer is mixed in the light emitting layer, then excitons generated in the light emitting layer are transported to the dopant, thus emitting light with high efficiency. With regard to this, since the wavelength of the host is shifted to the wavelength band of the dopant, light having a desired wavelength can be obtained according the type of the dopant.

Currently, the power consumption is required more than more as size of display becomes larger and larger in the portable display market. Therefore, the power consumption is a very important factor in the portable display with a limited power source of the battery, and efficiency and life span issue must also be solved.

Efficiency, life span, driving voltage, and the like are correlated with each other. For example, if efficiency is increased, then driving voltage is relatively lowered, and the crystallization of an organic material due to Joule heating generated during operation is reduced as driving voltage is lowered, as a result of which life span shows a tendency to increase. However, efficiency cannot be maximized only by simply improving the organic material layer. This is because long life span and high efficiency can be simultaneously achieved when energy levels and $T_1$ values among the respective layers included in the organic material layer, inherent material properties (mobility, interfacial properties, etc.) and the like are optimal combination.

Therefore, there is a need to develop host material, in particular, phosphorescent host material that has high thermal stability and can achieve efficient charge balance in the light-emitting layer.

Object, Technical Solution and Effects of the Invention

The object of the present invention is to provide an organic electric element comprising a compound capable of lowering the driving voltage of the element and improving the luminous efficiency, color purity, stability and life time, and an electronic device thereof.

In an aspect of the present invention, the present invention provides an organic electric element comprising a compound represented by the following formulas 1 and 2.

<Formula 1>

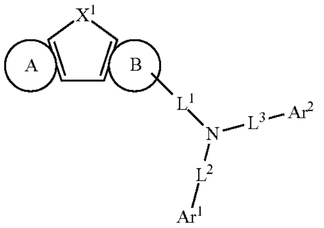

<Formula 2>

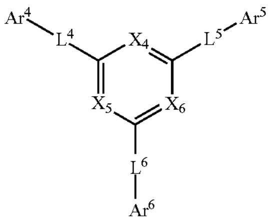

In another aspect of the present invention, the present invention provides an organic electric element using the compound represented by formulas above and an electronic device thereof.

By employing a mixture of the compounds represented by Formulas 1 and 2 of the present invention to the organic material layer of the organic electric element, the driving voltage can be lowered, and the luminous efficiency and lifetime of the element can be improved.

BRIEF DESCRIPTION OF THE DRAWINGS

The FIGS. 1 to 3 illustrate an example of an organic electroluminescent element according to an embodiment of the present invention.

DESCRIPTION OF REFERENCE NUMERALS

Figure 1:
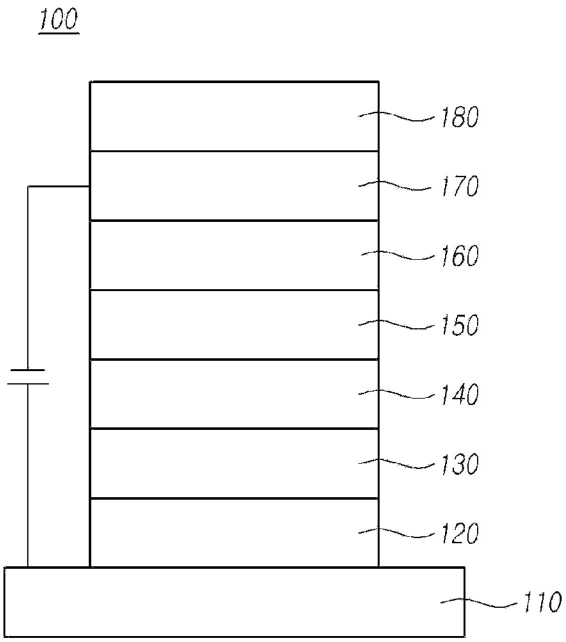

| |
|---|
| 100, 200, 300: an organic electric element |
| 110: a first electrode |
| 120: a hole injection layer |
| 130: a hole transport layer |
| 140: a light emitting layer |
| 150: an electron transport layer |
| 160: an electron injection layer |
| 170: a second electrode |
| 180: a light efficiency improving layer |
| 210: a buffer layer |
| 220: an emission-auxiliary layer |
| 320: a first hole injection layer |
| 330: a first hole transport layer |
| 340: a first light emitting layer |
| 350: a first electron transport layer |
| 360: a first charge generation layer |
| 361: a second charge generation layer |
| 420: a second hole injection layer |
| 430: a second hole transport layer |
| 440: a second light emitting layer |
| 450: a second electron transport layer |
| CGL: a charge generation layer |
| ST1: a first stack |
| ST2: a second stack |

DETAILED DESCRIPTION

Unless otherwise stated, the term "aryl group" or "arylene group" as used herein has, but not limited to, 6 to 60 carbon atoms. The aryl group or arylene group in the present invention may comprise a monocyclic ring, ring assemblies, a fused polycyclic system, spiro-compounds and the like. In addition, unless otherwise stated, a fluorenyl group may be comprised in an aryl group and a fluorenylene group may be comprised in an arylene group.

Unless otherwise stated, the term "fluorenyl group", "fluorenylene group" or "fluorentriyl group" as used herein means univalent, bivalent or trivalent functional group in which R, R' and R" are all hydrogen in the following structure, "substituted fluorenyl group", "substituted fluorenylene group" or "substituted fluorentriyl group" means that at least any one of R, R' and R" is a substituent other than hydrogen, and the case where R and R' are bonded to each other to form the spiro compound together with the carbon bonded to them is comprised. In this specification, a fluorenyl group, a fluorenylene group, and a fluorentriyl group may be referred to as a fluorene group regardless of the valence.

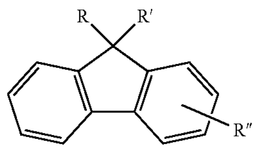

The term "spiro-compound" as used herein has a spiro union which means union having one atom as the only common member of two rings. The common atom is designated as 'spiro atom'. The compounds are defined as 'monospiro-', 'dispiro-' or 'trispiro-' depending on the number of spiro atoms in one compound.

The term "heterocyclic group" used in the specification comprises a non-aromatic ring as well as an aromatic ring like "heteroaryl group" or "heteroarylene group" and comprises a monocyclic ring, ring assemblies, a fused polycyclic system, spiro compounds, and the like. In addition, unless otherwise stated, the term "heterocyclic group" means, but not limited to, a ring containing one or more heteroatoms and having 2 to 60 carbon atoms. Unless otherwise stated, the term "heteroatom" as used herein represents N, O, S, P or Si and comprises the compound comprising the heteroatom group such as $SO_2$, P═O etc. instead of carbon forming a ring such as the following compound.

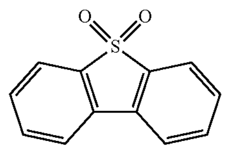 [SMILES: O=S1(=O)c2ccccc2-c2ccccc21]

The term "aliphatic ring group" as used herein refers to a cyclic hydrocarbon except for aromatic hydrocarbons, and comprises a monocyclic ring, ring assemblies, a fused polycyclic system, spiro compounds, and the like, and unless otherwise specified, it means a ring of 3 to 60 carbon atoms, but not limited thereto. For example, a fused ring formed by benzene being an aromatic ring with cyclohexane being a non-aromatic ring corresponds to aliphatic ring group.

In this specification, a 'group name' corresponding to an aryl group, an arylene group, a heterocyclic group, and the like exemplified for each symbol and its substituent may be written in the name of functional group reflecting the valence, and may also be described as the name of a parent compound. For example, in the case of phenanthrene which is a kind of aryl group, it may be described by distinguishing valence such as 'phenanthryl (group)' when it is 'monovalent group', and 'phenanthrylene (group)' when it is 'divalent group', and regardless of its valence, it may also be described as 'phenanthrene' which is a parent compound name. Similarly, in the case of pyrimidine, it may be described as 'pyrimidine' regardless of its valence, and it may also be described as the name of corresponding functional group such as pyrimidinyl (group) when it is 'monovalent group', and 'pyrimidinylene (group)' when it is 'divalent group'.

In addition, in the present specification, the numbers and alphabets indicating a position may be omitted when describing a compound name or a substituent name, For example, pyrido[4,3-d]pyrimidine, benzopuro[2,3-d]pyrimidine and 9,9-dimethyl-9H-fluorene can be described as pyridopyrimidine, benzofurropyrimidine and dimethylfluorene, respectively. Therefore, both benzo[g]quinoxaline and benzo[f] quinoxaline can be described as benzoquinoxaline.

In addition, unless otherwise expressed, when any formula of the present invention is represented by the following formula, the substituent according to the index may be defined as follows.

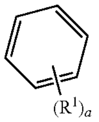

In the above formula, when a is an integer of zero, the substituent $R^1$ is absent, that is, hydrogen atoms are bonded to all the carbon constituting the benzene ring. Here, Formula or compound may be described while omitting the indication of hydrogen bonded to carbon. In addition, one substituent $R^1$ is bonded to any carbon of the carbons forming the benzene ring when "a" is an integer of 1. Similarly, when "a" is an integer of 2 or 3, for example, as in the following formulas, substituents $R^1$s may be bonded to the carbon of the benzene ring. Also, when "a" is an integer of 4 to 6, substituents $R^1$s are bonded to the carbon of the benzene ring in a similar manner. Further, when "a" is an integer of 2 or more, $R^1$s may be the same as or different from each other.

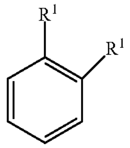

(a = 2)

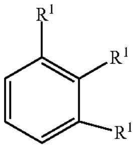

(a = 3)

In addition, unless otherwise specified in the present specification, the ring formed by bonding adjacent groups to each other may be selected from the group consisting of a $C_6$-$C_{60}$ aromatic ring group, a fluorenyl group, a $C_2$-$C_{60}$ heterocyclic group containing at least one heteroatom selected from the group consisting of O, N, S, Si, and P, and a $C_3$-$C_{60}$ aliphatic ring.

Hereinafter, referring to FIGS. 1 to 3, a lamination structure of an organic electric element including the compound of the present invention will be described.

In the reference numbers assigned to the components of each drawing, it should be noted that the same elements will be designated by the same reference numerals although they are shown in different drawings. In addition, in the following description of the present invention, a detailed description of known functions and configurations incorporated herein will be omitted when it may make the subject matter of the present invention rather unclear.

In addition, terms, such as first, second, A, B, (a), (b) or the like may be used herein when describing components of the present invention. Each of these terminologies is not used for defining an essence, order or sequence of a corresponding component but used merely to distinguish the corresponding component from other component(s). It will be understood that the expression "one component is "connected," "coupled" or "joined" to another component" comprises the case where a third component may be "connected," "coupled," and "joined" between the first and second components as well as the case where the first component may be directly connected, coupled or joined to the second component.

In addition, it will be understood that when an element such as a layer, film, region or substrate is referred to as being "on" or "over" another element, it can be directly on the other element or intervening elements may also be present. In contrast, when an element is referred to as being "directly on" another element, there are no intervening elements present.

Figure 2:
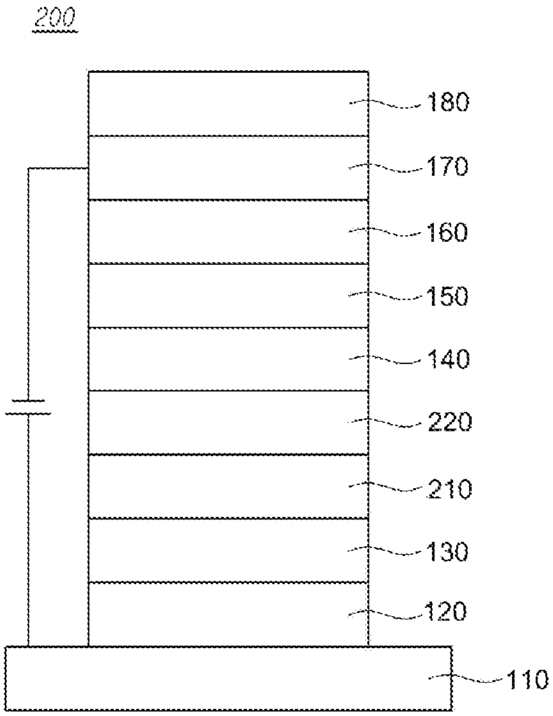
Figure 3:
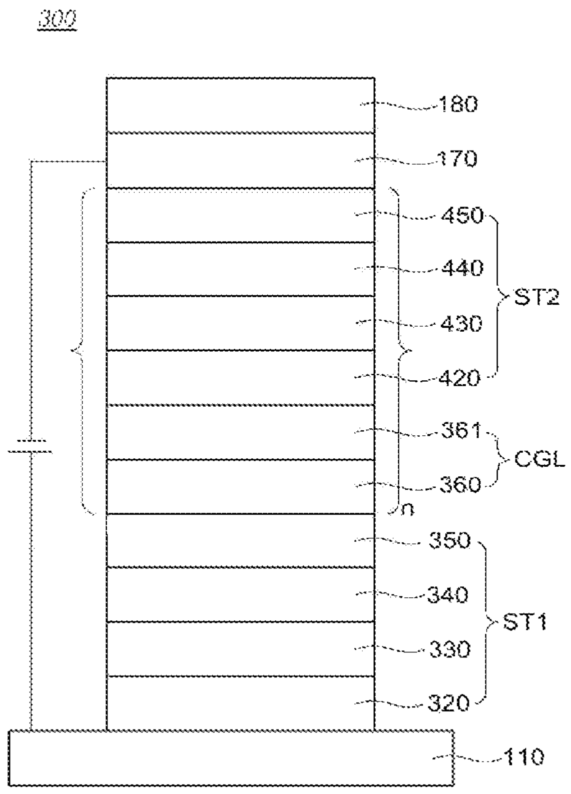

The FIGS. 1 to 3 are structures for showing an example of an organic electric element according to an embodiment of the present invention.

Referring to the FIG. 1, an organic electric element 100 according to an embodiment of the present invention includes a first electrode 110 formed on a substrate (not shown), a second electrode 170, and an organic material layer formed between the first electrode 110 and the second electrode 170.

The first electrode 110 may be an anode (positive electrode), and the second electrode 170 may be a cathode (negative electrode). In the case of an inverted organic electric element, the first electrode may be a cathode, and the second electrode may be an anode.

The organic material layer may be comprised a hole injection layer 120, a hole transport layer 130, a light emitting layer 140, an electron transport layer 150, and an electron injection layer 160. Specifically, a hole injection layer 120, a hole transport layer 130, a light emitting layer 140, an electron transport layer 150, and an electron injection layer 160 are formed on the first electrode 110 in sequence.

Preferably, a layer for improving the luminous efficiency 180 may be formed on one side of sides of the first electrode 110 or one side of sides of the second electrode 170, wherein the one side is not facing the organic material layer. If a layer for improving the luminous efficiency 180 is formed, the luminous efficiency of an organic electric element can be improved.

For example, the light efficiency improving layer 180 may be formed on the second electrode 170, as a result, in the case of a top emission organic light emitting diode, the optical energy loss due to Surface Plasmon Polaritons (SPPs) at the second electrode 170 may be reduced and in the case of a bottom emission organic light emitting diode, the light efficiency improving layer 180 may serve as a buffer for the second electrode 170.

A buffer layer 210 or an emission-auxiliary layer 220 may be further formed between the hole transport layer 130 and the light emitting layer 140. This will be described with reference to FIG. 2.

Referring to FIG. 2, the organic electric element 200 according to another embodiment of the present invention may comprise a hole injection layer 120, a hole transport layer 130, a buffer layer 210, an emission-auxiliary layer 220, a light emitting layer 140, the electron transport layer 150, the electron injection layer 160, and a second electrode 170 formed on a first electrode 110 in sequence, and a light efficiency improving layer 180 may be formed on the second electrode 170.

Although not shown in FIG. 2, an electron transport auxiliary layer may be further formed between the light emitting layer 140 and the electron transport layer 150.

In addition, according to another embodiment of the present invention, the organic material layer may be a form consisting of a plurality of stacks, wherein the stacks comprise a hole transport layer, a light emitting layer, and an electron transport layer, respectively. This will be described with reference to FIG. 3.

Referring to FIG. 3, two or more sets of stacks of the organic material layers ST1 and ST2 may be formed between the first electrode 110 and the second electrode 170 in the organic electric element 300 according to another embodiment of the present invention, wherein the organic material layers are consisted of multiple layers, respectively, and the charge generation layer CGL may be formed between the stacks of the organic material layer.

Specifically, the organic electric element according to the embodiment of the present invention may comprise the first electrode 110, the first stack ST1, the charge generation layer CGL, the second stack ST2, and the second electrode 170 and the light efficiency improving layer 180.

The first stack ST1 is an organic layer formed on the first electrode 110, and the first stack ST1 may comprise the first hole injection layer 320, the first hole transport layer 330, the first light emitting layer 340 and the first electron transport layer 350 and the second stack ST2 may comprise a second hole injection layer 420, a second hole transport layer 430, a second light emitting layer 440 and a second electron transport layer 450. As such, the first stack and the second stack may be the organic layers having the same or different stacked structures.

The charge generation layer CGL may be formed between the first stack ST1 and the second stack ST2. The charge generation layer CGL may comprise a first charge generation layer 360 and a second charge generation layer 361. The charge generating layer CGL is formed between the first light emitting layer 340 and the second light emitting layer 440 to increase the current efficiency generated in each light emitting layer and to smoothly distribute charges.

The first light emitting layer 340 may comprise a light emitting material comprising a blue host doped with a blue fluorescent dopant and the second light emitting layer 440 may comprise a light emitting material comprising a green host doped with a greenish yellow dopant and a red dopant together, but the material of the first light emitting layer 340 and the second light emitting layer 440 according to an embodiment of the present invention is not limited thereto.

In FIG. 3, n may be an integer of 1 to 5 and the charge generation layer CGL and the third stack may be further stacked on the second stack ST2 when n is 2.

When a plurality of light emitting layers are formed in a multi-layer stack structure as shown in FIG. 3, it is possible to manufacture an organic electroluminescent element that emits not only white light but also various colors, wherein the white light is emitted by the mixing effect of light emitted from each light emitting layer.

The compound represented by Formula 1 can be used as material of a hole injection layer 120, 320, 420, a hole transport layer 130, 330, 430, a buffer layer 210, an emission-auxiliary layer 220, an electron transport layer 150, 350, 450, an electron injection layer 160, a light emitting layer 140, 340, 440, or a layer for improving luminous efficiency 180, preferably, a mixture of the compound of Formula 1 and the compound of Formula 2 can be used as host of a light emitting layer 140, 340, 440 and/or the compound of Formula 1 can be used as material of a hole transport band layer such as a hole transport layer 130, 330, 430 and/or an emission-auxiliary layer 220.

Even if the core is the same core, the band gap, the electrical characteristics, the interface characteristics and the like may be different depending on which substituent is bonded at which position. Therefore, it is necessary to study the selection of the core and the combination of the core and the sub-substituent bonded to the core. In particular, long life span and high efficiency can be simultaneously achieved when the optimal combination of energy levels and $T_1$ values, inherent material properties (mobility, interfacial properties, etc.), and the like among the respective layers of an organic material layer is achieved.

Therefore, energy level and $T_1$ value between the respective layers of the organic material layer, inherent material properties (mobility, interfacial properties, etc.) and the like can be optimized by using a mixture of the compound of Formula 1 and the compound of Formula 2 as host of a light emitting layer 140, 340, 440 and/or by using a the compound of Formula 1 as material of a hole transport band layer such as a hole transport layer 130, 330, 430 and/or an emission-auxiliary layer 220. As a result, the lifetime and efficiency of the organic electric element can be improved simultaneously.

The organic electric element according to an embodiment of the present invention may be manufactured using various deposition methods. The organic electric element according to an embodiment of the present invention may be manufactured using a PVD (physical vapor deposition) method or CVD (chemical vapor deposition) method. For example, the organic electric element may be manufactured by depositing a metal, a conductive metal oxide, or a mixture thereof on the substrate to form the anode 110, forming the organic material layer comprising the hole injection layer 120, the hole transport layer 130, the light emitting layer 140, the electron transport layer 150, and the electron injection layer 160 thereon, and then depositing a material, which can be used as the cathode 170, thereon. Also, an emission-auxiliary layer 220 may be formed between a hole transport layer 130 and a light emitting layer 140, and an electron transport auxiliary layer (not shown) may be further formed between a light emitting layer 140 and an electron transport layer 150 and, a stacked structure may be formed, as described above.

In addition, the organic material layer may be manufactured in such a manner that the fewer layers are formed using various polymer materials by a soluble process or solvent process, for example, spin coating, nozzle printing, inkjet printing, slot coating, dip coating, roll-to-roll, doctor blading, screen printing, or thermal transfer, instead of deposition. Since the organic material layer according to the present invention may be formed in various ways, the scope of protection of the present invention is not limited by a method of forming the organic material layer.

The organic electric element according to an embodiment of the present invention may be of a top emission type, a bottom emission type, or a dual emission type depending on the material used.

In addition, the organic electric element according to an embodiment of the present invention may be selected from the group consisting of an organic light emitting diode, an organic solar cell, an organic photo conductor, an organic transistor, an element for monochromatic illumination and an element for quantum dot display.

Another embodiment of the present invention provides an electronic device including a display device which includes the above described organic electric element, and a control unit for controlling the display device. Here, the electronic device may be a wired/wireless communication terminal which is currently used or will be used in the future, and covers all kinds of electronic devices including a mobile communication terminal such as a cellular phone, a personal digital assistant (PDA), an electronic dictionary, a point-to-multipoint (PMP), a remote controller, a navigation unit, a game player, various kinds of TVs, and various kinds of computers.

Hereinafter, compound and an organic electric element according to an aspect of the present invention and will be described.

In one aspect of the present invention, the present invention provides an organic electric element comprising a first electrode, a second electrode, and an organic material layer formed between the first electrode and the second electrode, wherein the organic material layer comprises a phosphorescent light emitting layer, and host of the phosphorescent light emitting layer comprises a first compound of Formula 1 and a second compound of Formula 2.

<Formula 1>

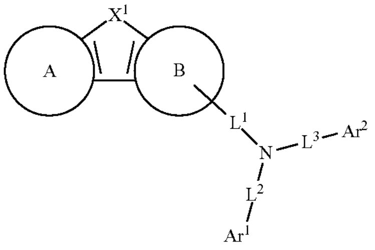

<Formula 2>

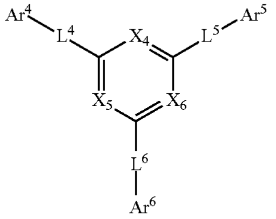

First, Formula 1 will be described.

In Formula 1, each of symbols may be defined as follows.

A ring and B ring are each independently a $C_6$-$C_{60}$ aromatic ring group or a $C_2$-$C_{60}$ heterocyclic group comprising at least one heteroatom selected from the group consisting of O, N, S, Si and P, and at least one of A ring and B ring is a $C_{10}$ or more aromatic ring group.

When at least one of A ring and B ring is an aromatic ring group, the aromatic ring group is preferably a $C_6$-$C_{20}$ aromatic ring group, more preferably a $C_6$-$C_{14}$ aromatic ring group, for example, benzene, naphthalene, phenanthrene, anthracene, and the like.

A ring may be substituted with one or more same or different $R^1$ (s), B Ring may be substituted with one or more same or different $R^2$(s).

$R^1$ and $R^2$ are each independently selected from the group consisting of hydrogen, deuterium, halogen, a cyano group, a nitro group, a $C_6$-$C_{60}$ aryl group, a fluorenyl group, a $C_2$-$C_{60}$ heterocyclic group comprising at least one heteroatom of O, N, S, Si and P, a $C_3$-$C_{60}$ aliphatic ring, a $C_1$-$C_{30}$ alkyl group, a $C_2$-$C_{30}$ alkenyl group, a $C_2$-$C_{30}$ alkynyl group, a $C_1$-$C_{30}$ alkoxyl group and a $C_6$-$C_{30}$ aryloxy group.

When at least one of $R^1$ and $R^2$ is an aryl group, the aryl group may be preferably a $C_6$-$C_{30}$ aryl group, more preferably a $C_6$-$C_{18}$ aryl group, for example, phenyl, naphthyl, biphenyl, terphenyl, and the like.

When at least one of $R^1$ and $R^2$ is a heterocyclic group, the heterocyclic group may be preferably a $C_2$-$C_{30}$ heterocyclic group, more preferably a $C_2$-$C_{18}$ heterocyclic group, for example, carbazole, phenylcarbazole, dibenzothiophene, dibenzofuran, and the like.

When at least one of $R^1$ and $R^2$ is an alkyl group, the alkyl group may be preferably a $C_1$-$C_{10}$ alkyl group, more preferably a $C_1$-$C_4$ alkyl group, for example, methyl, t-butyl and the like.

Preferably, A ring and B ring may be each independently selected from the group consisting of Formulas a-1 to a-9.

<Formula a-1>

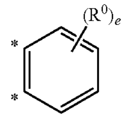

<Formula a-2>

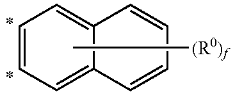

<Formula a-3>

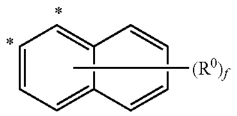

<Formula a-4>

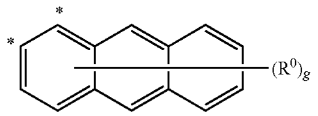

<Formula a-5>

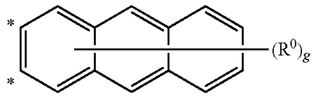

<Formula a-6>

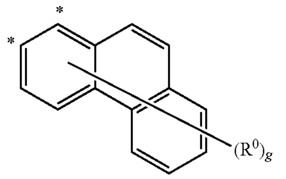

<Formula a-7>

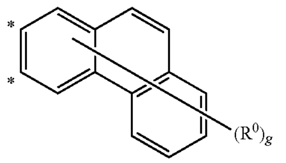

<Formula a-8>

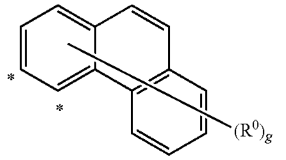

<Formula a-9>

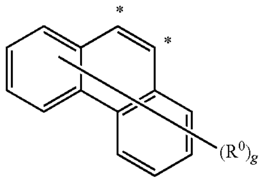

In Formulas a-1 to a-9, * represents the condensed position, $R^0$ is defined the same as $R^1$ or $R^2$ in Formula 1, e is an integer of 0 to 4, f is an integer of 0 to 6, g is an integer of 0 to 8, when they are each an integer of 2 or more, $R^0$s are the same as or different from each other.

$X^1$ is O, S or C(R')(R").

R' and R" are each independently selected from the group consisting of hydrogen, deuterium, halogen, a cyano group, a nitro group, a $C_6$-$C_{60}$ aryl group, a fluorenyl group, a $C_2$-$C_{60}$ heterocyclic group comprising at least one heteroatom selected from the group consisting of O, N, S, Si and P, a $C_3$-$C_{60}$ aliphatic ring, a $C_1$-$C_{30}$ alkyl group, a $C_2$-$C_{30}$ alkenyl group, a $C_2$-$C_{30}$ alkynyl group, a $C_1$-$C_{30}$ alkoxyl group and a $C_6$-$C_{30}$ aryloxy group, and R' and R" may be linked to each other to form a ring, and R' and R" may be linked to each other to form a ring. When R' and R" are linked to each other to form a ring, a spiro compound may be formed together with C to which they are attached.

When at least one of R' and R" is an aryl group, the aryl group may be preferably a $C_6$-$C_{20}$ aryl group, more preferably a $C_6$-$C_{18}$ aryl group, for example, phenyl, naphthyl, biphenyl, terphenyl, and the like.

When at least one of R' and R" is an alkyl group, the alkyl group may be preferably a $C_1$-$C_{10}$ alkyl group, more preferably a $C_1$-$C_4$ alkyl group, for example, methyl, t-butyl and the like.

$L^1$ to $L^3$ are each independently selected from the group consisting of a single bond, a $C_6$-$C_{60}$ arylene group, a fluorenylene group, a $C_2$-$C_{60}$ heterocyclic group comprising at least one heteroatom selected from the group consisting of O, N, S, Si and P, and a $C_3$-$C_{60}$ aliphatic ring.

When at least one of $L^1$ to $L^3$ is an arylene group, the arylene group may be preferably a $C_6$-$C_{20}$ arylene group, more preferably a $C_6$-$C_{18}$ arylene group, for example, phenylene, naphthalene, biphenyl, terphenyl and the like.

When at least one of $L^1$ to $L^3$ is a heterocyclic group, the heterocyclic group may be preferably a $C_2$-$C_{30}$ heterocyclic group, more preferably a $C_2$-$C_{18}$ heterocyclic group, for example, carbazole, phenylcarbazole, dibenzothiophene, dibenzofuran, and the like.

When at least one of $L^1$ to $L^3$ is a fluorenylene group, the fluorenylene group may be 9,9-dimethylfluorene, 9,9-diphenylfluorene, and the like.

$Ar^1$ and $Ar^2$ are each independently selected from the group consisting of a $C_6$-$C_{60}$ aryl group, a fluorenyl group, a $C_2$-$C_{60}$ heterocyclic group comprising at least one heteroatom selected from the group consisting of O, N, S, Si and P, and a $C_3$-$C_{60}$ aliphatic ring.

When at least one of $Ar^1$ and $Ar^2$ is an aryl group, the aryl group may be preferably a $C_6$-$C_{20}$ aryl group, more preferably a $C_6$-$C_{18}$ aryl group, for example, phenyl, naphthyl, biphenyl, terphenyl, and the like.

When at least one of $Ar^1$ and $Ar^2$ is a heterocyclic group, the heterocyclic group may be preferably a $C_2$-$C_{30}$ heterocyclic group, more preferably a $C_2$-$C_{18}$ heterocyclic group, for example, carbazole, phenylcarbazole, dibenzothiophene, dibenzofuran, benzonaphthothiophene, benzonaphthofuran, and the like.

When at least one of $Ar^1$ and $Ar^2$ is a fluorenyl group, the fluorenyl group may be 9,9-dimethylfluorene, 9,9-diphenylfluorene, 9,9-dimethylbenzofluorene, and the like.

$L^1$ to $L^3$, $Ar^1$, $Ar^2$, $R^1$, $R^2$, R', R", and the ring formed by R' and R" may be each optionally substituted with one or more substituents selected from the group consisting of deuterium, halogen, a silane group unsubstituted or substituted with a $C_1$-$C_{20}$ alkyl group or a $C_6$-$C_{20}$ aryl group, a siloxane group, a boron group, a germanium group, a cyano group, a nitro group, a $C_1$-$C_{20}$ alkylthio group, a $C_1$-$C_{20}$ alkoxy group, a $C_6$-$C_{20}$ arylalkoxy group, a $C_1$-$C_{20}$ alkyl group, a $C_2$-$C_{20}$ alkenyl group, a $C_2$-$C_{20}$ alkynyl group, a $C_6$-$C_{20}$ aryl group, a fluorenyl group, a $C_2$-$C_{20}$ heterocyclic group containing at least one heteroatom of O, N, S, Si, and P, a $C_3$-$C_{20}$ aliphatic ring group, a $C_7$-$C_{20}$ arylalkyl group and $C_8$-$C_{20}$ arylalkenyl group.

Preferably, Formula 1 may be represented by one of Formula 1-A to Formula 1-C.

<Formula 1-A>

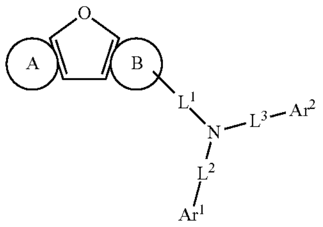

<Formula 1-B>

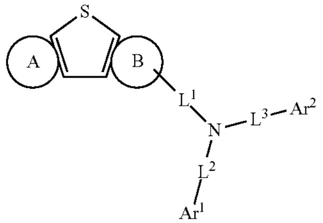

<Formula 1-C>

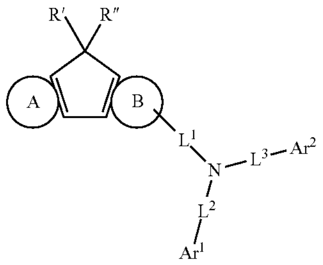

In Formula 1-A to Formula 1-C, A ring, B ring, $L^1$ to $L^3$, $Ar^1$, $Ar^2$, R' and R" are the same as defined for Formula 1.

Further, Formula 1 may be represented by one of Formula 1-1 to Formula 1-6.

<Formula 1-1>

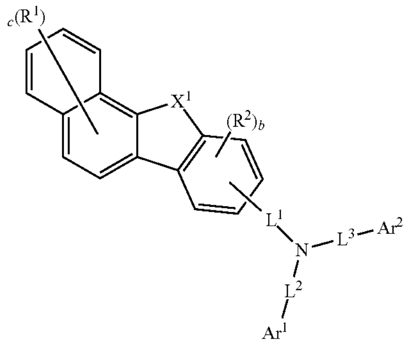

<Formula 1-2>

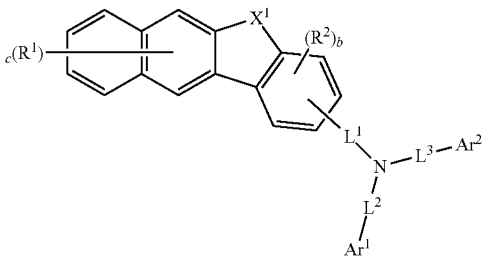

-continued

<Formula 1-3>

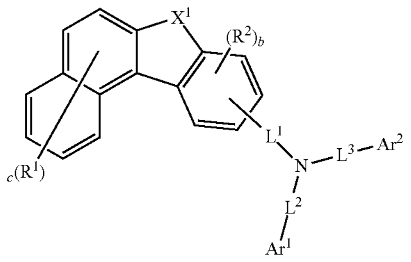

<Formula 1-4>

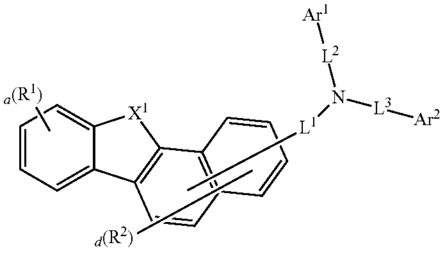

<Formula 1-5>

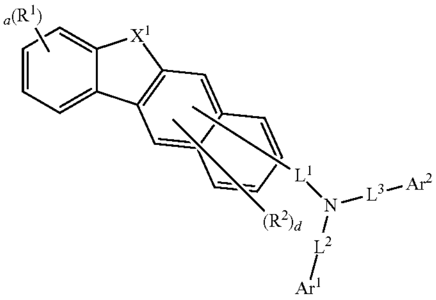

<Formula 1-6>

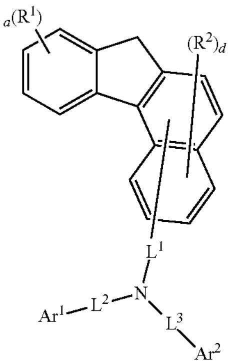

In Formula 1-1 to Formula 1-6, $X^1$, $R^1$, $R^2$, $L^1$ to $L^3$, $Ar^1$ and $Ar^2$ are the same as defined for Formula 1 and a is an integer of 0 to 4, b is an integer of 0 to 3, c is an integer of 0 to 6, and d is an integer of 0 to 5.

Specifically, the compound represented by Formula 1 may be one of the following compounds, but there is no limitation thereto.

P1-1

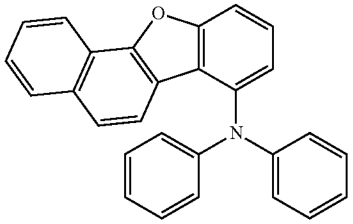

P1-2

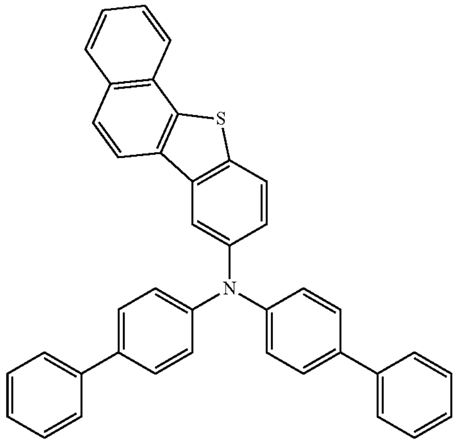

P1-3

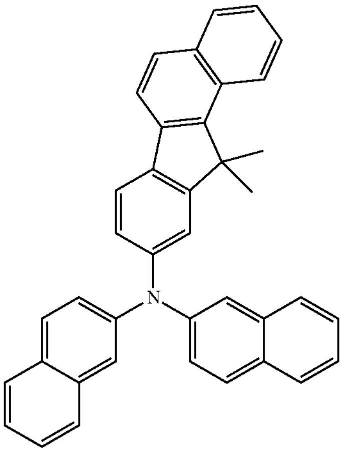

P1-4

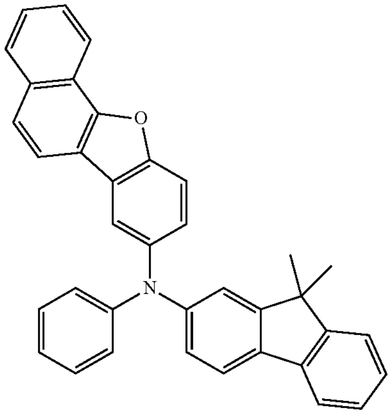

-continued
P1-5
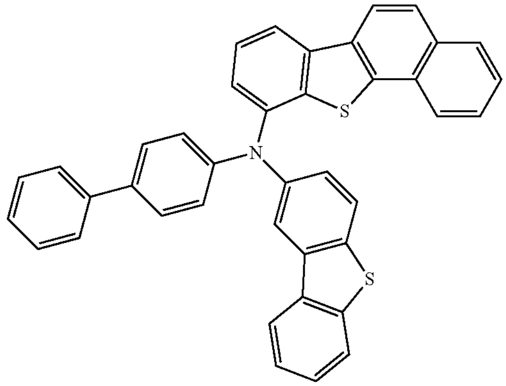
P1-6
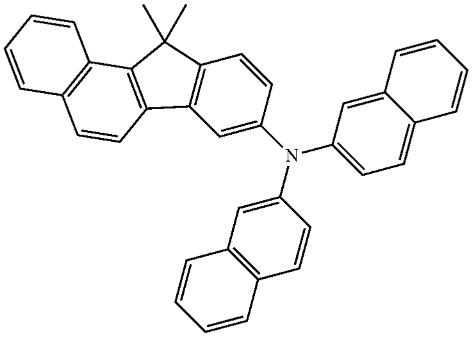
P1-7
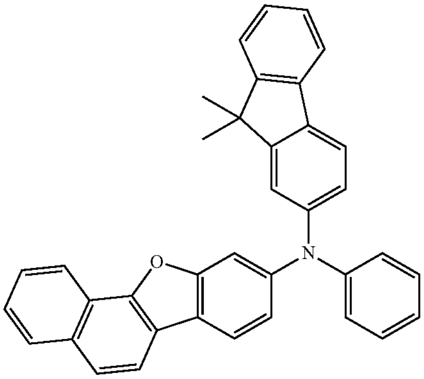
P1-8
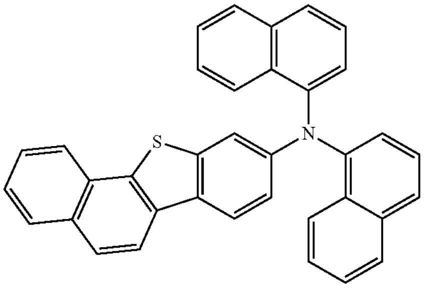
-continued
P1-9
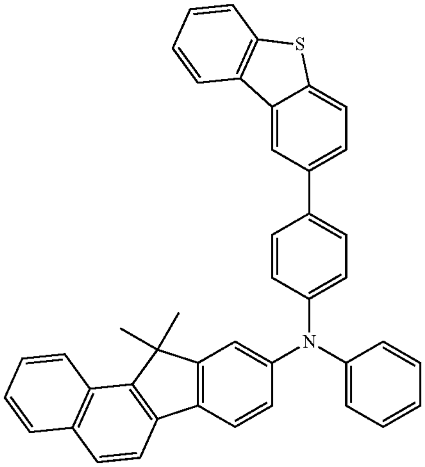
P1-10
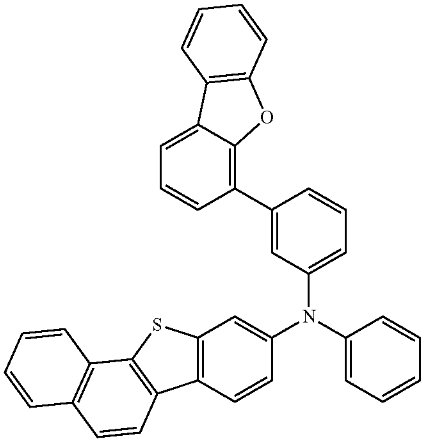
P1-11
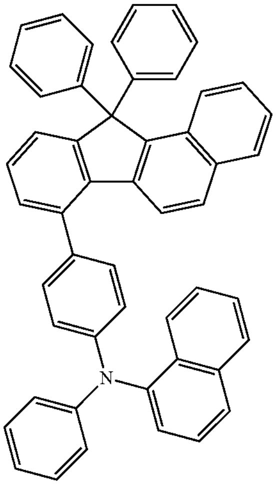

-continued
P1-12
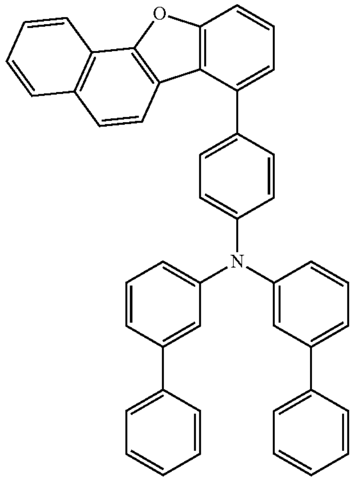
P1-13
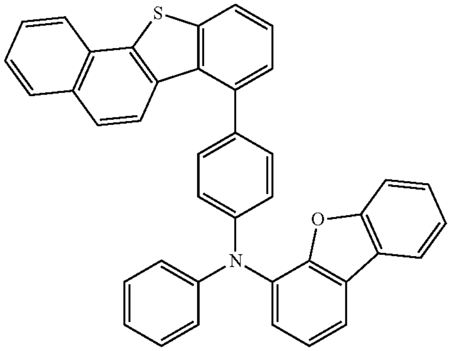
P1-14
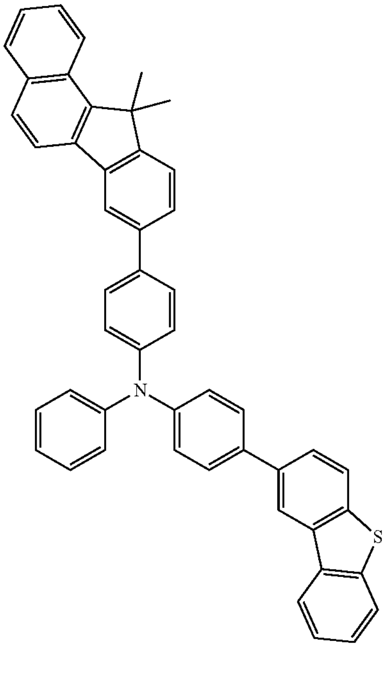
-continued
P1-15
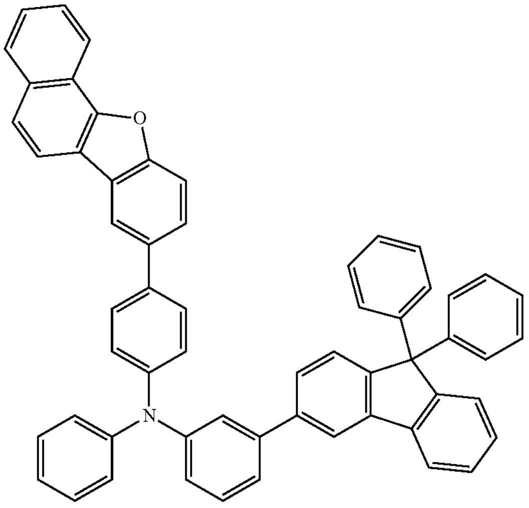
P1-16
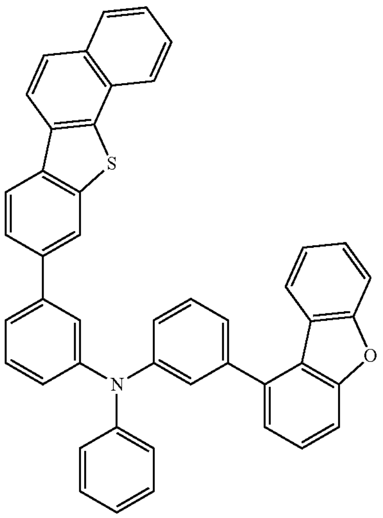
P1-17
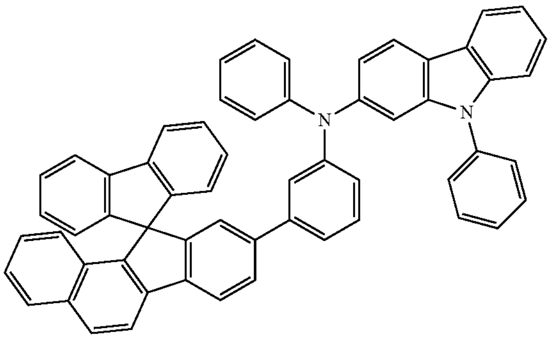

-continued
P1-18
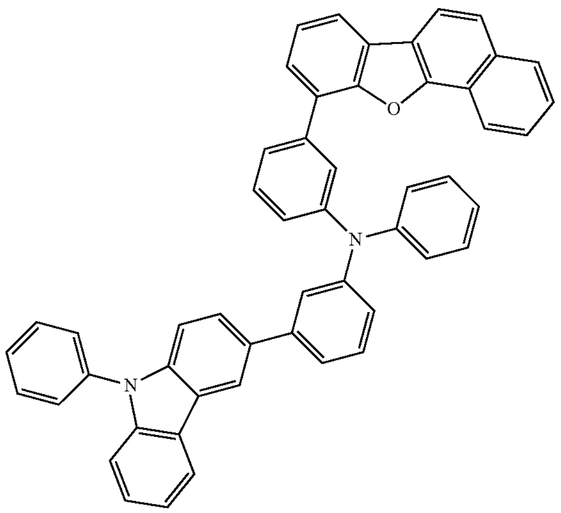
P1-19
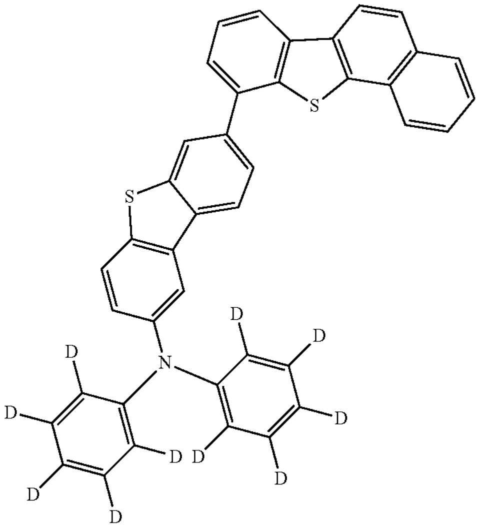
P1-20
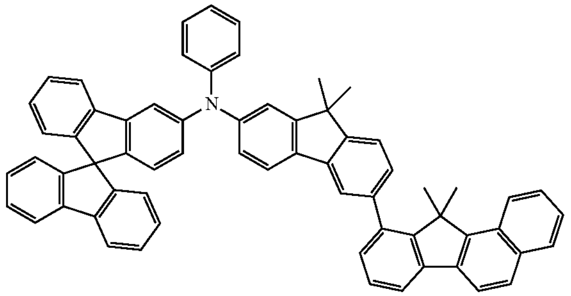
-continued
P1-21
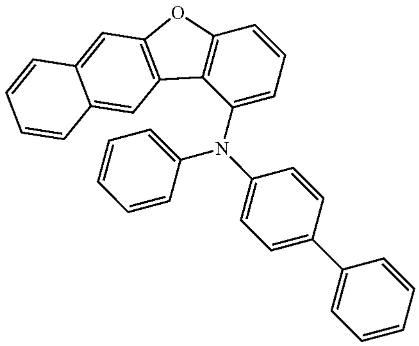
P1-22
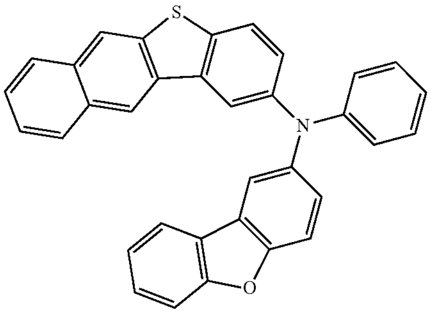
P1-23
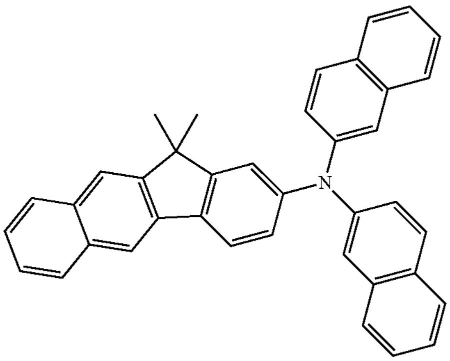
P1-24
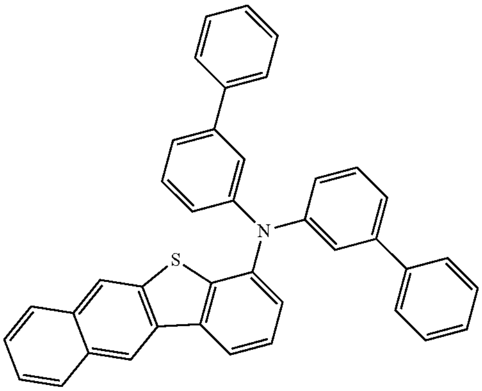

-continued
P1-25
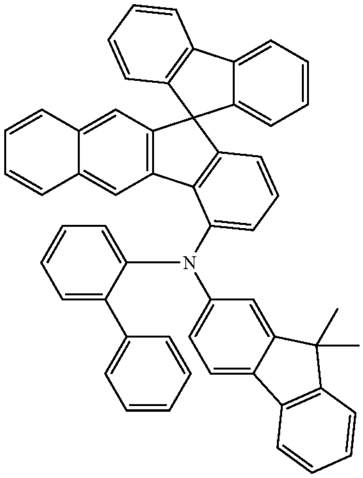
P1-26
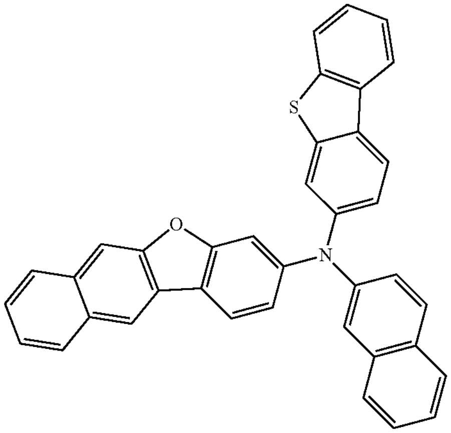
P1-27
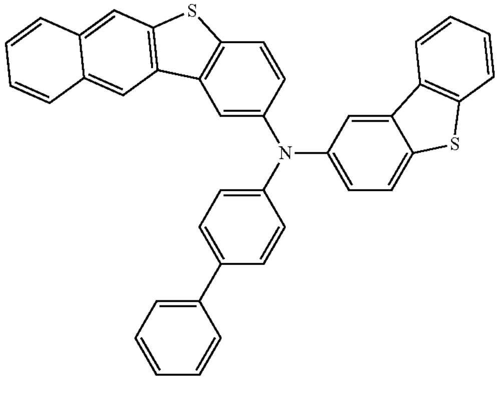
-continued
P1-28
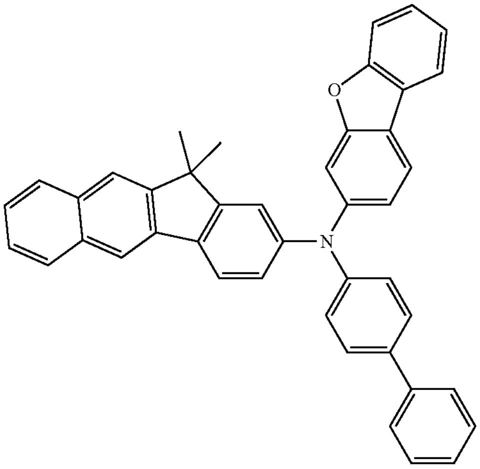
P1-29
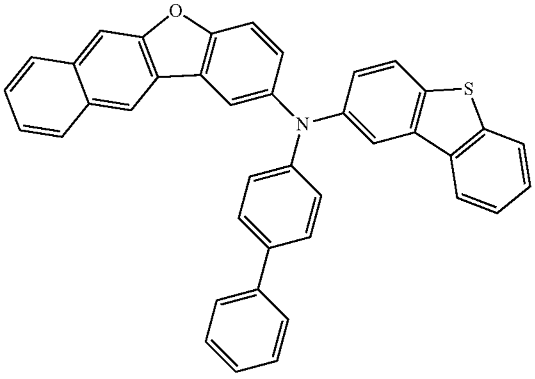
P1-30
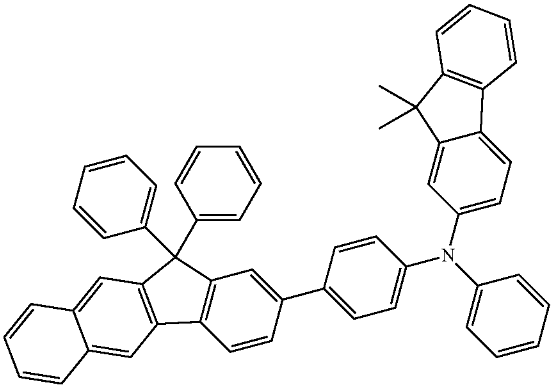

-continued
P1-31
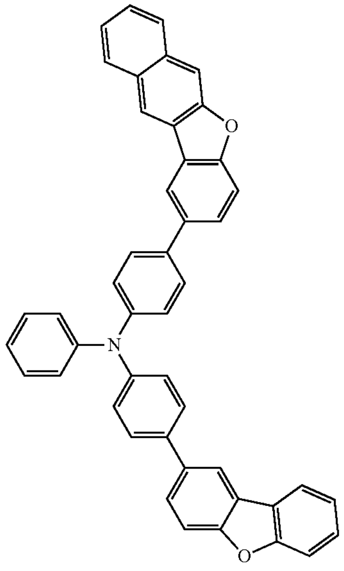
P1-32
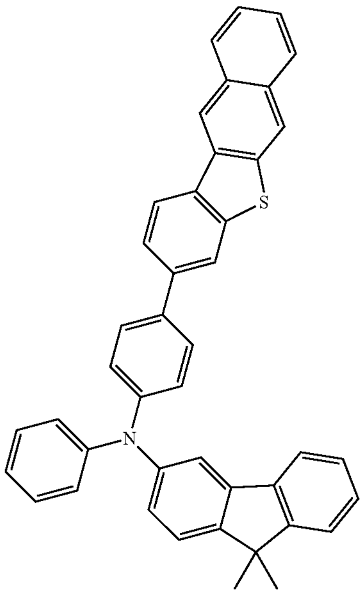
P1-33
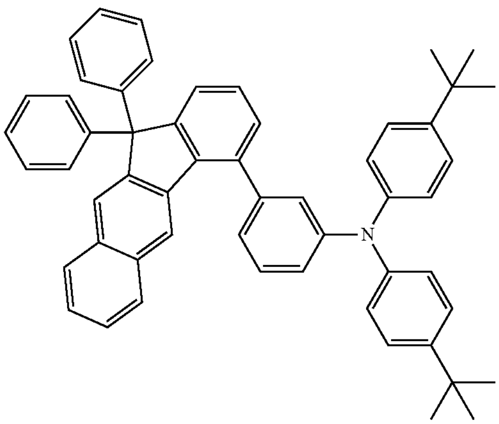
-continued
P1-34
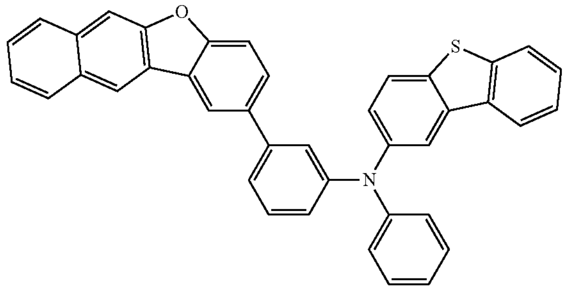
P1-35
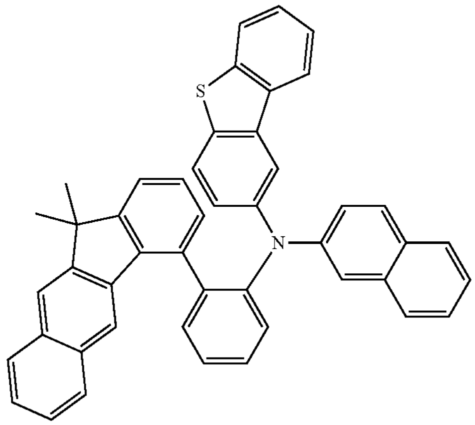
P1-36
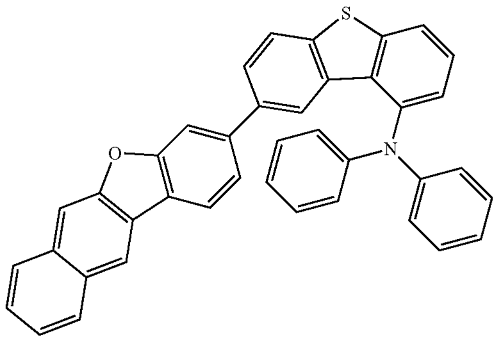
P1-37
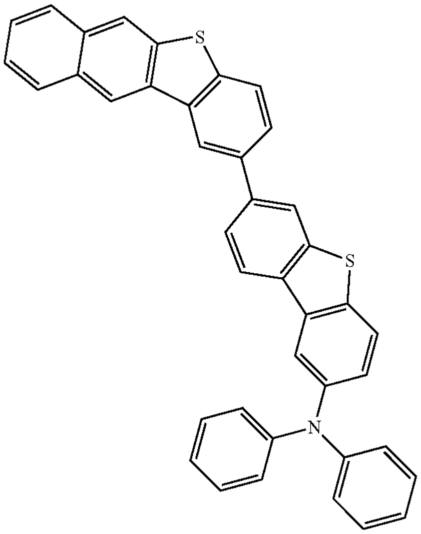

-continued
P1-38
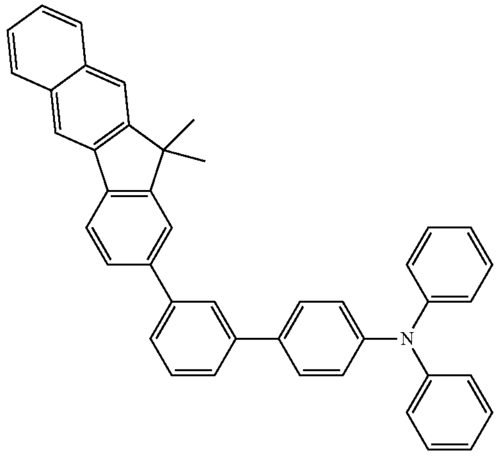
P1-39
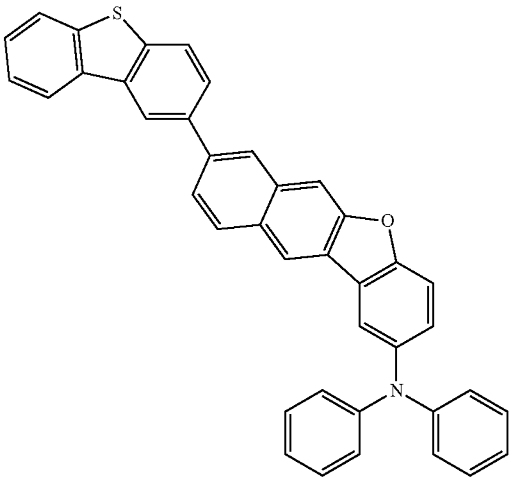
P1-40
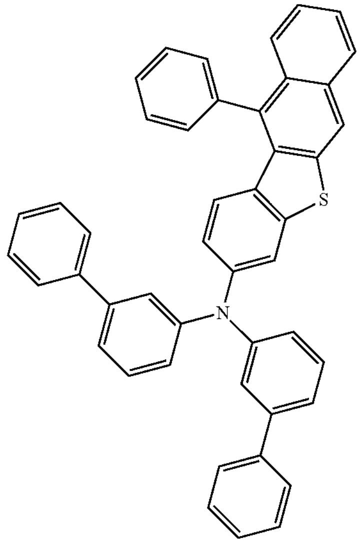
-continued
P1-41
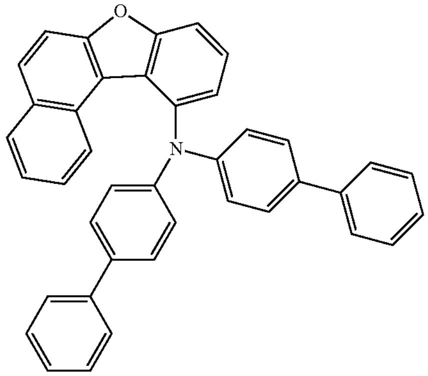
P1-42
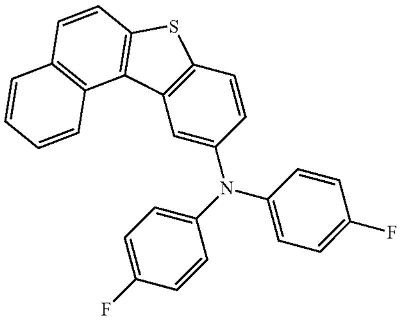
P1-43
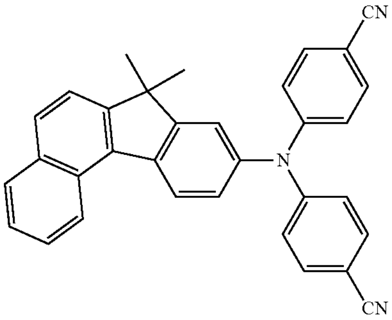
P1-44
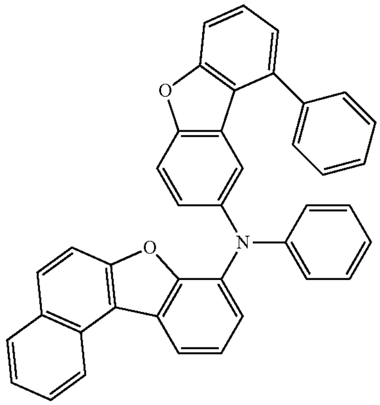

-continued
P1-45
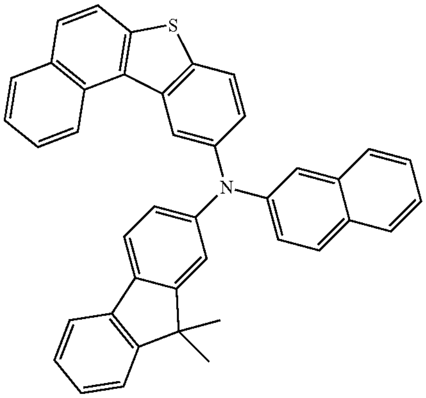
P1-46
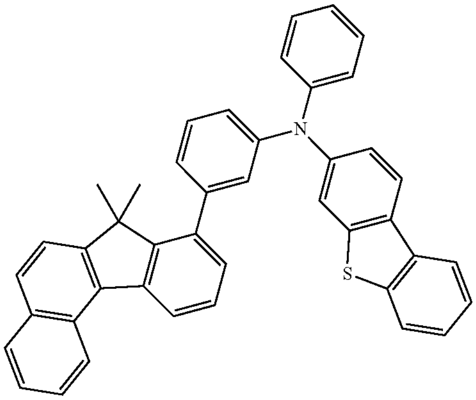
P1-47
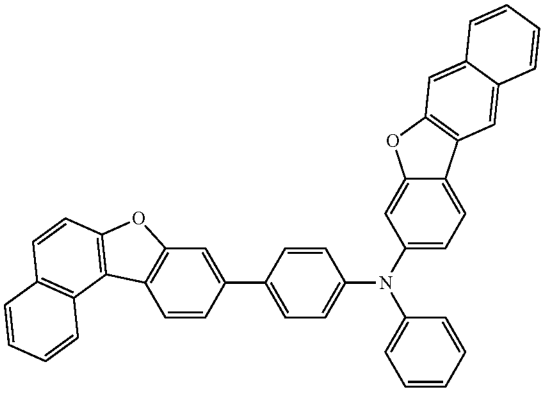
-continued
P1-48
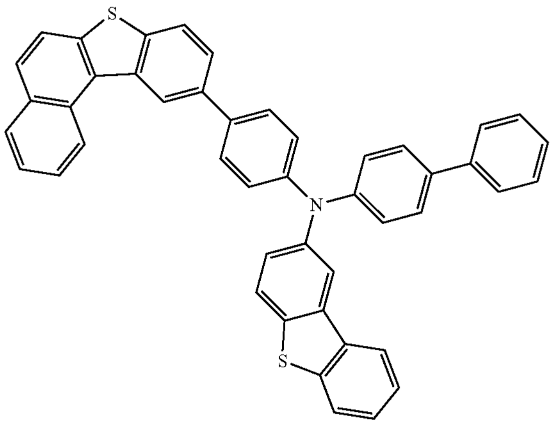
P1-49
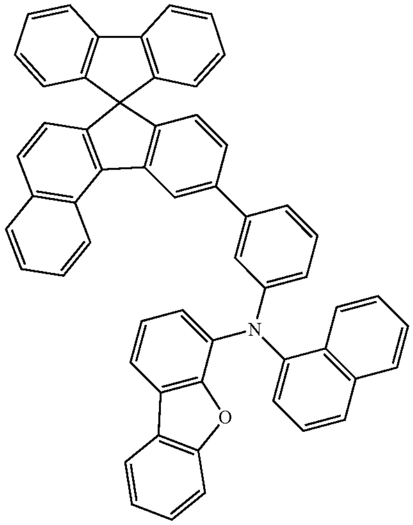
P1-50
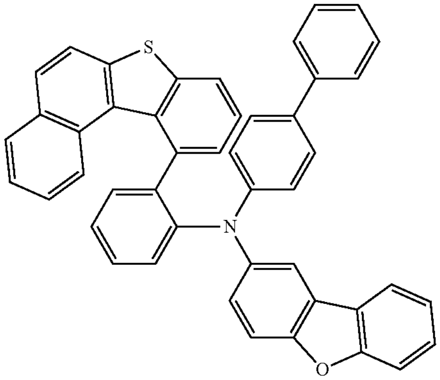

-continued
P1-51
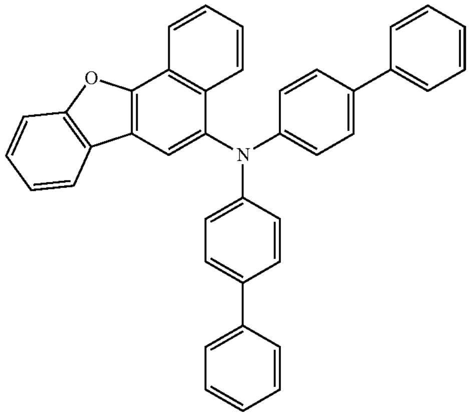
P1-52
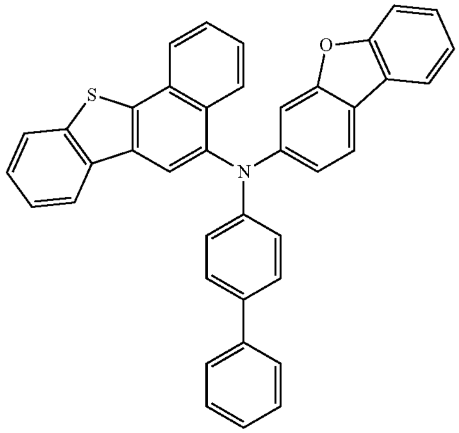
P1-53
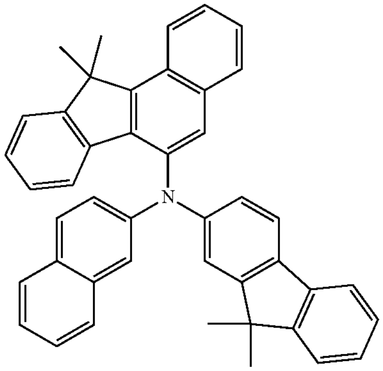
-continued
P1-54
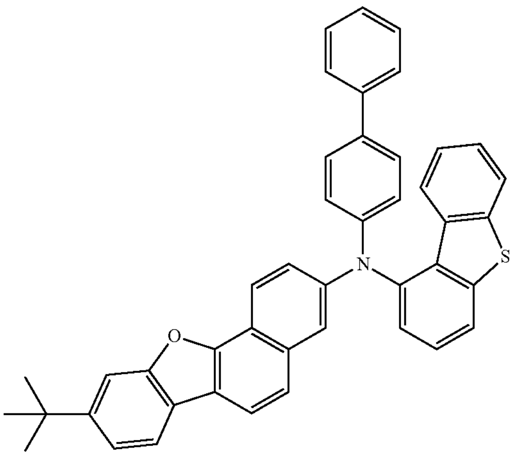
P1-55
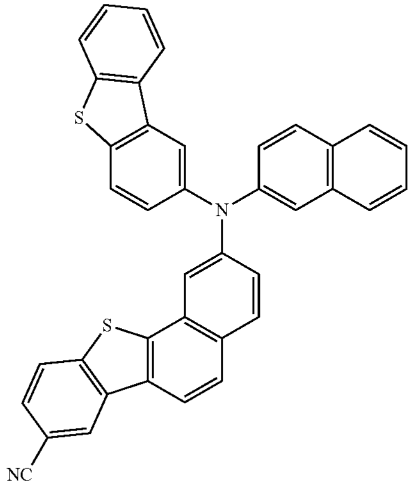
P1-56
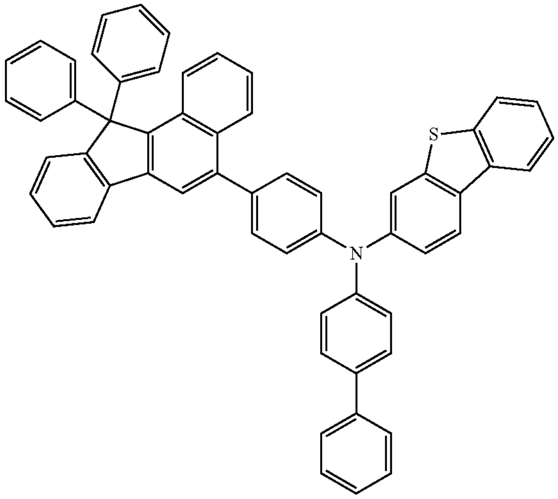

-continued
P1-57
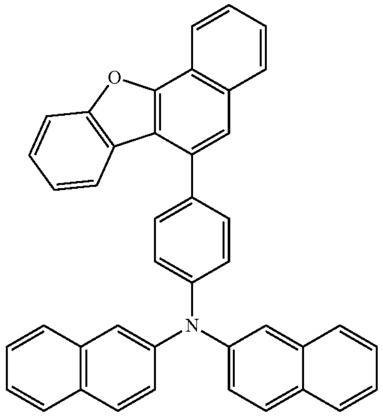
P1-58
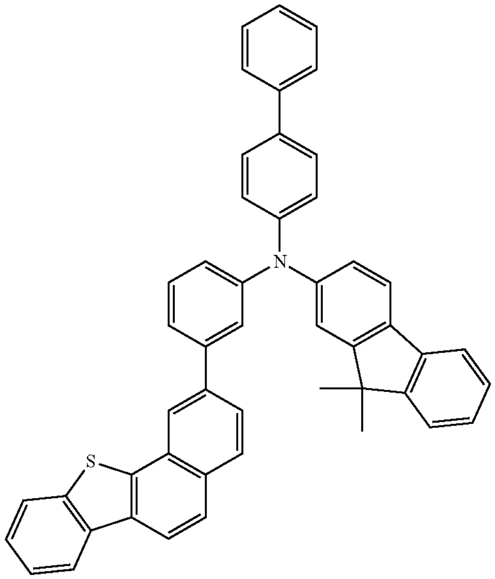
P1-59
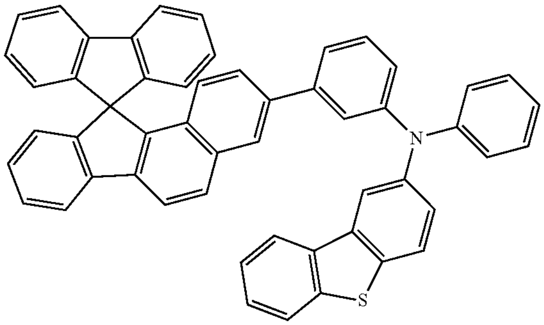
-continued
P1-60
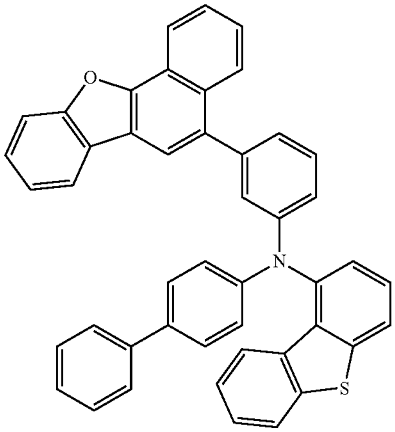
P1-61
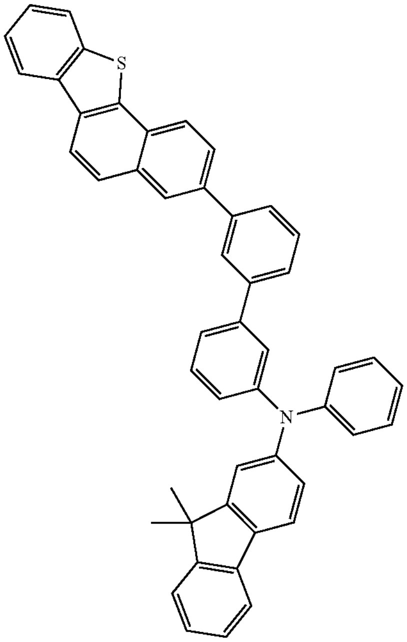
P1-62
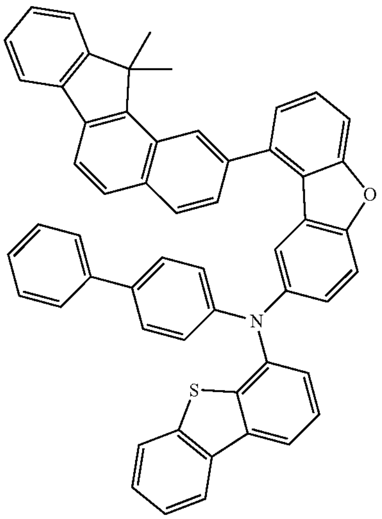

-continued
P1-63
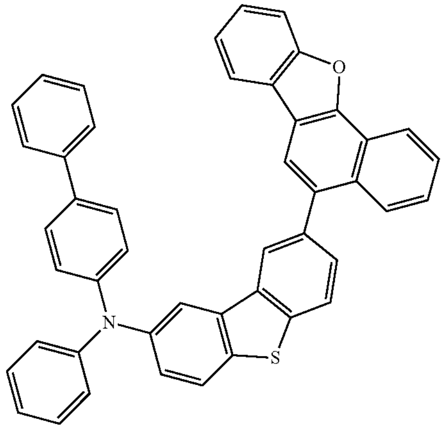
P1-64
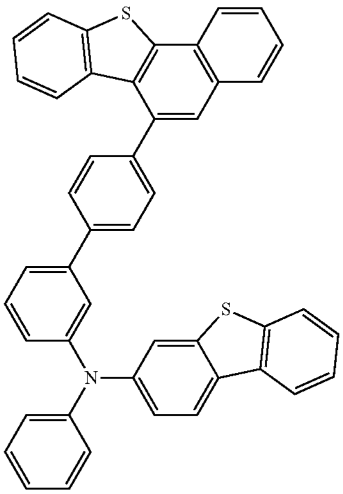
P1-65
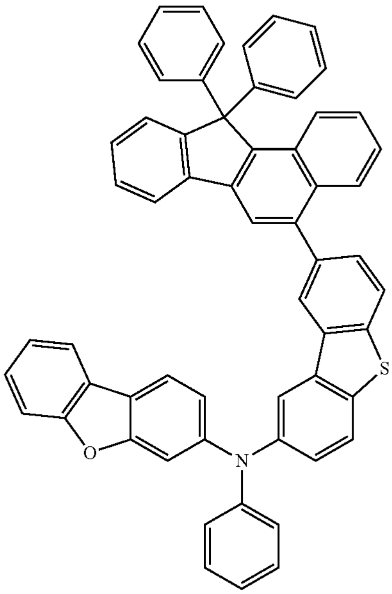
-continued
P1-66
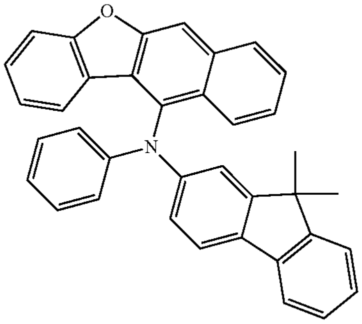
P1-67
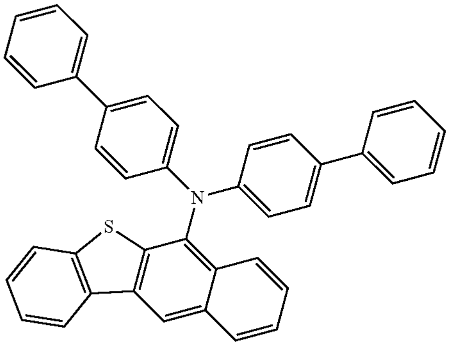
P1-68
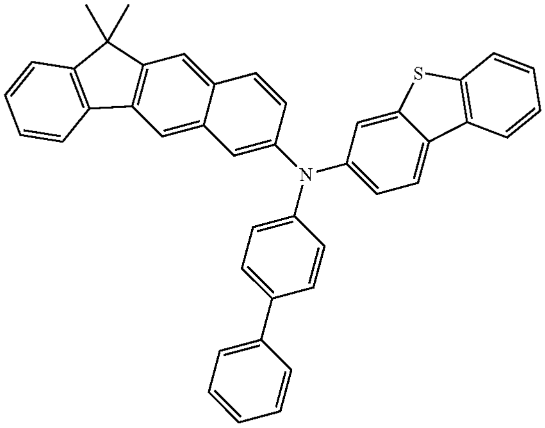
P1-69
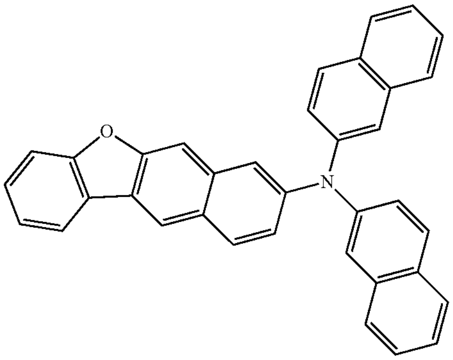

-continued
P1-70
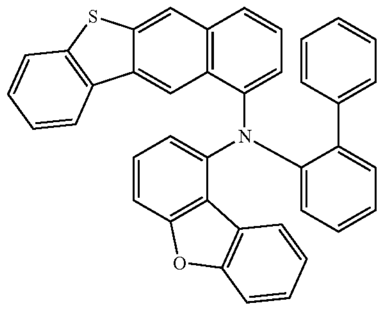
P1-71
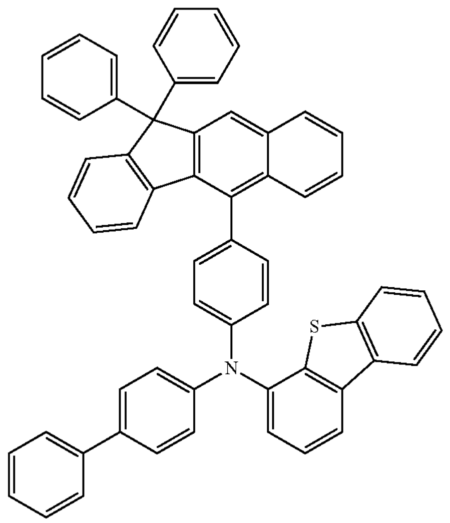
P1-72
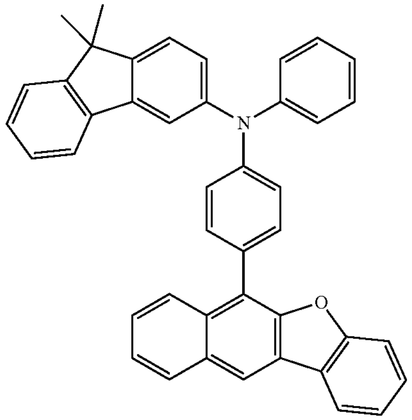
-continued
P1-73
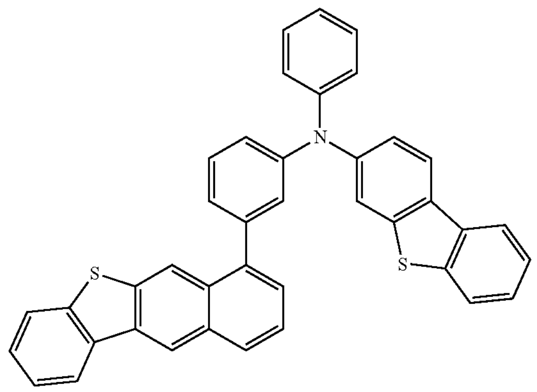
P1-74
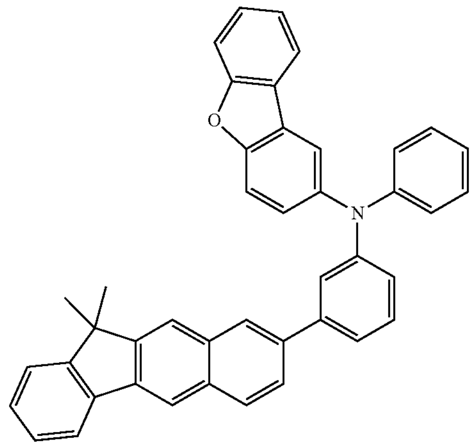
P1-75
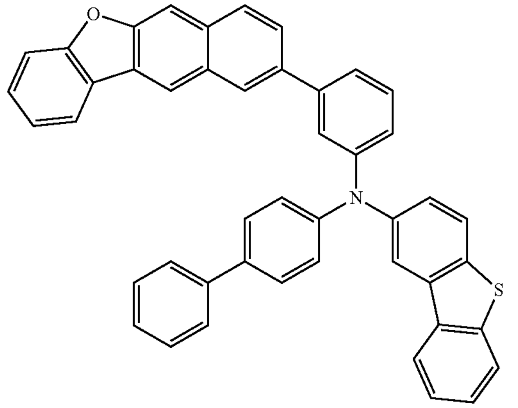

-continued
P1-76
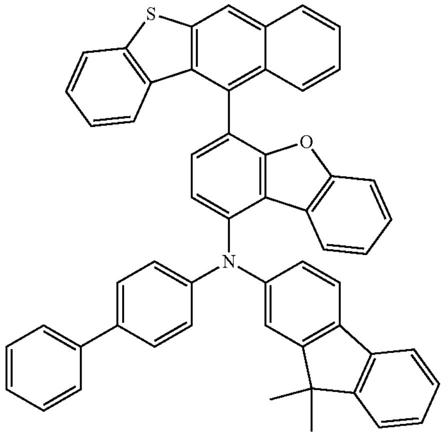
P1-77
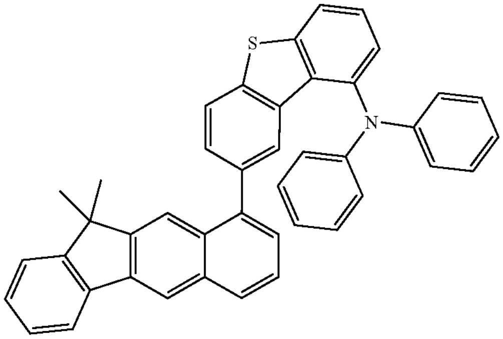
P1-78
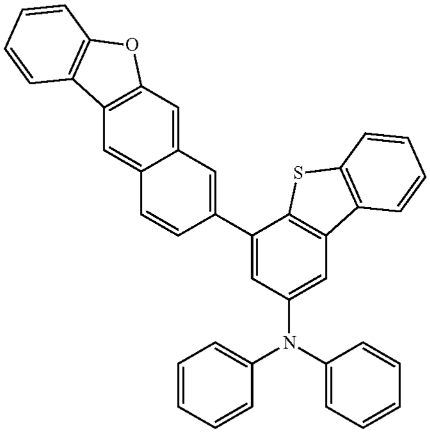
-continued
P1-79
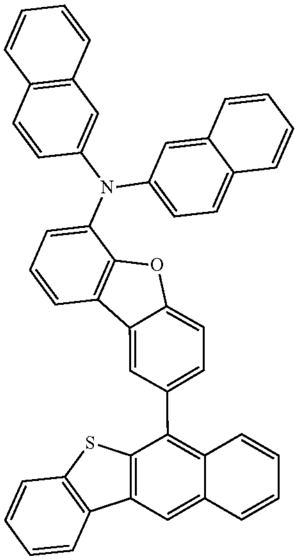
P1-80
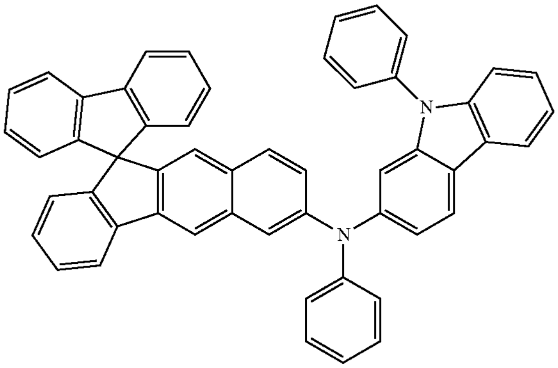
P1-81
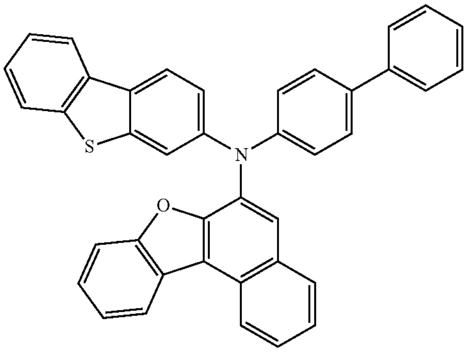
P1-82
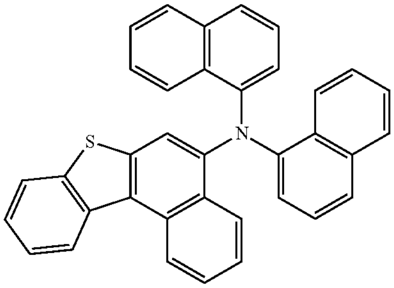

-continued
P1-83
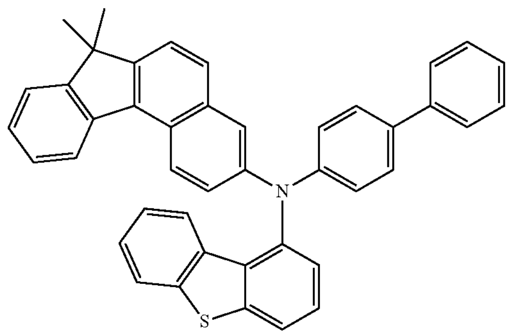
P1-84
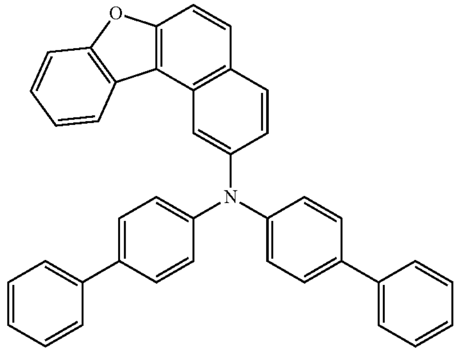
P1-85
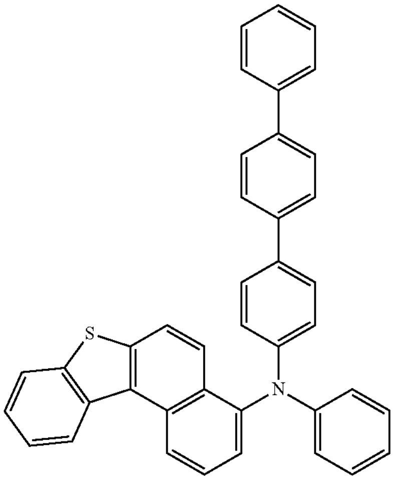
P1-86
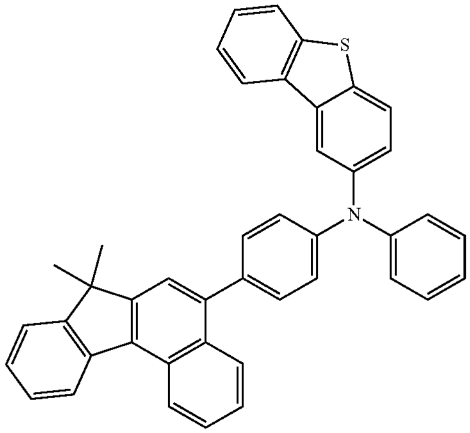
-continued
P1-87
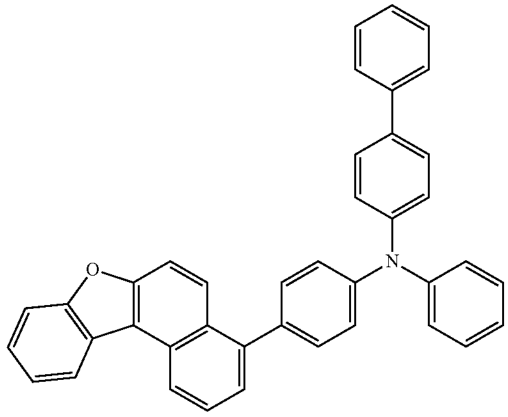
P1-88
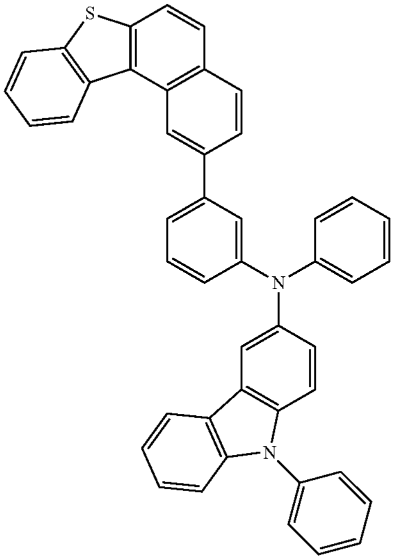
P1-89
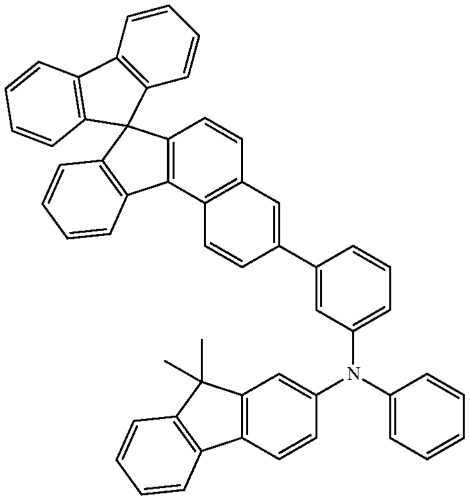

-continued
P1-90
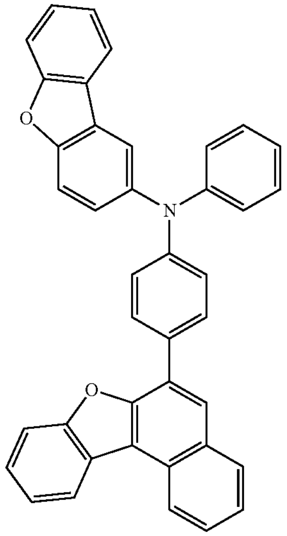
P1-91
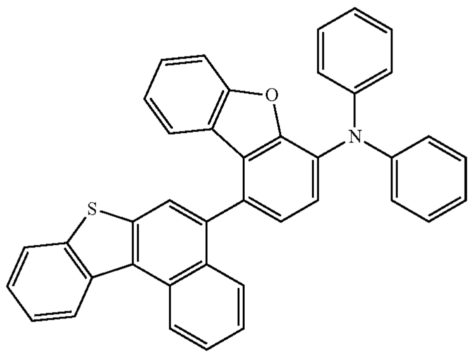
P1-92
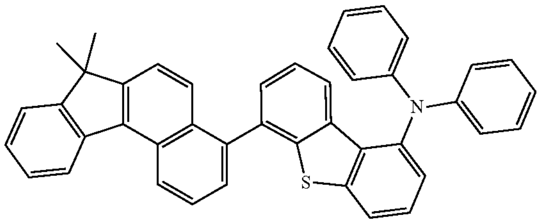
P1-93
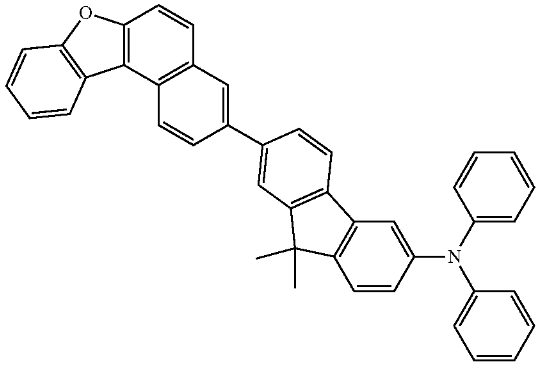
-continued
P1-94
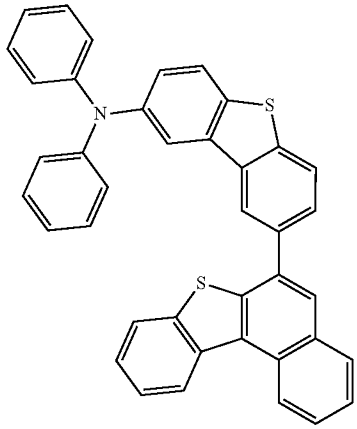
P1-95
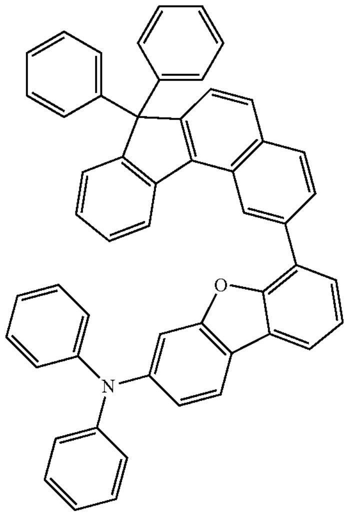
P1-96
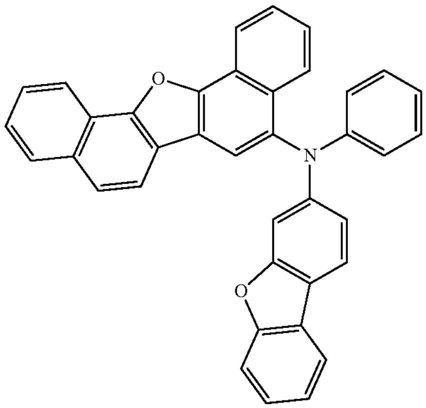

-continued
P1-97
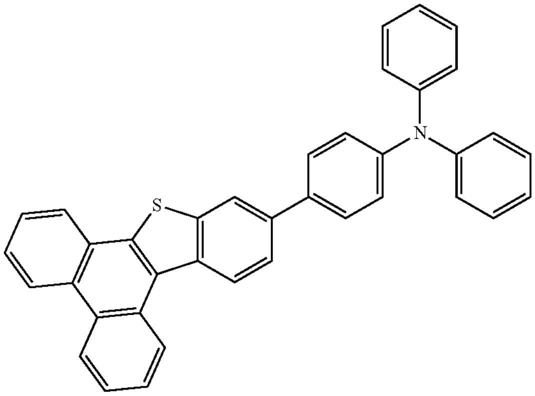
P1-98
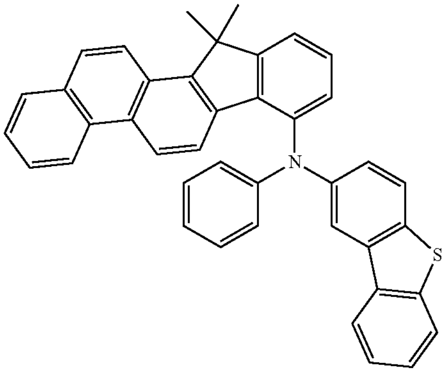
P1-99
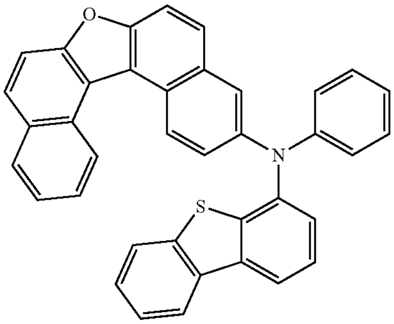
P1-100
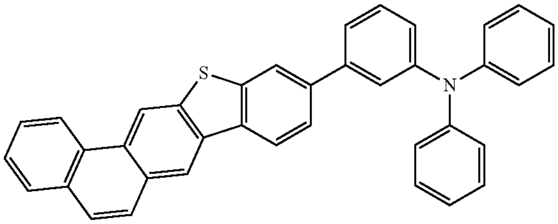
-continued
P1-101
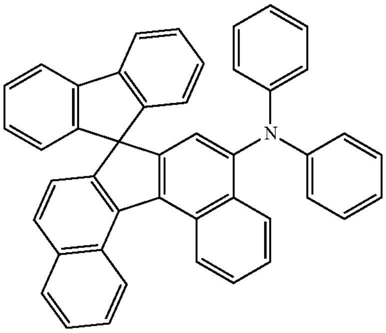
P1-102
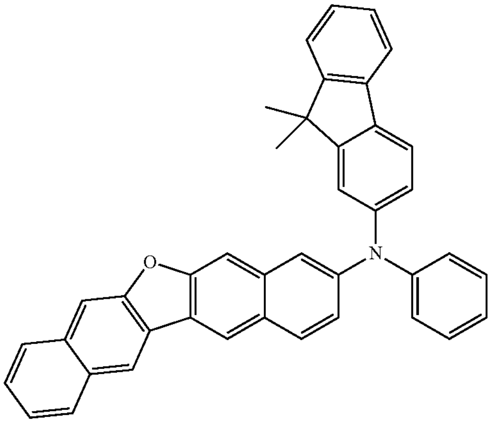
P1-103
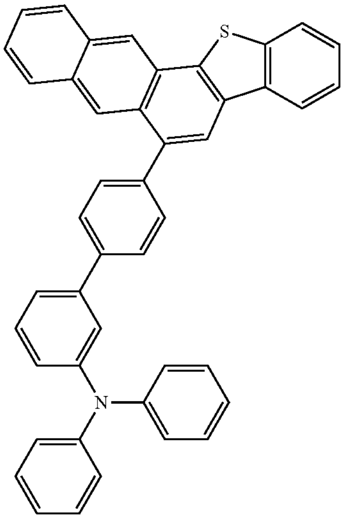

-continued

P1-104

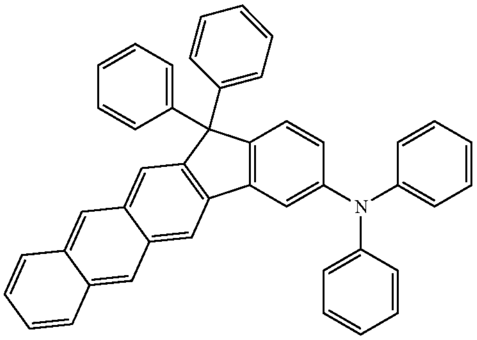

Next, the following Formula 2 will be described.

<Formula 2>

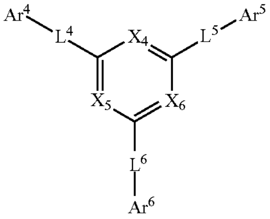

In Formula 2, each of symbols may be defined as follows.

$X_4$ to $X_6$ are each N or C(L-Ar), and at least one of $X_4$ to $X_6$ is N.

Accordingly, the ring comprising $X_4$ to $X_6$ may be pyridine and its derivatives, pyrimidine and its derivatives, or triazine and its derivatives.

L is selected from the group consisting of a single bond, a $C_6$-$C_{60}$ arylene group, a fluorenylene group, a $C_3$-$C_{60}$ aliphatic ring and a $C_2$-$C_{60}$ heterocyclic group comprising at least one heteroatom selected from the group consisting of O, N, S, Si and P, and when L is plural, Ls are the same as or different from each other.

Ar is selected from the group consisting of hydrogen, deuterium, halogen, a cyano group, a nitro group, a $C_6$-$C_{60}$ aryl group, a fluorenyl group, a $C_2$-$C_{60}$ heterocyclic group comprising at least one heteroatom selected from the group consisting of O, N, S, Si and P, a $C_3$-$C_{60}$ aliphatic ring, a $C_1$-$C_{30}$ alkyl group, a $C_2$-$C_{30}$ alkenyl group, a $C_2$-$C_{30}$ alkynyl group, a $C_1$-$C_{30}$ alkoxyl group and a $C_6$-$C_{30}$ aryloxy group, and when Ar is plural, Ars are the same as or different from each other.

$Ar^4$ to $Ar^6$ are each independently selected from the group consisting of a $C_6$-$C_{60}$ aryl group, a fluorenyl group, a $C_2$-$C_{60}$ heterocyclic group comprising at least one heteroatom selected from the group consisting of O, N, S, Si and P, and a $C_3$-$C_{60}$ aliphatic ring.

When at least one of $Ar^4$ to $Ar^6$ is an aryl group, the aryl group may be preferably a $C_6$-$C_{30}$ aryl group, more preferably a $C_6$-$C_{18}$ aryl group, for example, phenyl, biphenyl, naphthyl, terphenyl, anthracene, pyrene, phenanthrene, triphenylene, and the like.

When at least one of $Ar^4$ to $Ar^6$ is is a heterocyclic group, the heterocyclic group may be preferably a $C_2$-$C_{30}$ heterocyclic group, more preferably a $C_2$-$C_{21}$ heterocyclic group, for example, pyridine, dibenzothiophene, dibenzofuran, quinazoline, quinoxaline, quinoline, phenanthroline, imidazole, benzonaphthyridine, benzoquinoline, benzothienopyrimidine, benzofuropyrimidine, benzoacridine, dibenzoacridine, and the like.

When at least one of $Ar^4$ to $Ar^6$ is a fluorenyl group, the fluorenyl group may be 9,9-dimethylfluorene, 9,9-diphenylfluorene, 9,9-spirofluorene, and the like.

$L^4$ to $L^6$ are each independently selected from the group consisting of a single bond, a $C_6$-$C_{60}$ arylene group, a fluorenylene group, a $C_3$-$C_{60}$ aliphatic ring, and a $C_2$-$C_{60}$ heterocyclic group comprising at least one heteroatom selected from the group consisting of O, N, S, Si and P.

When at least one of $L^4$ to $L^6$ is an arylene group, the arylene group may be preferably a $C_6$-$C_{30}$ arylene group, more preferably a $C_6$-$C_{18}$ arylene group, for example, phenyl, biphenyl, naphthyl, terphenyl and the like.

When at least one of $L^4$ to $L^6$ is a heterocyclic group, the heterocyclic group may be preferably a $C_2$-$C_{30}$ heterocyclic group, more preferably a $C_2$-$C_{12}$ heterocyclic group, for example, pyridine, quinazoline, benzoquinazoline, quinoxaline, dibenzothiophene, dibenzofuran, and the like.

$Ar^4$ to $Ar^6$, Ar, $L^4$ to $L^6$ and L may be each optionally substituted with one or more substituents selected from the group consisting of deuterium, halogen, a silane group unsubstituted or substituted with a $C_1$-$C_{20}$ alkyl group or a $C_6$-$C_{20}$ aryl group, a siloxane group, a boron group, a germanium group, a cyano group, a nitro group, a $C_1$-$C_{20}$ alkylthio group, a $C_1$-$C_{20}$ alkoxy group, a $C_6$-$C_{20}$ arylalkoxy group, a $C_1$-$C_{20}$ alkyl group, a $C_2$-$C_{20}$ alkenyl group, a $C_2$-$C_{20}$ alkynyl group, a $C_6$-$C_{20}$ aryl group, a fluorenyl group, a $C_2$-$C_{20}$ heterocyclic group containing at least one heteroatom of O, N, S, Si, and P, a $C_3$-$C_{20}$ aliphatic ring group, a $C_7$-$C_{20}$ arylalkyl group and $C_8$-$C_{20}$ arylalkenyl group.

Preferably, Formula 2 may be represented by one of Formula 2-A to Formula 2-C.

<Formula 2-A>

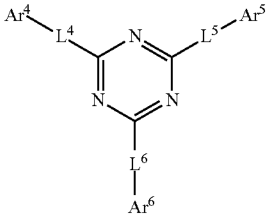

<Formula 2-B>

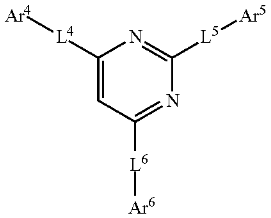

<Formula 2-C>

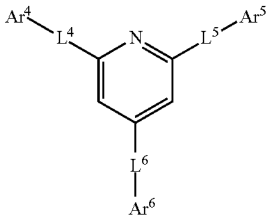

In formula 2-A to Formula 2-C, $Ar^4$ to $Ar^6$, $L^4$ to $L^6$ are the same as defined for Formula 2.

In addition, preferably, Formula 2 may be represented by one of Formula 2-1 to Formula 2-8.

<Formula 2-1>

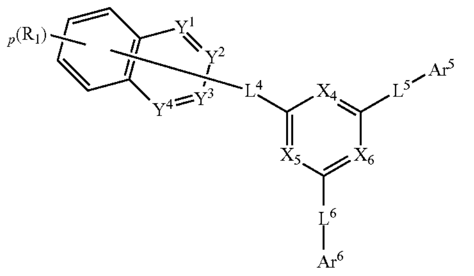

<Formula 2-2>

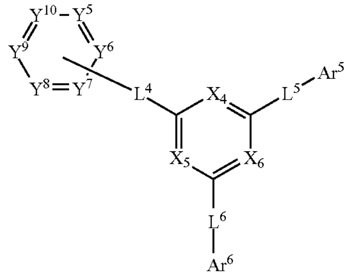

<Formula 2-3>

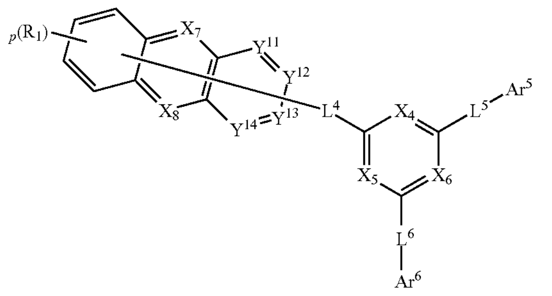

<Formula 2-4>

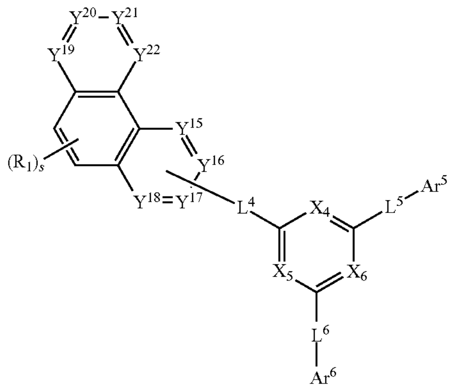

-continued

<Formula 2-5>

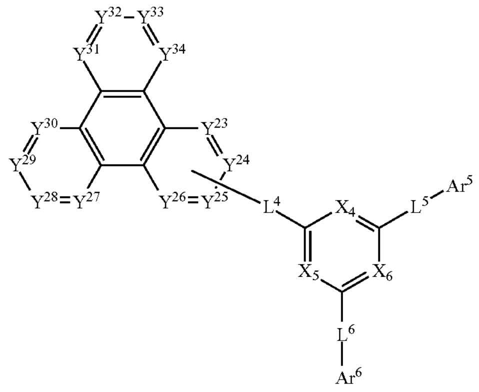

<Formula 2-6>

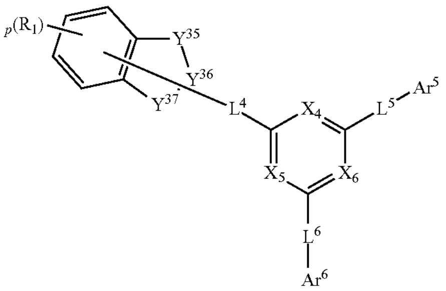

<Formula 2-7>

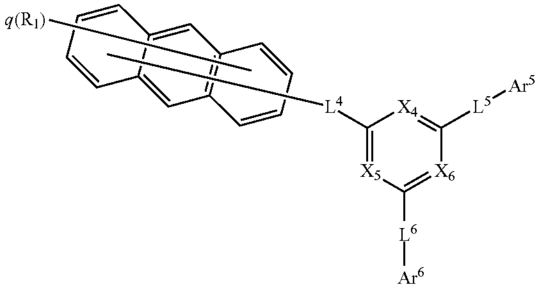

<Formula 2-8>

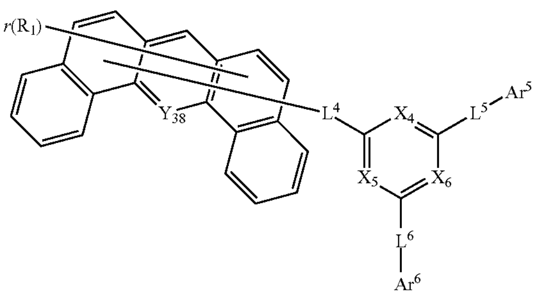

In Formula 2-1 to Formula 2-8, $Ar^5$, $Ar^6$, $L^4$ to $L^6$, and $X_4$ to $X_6$ are the same as defined for Formula 2.

$R_1$ is selected from the group consisting of hydrogen, deuterium, halogen, a cyano group, a nitro group, a $C_6$-$C_{20}$ aryl group, a fluorenyl group, a $C_2$-$C_{20}$ heterocyclic group comprising at least one heteroatom selected from the group consisting of O, N, S, Si and P, a $C_3$-$C_{20}$ aliphatic ring, a fused ring of a $C_3$-$C_{20}$ aliphatic ring with a $C_6$-$C_{20}$ aromatic ring, a $C_1$-$C_{20}$ alkyl group, a $C_2$-$C_{20}$ alkenyl group, a $C_2$-$C_{20}$ alkynyl group, a $C_1$-$C_{20}$ alkoxyl group, a $C_6$-$C_{20}$ aryloxy group and $-L_3$-$N(R_5)(R_6)$, and adjacent groups may be linked to each other to form a ring.

p is an integer of 0 to 4, q is an integer of 0 to 9, r is an integer of 0 to 5, s is an integer of 0 to 2, when p, q, r or s are an integer of 2 or more, $R_1$s are the same as or different from each other.

$X_7$ and $X_8$ are each independently a single bond, N-($L_2$-$Ar_2$), O, S or C($R_2$)($R_3$), and at least one of $X_7$ and $X_8$ is not a single bond. That is, at least one of $X_7$ and $X_8$ is N-($L_2$-$Ar_2$), O, S or C($R_2$)($R_3$).

$Y^1$ to $Y^{38}$ are each independently C, C($R_4$) or N, and adjacent $R_4$s may be linked to each other to form a ring.

$R_2$ to $R_4$ are each independently selected from the group consisting of hydrogen, deuterium, halogen, a cyano group, a nitro group, a $C_6$-$C_{20}$ aryl group, a fluorenyl group, a $C_2$-$C_{20}$ heterocyclic group comprising at least one heteroatom selected from the group consisting of O, N, S, Si and P, a $C_3$-$C_{20}$ aliphatic ring, a fused ring of a $C_3$-$C_{20}$ aliphatic ring with a $C_6$-$C_{20}$ aromatic ring, a $C_1$-$C_{20}$ alkyl group, a $C_2$-$C_{20}$ alkenyl group, a $C_2$-$C_{20}$ alkynyl group, a $C_1$-$C_{20}$ alkoxyl group, a $C_6$-$C_{20}$ aryloxy group, and -$L_3$-N($R_5$)($R_6$), and $R_2$ and $R_3$ may be bonded to each other to form a ring, adjacent $R_4$s may be bonded to each other to form a ring.

$L_2$ and $L_3$ are each independently selected from the group consisting of a single bond; a $C_6$-$C_{20}$ arylene group, a fluorenylene group, a $C_2$-$C_{20}$ heterocyclic group comprising at least one heteroatom selected from the group consisting of O, N, S, Si and P, a $C_3$-$C_{20}$ aliphatic ring and a combination thereof.

$Ar_2$ is selected from the group consisting of a $C_6$-$C_{20}$ aryl group, a fluorenyl group, a $C_2$-$C_{20}$ heterocyclic group comprising at least one heteroatom selected from the group consisting of O, N, S, Si and P, a $C_3$-$C_{20}$ aliphatic ring and a combination thereof.

$R_5$ and $R_6$ are each independently selected from the group consisting of a $C_6$-$C_{20}$ aryl group, a fluorenyl group, a $C_2$-$C_{20}$ heterocyclic group comprising at least one heteroatom selected from the group consisting of O, N, S, Si and P, a $C_3$-$C_{20}$ aliphatic ring and a combination thereof.

With the proviso that a compound represented by the following formulas 2-3-1 to 2-3-4 are excluded from Formula 2-3.

<Formula 2-3-1>

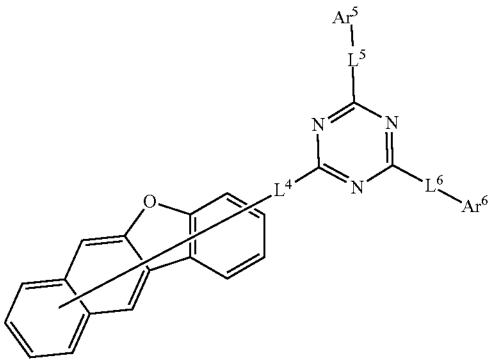

-continued

<Formula 2-3-2>

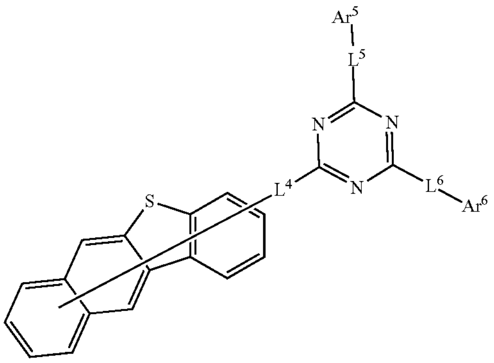

<Formula 2-3-3>

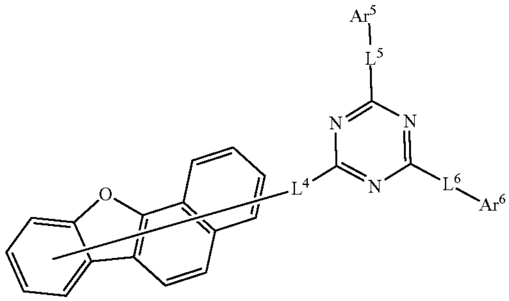

<Formula 2-3-4>

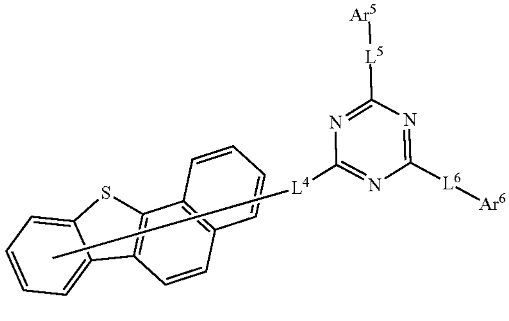

In Formula 2-3-1 to Formula 2-3-4, $L^4$ to $L^6$, $Ar^5$, $Ar^6$ are the same as defined for Formula 2.

Specifically, the compound represented by Formula 2 may be one of the following compounds, but there is no limitation thereto.

-continued
3-1
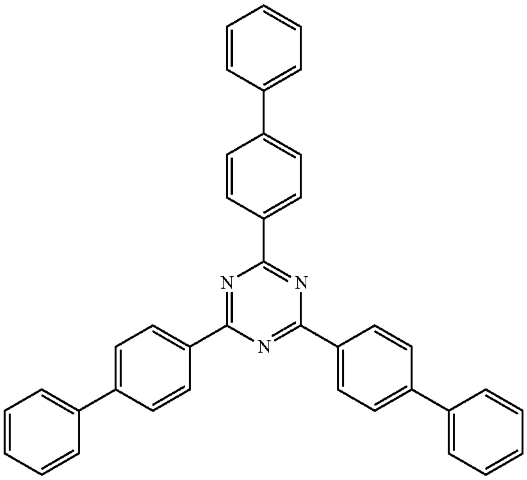
3-2
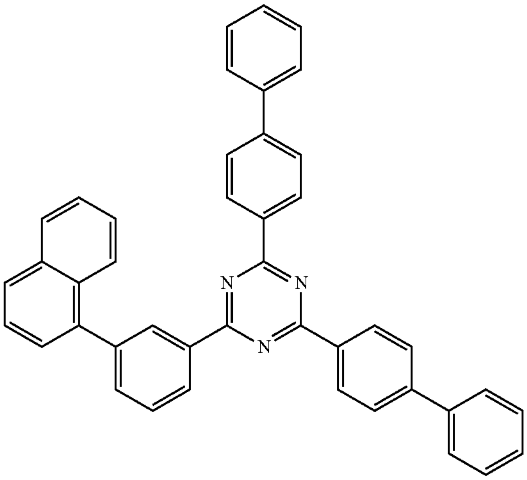
3-3
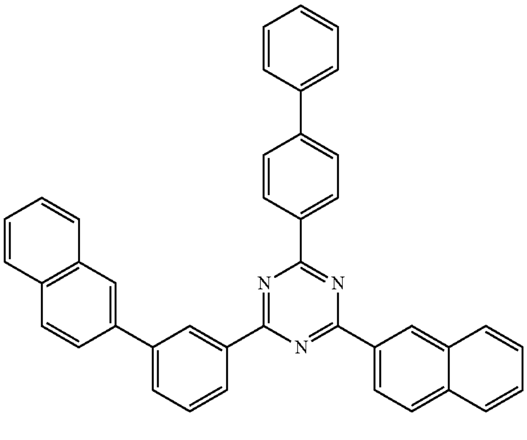
3-4
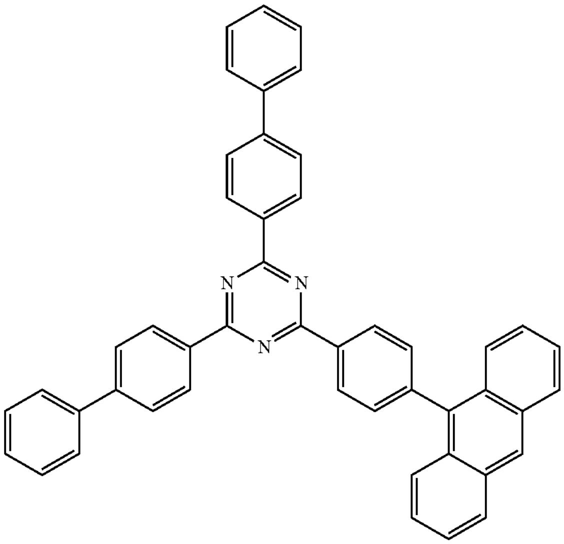
3-5
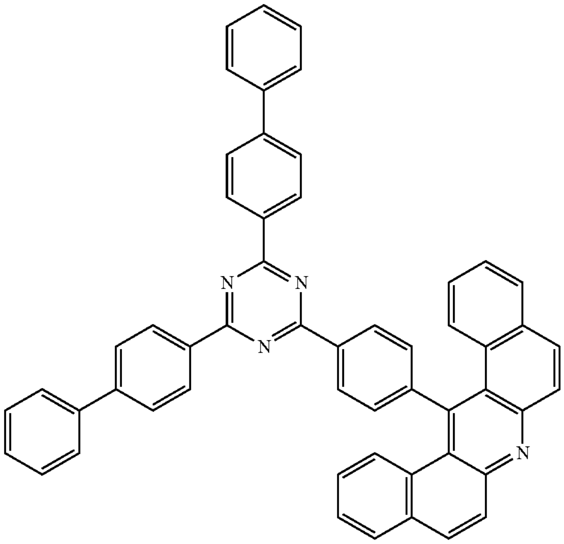
3-6
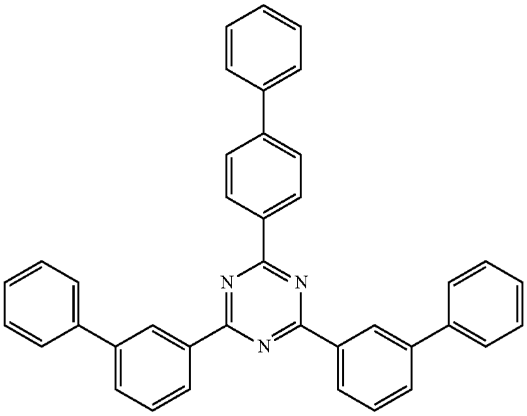

-continued
3-7
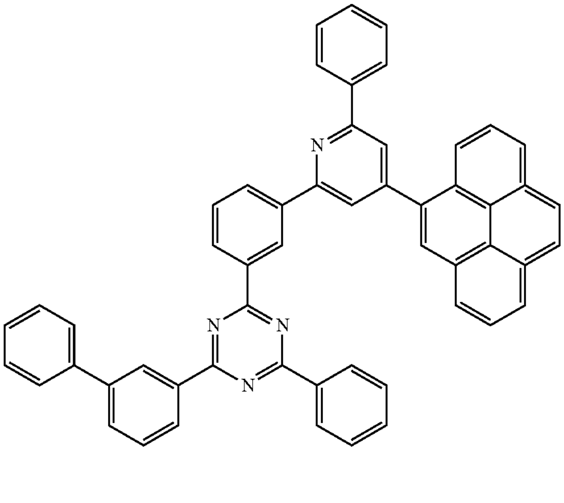
3-8
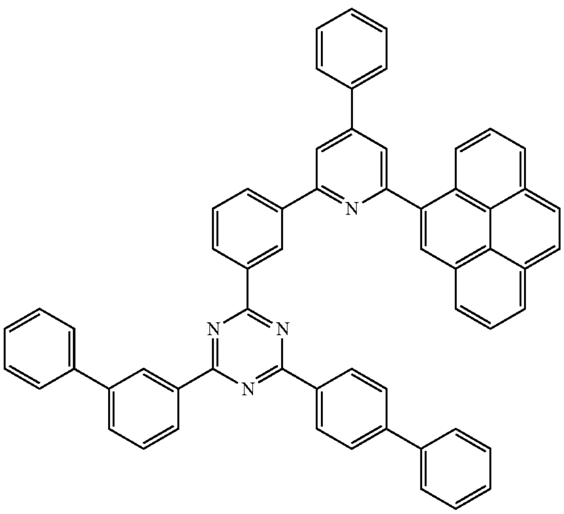
3-9
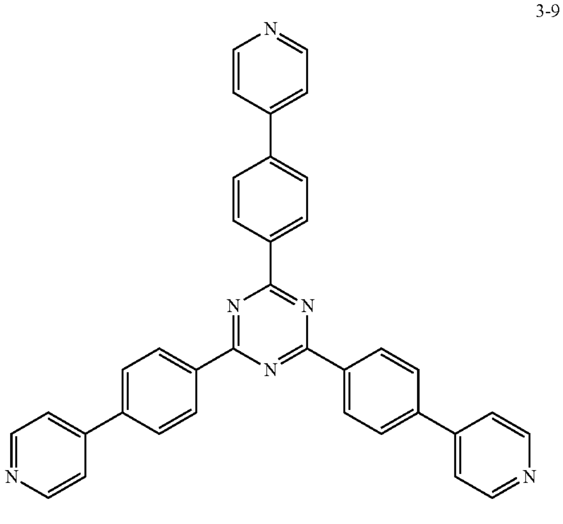
-continued
3-10
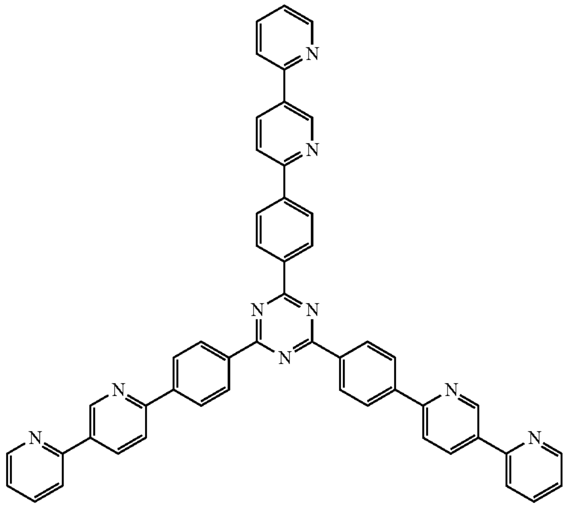
3-11
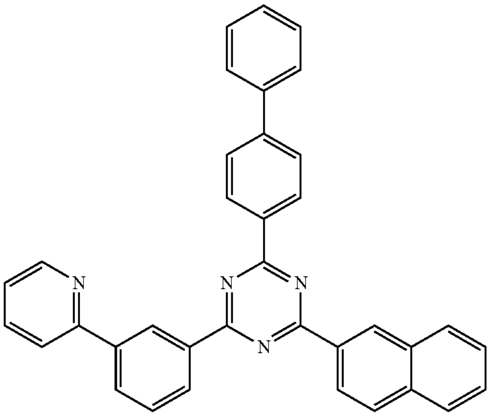
3-12
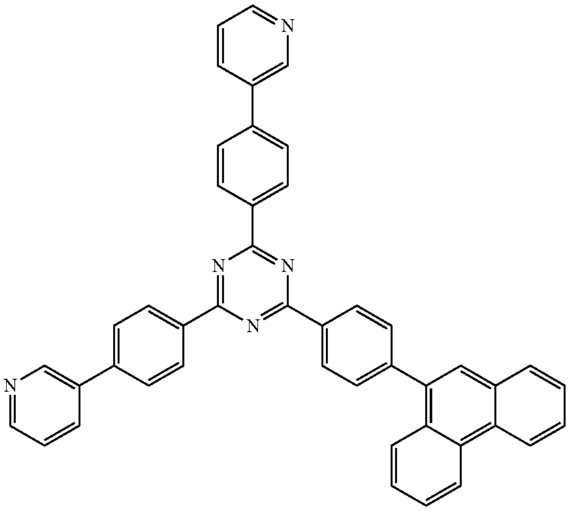

-continued
3-13
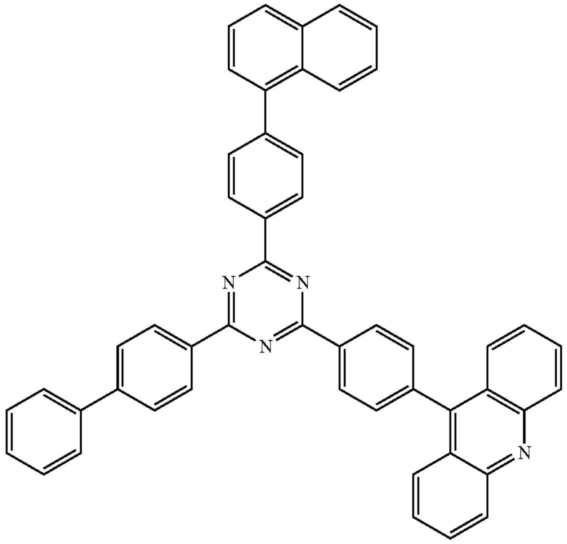
3-14
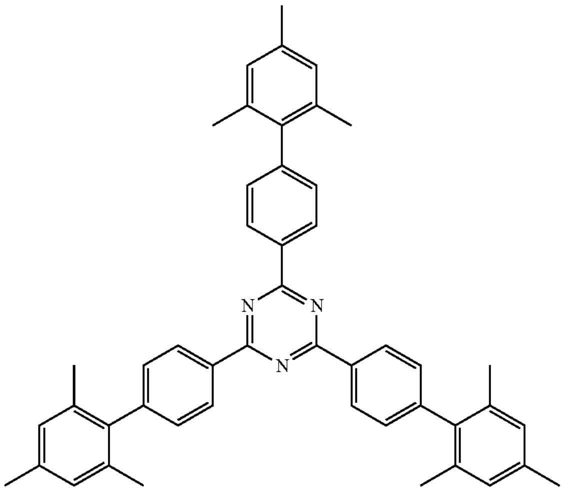
3-15
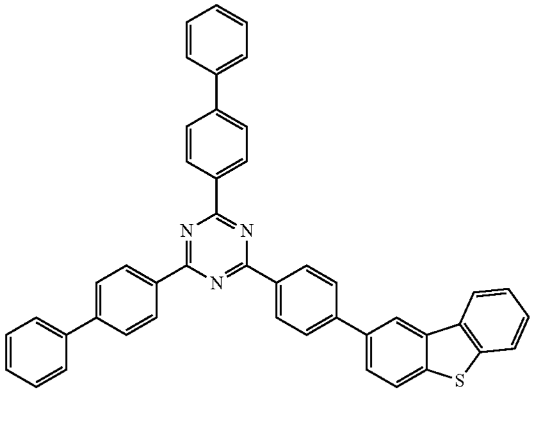
-continued
3-16
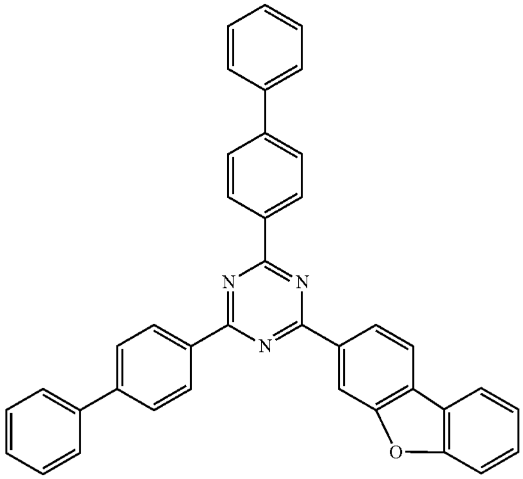
3-17
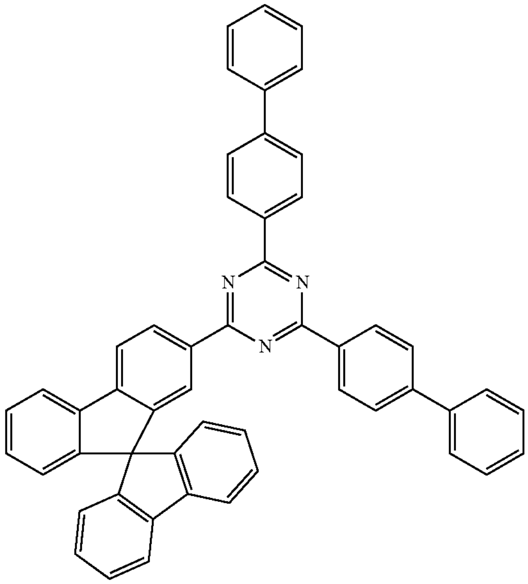
3-18
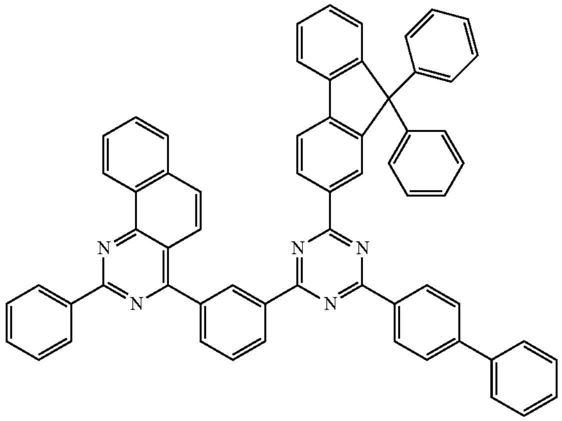

-continued
3-19
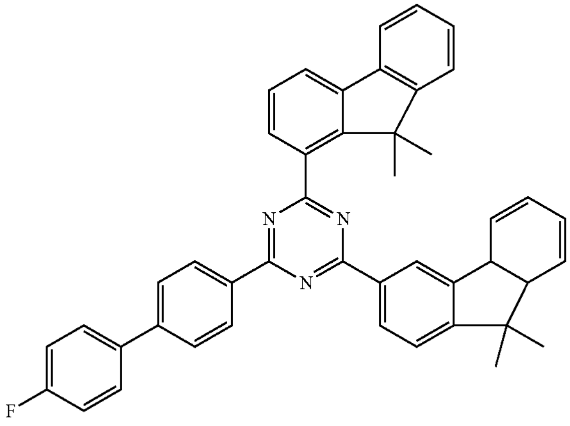
3-20
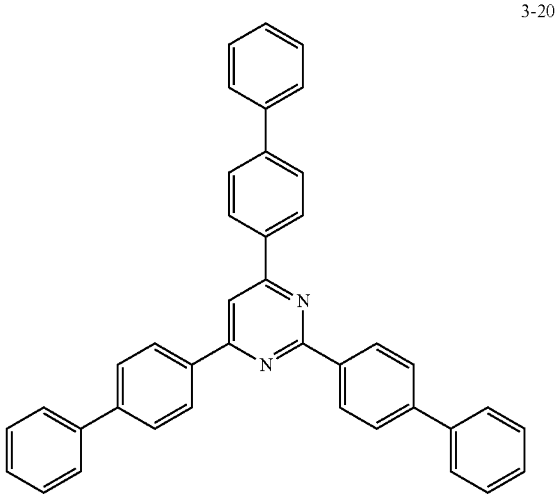
3-21
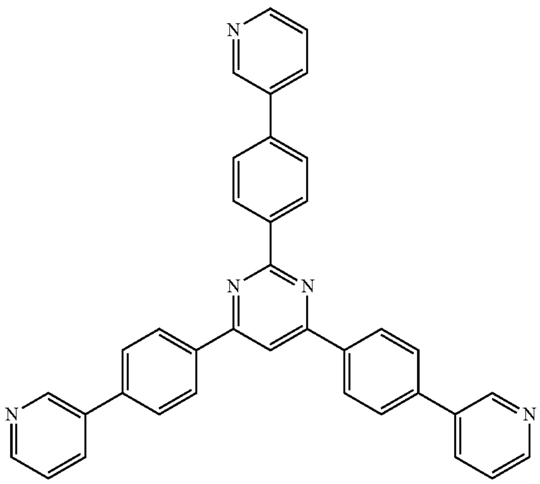
-continued
3-22
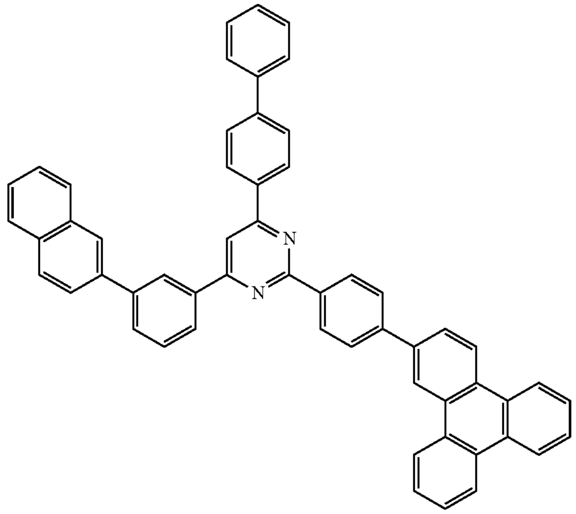
3-23
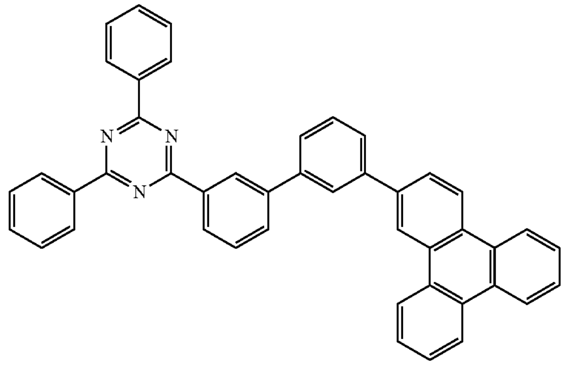
3-24
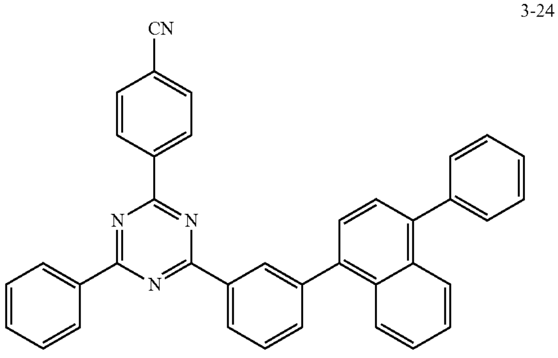

-continued
3-25
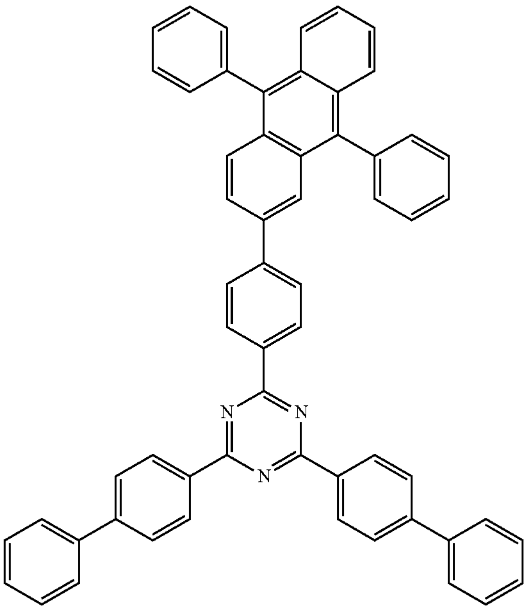
3-26
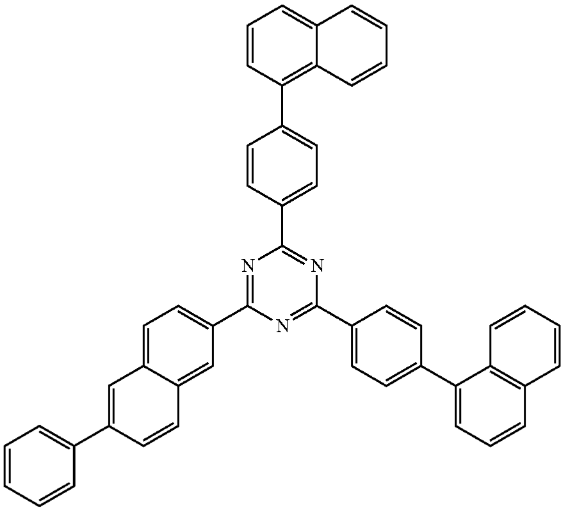
3-27
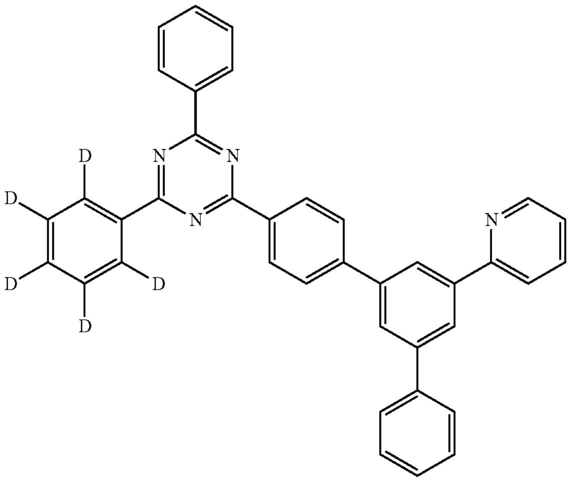
-continued
3-28
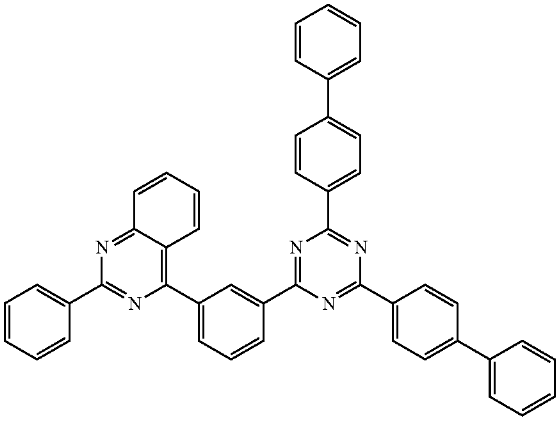
3-29
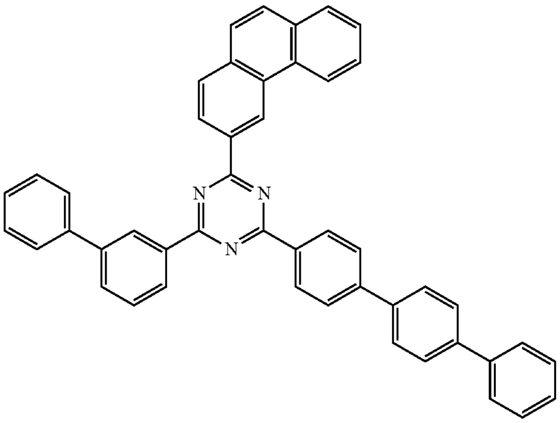
3-30
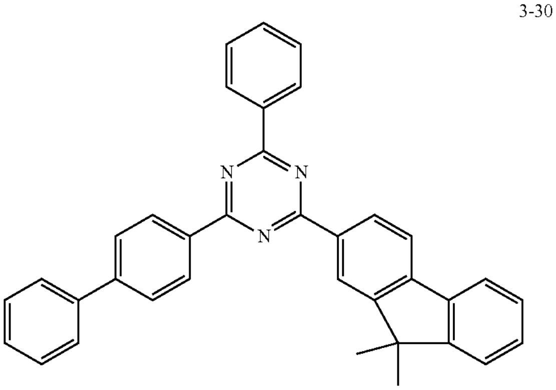

-continued
3-31
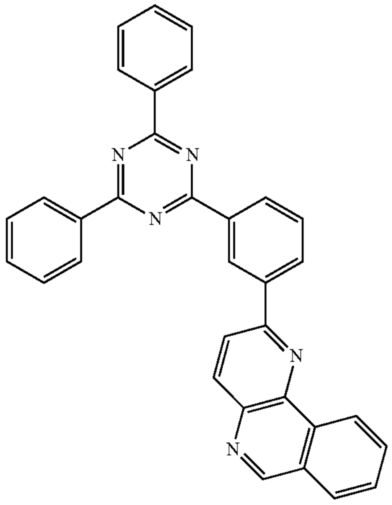
3-32
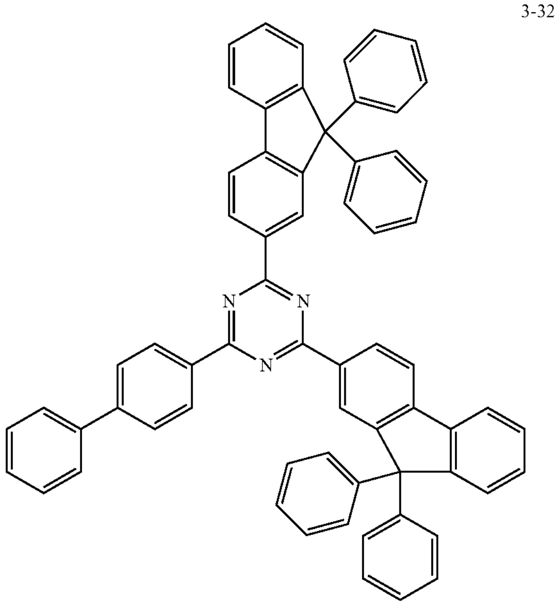
-continued
3-33
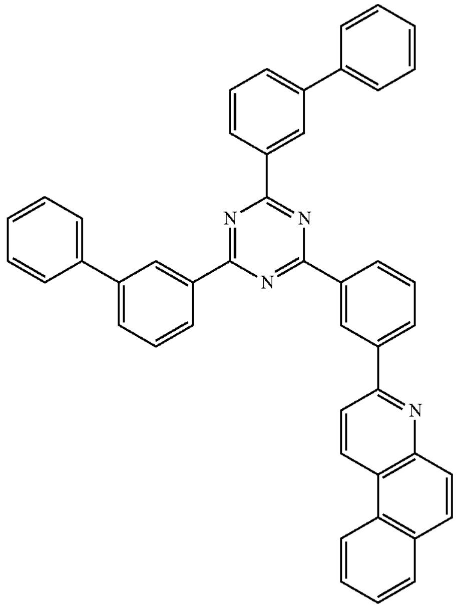
3-34
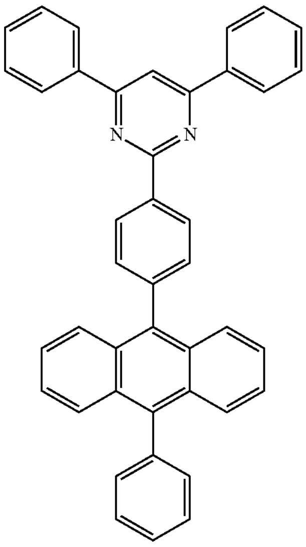
3-35
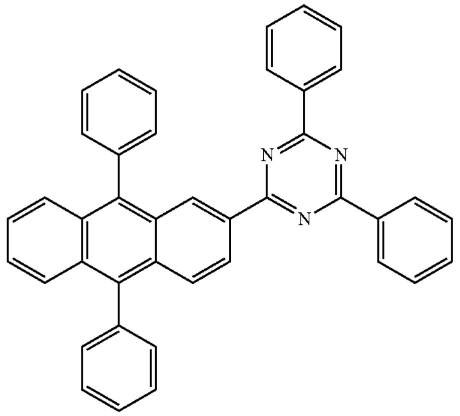

-continued
3-36
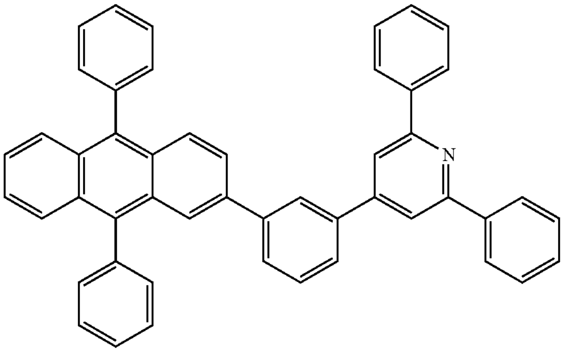
3-37
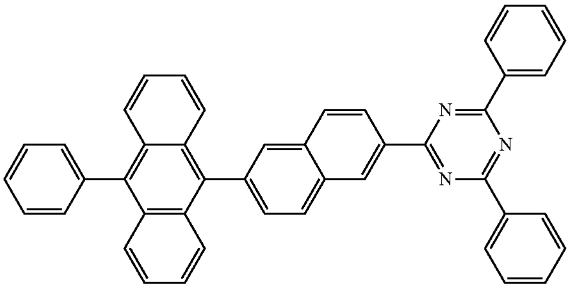
3-38
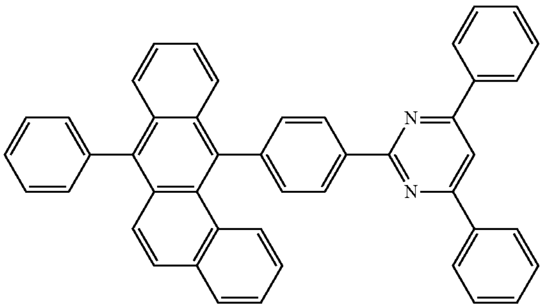
3-39
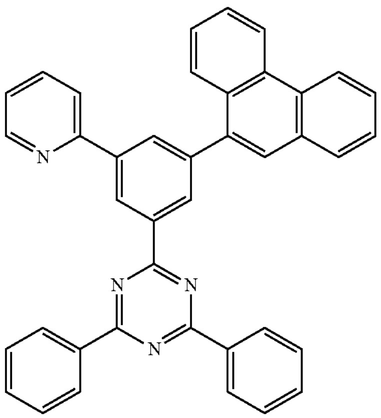
-continued
3-40
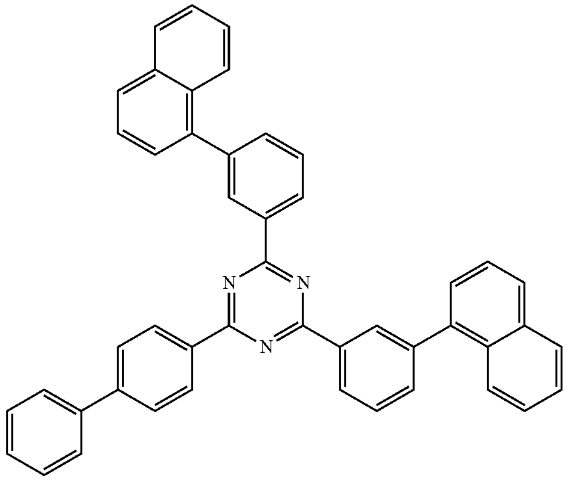
3-41
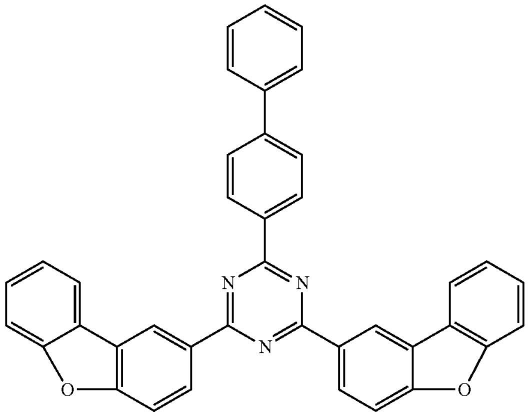
3-42
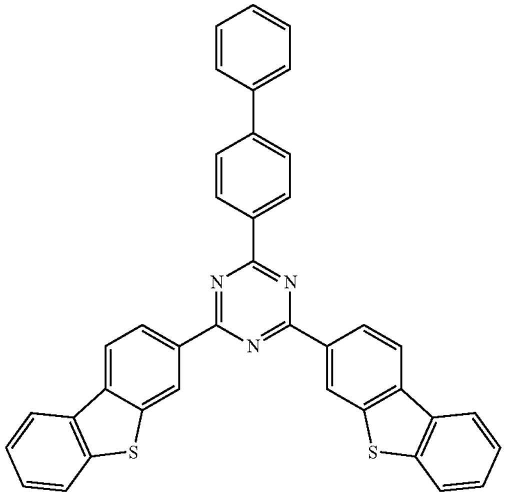

-continued
3-43
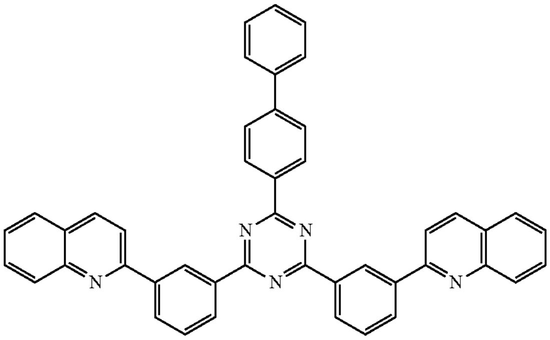
3-44
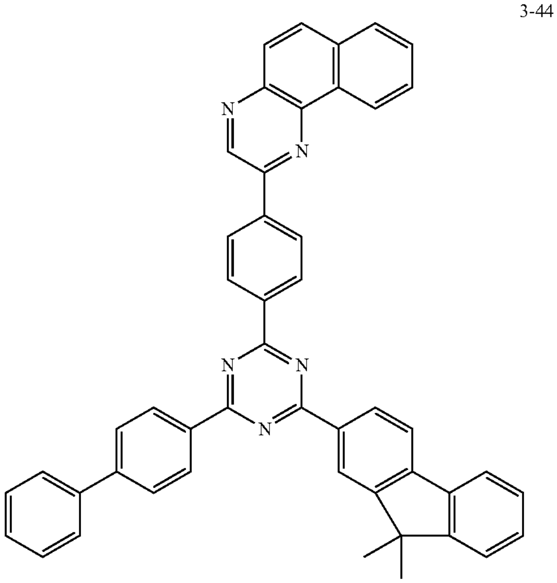
3-46
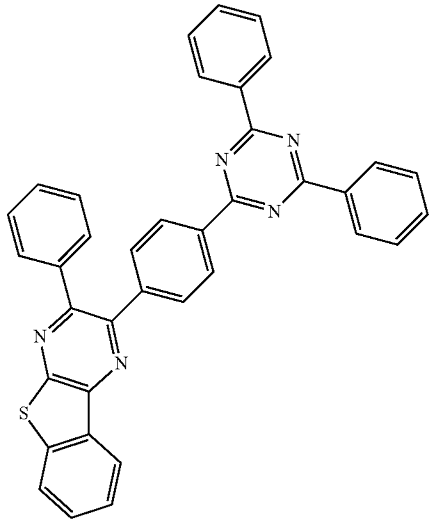
-continued
3-47
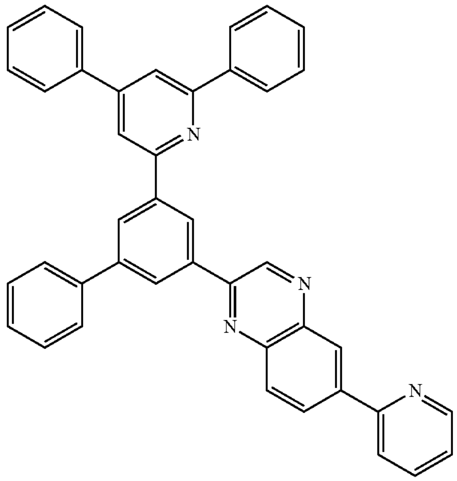
3-48
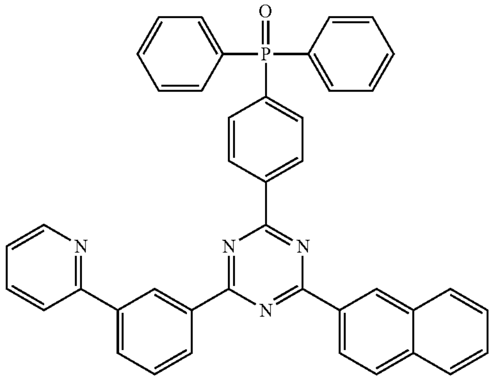
3-49
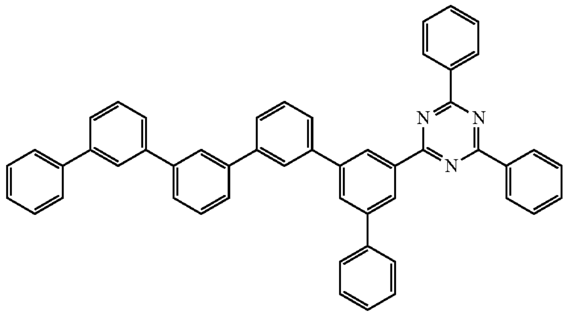
3-50
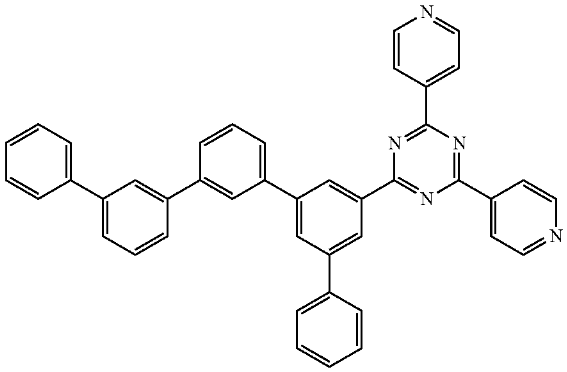

-continued
3-51
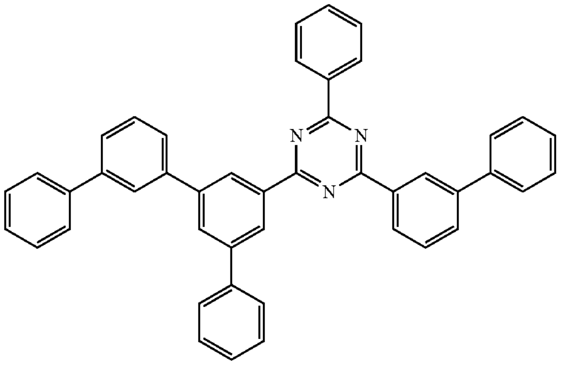
3-52
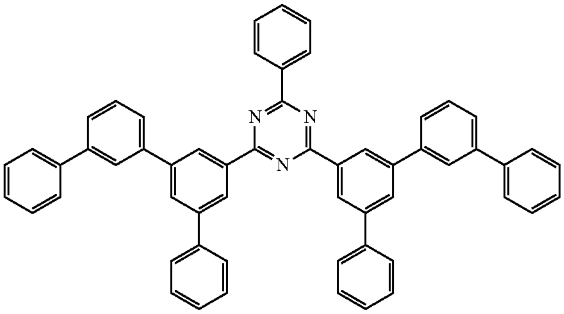
3-53
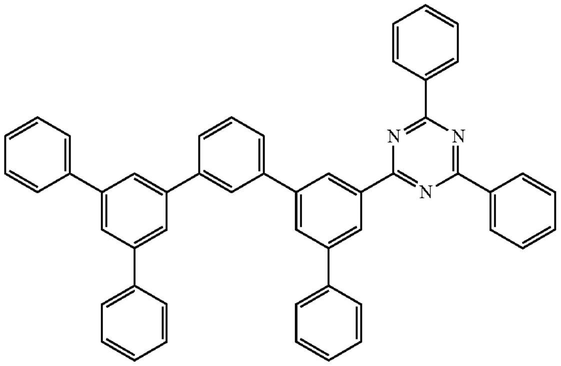
3-54
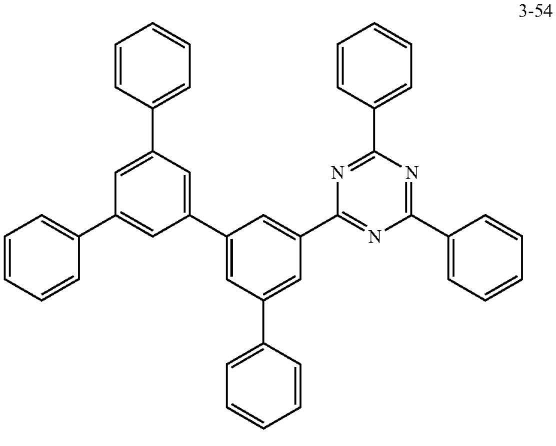
-continued
3-55
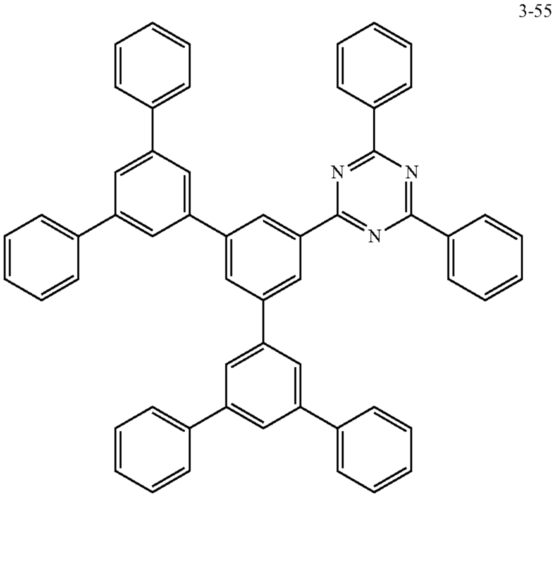
3-56
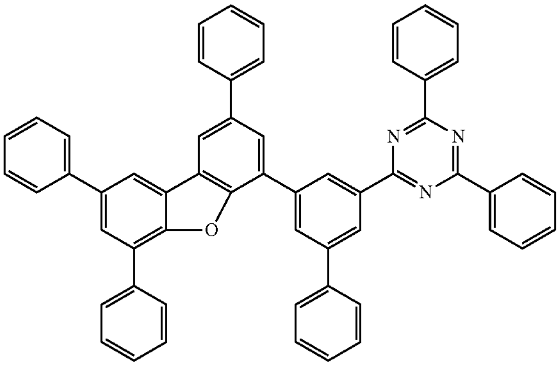
3-57
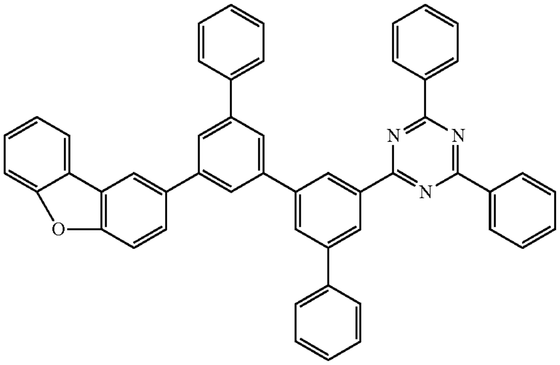

-continued
3-58
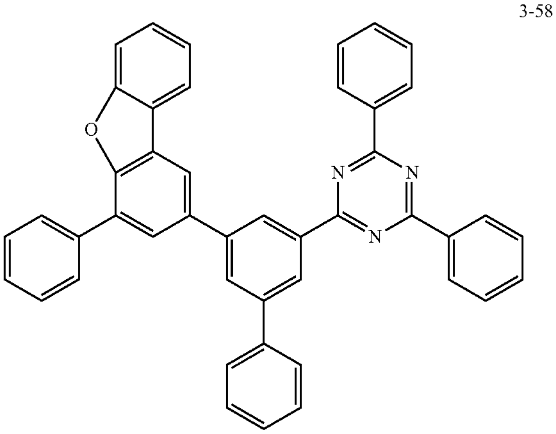
3-59
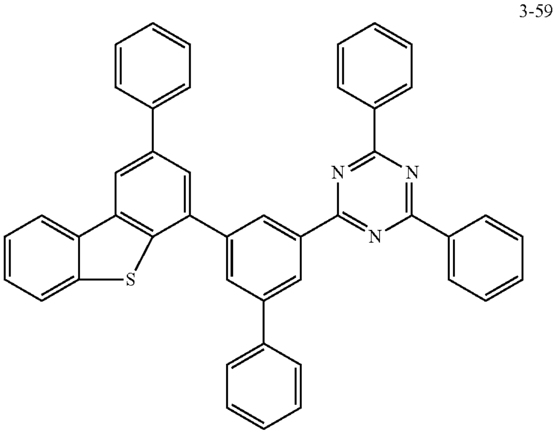
3-60
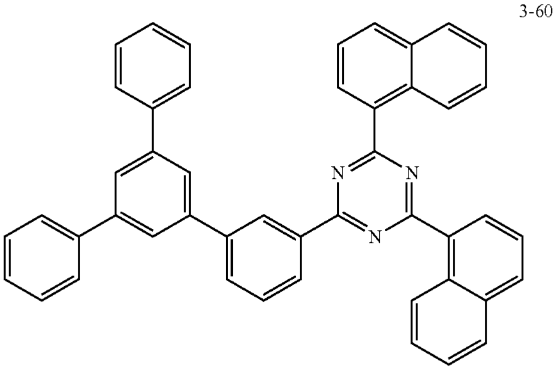
3-61
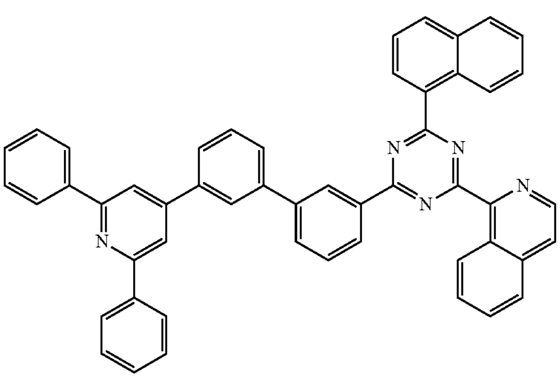
-continued
3-62
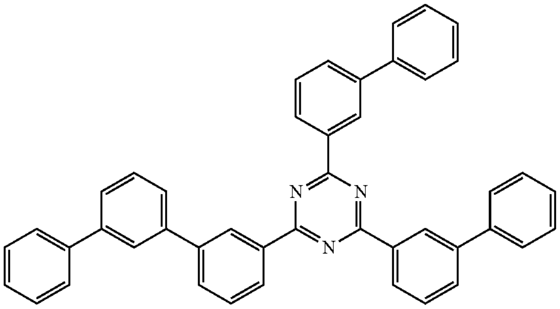
3-63
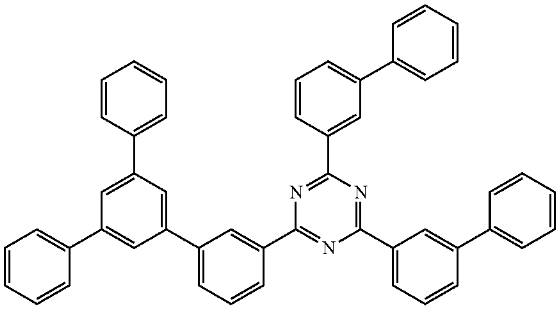
3-64
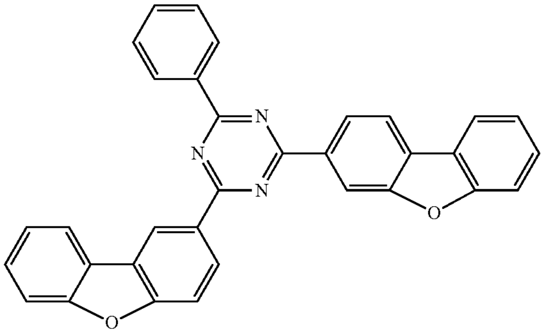
3-65
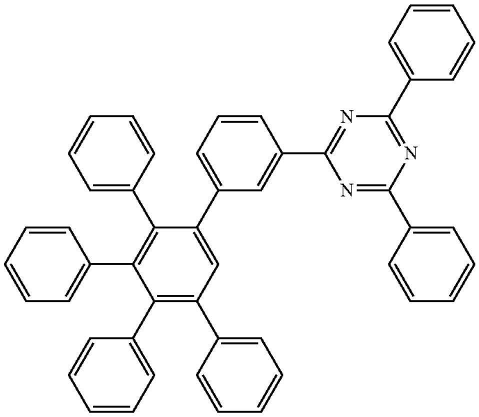

-continued
3-66
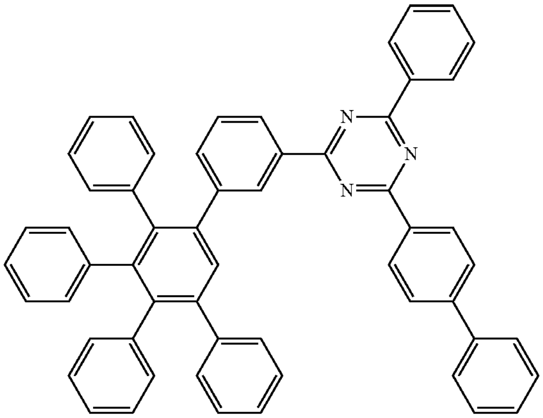
3-67
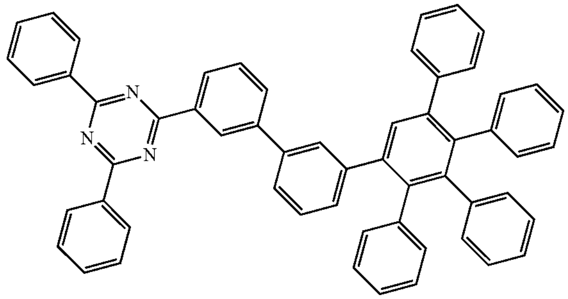
3-68
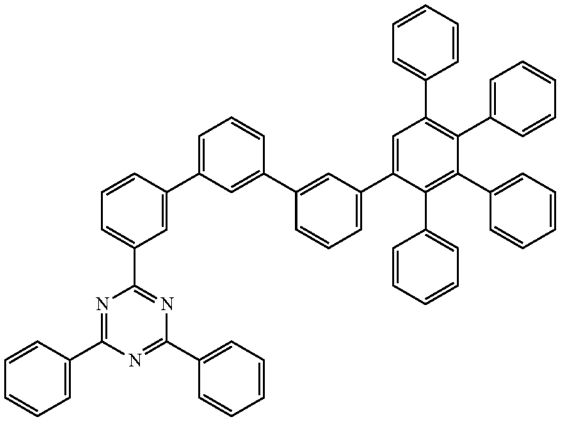
-continued
3-69
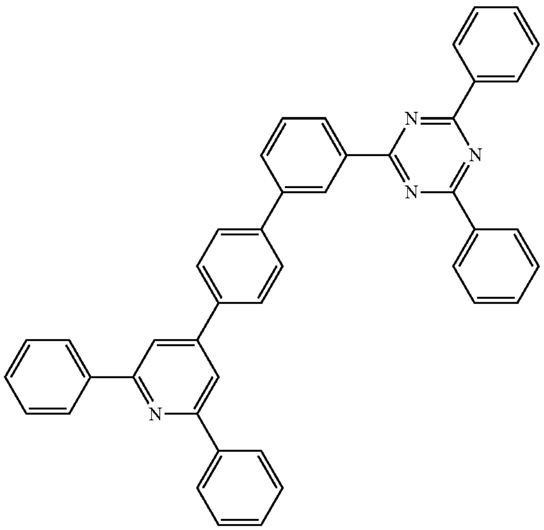
3-70
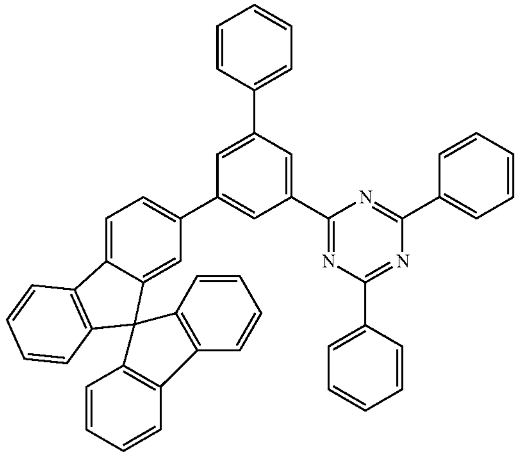
3-71
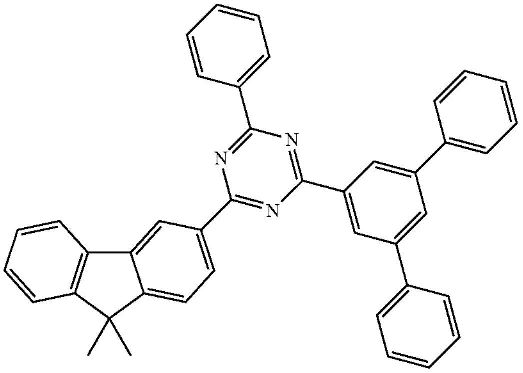

-continued
3-72
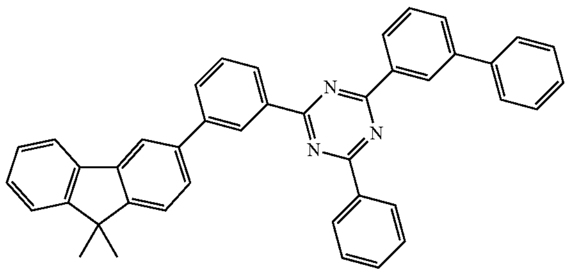
3-73
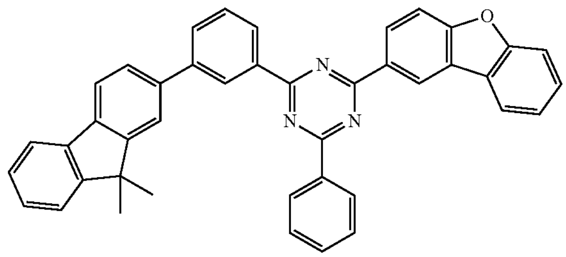
3-74
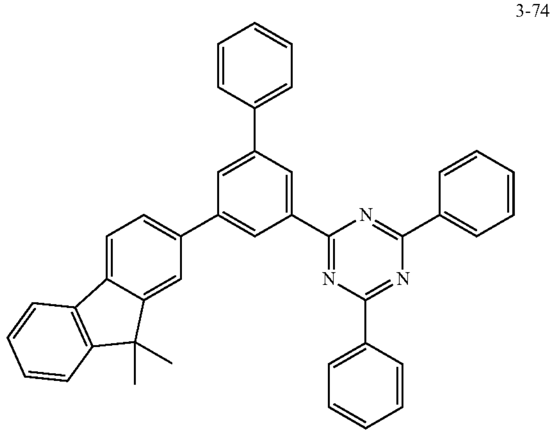
3-75
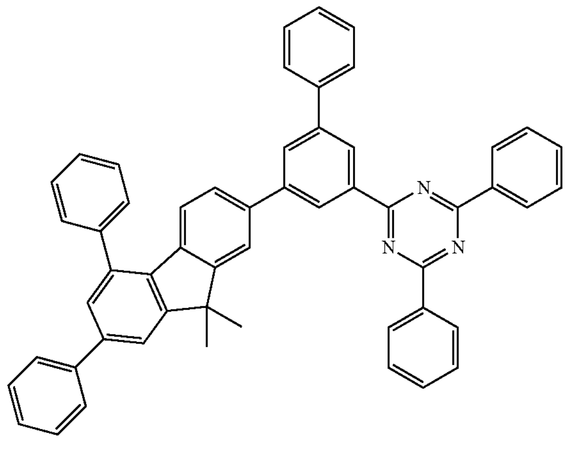
-continued
3-76
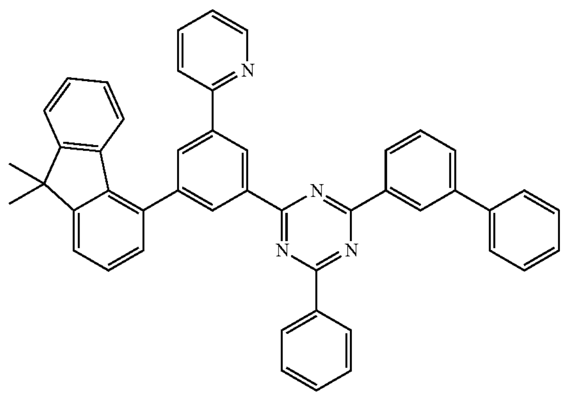
3-77
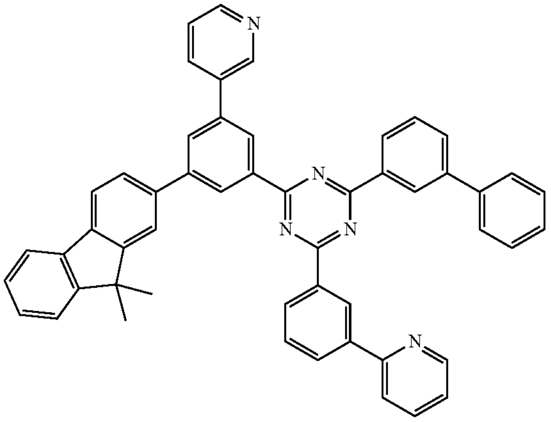
3-78
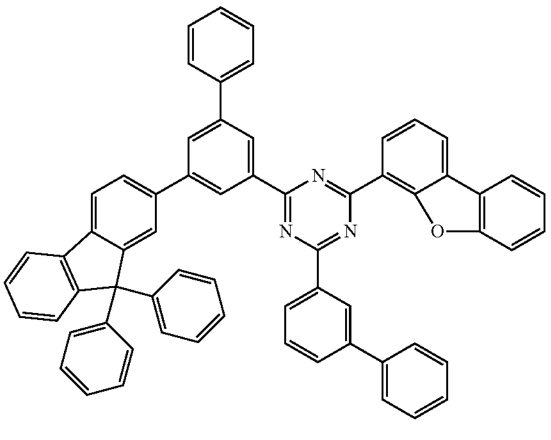

-continued
3-79
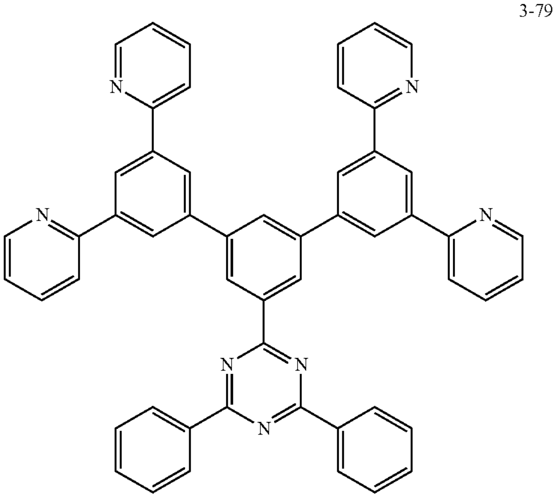
3-80
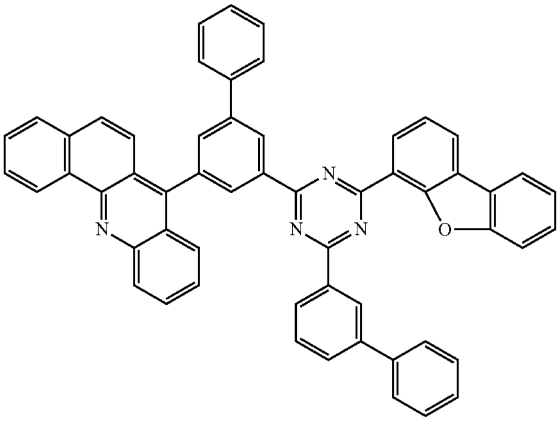
3-81
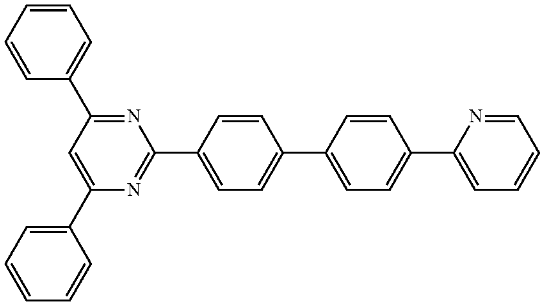
3-82
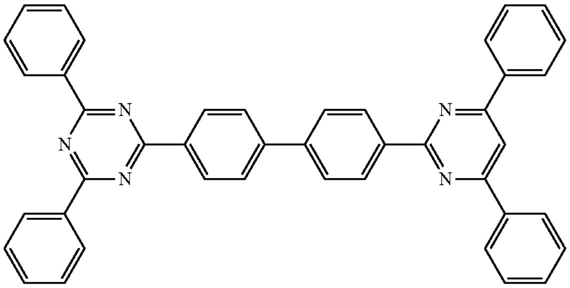
-continued
3-83
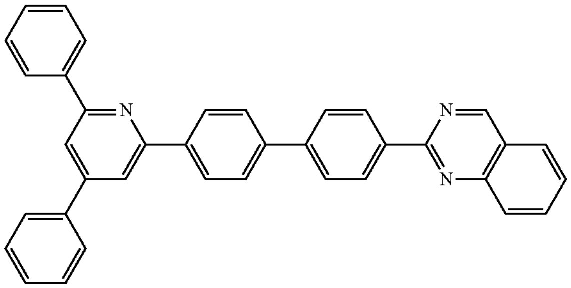
3-84
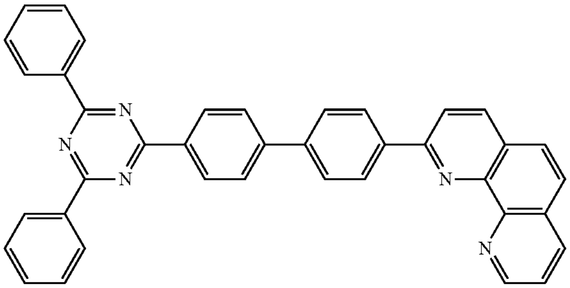
3-85
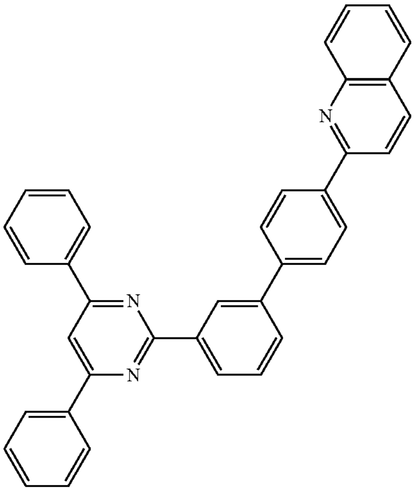
3-86
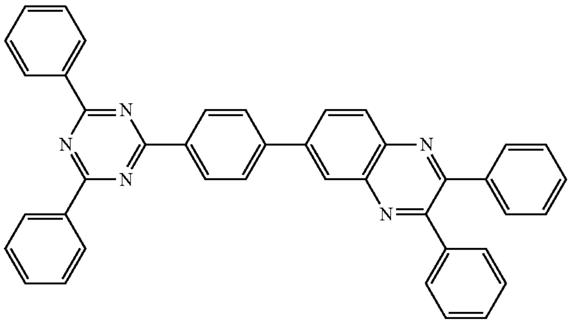

-continued
3-87
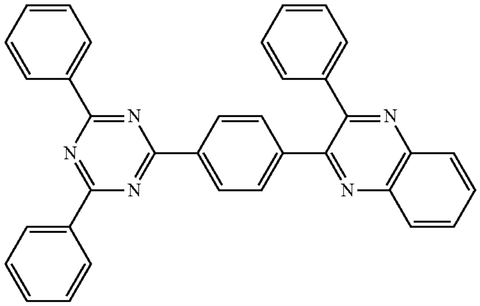
3-88
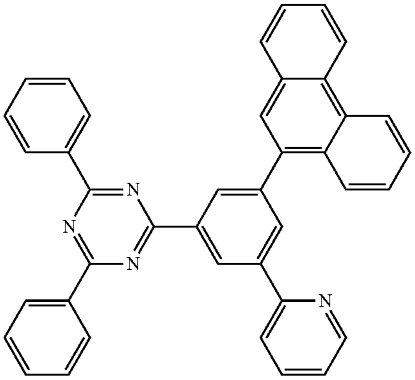
3-89
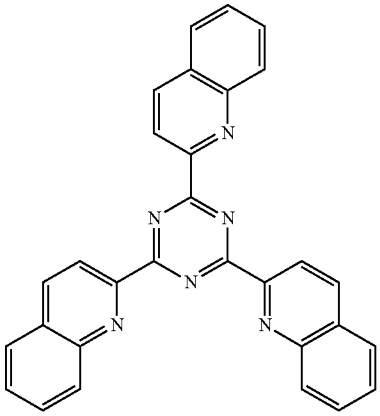
3-90
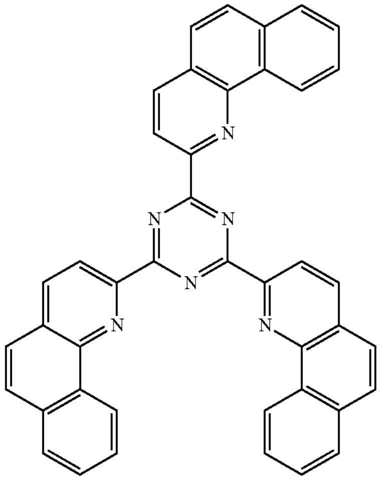
-continued
3-91
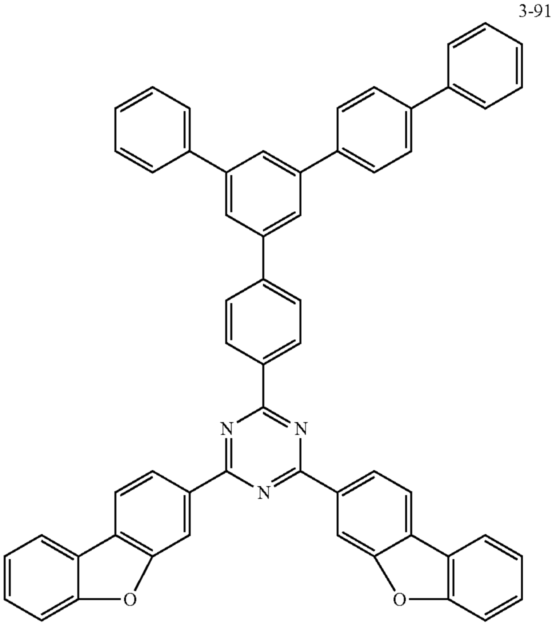
3-92
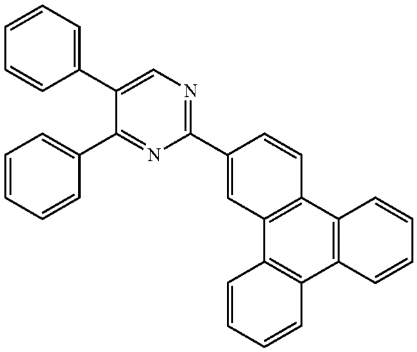
3-93
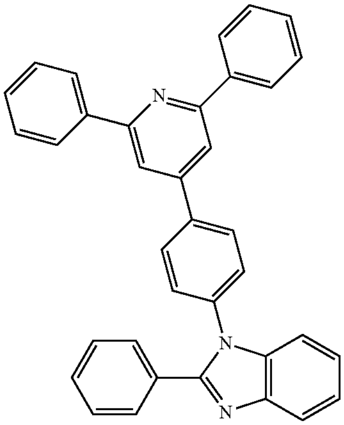

-continued
3-94
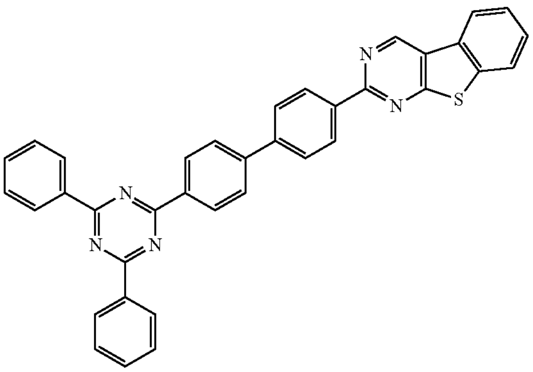
3-95
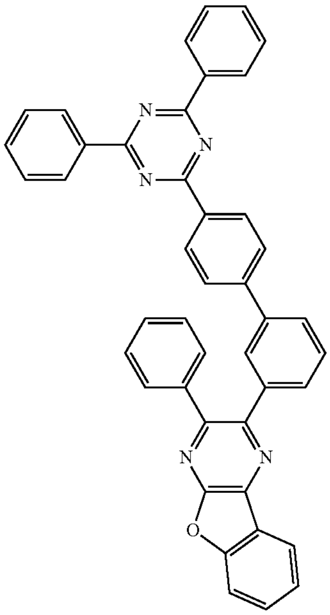
3-96
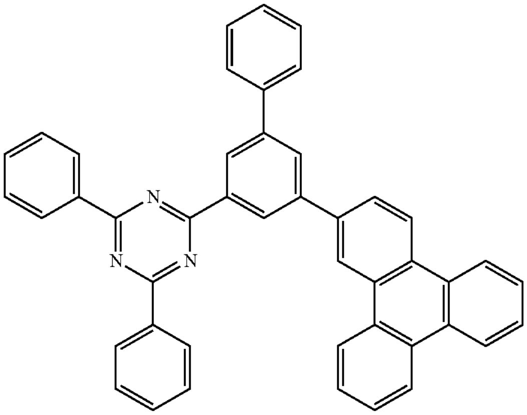
-continued
3-97
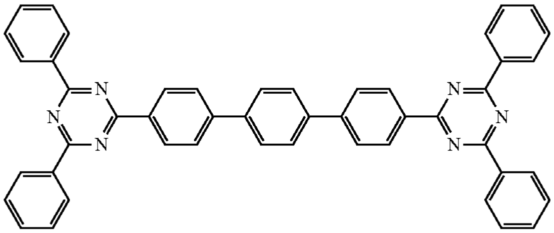
3-98
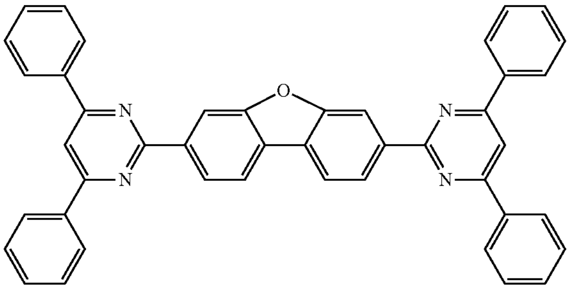
3-99
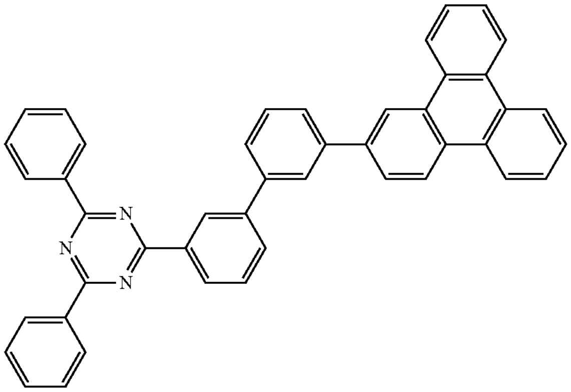
3-100
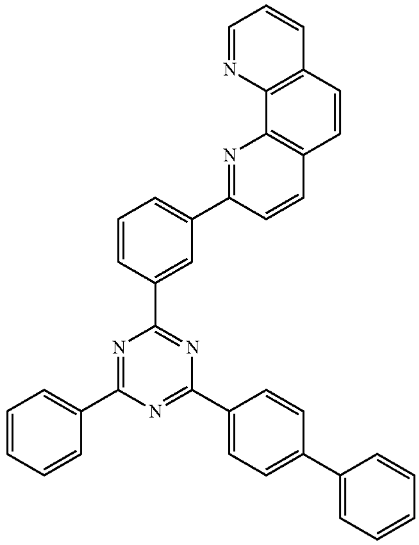

-continued
3-101
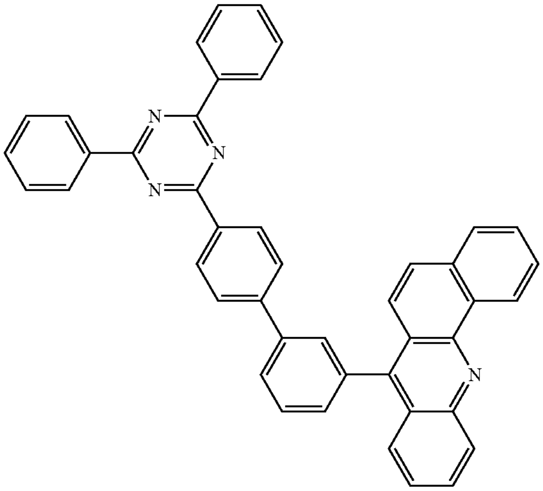
3-102
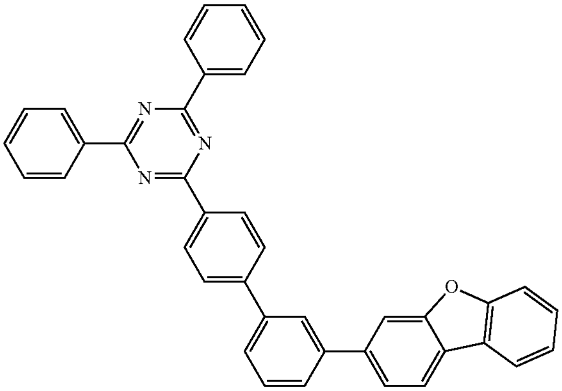
3-103
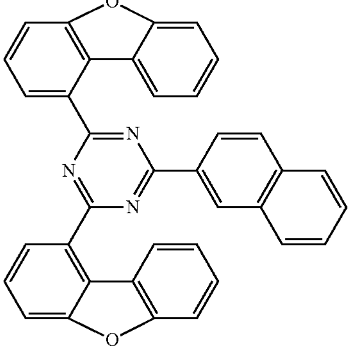
-continued
3-104
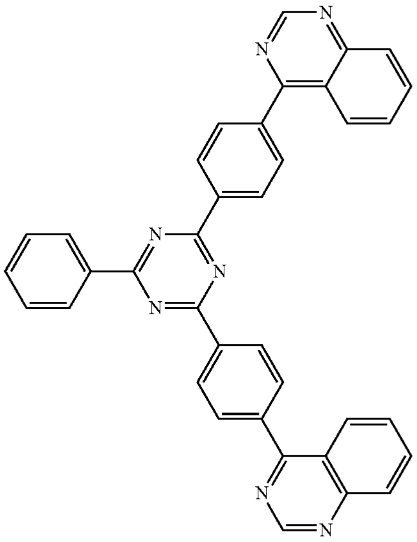
3-105
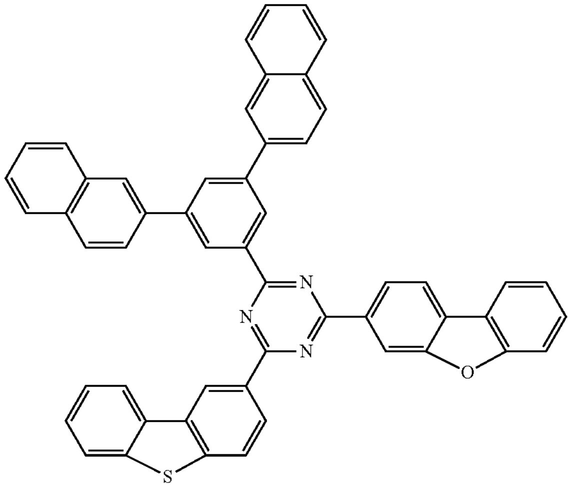
3-106
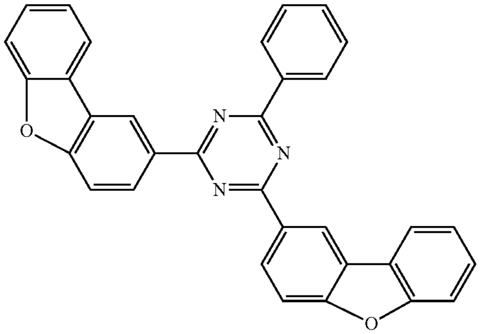

-continued
3-107
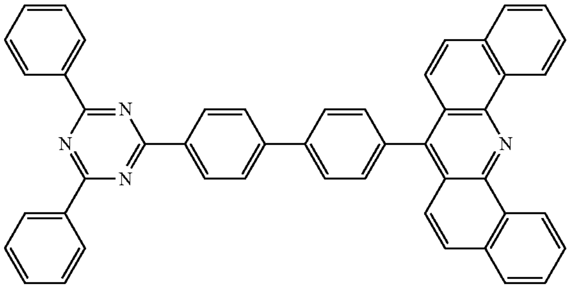
3-108
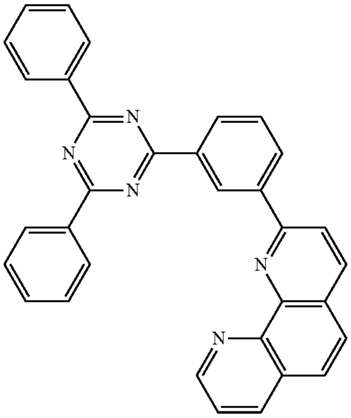
3-109
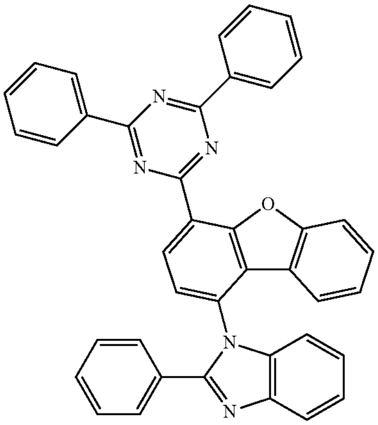
-continued
3-110
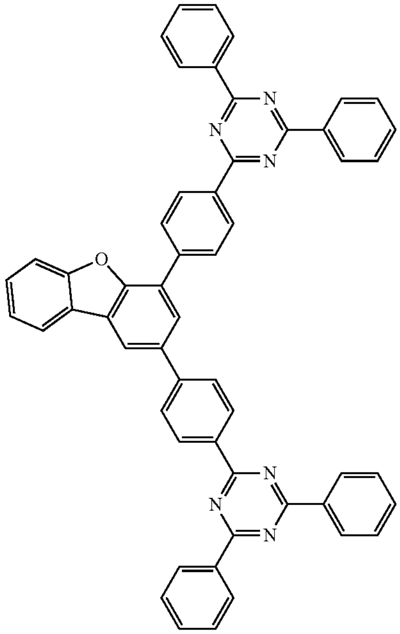
3-111
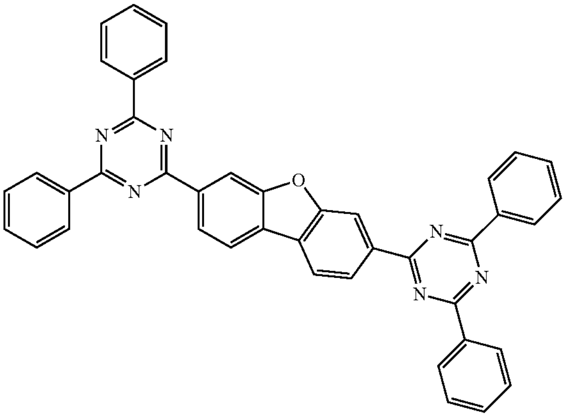

-continued
3-112
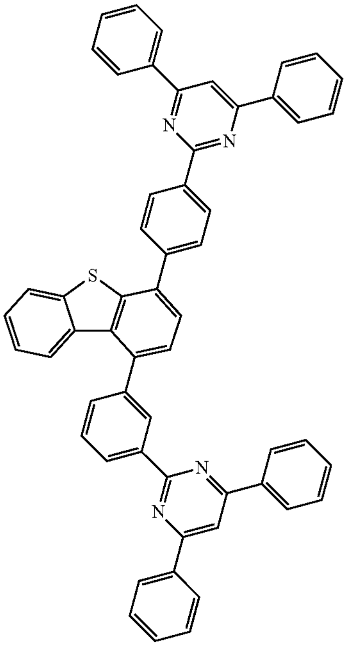
3-113
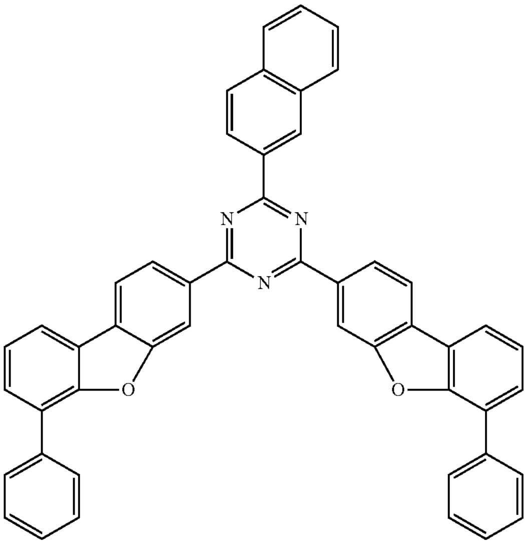
3-114
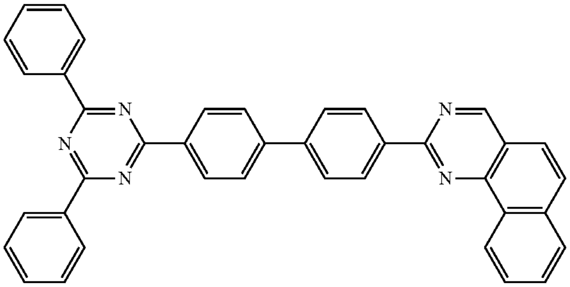
-continued
3-115
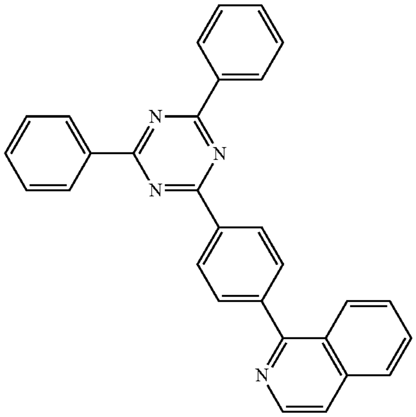
3-116
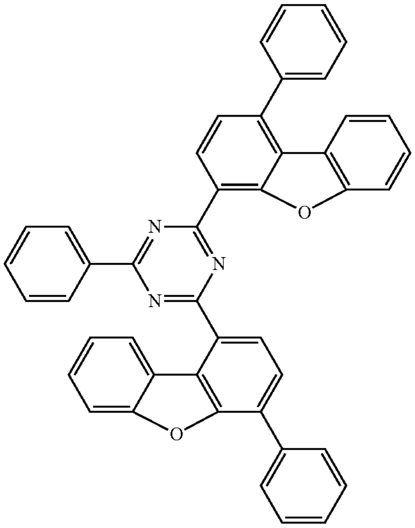
3-117
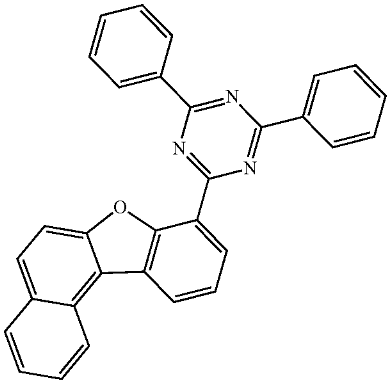

-continued
3-118
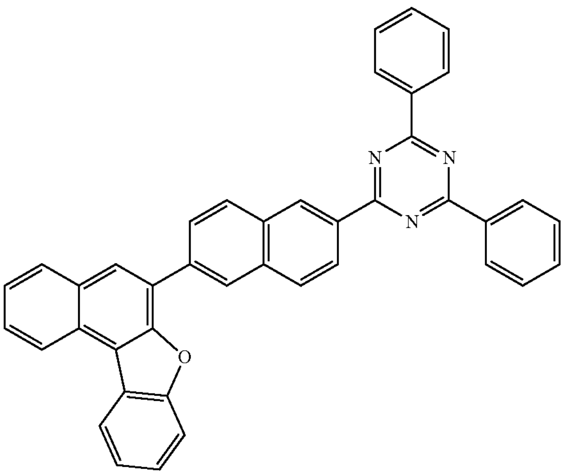
3-119
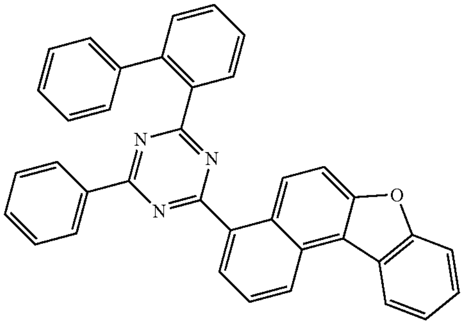
3-120
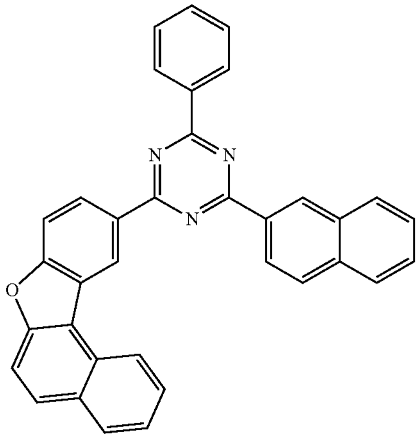
3-121
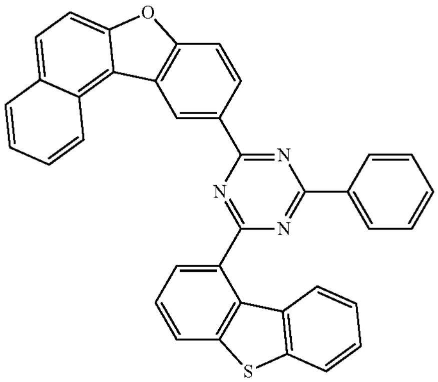
-continued
3-122
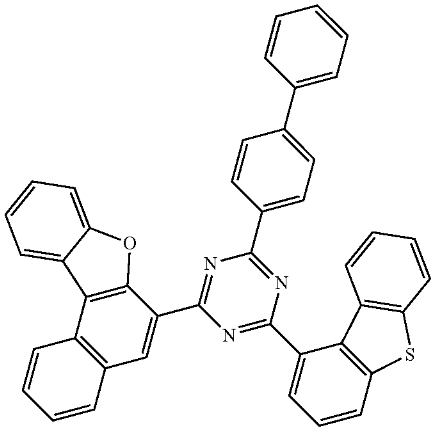
3-123
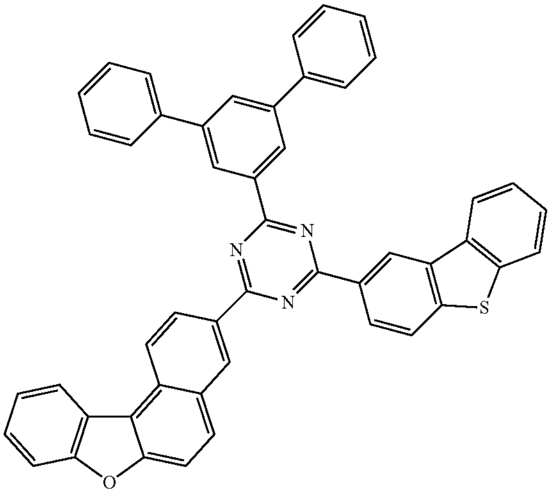
3-124
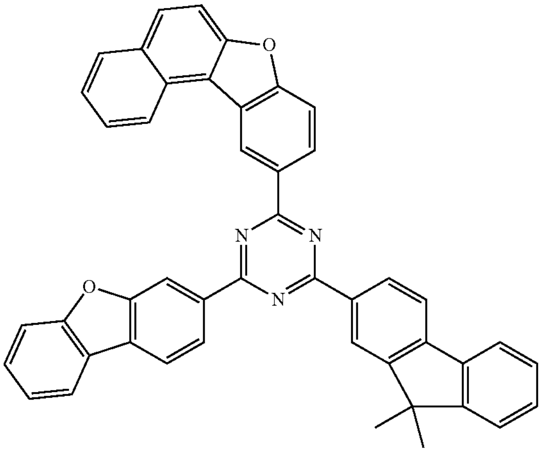

-continued
3-125
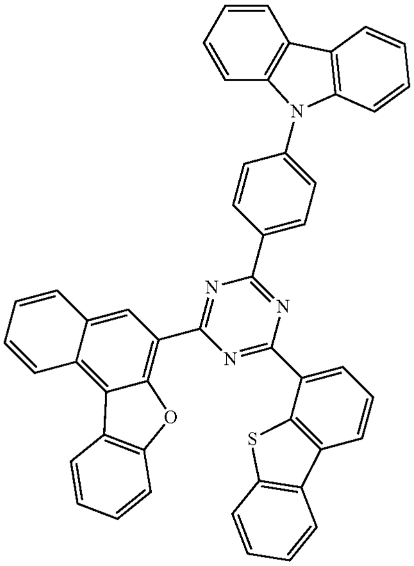
3-126
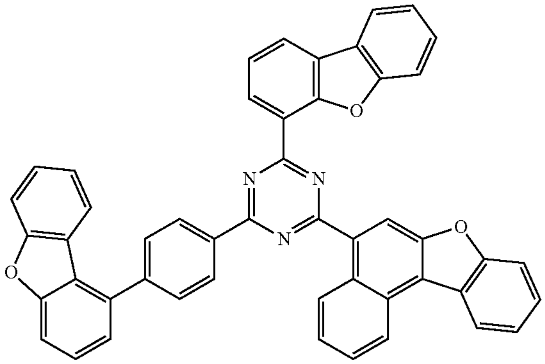
3-127
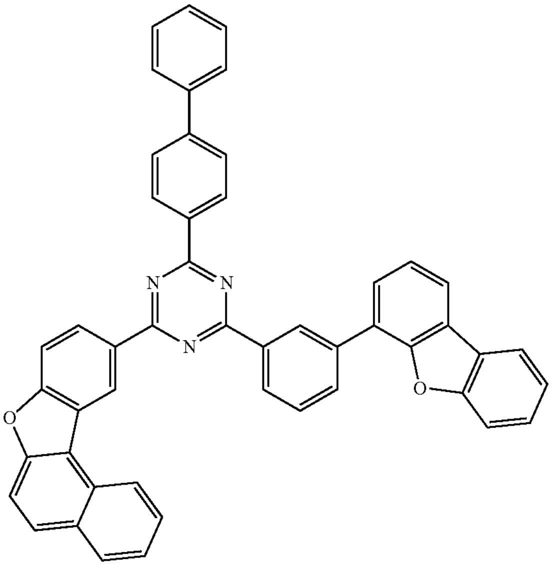
-continued
3-128
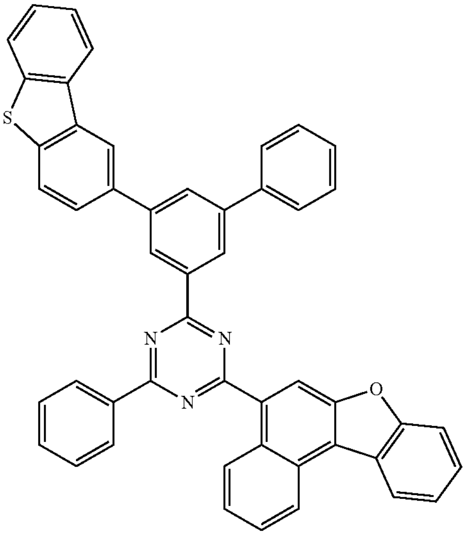
3-129
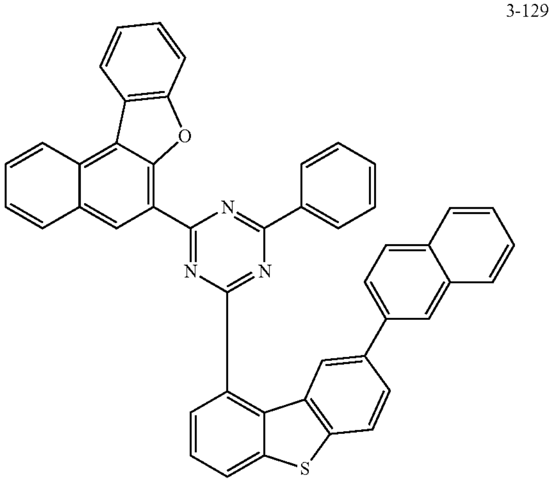
3-130
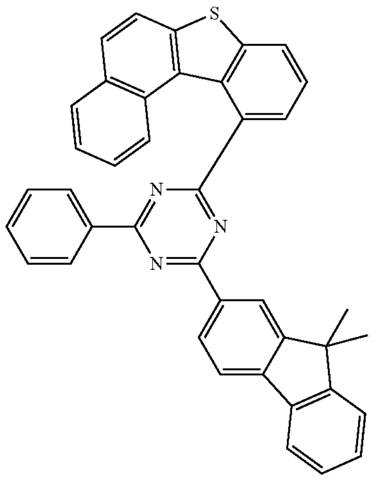

-continued
3-131
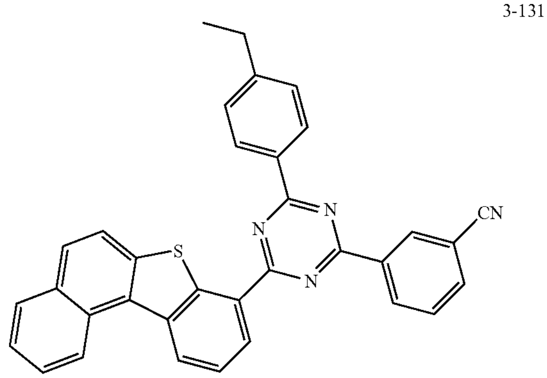
3-132
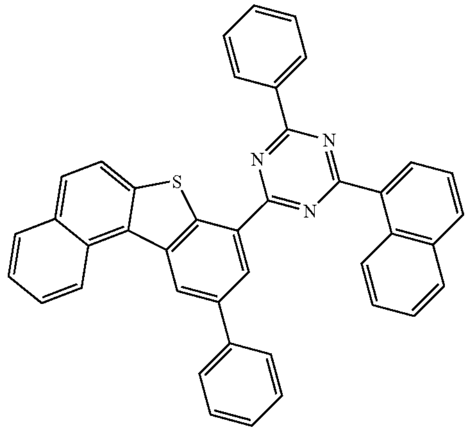
3-133
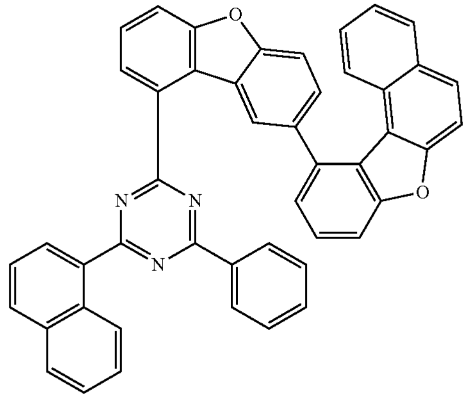
3-134
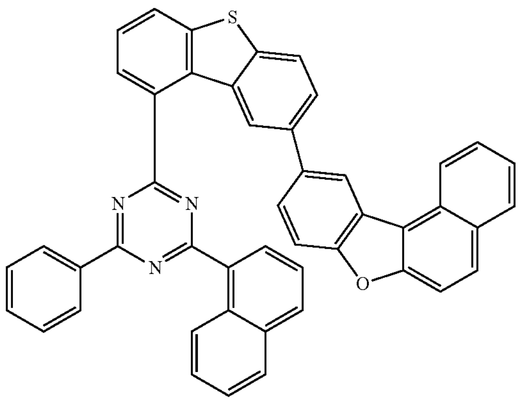
-continued
3-135
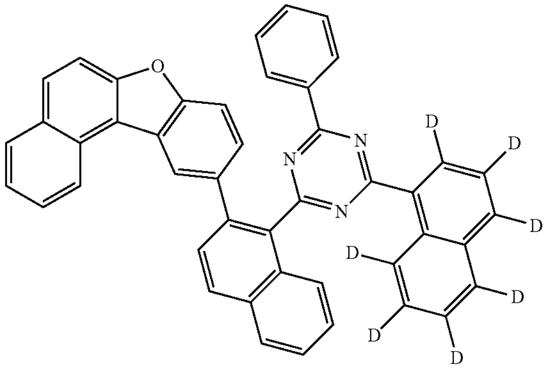
3-136
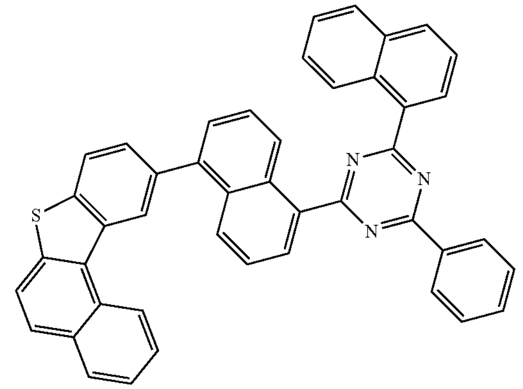
3-137
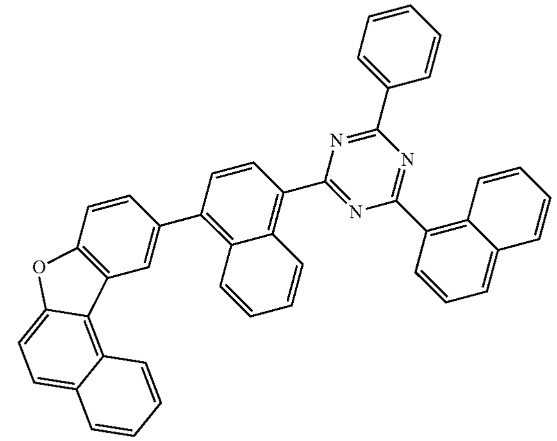
3-138
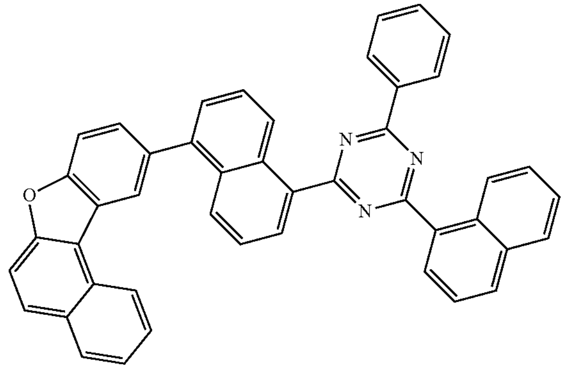

-continued 3-139

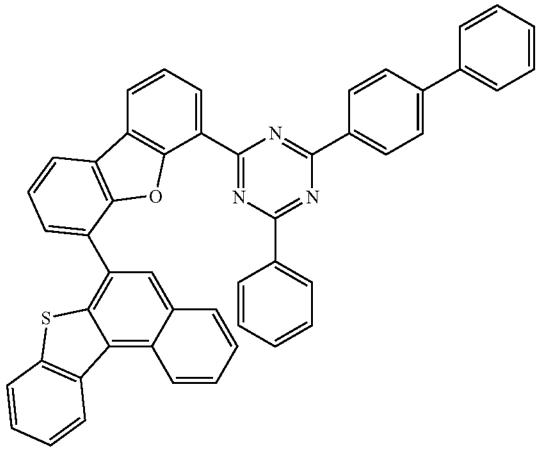

3-140

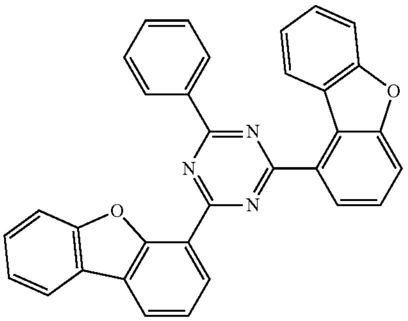

3-141

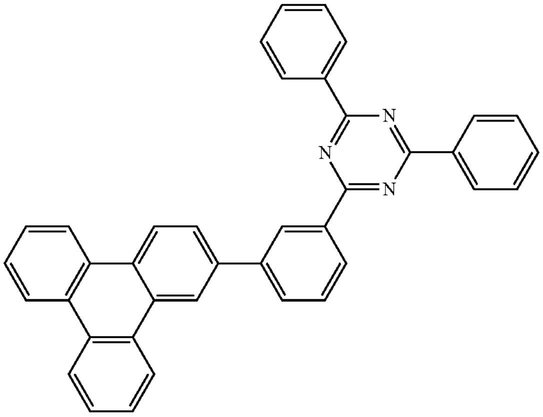

.

In one embodiment of the present invention, it is preferable to use a mixture of the first compound and the second compound in a weight ratio of 2:8 to 8:2 as the host material.

In another embodiment of the present invention, the organic material layer further comprises a hole transport band layer having one or more layers and formed between the light emitting layer and the anode, the hole transport band layer comprises at least one of a hole transport layer and an emission-auxiliary layer, and comprises the compound represented by Formula 1.

Hereinafter, synthesis example of the compound represented by Formula 1 and Formula 2 and preparation method of an organic electric element according to the present invention will be described by way of examples. However, the present invention is not limited to the following examples.

SYNTHESIS EXAMPLE

[Synthesis Example 1] Formula 1

The compound (final product 1) represented by Formula 1 according to the present invention may be synthesized by a reaction route as shown in Reaction Scheme 1, but is not limited thereto.

<Reaction Scheme 1>

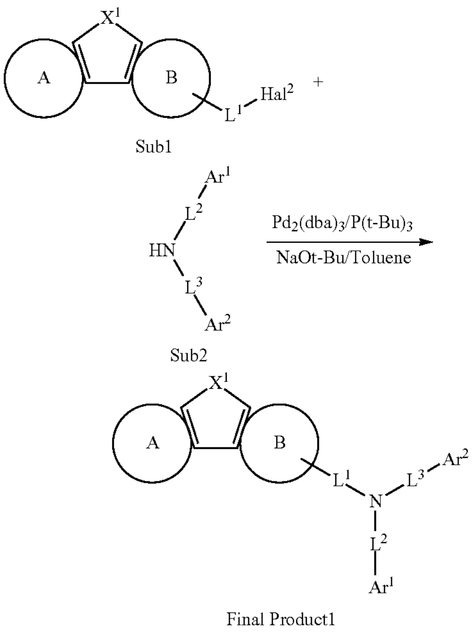

($Hal^2$ is Br or Cl.)

I. Synthesis Example of Sub1

Sub 1 of Reaction Scheme 1 may be synthesized by the reaction route of the following Reaction Scheme 2, but is not limited thereto.

<Reaction Scheme 2>

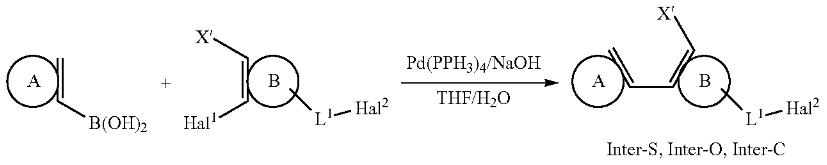

-continued

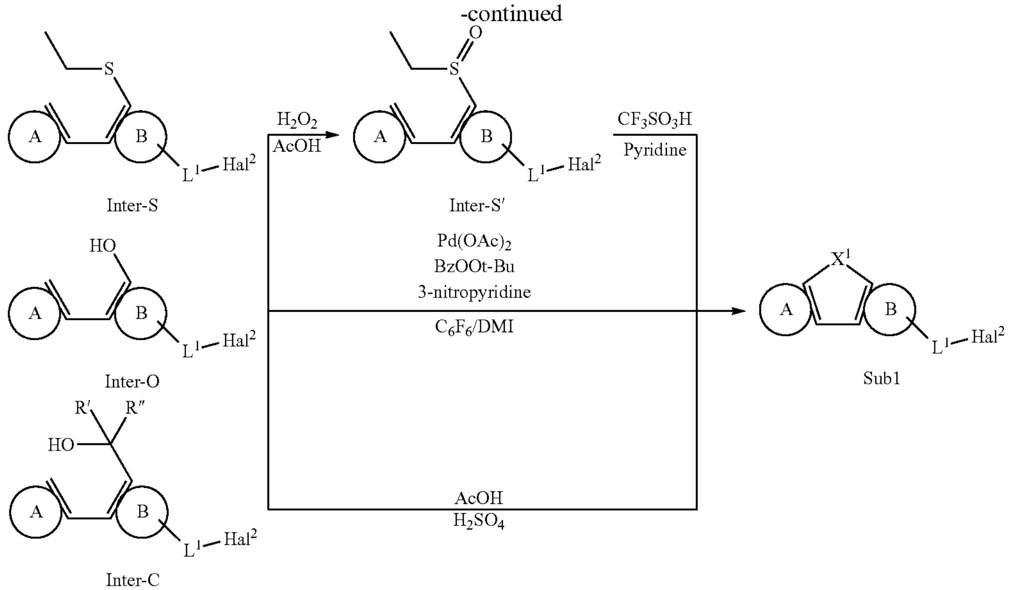

(Hal[1] is I or Br, and Hal[2] is Br or Cl.)
X' = S(Et), OH, CR'R"OH

1. Synthesis Example of Sub1-5

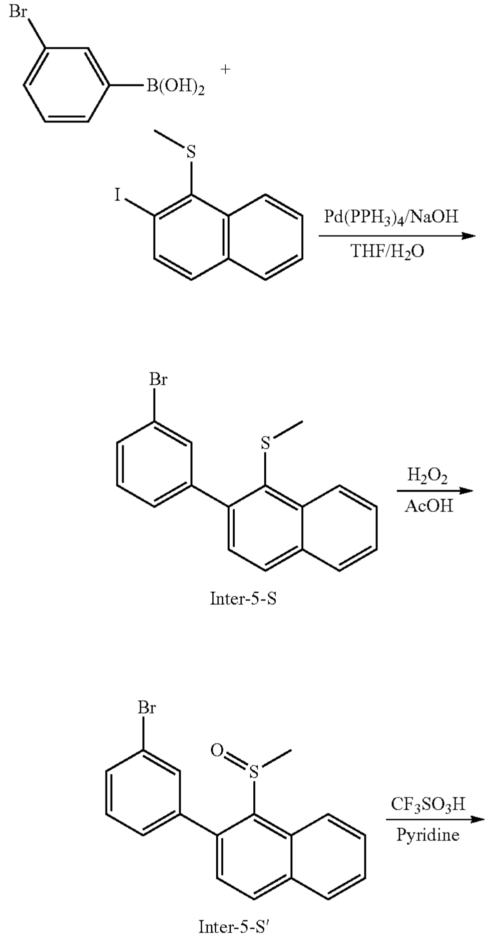

-continued

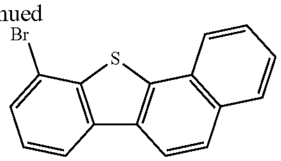

Sub1-5

(1) Synthesis Example of Inter-5-S

After (3-bromophenyl)boronic acid (50.0 g, 249 mmol) was dissolved in THF (1.25 L), (2-iodonaphthalen-1-yl)(methyl)sulfane (74.7 g, 249 mmol), NaOH (29.9 g, 747 mmol), $Pd(PPh_3)_4$ (17.3 g, 14.9 mmol) and water (620 mL) were added to the solution, and the mixture was stirred at 80° C. When the reaction was completed, the reaction product was extracted with $CH_2Cl_2$ and water. An organic layer was dried over $MgSO_4$ and concentrated. Then, the concentrate was separated by a silica gel column and recrystallized to obtain 68.0 g (yield: 83%) of the product.

(2) Synthesis Example of Inter-5-S'

Acetic acid (830 mL) and 35% Hydrogen peroxide ($H_2O_2$) (60 mL) were added to Inter-5-S (68.0 g, 207 mmol), and the mixture was stirred at room temperature. When the reaction was completed, the reaction product was neutralized with an aqueous NaOH solution, and extracted with EA (ethylacetate) and water. An organic layer was dried over $MgSO_4$ and concentrated. Then, the concentrate was separated by a silica gel column and recrystallized to obtain 65.6 g (yield: 92%) of the product.

(3) Synthesis Example of Sub1-5

An excess of trifluoromethane-sulfonic acid was added to Inter-5-S' (65.6 g, 190 mmol), and the solution was stirred at room temperature for 24 hours. Then, water and pyridine (8:1) were slowly added the solution and the mixture was refluxed for 30 minutes. After lowering the temperature of the mixture, the mixture was extracted with $CH_2Cl_2$ and water. An organic layer was dried over $MgSO_4$ and concentrated. Then, the concentrate was separated by a silica gel column and recrystallized to obtain 36.9 g (yield: 62%) of the product.

2. Synthesis Example of Sub1-16

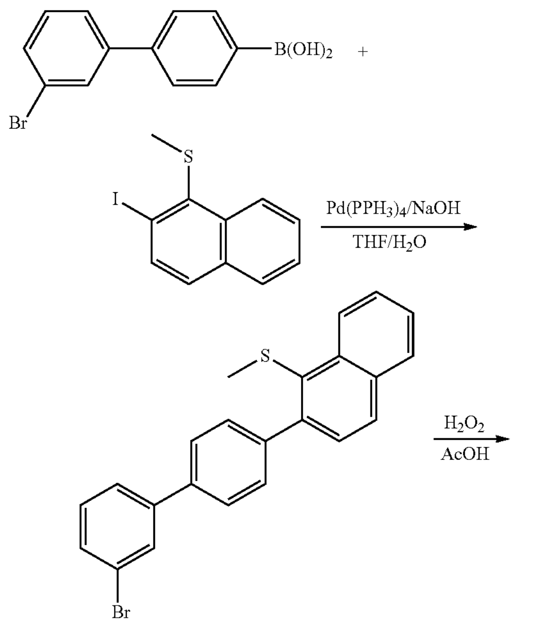

Inter-16-S

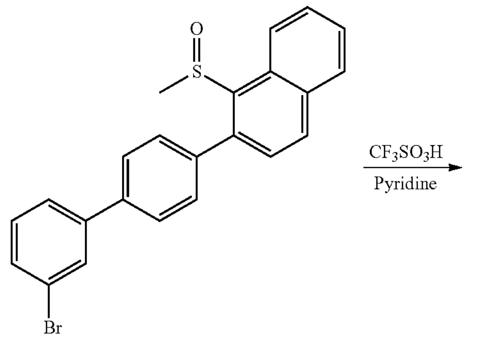

Inter-16-S'

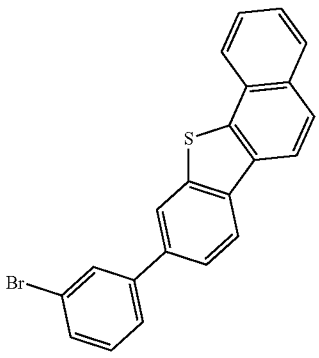

Sub1-16

(1) Synthesis Example of Inter-16-S

Synthesis was carried out in the same manner as for the synthesis of Inter-5-S using (3'-bromo-[1,1'-biphenyl]-4-yl) boronic acid (50.0 g, 181 mmol), (2-iodonaphthalen-1-yl)(methyl)sulfane (54.2 g, 181 mmol), NaOH (21.7 g, 542 mmol), $Pd(PPh_3)_4$ (12.5 g, 10.8 mmol), THF and water to obtain 59.3 g (yield: 81%) of the product.

(2) Synthesis Example of Inter-16-S'

Synthesis was carried out in the same manner as for the synthesis of Inter-5-S' using Inter16-S (59.3 g, 146 mmol), acetic acid (590 mL) and 35% hydrogen peroxide ($H_2O_2$) (41.8 mL) to obtain 57.9 g (yield: 94%) of the product.

(3) Synthesis Example of Sub1-16

An excess of trifluoromethane-sulfonic acid was added to Inter16-S' (57.9 g, 138 mmol), and synthesis was carried out in the same manner as for the synthesis of Sub1-5 to obtain 40.1 g (yield: 75%) of the product.

3. Synthesis Example of Sub1-28

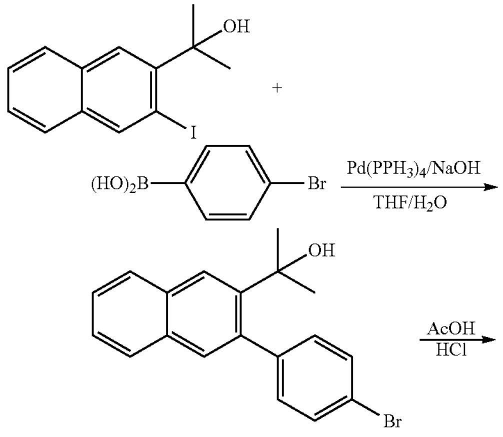

Inter-28-C

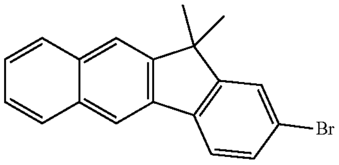

Sub1-28

(1) Synthesis Example of Inter-28-C

Synthesis was carried out in the same manner as for the synthesis of Inter-5-S using (4-bromophenyl)boronic acid (50.0 g, 249 mmol), 2-(3-iodonaphthalen-2-yl)propan-2-01 (77.7 g, 249 mmol), NaOH (29.9 g, 747 mmol), $Pd(PPh_3)_4$ (17.3 g, 14.9 mmol), THF and water to obtain 65.4 g (yield: 77%) of the product.

(2) Synthesis Example of Sub1-28

Acetic acid (479 mL) and HCl (77 mL) were added to Inter-28-C (65.4 g, 192 mmol) and the mixture was stirred at 120° C. for 12 hours. When the reaction was completed, the reaction product was extracted with $CH_2Cl_2$ and water. An organic layer was dried over $MgSO_4$ and concentrated. Then, the concentrate was separated by a silica gel column and recrystallized to obtain 52.1 g (yield: 84%) of the product.

4. Synthesis Example of Sub1-29

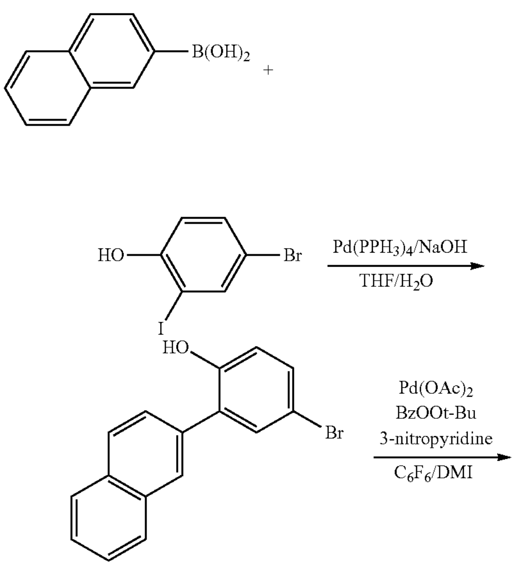

Inter-29-O

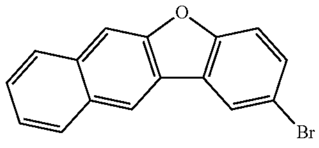

Sub1-29

(1) Synthesis Example of Inter-29-O

Synthesis was carried out in the same manner as for the synthesis of Inter-5-S using naphthalen-2-ylboronic acid (50.0 g, 291 mmol), 4-bromo-2-iodophenol (86.9 g, 291 mmol), NaOH (34.9 g, 872 mmol), $Pd(PPh_3)_4$ (20.2 g, 17.4 mmol), THF and water to obtain 66.1 g (yield: 76%) of the product.

(2) Synthesis Example of Sub1-29

$Pd(OAc)_2$ (2.48 g, 11.1 mmol), 3-nitropyridine (1.37 g, 11.1 mmol), BzOOt-Bu (tert-butyl peroxybenzoate) (85.8 g, 442 mmol), $C_6F_6$ (hexafluorobenzene) (330 mL) and DMI (N,N'-dimethylimidazolidinone) (221 mL) were added to Inter-29-O (66.1 g, 221 mmol), and the mixture was refluxed at 90° C. for 3 hours. When the reaction was completed, the reaction product was cooled to room temperature and extracted with EA and water. An organic layer was dried over $MgSO_4$ and concentrated. Then, the concentrate was separated by a silica gel column and recrystallized to obtain 26.9 g (yield: 41%) of the product.

5. Synthesis Example of Sub1-49

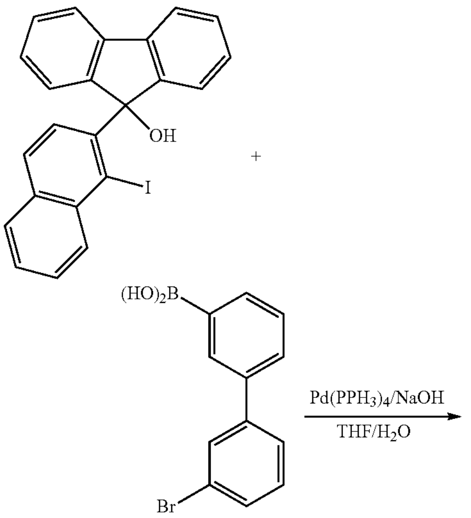

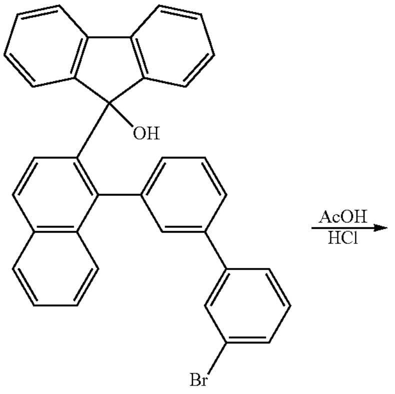

Inter-49-C

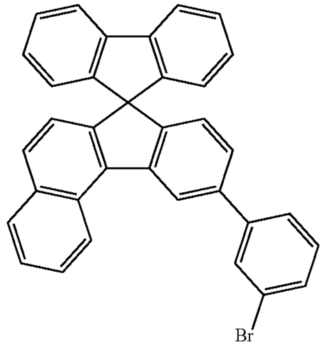

Sub1-49

(1) Synthesis Example of Inter-49-C

Synthesis was carried out in the same manner as for the synthesis of Inter-5-S using (3'-bromo-[1,1'-biphenyl]-3-yl) boronic acid (50.0 g, 181 mmol), 9-(1-iodonaphthalen-2-yl)-9H-fluoren-9-ol (78.4 g, 181 mmol), NaOH (21.7 g, 542 mmol), $Pd(PPh_3)_4$ (12.5 g, 10.8 mmol), THF and water to obtain 69.2 g (yield: 71%) of the product.

(2) Synthesis Example of Sub1-49

Synthesis was carried out in the same manner as for the synthesis of Sub1-28 using Inter-49-C (69.2 g, 128 mmol), acetic acid (320 mL) and HCl (51 mL) to obtain 48.8 g (yield: 73%) of the product.

6. Synthesis Example of Sub1-52

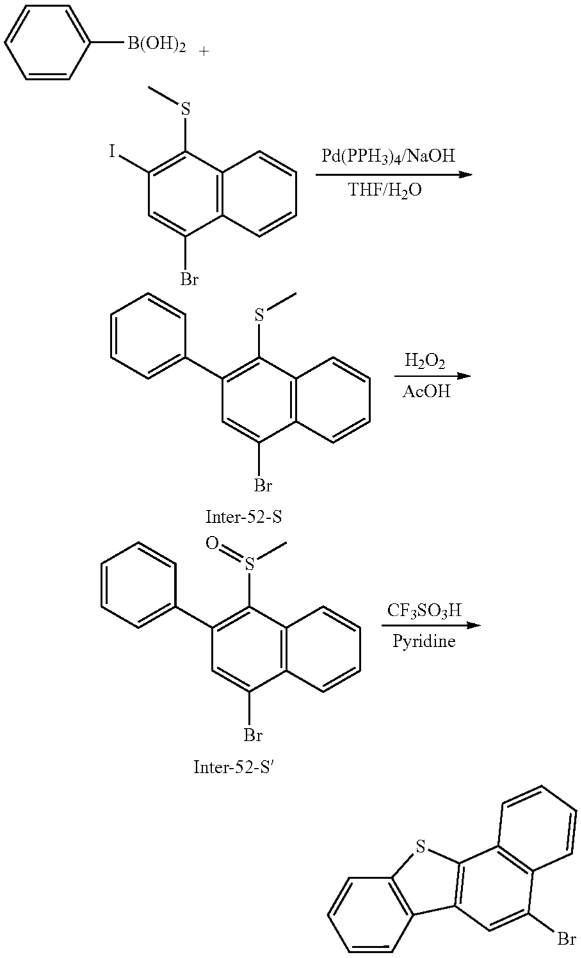

Inter-52-S

Inter-52-S'

Sub1-52

(1) Synthesis Example of Inter-52-S

Synthesis was carried out in the same manner as for the synthesis of Inter-5-S using phenylboronic acid (50.0 g, 410 mmol), (4-bromo-2-iodonaphthalen-1-yl)(methyl)sulfane (155 g, 410 mmol), NaOH (49.2 g, 1230 mmol), $Pd(PPh_3)_4$ (28.4 g, 24.6 mmol), THF and water to obtain 102.6 g (yield: 76%) of the product.

(2) Synthesis Example of Inter-52-S'

Synthesis was carried out in the same manner as for the synthesis of Inter-5-S' using Inter52-S (102.6 g, 312 mmol), acetic acid (1.25 L) and 35% Hydrogen peroxide ($H_2O_2$) (89.0 mL) to obtain 103.3 g (yield: 96%) of the product.

(3) Synthesis Example of Sub1-52

An excess of trifluoromethane-sulfonic acid was added to Inter52-S' (103.3 g, 299 mmol), and synthesis was carried out in the same manner as for the synthesis of Sub1-5 to obtain 67.5 g (yield: 72%) of the product.

7. Synthesis Example of Sub1-66

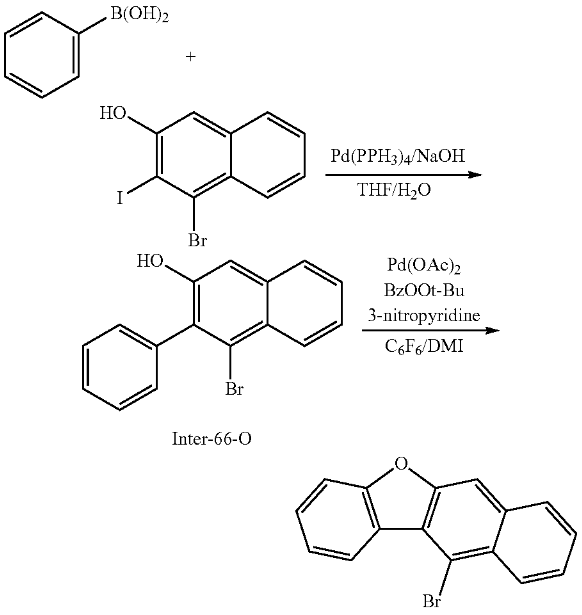

Inter-66-O

Sub1-66

(1) Synthesis Example of Inter-66-0

Synthesis was carried out in the same manner as for the synthesis of Inter-5-S using phenylboronic acid (50.0 g, 410 mmol), 4-bromo-3-iodonaphthalen-2-ol (143.1 g, 410 mmol), NaOH (28.4 g, 1230 mmol), $Pd(PPh_3)_4$ (28.4 g, 24.6 mmol), THF and water to obtain 92.0 g (yield: 75%) of the product.

(2) Synthesis Example of Sub1-66

$Pd(OAc)_2$ (3.45 g, 15.4 mmol), 3-nitropyridine (1.91 g, 15.4 mmol), BzOOt-Bu (tert-butyl peroxybenzoate) (119.5 g, 615 mmol), $C_6F_6$ (hexafluorobenzene) (460 mL) and DMI (N,N'-dimethylimidazolidinone) (310 mL) were added to Inter-66-O (92.0 g, 308 mmol) and synthesis was carried out in the same manner as for the synthesis of Sub1-29 to obtain 57.6 g (yield: 63%) of the product.

8. Synthesis Example of Sub1-81

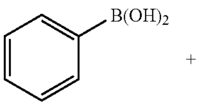

-continued

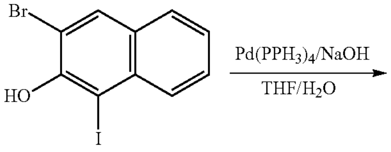

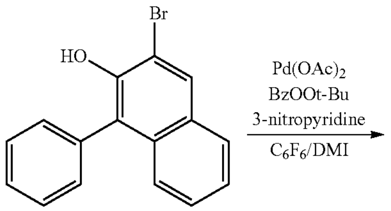

Inter-81-O

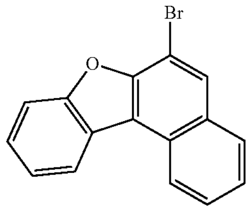

Sub1-81

(1) Synthesis Example of Inter-81-O

Synthesis was carried out in the same manner as for the synthesis of Inter-5-S using phenylboronic acid (50.0 g, 410 mmol), 3-bromo-1-iodonaphthalen-2-ol (143.1 g, 410 mmol), NaOH (28.4 g, 1230 mmol), $Pd(PPh_3)_4$ (28.4 g, 24.6 mmol), THF and water to obtain 88.3 g (yield: 72%) of the product.

(2) Synthesis Example of Sub1-81

$Pd(OAc)_2$ (3.31 g, 14.8 mmol), 3-nitropyridine (1.83 g, 14.8 mmol), BzOOt-Bu (tert-butyl peroxybenzoate) (114.7 g, 591 mmol), $C_6F_6$ (hexafluorobenzene) (440 mL) and DMI (N,N'-dimethylimidazolidinone) (295 mL) were added to Inter-81-O (88.3 g, 295 mmol) and synthesis was carried out in the same manner as for the synthesis of Sub1-29 to obtain 58.8 g (yield: 67%) of the product.

The Compound belonging to Sub1 may be a compound as follows, but is not limited thereto, and Table 1 shows FD-MS (Field Desorption-Mass Spectrometry) values of the following compounds.

Sub1-1

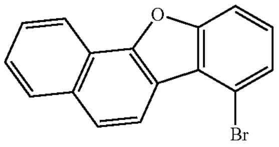

-continued

Sub1-2

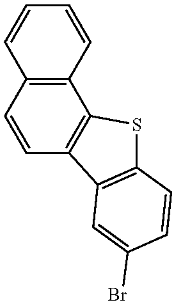

Sub1-3

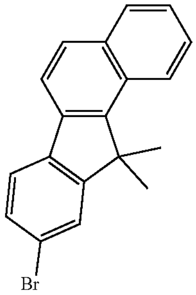

Sub1-4

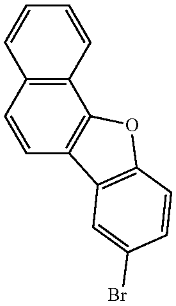

Sub1-5

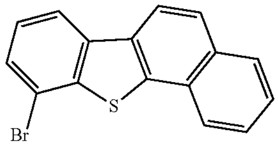

Sub1-6

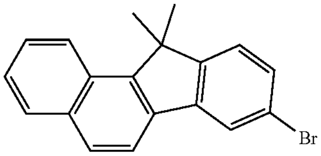

Sub1-7

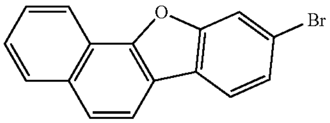

Sub1-8

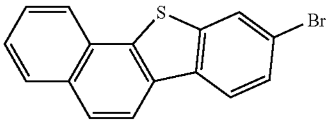

-continued
Sub1-9
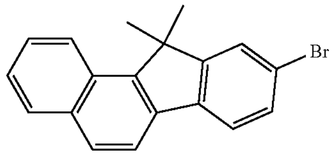
Sub1-10
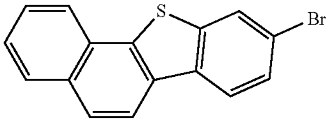
Sub1-11
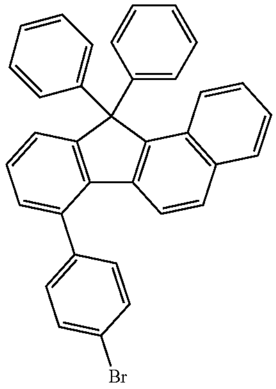
Sub1-12
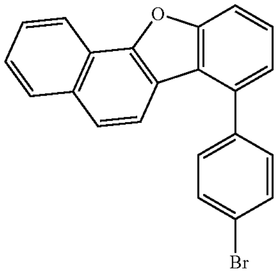
Sub1-13
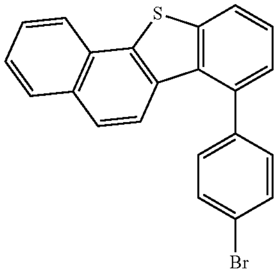
-continued
Sub1-14
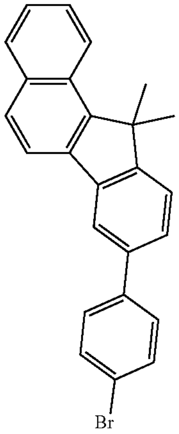
Sub1-15
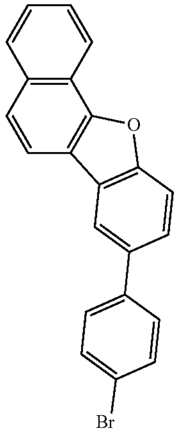
Sub1-16
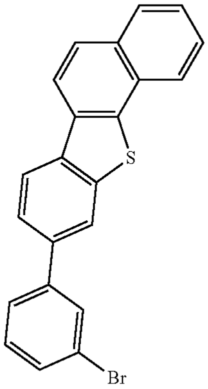
Sub1-17
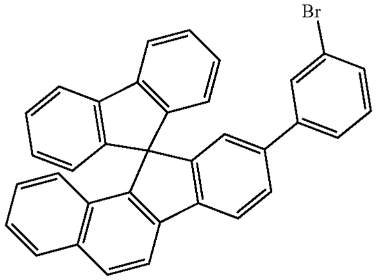

-continued
Sub1-18
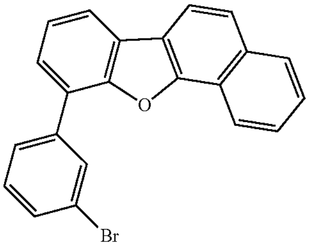
Sub1-19
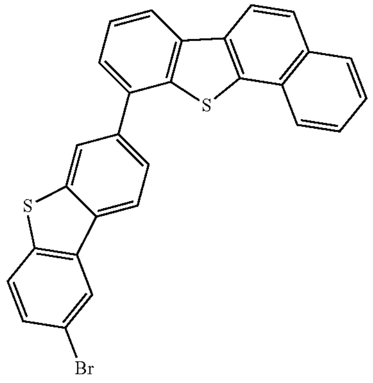
Sub1-20
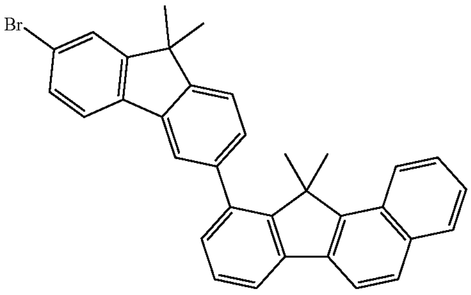
Sub1-21
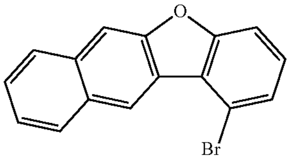
Sub1-22
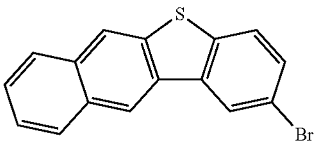
Sub1-23
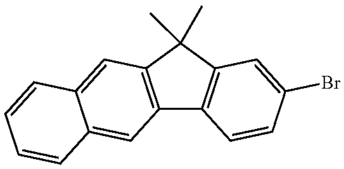
Sub1-24
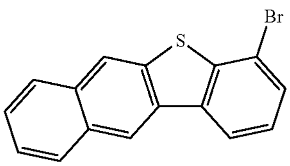
-continued
Sub1-25
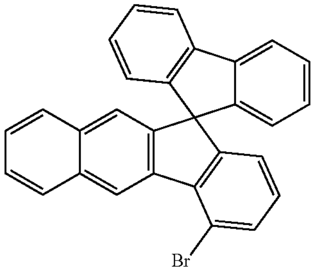
Sub1-26
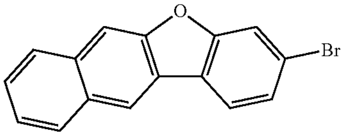
Sub1-27
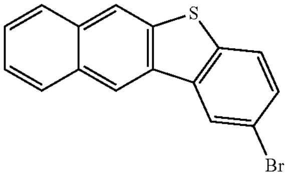
Sub1-28
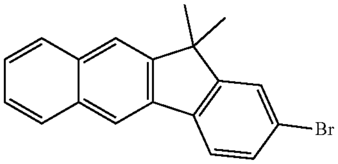
Sub1-29
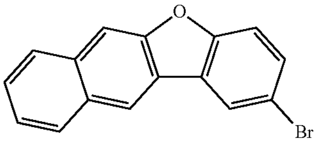
Sub1-30
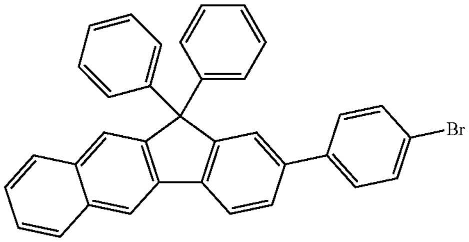
Sub1-31
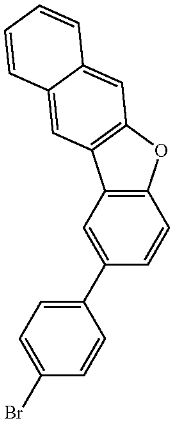

-continued
Sub1-32
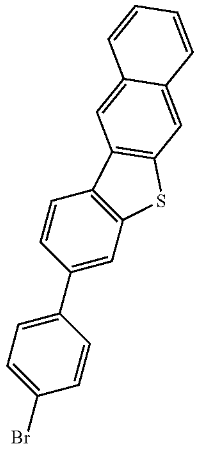
Sub1-33
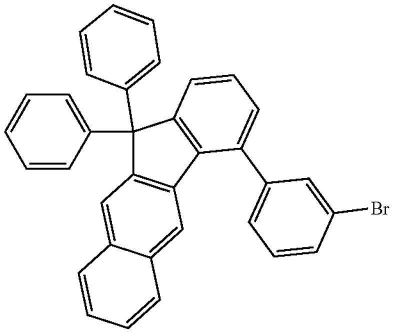
Sub1-34
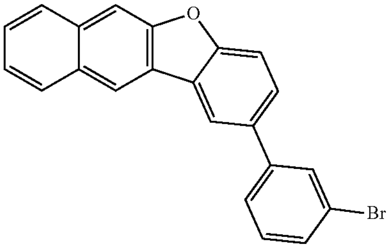
Sub1-35
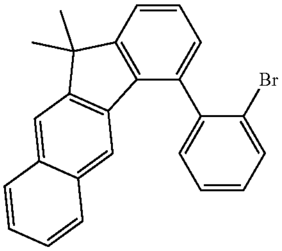
Sub1-36
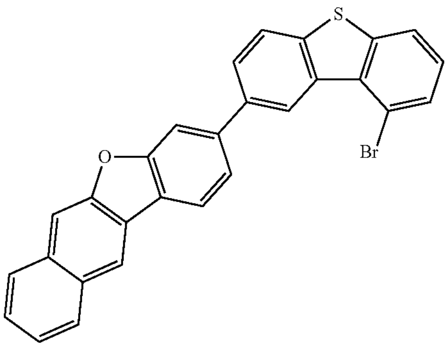
-continued
Sub1-37
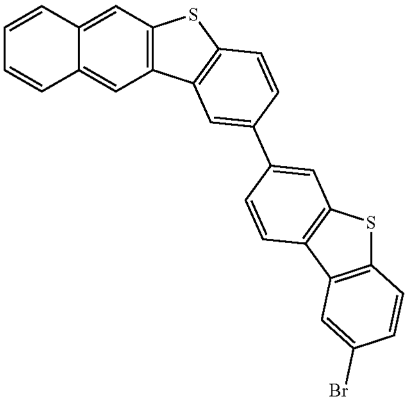
Sub1-38
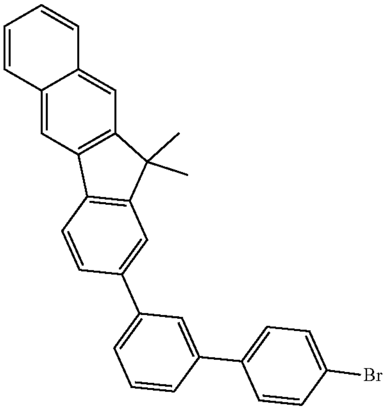
Sub1-39
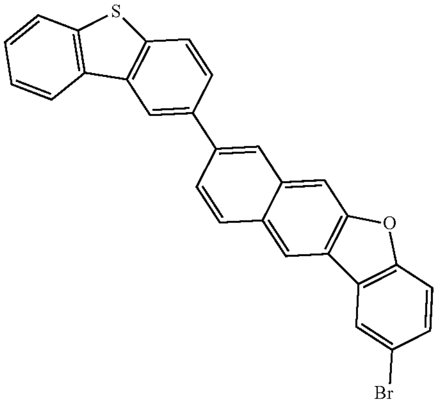
Sub1-40
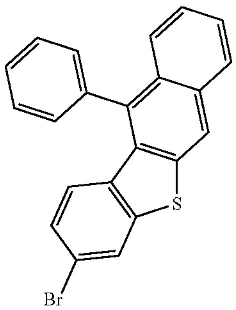

-continued
Sub1-41
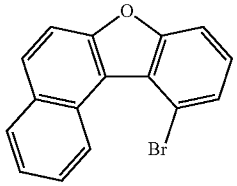
Sub1-42
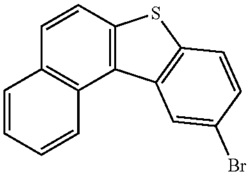
Sub1-43
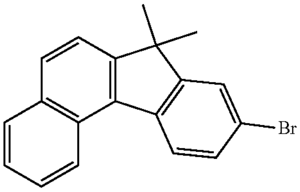
Sub1-44
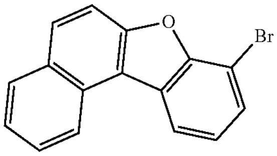
Sub1-45
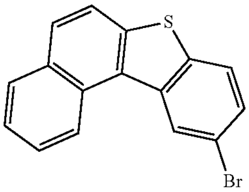
Sub1-46
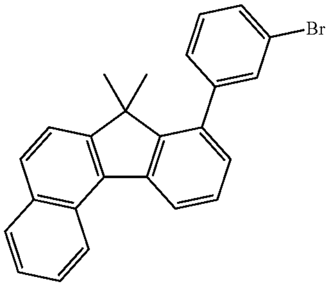
Sub1-47
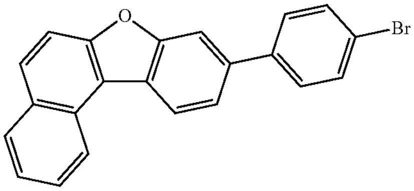
-continued
Sub1-48
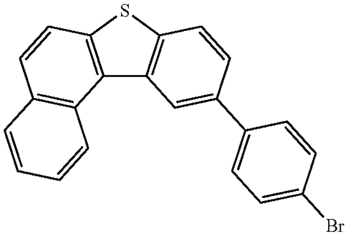
Sub1-49
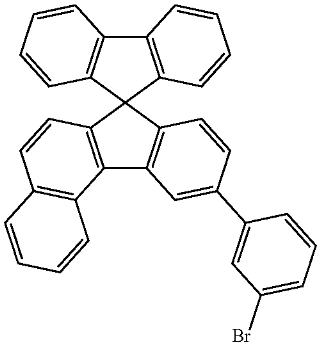
Sub1-50
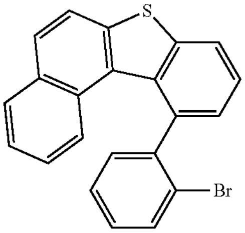
Sub1-51
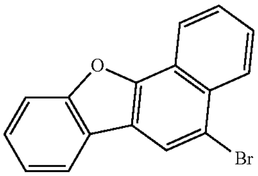
Sub1-52
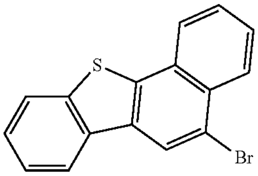
Sub1-53
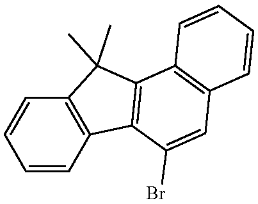
Sub1-54
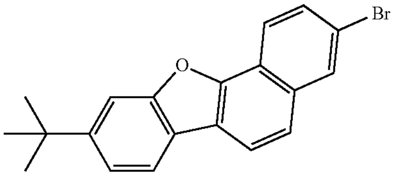

-continued
Sub1-55
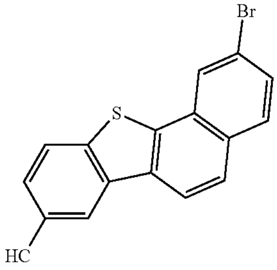
Sub1-56
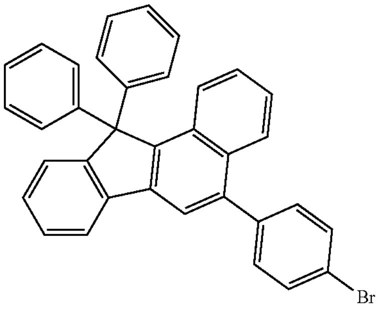
Sub1-57
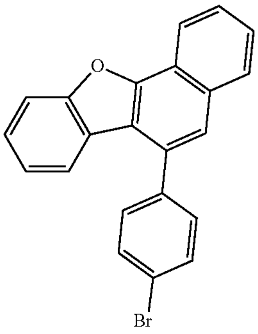
Sub1-58
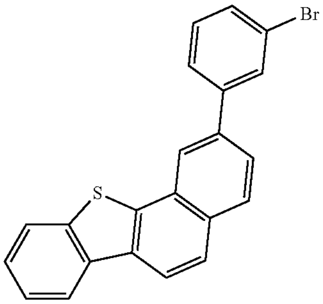
Sub1-59
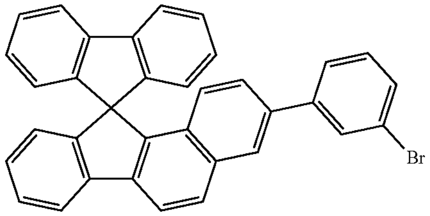
-continued
Sub1-60
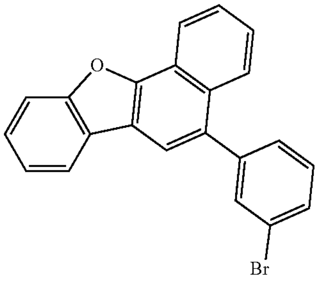
Sub1-61
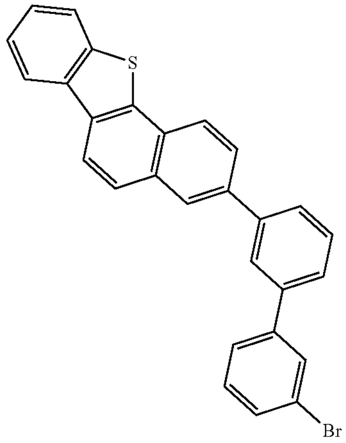
Sub1-62
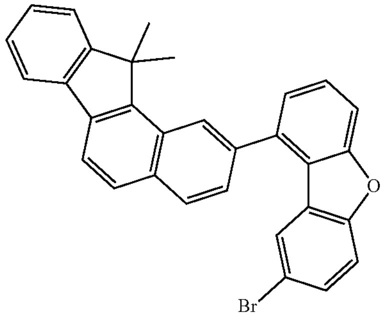
Sub1-63
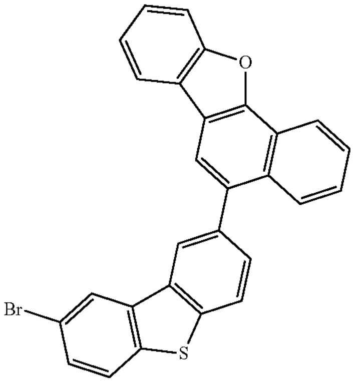

-continued
Sub1-64
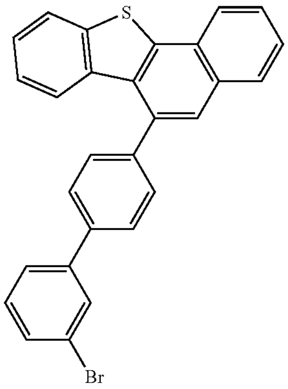
Sub1-65
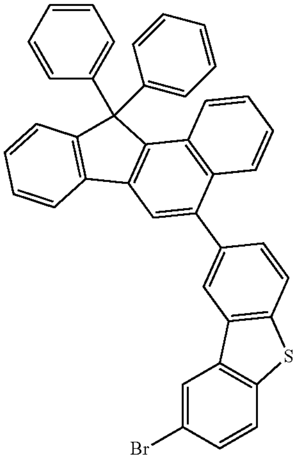
Sub1-66
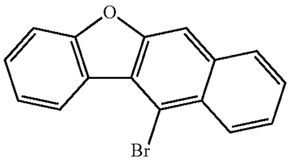
Sub1-67
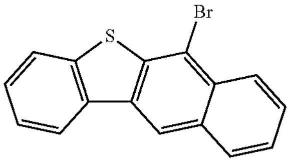
Sub1-68
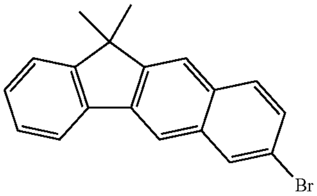
Sub1-69
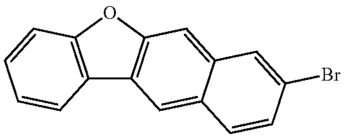
-continued
Sub1-70
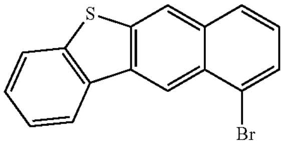
Sub1-71
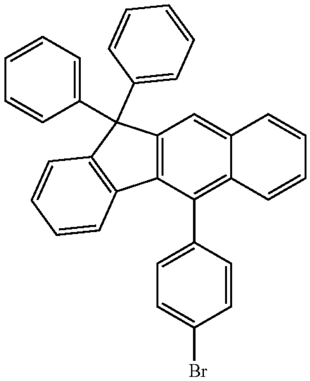
Sub1-72
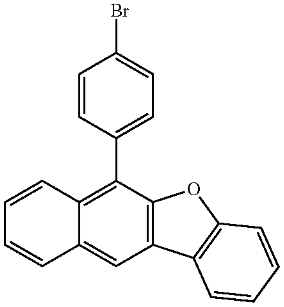
Sub1-73
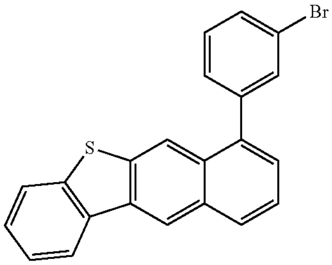
Sub1-74
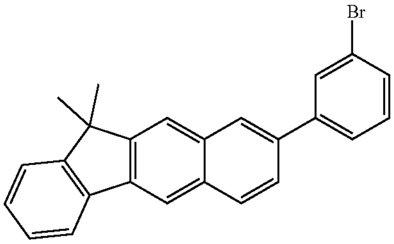
Sub1-75
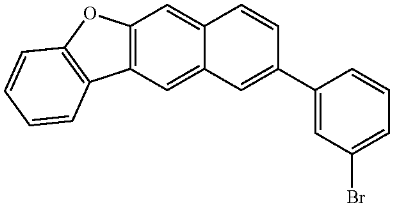

Sub1-76
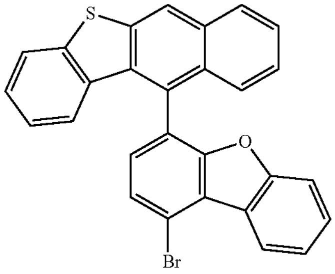
Sub1-77
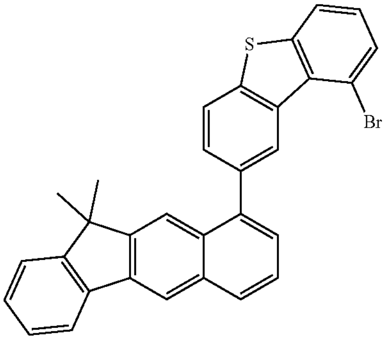
Sub1-78
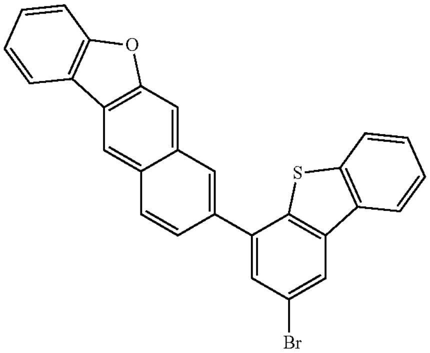
Sub1-79
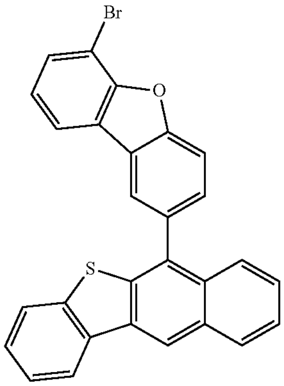
Sub1-80
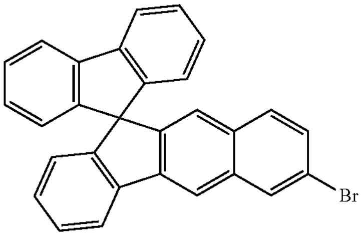
Sub1-81
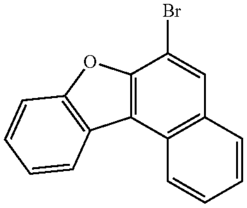
Sub1-82
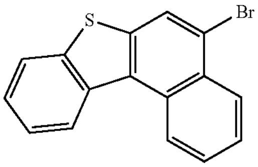
Sub1-83
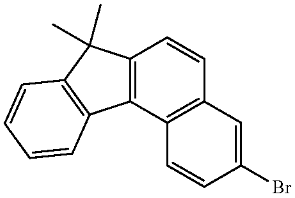
Sub1-84
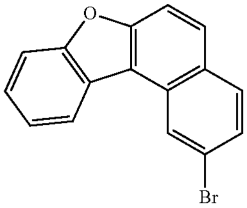
Sub1-85
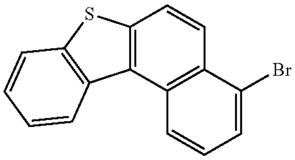
Sub1-86
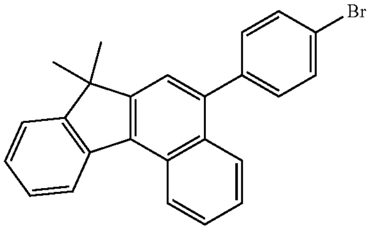
Sub1-87
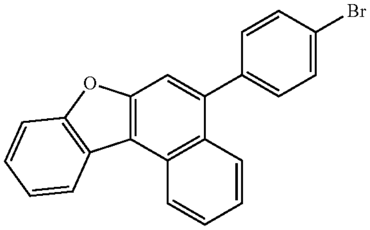

-continued
Sub1-88
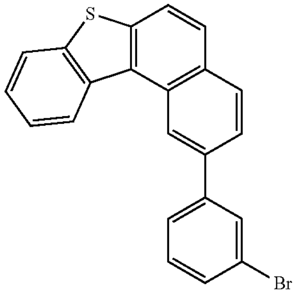
Sub1-89
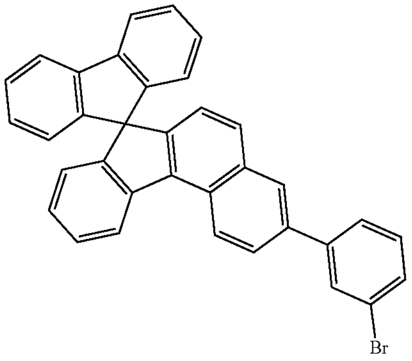
Sub1-90
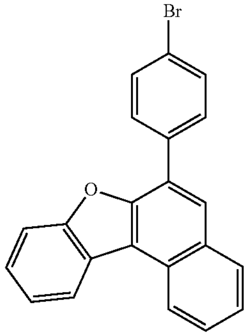
Sub1-91
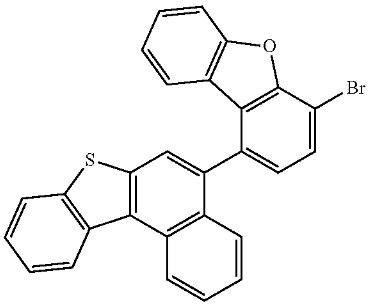
Sub1-92
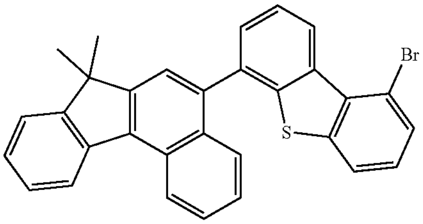
-continued
Sub1-93
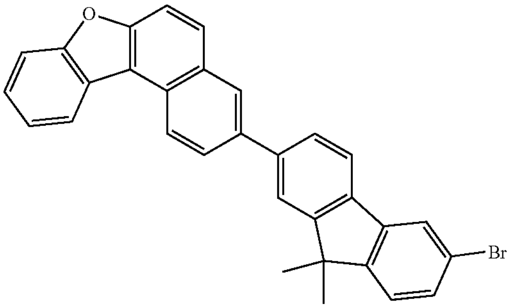
Sub1-94
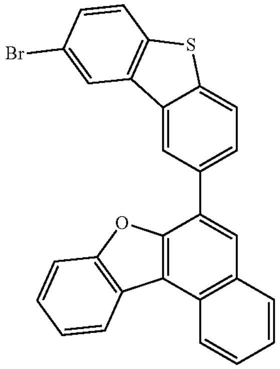
Sub1-95
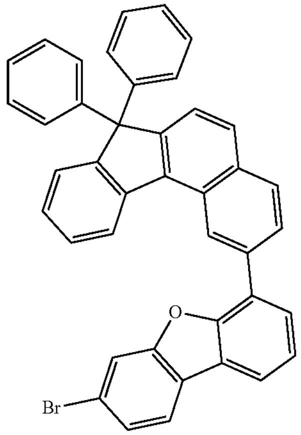
Sub1-96
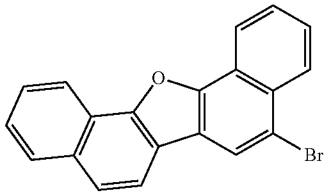
Sub1-97
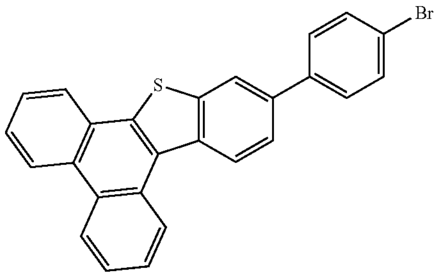

-continued

Sub1-98

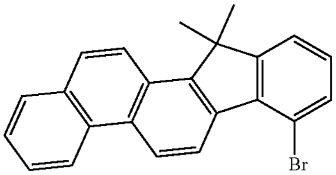

Sub1-99

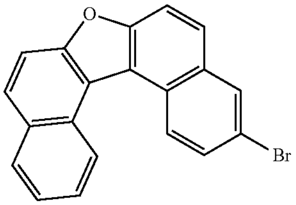

Sub1-100

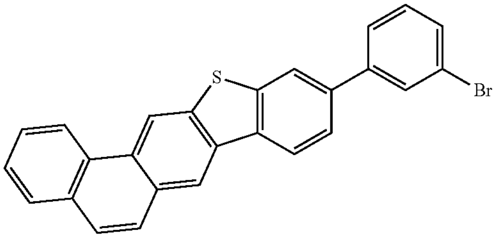

Sub1-101

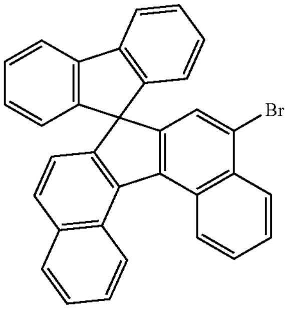

Sub1-102

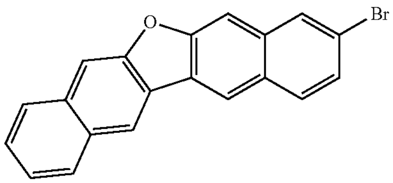

Sub1-103

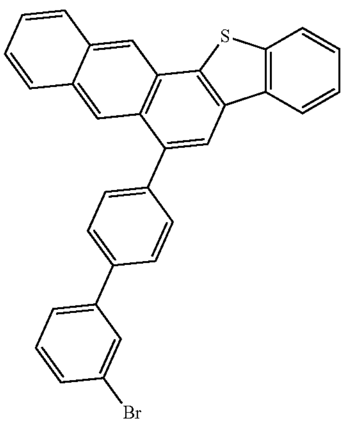

-continued

Sub1-104

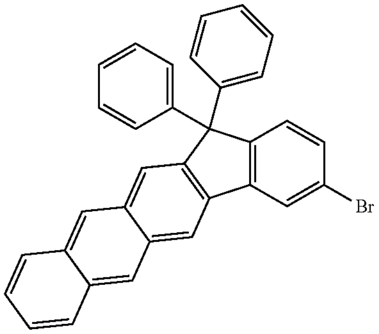

TABLE 1

| Compound | FD-MS |
|---|---|
| Sub1-1 | m/z = 295.98($C_{16}H_9BrO$ = 297.15) |
| Sub1-2 | m/z = 311.96($C_{16}H_9BrS$ = 313.21) |
| Sub1-3 | m/z = 322.04($C_{19}H_{15}Br$ = 323.23) |
| Sub1-4 | m/z = 295.98($C_{16}H_9BrO$ = 297.15) |
| Sub1-5 | m/z = 311.96($C_{16}H_9BrS$ = 313.21) |
| Sub1-6 | m/z = 322.04($C_{19}H_{15}Br$ = 323.23) |
| Sub1-7 | m/z = 295.98($C_{16}H_9BrO$ = 297.15) |
| Sub1-8 | m/z = 311.96($C_{16}H_9BrS$ = 313.21) |
| Sub1-9 | m/z = 322.04($C_{19}H_{15}Br$ = 323.23) |
| Sub1-10 | m/z = 311.96($C_{16}H_9BrS$ = 313.21) |
| Sub1-11 | m/z = 522.10($C_{35}H_{23}Br$ = 523.47) |
| Sub1-12 | m/z = 372.01($C_{22}H_{13}BrO$ = 373.25) |
| Sub1-13 | m/z = 387.99($C_{22}H_{13}BrS$ = 389.31) |
| Sub1-14 | m/z = 398.07($C_{25}H_{19}Br$ = 399.33) |
| Sub1-15 | m/z = 372.01($C_{22}H_{13}BrO$ = 373.25) |
| Sub1-16 | m/z = 387.99($C_{22}H_{13}BrS$ = 389.31) |
| Sub1-17 | m/z = 520.08($C_{35}H_{21}Br$ = 521.46) |
| Sub1-18 | m/z = 372.01($C_{22}H_{13}BrO$ = 373.25) |
| Sub1-19 | m/z = 493.98($C_{28}H_{15}BrS_2$ = 495.45) |
| Sub1-20 | m/z = 514.13($C_{34}H_{27}Br$ = 515.49) |
| Sub1-21 | m/z = 295.98($C_{16}H_9BrO$ = 297.15) |
| Sub1-22 | m/z = 311.96($C_{16}H_9BrS$ = 313.21) |
| Sub1-23 | m/z = 322.04($C_{19}H_{15}Br$ = 323.23) |
| Sub1-24 | m/z = 311.96($C_{19}H_9BrS$ = 313.21) |
| Sub1-25 | m/z = 444.05($C_{29}H_{17}Br$ = 445.36) |
| Sub1-26 | m/z = 295.98($C_{16}H_9BrO$ = 297.15) |
| Sub1-27 | m/z = 311.96($C_{16}H_9BrS$ = 313.21) |
| Sub1-28 | m/z = 322.04($C_{19}H_{15}Br$ = 323.23) |
| Sub1-29 | m/z = 295.98($C_{16}H_9BrO$ = 297.15) |
| Sub1-30 | m/z = 522.10($C_{35}H_{23}Br$ = 523.47) |
| Sub1-31 | m/z = 372.01($C_{22}H_{13}BrO$ = 373.25) |
| Sub1-32 | m/z = 387.99($C_{22}H_{13}BrS$ = 389.31) |
| Sub1-33 | m/z = 522.10($C_{35}H_{23}Br$ = 523.47) |
| Sub1-34 | m/z = 372.01($C_{22}H_{13}BrO$ = 373.25) |
| Sub1-35 | m/z = 398.07($C_{25}H_{19}Br$ = 399.33) |
| Sub1-36 | m/z = 478.00($C_{28}H_{15}BrOS$ = 479.39) |
| Sub1-37 | m/z = 493.98($C_{28}H_{15}BrS_2$ = 495.45) |
| Sub1-38 | m/z = 474.10($C_{31}H_{23}Br$ = 475.43) |
| Sub1-39 | m/z = 478.00($C_{28}H_{15}BrOS$ = 479.39) |
| Sub1-40 | m/z = 387.99($C_{22}H_{13}BrS$ = 389.31) |
| Sub1-41 | m/z = 295.98($C_{16}H_9BrO$ = 297.15) |
| Sub1-42 | m/z = 311.96($C_{16}H_9BrS$ = 313.21) |
| Sub1-43 | m/z = 322.04($C_{19}H_{15}Br$ = 323.23) |
| Sub1-44 | m/z = 295.98($C_{16}H_9BrO$ = 297.15) |
| Sub1-45 | m/z = 311.96($C_{16}H_9BrS$ = 313.21) |
| Sub1-46 | m/z = 398.07($C_{25}H_{19}Br$ = 399.33) |
| Sub1-47 | m/z = 372.01($C_{22}H_{13}BrO$ = 373.25) |
| Sub1-48 | m/z = 387.99($C_{22}H_{13}BrS$ = 389.31) |
| Sub1-49 | m/z = 520.08($C_{35}H_{21}Br$ = 521.46) |
| Sub1-50 | m/z = 387.99($C_{22}H_{13}BrS$ = 389.31) |
| Sub1-51 | m/z = 295.98($C_{16}H_9BrO$ = 297.15) |
| Sub1-52 | m/z = 311.96($C_{16}H_9BrS$ = 313.21) |
| Sub1-53 | m/z = 322.04($C_{19}H_{15}Br$ = 323.23) |
| Sub1-54 | m/z = 352.05($C_{20}H_{17}BrO$ = 353.26) |
| Sub1-55 | m/z = 336.96($C_{17}H_8BrNS$ = 338.22) |
| Sub1-56 | m/z = 522.10($C_{35}H_{23}Br$ = 523.47) |
| Sub1-57 | m/z = 372.01($C_{22}H_{13}BrO$ = 373.25) |

TABLE 1-continued

| Compound | FD-MS |
|---|---|
| Sub1-58 | m/z = 387.99($C_{22}H_{13}BrS$ = 389.31) |
| Sub1-59 | m/z = 520.08($C_{35}H_{21}Br$ = 521.46) |
| Sub1-60 | m/z = 372.01($C_{22}H_{13}BrO$ = 373.25) |
| Sub1-61 | m/z = 464.02($C_{26}H_{17}BrS$ = 465.41) |
| Sub1-62 | m/z = 488.08($C_{31}H_{21}BrO$ = 489.41) |
| Sub1-63 | m/z = 478.00($C_{28}H_{15}BrOS$ = 479.39) |
| Sub1-64 | m/z = 464.02($C_{28}H_{17}BrS$ = 465.41) |
| Sub1-65 | m/z = 628.09($C_{41}H_{25}BrS$ = 629.62) |
| Sub1-66 | m/z = 295.98($C_{16}H_9BrO$ = 297.15) |
| Sub1-67 | m/z = 311.96($C_{16}H_9BrS$ = 313.21) |
| Sub1-68 | m/z = 322.04($C_{19}H_{15}Br$ = 323.23) |
| Sub1-69 | m/z = 295.98($C_{16}H_9BrO$ = 297.15) |
| Sub1-70 | m/z = 311.96($C_{16}H_9BrS$ = 313.21) |
| Sub1-71 | m/z = 522.10($C_{35}H_{23}Br$ = 523.47) |
| Sub1-72 | m/z = 388.05($C_{23}H_{17}BrO$ = 389.29) |
| Sub1-73 | m/z = 387.99($C_{22}H_{13}BrS$ = 389.31) |
| Sub1-74 | m/z = 414.10($C_{26}H_{23}Br$ = 415.37) |
| Sub1-75 | m/z = 388.05($C_{23}H_{17}BrO$ = 389.29) |
| Sub1-76 | m/z = 478.00($C_{28}H_{15}BrOS$ = 479.39) |
| Sub1-77 | m/z = 504.05($C_{31}H_{21}BrS$ = 505.47) |
| Sub1-78 | m/z = 478.00($C_{28}H_{15}BrOS$ = 479.39) |
| Sub1-79 | m/z = 478.00($C_{28}H_{15}BrOS$ = 479.39) |
| Sub1-80 | m/z = 444.05($C_{29}H_{17}Br$ = 445.36) |
| Sub1-81 | m/z = 295.98($C_{16}H_9BrO$ = 297.15) |
| Sub1-82 | m/z = 311.96($C_{16}H_9BrS$ = 313.21) |
| Sub1-83 | m/z = 322.04($C_{19}H_{15}Br$ = 323.23) |
| Sub1-84 | m/z = 295.98($C_{16}H_9BrO$ = 297.15) |
| Sub1-85 | m/z = 311.96($C_{16}H_9BrS$ = 313.21) |
| Sub1-86 | m/z = 398.07($C_{25}H_{19}Br$ = 399.33) |
| Sub1-87 | m/z = 372.01($C_{22}H_{13}BrO$ = 373.25) |
| Sub1-88 | m/z = 387.99($C_{22}H_{13}BrS$ = 389.31) |
| Sub1-89 | m/z = 520.08($C_{35}H_{21}Br$ = 521.46) |
| Sub1-90 | m/z = 372.01($C_{22}H_{13}BrO$ = 373.25) |
| Sub1-91 | m/z = 478.00($C_{28}H_{15}BrOS$ = 479.39) |
| Sub1-92 | m/z = 504.05($C_{31}H_{21}BrS$ = 505.47) |
| Sub1-93 | m/z = 488.08($C_{31}H_{21}BrO$ = 489.41) |
| Sub1-94 | m/z = 493.98($C_{28}H_{15}BrS_2$ = 495.45) |
| Sub1-95 | m/z = 612.11($C_{41}H_{25}BrO$ = 613.55) |
| Sub1-96 | m/z = 346.00($C_{20}H_{11}BrO$ = 347.21) |
| Sub1-97 | m/z = 438.01($C_{26}H_{15}BrS$ = 439.37) |
| Sub1-98 | m/z = 372.05($C_{23}H_{17}Br$ = 373.29) |
| Sub1-99 | m/z = 346.00($C_{20}H_{11}BrO$ = 347.21) |
| Sub1-100 | m/z = 438.01($C_{26}H_{15}BrS$ = 439.37) |
| Sub1-101 | m/z = 494.07($C_{33}H_{19}Br$ = 495.42) |
| Sub1-102 | m/z = 346.00($C_{20}H_{11}BrO$ = 347.21) |
| Sub1-103 | m/z = 514.04($C_{32}H_{19}BrS$ = 515.47) |
| Sub1-104 | m/z = 496.08($C_{33}H_{21}Br$ = 497.44) |

II. Synthesis of Sub2

Sub2 of Reaction Scheme 1 may be synthesized by the reaction route of Scheme 3 below (disclosed in Korean Patent Registration No. 10-1251451 of the present applicant (published on Apr. 5, 2013)), but is not limited thereto.

<Reaction Scheme 3>

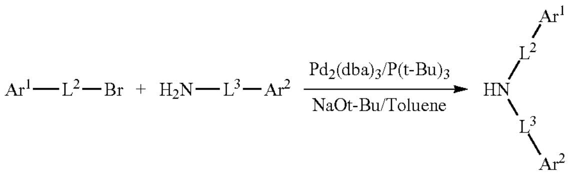

Sub2

Compounds belonging to Sub2 may be a compound as follows, but is not limited thereto, and Table 2 shows FD-MS values of the following compounds.

Sub2-1

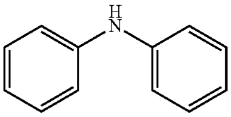

Sub2-2

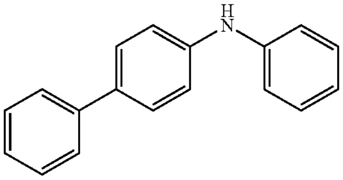

Sub2-3

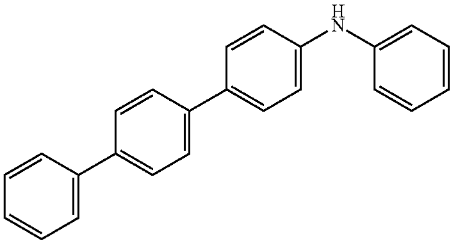

Sub2-4

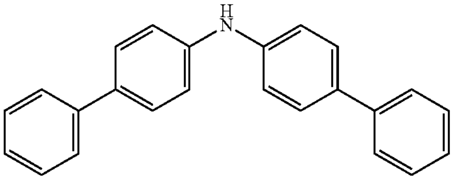

Sub2-5

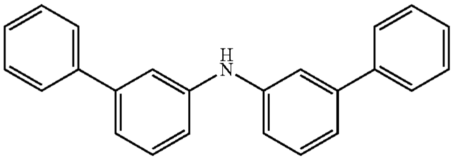

Sub2-6

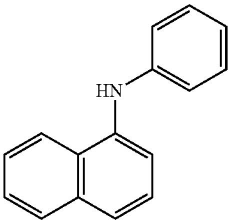

Sub2-7

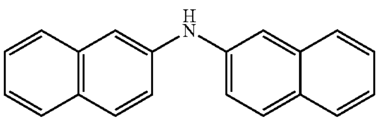

Sub2-8

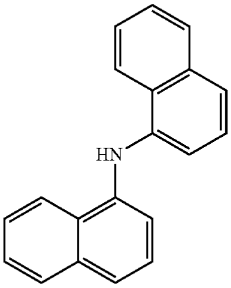

-continued
Sub2-9
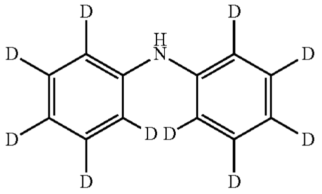
Sub2-10
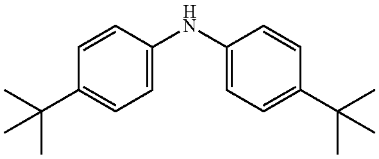
Sub2-11
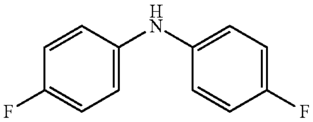
Sub2-12
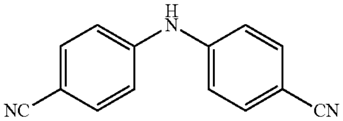
Sub2-13
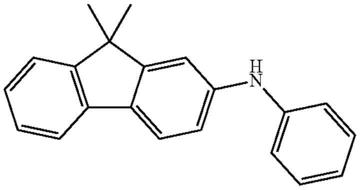
Sub2-14
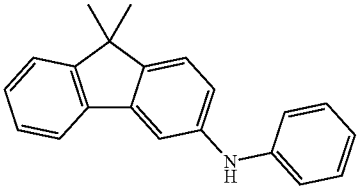
Sub2-15
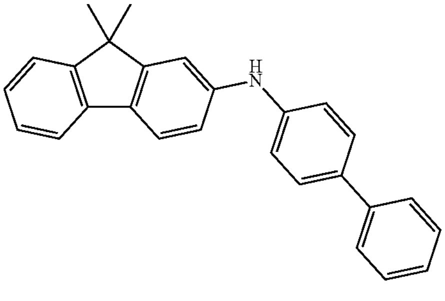
Sub2-16
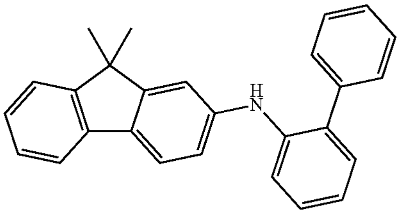
-continued
Sub2-17
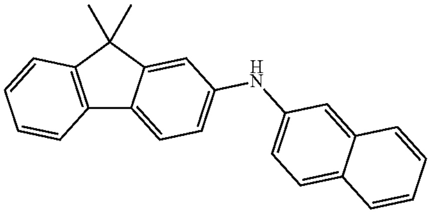
Sub2-18
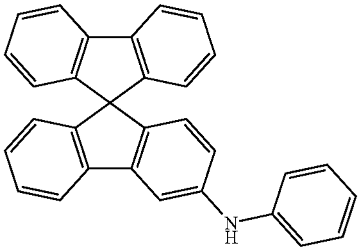
Sub2-19
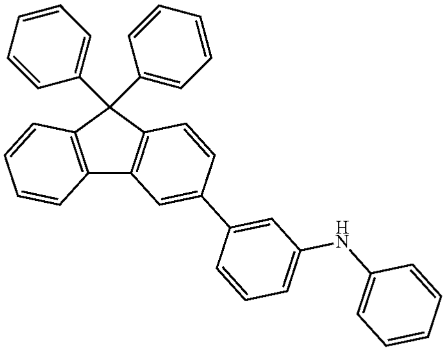
Sub2-20
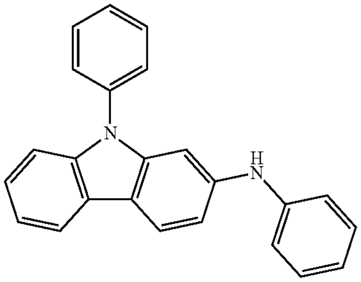
Sub2-21
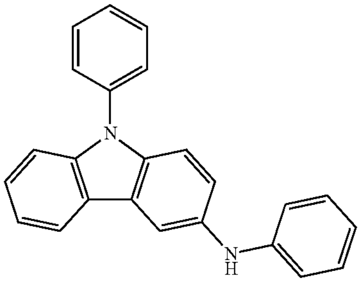

-continued
Sub2-22
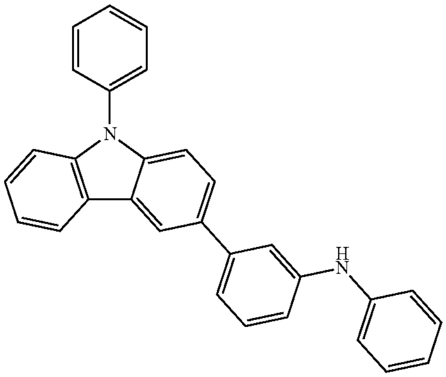
Sub2-23
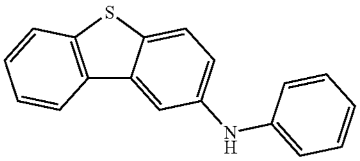
Sub2-24
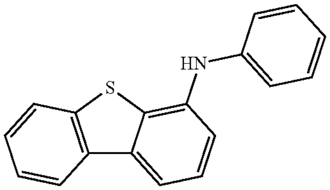
Sub2-25
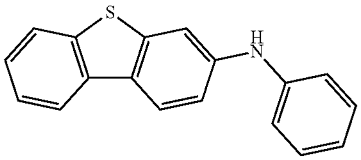
Sub2-26
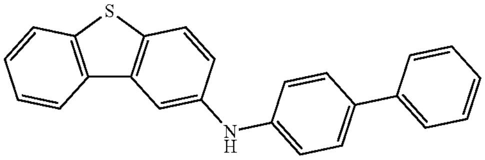
Sub2-27
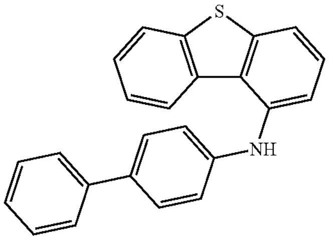
Sub2-28
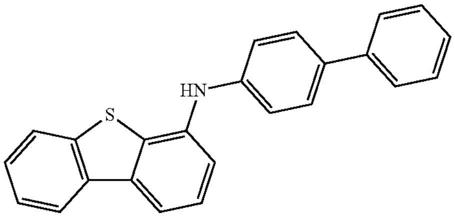
-continued
Sub2-29
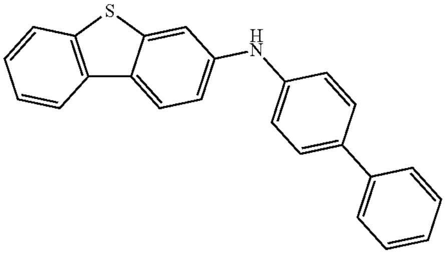
Sub2-30
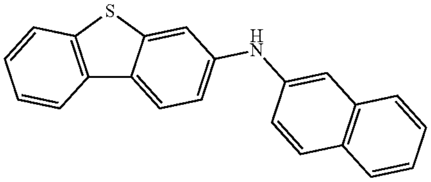
Sub2-31
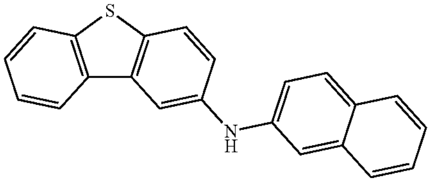
Sub2-32
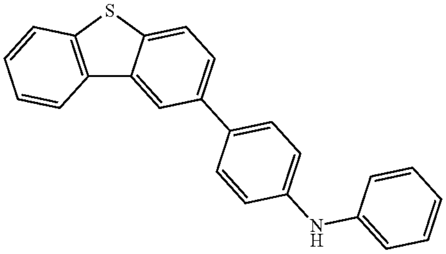
Sub2-33
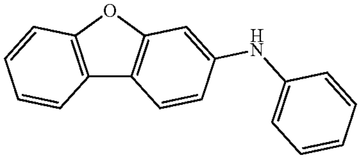
Sub2-34
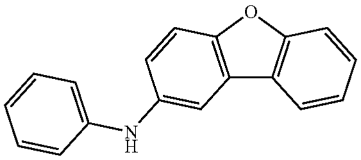
Sub2-35
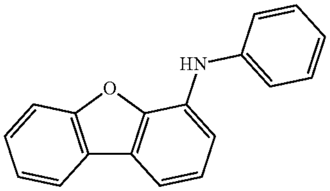

-continued
Sub2-36
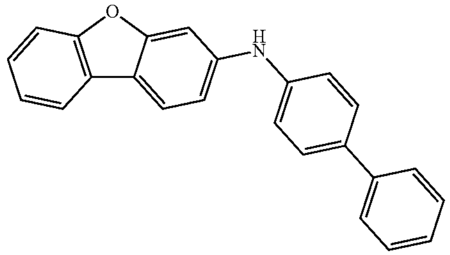
Sub2-37
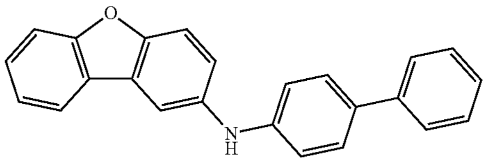
Sub2-38
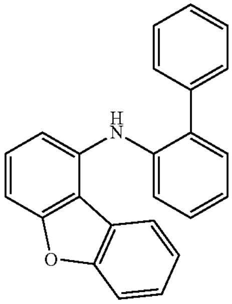
Sub2-39
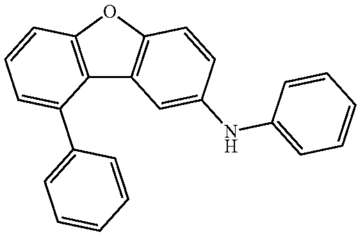
Sub2-40
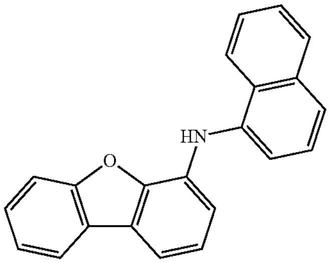
-continued
Sub2-41
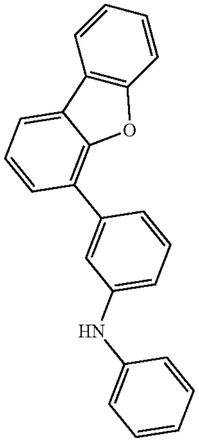
Sub2-42
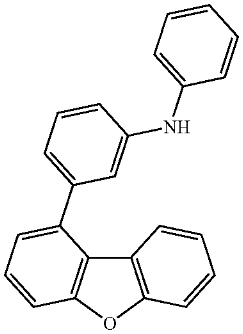
Sub2-43
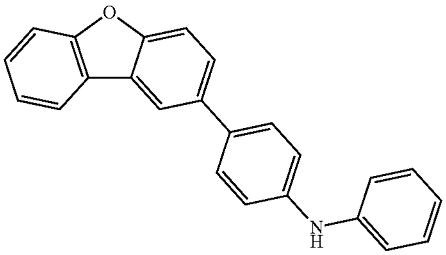
Sub2-44
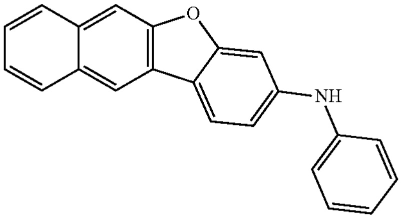
TABLE 2
| Compound | FD-MS |
|---|---|
| Sub2-1 | m/z = 169.09($C_{12}H_{11}N$ = 169.23) |
| Sub2-2 | m/z = 245.12($C_{18}H_{15}N$ = 245.33) |
| Sub2-3 | m/z = 321.15($C_{24}H_{19}N$ = 321.42) |
| Sub2-4 | m/z = 321.15($C_{24}H_{19}N$ = 321.42) |
| Sub2-5 | m/z = 321.15($C_{24}H_{19}N$ = 321.42) |
| Sub2-6 | m/z = 219.10($C_{16}H_{13}N$ = 219.29) |
| Sub2-7 | m/z = 269.12($C_{20}H_{15}N$ = 269.35) |
| Sub2-8 | m/z = 269.12($C_{20}H_{15}N$ = 269.35) |
| Sub2-9 | m/z = 179.15($C_{12}HD_{10}N$ = 179.29) |
| Sub2-10 | m/z = 281.21($C_{20}H_{27}N$ = 281.44) |

TABLE 2-continued

| Compound | FD-MS |
| --- | --- |
| Sub2-11 | m/z = 205.07($C_{12}H_9F_2N$ = 205.21) |
| Sub2-12 | m/z = 219.08($C_{14}H_9N_3$ = 219.25) |
| Sub2-13 | m/z = 285.15($C_{21}H_{19}N$ = 285.39) |
| Sub2-14 | m/z = 285.15($C_{21}H_{19}N$ = 285.39) |
| Sub2-15 | m/z = 361.18($C_{27}H_{23}N$ = 361.49) |
| Sub2-16 | m/z = 361.18($C_{27}H_{23}N$ = 361.49) |
| Sub2-17 | m/z = 335.17($C_{25}H_{21}N$ = 335.45) |
| Sub2-18 | m/z = 407.17($C_{31}H_{21}N$ = 407.52) |
| Sub2-19 | m/z = 485.21($C_{37}H_{27}N$ = 485.63) |
| Sub2-20 | m/z = 334.15($C_{24}H_{18}N_2$ = 334.42) |
| Sub2-21 | m/z = 334.15($C_{24}H_{18}N_2$ = 334.42) |
| Sub2-22 | m/z = 410.18($C_{30}H_{22}N_2$ = 410.52) |
| Sub2-23 | m/z = 275.08($C_{18}H_{13}NS$ = 275.37) |
| Sub2-24 | m/z = 275.08($C_{18}H_{13}NS$ = 275.37) |
| Sub2-25 | m/z = 275.08($C_{18}H_{13}NS$ = 275.37) |
| Sub2-26 | m/z = 351.11($C_{24}H_{17}NS$ = 351.47) |
| Sub2-27 | m/z = 351.11($C_{24}H_{17}NS$ = 351 .47) |
| Sub2-28 | m/z = 351.11($C_{24}H_{17}NS$ = 351.47) |
| Sub2-29 | m/z = 351.11($C_{24}H_{17}NS$ = 351 .47) |
| Sub2-30 | m/z = 325.09($C_{22}H_{15}NS$ = 325.43) |
| Sub2-31 | m/z = 325.09($C_{22}H_{15}NS$ = 325.43) |
| Sub2-32 | m/z = 351.11($C_{24}H_{17}NS$ = 351.47) |
| Sub2-33 | m/z = 259.1($C_{18}H_{13}NO$ = 259.31) |
| Sub2-34 | m/z = 259.10($C_{18}H_{13}NO$ = 259.31) |
| Sub2-35 | m/z = 259.1($C_{18}H_{13}NO$ = 259.31) |
| Sub2-36 | m/z = 335.13($C_{24}H_{17}NO$ = 335.41) |
| Sub2-37 | m/z = 335.13($C_{24}H_{17}NO$ = 335.41) |
| Sub2-38 | m/z = 335.13($C_{24}H_{17}NO$ = 335.41) |
| Sub2-39 | m/z = 335.13($C_{24}H_{17}NO$ = 335.41) |
| Sub2-40 | m/z = 309.12($C_{22}H_{15}NO$ = 309.37) |
| Sub2-41 | m/z = 335.13($C_{24}H_{17}NO$ = 335.41) |
| Sub2-42 | m/z = 335.13($C_{24}H_{17}NO$ = 335.41) |
| Sub2-43 | m/z = 335.13($C_{24}H_{17}NO$ = 335.41) |
| Sub2-44 | m/z = 309.12($C_{22}H_{15}NO$ = 309.37) |

III. Synthesis of Final Product

1. Synthesis Example of P1-5

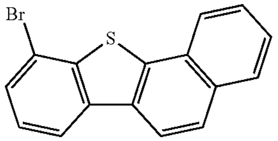

+

Sub1-5

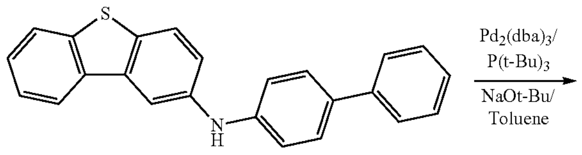

Sub2-26

-continued

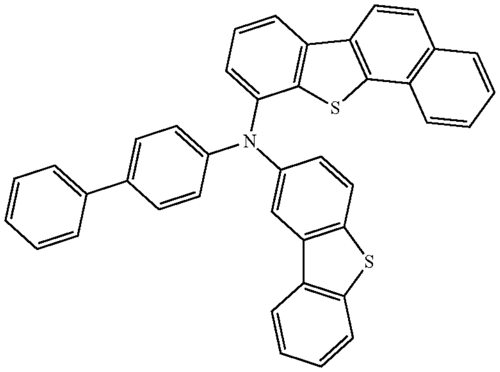

P1-5

Toluene (160 mL), Sub2-26 (11.2 g, 31.9 mmol), $Pd_2(dba)_3$ (0.88 g, 0.96 mmol), $P(t\text{-}Bu)_3$ (0.39 g, 1.92 mmol) and NaOt-Bu (6.1 g, 63.9 mmol) were added to Sub1-5 (10.0 g, 31.9 mmol) and the mixture was stirred at 100° C. When the reaction was completed, the reaction product was extracted with $CH_2Cl_2$ and water. An organic layer was dried over $MgSO_4$ and concentrated. Then, the concentrate was separated by a silica gel column and recrystallized to obtain 13.8 g (yield: 74%) of the product.

2. Synthesis Example of P1-16

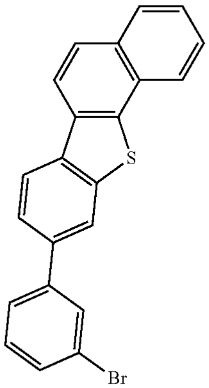

+

Sub1-16

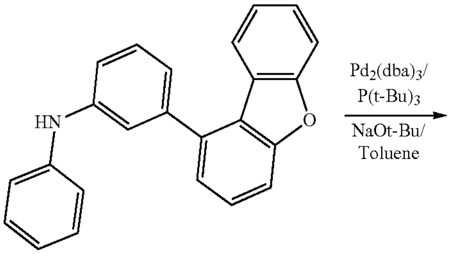

Sub2-42

-continued

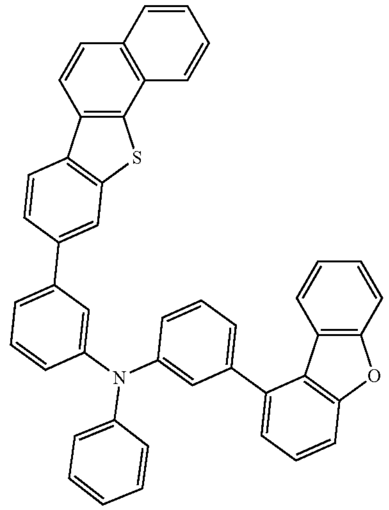

P1-16

Toluene, Sub2-42 (8.6 g, 25.7 mmol), $Pd_2(dba)_3$ (0.71 g, 0.77 mmol), $P(t\text{-}Bu)_3$ (0.31 g, 1.54 mmol) and NaOt-Bu (4.9 g, 51.4 mmol) were added to Sub1-16 (10.0 g, 25.7 mmol), and synthesis was carried out in the same manner as for the synthesis of P1-5 to obtain 12.6 g (yield: 76%) of the product.

3. Synthesis Example of P1-28

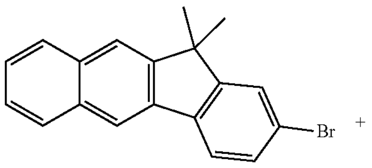

Sub1-28

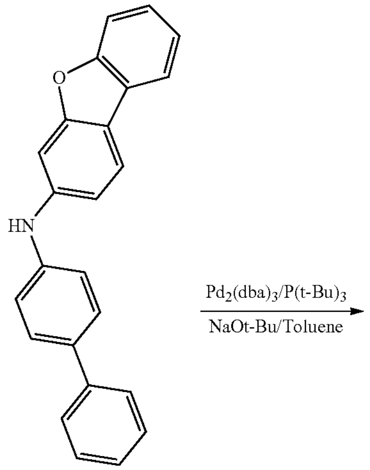

Sub2-36

-continued

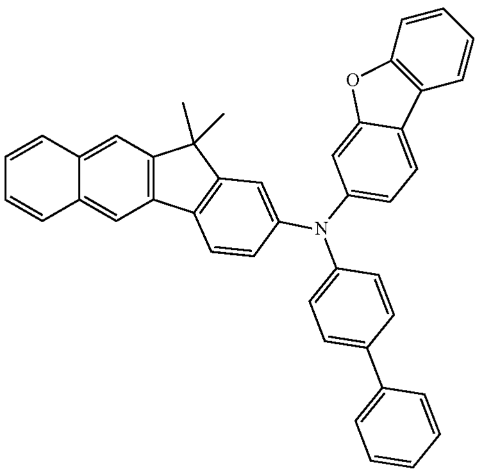

P1-28

Toluene, Sub2-36 (10.4 g, 30.9 mmol), $Pd_2(dba)_3$ (0.85 g, 0.93 mmol), $P(t\text{-}Bu)_3$ (0.38 g, 1.86 mmol) and NaOt-Bu (5.9 g, 61.9 mmol) were added to Sub1-28 (10.0 g, 30.9 mmol), and synthesis was carried out in the same manner as for the synthesis of P1-5 to obtain 13.0 g (yield: 73%) of the product.

4. Synthesis Example of P1-29

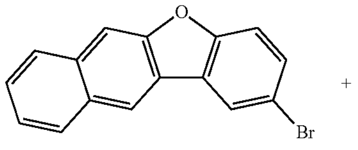

Sub1-29

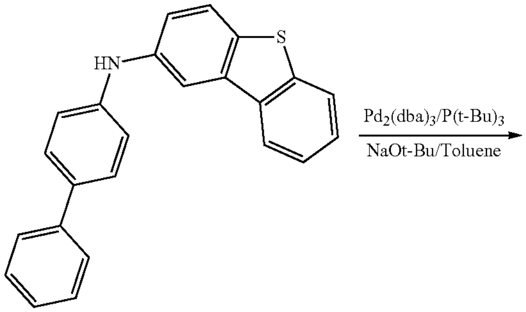

Sub2-26

-continued

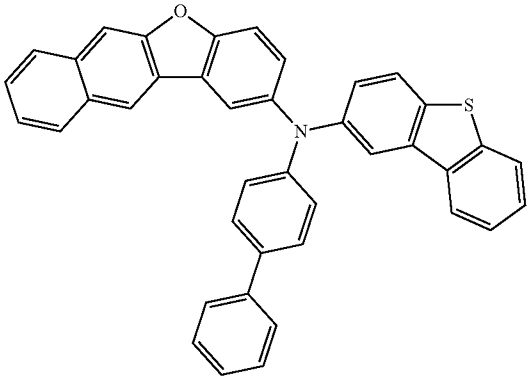

P1-29

Toluene, Sub2-26 (11.8 g, 33.7 mmol), $Pd_2(dba)_3$ (0.92 g, 1.01 mmol), $P(t\text{-}Bu)_3$ (0.41 g, 2.02 mmol) and NaOt-Bu (6.5 g, 67.3 mmol) were added to Sub1-29 (10.0 g, 33.7 mmol), and synthesis was carried out in the same manner as for the synthesis of P1-5 to obtain 13.0 g (yield: 68%) of the product.

5. Synthesis Example of P1-49

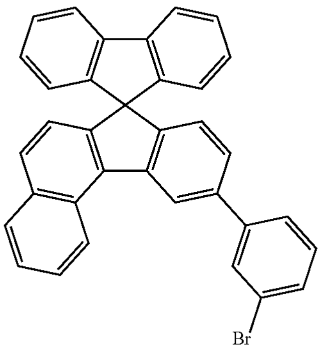

Sub1-49

+

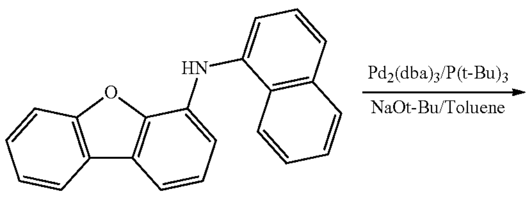

Sub2-40

-continued

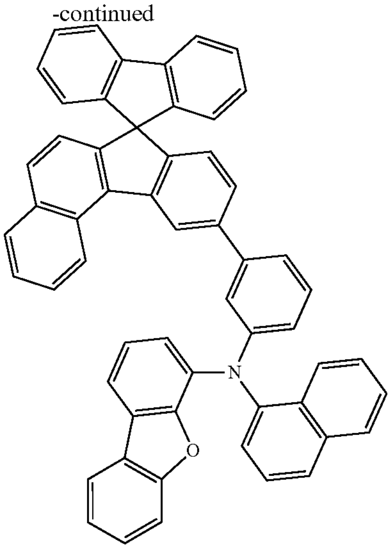

P1-49

Toluene, Sub2-40 (5.9 g, 19.2 mmol), $Pd_2(dba)_3$ (0.53 g, 0.58 mmol), $P(t\text{-}Bu)_3$ (0.23 g, 1.15 mmol) and NaOt-Bu (3.7 g, 38.4 mmol) were added to Sub1-49 (10.0 g, 19.2 mmol), and synthesis was carried out in the same manner as for the synthesis of P1-5 to obtain 10.6 g (yield: 74%) of the product.

6. Synthesis Example of P1-52

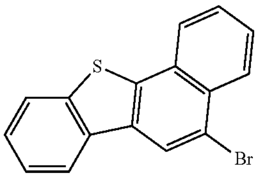

Sub1-52

+

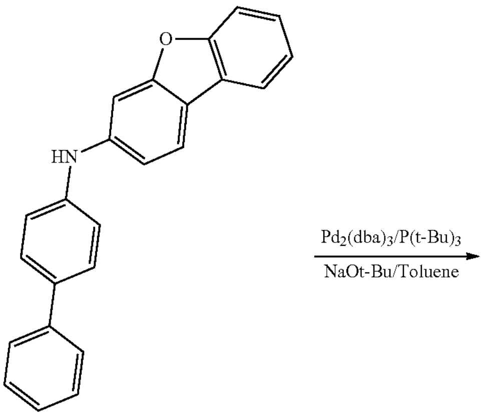

Sub2-36

-continued

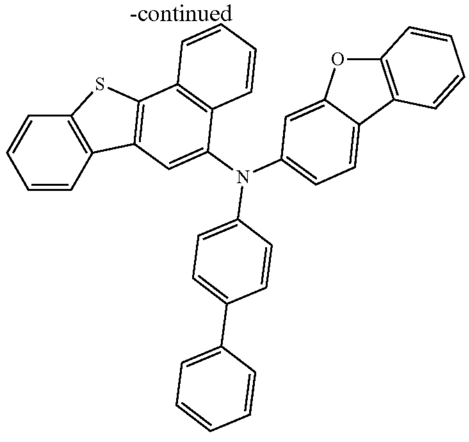

P1-52

Sub2-36 (10.7 g, 31.9 mmol), $Pd_2(dba)_3$ (0.88 g, 0.96 mmol), $P(t\text{-}Bu)_3$ (0.39 g, 1.92 mmol) and NaOt-Bu (6.1 g, 63.9 mmol) were added to Sub1-52 (10.0 g, 31.9 mmol), and synthesis was carried out in the same manner as for the synthesis of P1-5 to obtain 12.0 g (yield: 66%) of the product.

7. Synthesis Example of P1-66

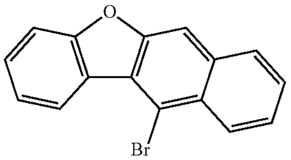

+

Sub1-66

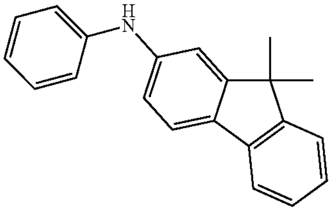

$Pd_2(dba)_3/P(t\text{-}Bu)_3$

NaOt-Bu/Toluene

Sub2-13

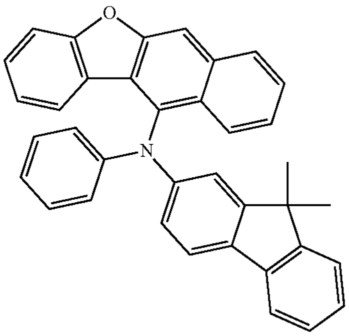

P1-66

Toluene, Sub2-13 (8.7 g, 30.4 mmol), $Pd_2(dba)_3$ (0.83 g, 0.91 mmol), $P(t\text{-}Bu)_3$ (0.37 g, 1.82 mmol) and NaOt-Bu (5.8 g, 60.7 mmol) were added to Sub1-66 (10.0 g, 30.4 mmol), and synthesis was carried out in the same manner as for the synthesis of P1-5 to obtain 10.5 g (yield: 69%) of the product.

8. Synthesis Example of P1-81

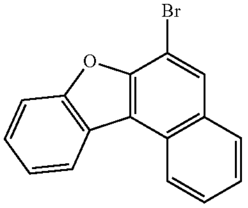

+

Sub1-81

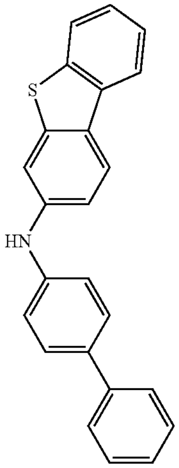

$Pd_2(dba)_3/P(t\text{-}Bu)_3$

NaOt-Bu/Toluene

Sub2-29

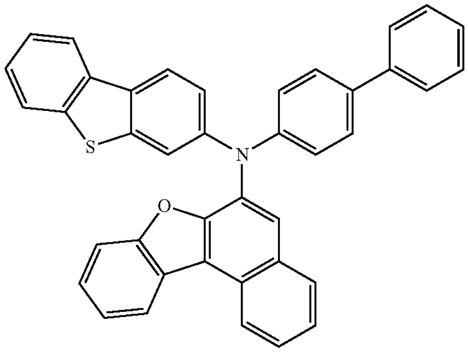

P1-81

Sub2-29 (11.8 g, 33.7 mmol), $Pd_2(dba)_3$ (0.92 g, 1.01 mmol), $P(t\text{-}Bu)_3$ (0.41 g, 2.02 mmol) and NaOt-Bu (6.5 g, 67.3 mmol) were added to Sub1-81 (10.0 g, 33.7 mmol), and synthesis was carried out in the same manner as for the synthesis of P1-5 to obtain 12.8 g (yield: 67%) of the product.

FD-MS values of compounds P1-1 to P1-104 of the present invention prepared according to the above synthesis examples are shown in Table 3 below.

TABLE 3

| Compound | FD-MS |
|---|---|
| P1-1 | m/z = 385.15($C_{28}H_{19}NO$ = 385.47) |
| P1-2 | m/z = 553.19($C_{40}H_{27}NS$ = 553.72) |
| P1-3 | m/z = 511.23($C_{39}H_{29}N$ = 511.67) |
| P1-4 | m/z = 501.21($C_{37}H_{27}NO$ = 501.63) |
| P1-5 | m/z = 583.14($C_{40}H_{25}NS_2$ = 583.77) |
| P1-6 | m/z = 511.23($C_{39}H_{29}N$ = 511.67) |
| P1-7 | m/z = 501.21($C_{37}H_{27}NO$ = 501.63) |
| P1-8 | m/z = 501.16($C_{36}H_{23}NS$ = 501.65) |
| P1-9 | m/z = 593.22($C_{43}H_{31}NS$ = 593.79) |
| P1-10 | m/z = 567.17($C_{40}H_{25}NOS$ = 567.71) |
| P1-11 | m/z = 661.28($C_{51}H_{35}N$ = 661.85) |
| P1-12 | m/z = 613.24($C_{46}H_{31}NO$ = 613.76) |
| P1-13 | m/z = 567.17($C_{40}H_{25}NOS$ = 567.71) |
| P1-14 | m/z = 669.25($C_{49}H_{35}NS$ = 669.89) |
| P1-15 | m/z = 777.30($C_{59}H_{39}NO$ = 777.97) |
| P1-16 | m/z = 643.20($C_{46}H_{29}NOS$ = 643.8) |
| P1-17 | m/z = 774.30($C_{59}H_{38}N_2$ = 774.97) |
| P1-18 | m/z = 702.27($C_{52}H_{34}N_2O$ = 702.86) |
| P1-19 | m/z = 593.21($C_{40}H_{15}D_{10}NS_2$ = 593.83) |
| P1-20 | m/z = 841.37($C_{65}H_{47}N$ = 842.10) |
| P1-21 | m/z = 461.18($C_{34}H_{23}NO$ = 461.56) |
| P1-22 | m/z = 491.13($C_{34}H_{21}NOS$ = 491.61) |
| P1-23 | m/z = 511.23($C_{39}H_{29}N$ = 511.67) |
| P1-24 | m/z = 553.19($C_{40}H_{27}NS$ = 553.72) |
| P1-25 | m/z = 725.31($C_{56}H_{39}N$ = 725.94) |
| P1-26 | m/z = 541.15($C_{38}H_{23}NOS$ = 541.67) |
| P1-27 | m/z = 583.14($C_{40}H_{25}NS_2$ = 583.77) |
| P1-28 | m/z = 557.24($C_{43}H_{31}NO$ = 557.73) |
| P1-29 | m/z = 567.17($C_{40}H_{25}NOS$ = 567.71) |
| P1-30 | m/z = 727.32($C_{56}H_{41}N$ = 727.95) |
| P1-31 | m/z = 627.22($C_{46}H_{29}NO_2$ = 627.74) |
| P1-32 | m/z = 593.22($C_{43}H_{31}NS$ = 593.79) |
| P1-33 | m/z = 723.39($C_{55}H_{49}N$ = 724.00) |
| P1-34 | m/z = 567.17($C_{40}H_{25}NOS$ = 567.71) |
| P1-35 | m/z = 643.23($C_{47}H_{33}NS$ = 643.85) |
| P1-36 | m/z = 567.17($C_{40}H_{25}NOS$ = 567.71) |
| P1-37 | m/z = 583.14($C_{40}H_{25}NS_2$ = 583.77) |
| P1-38 | m/z = 563.26($C_{43}H_{33}N$ = 563.74) |
| P1-39 | m/z = 567.17($C_{40}H_{25}NOS$ = 567.71) |
| P1-40 | m/z = 629.22($C_{46}H_{31}NS$ = 629.82) |
| P1-41 | m/z = 537.21($C_{40}H_{27}NO$ = 537.66) |
| P1-42 | m/z = 437.10($C_{28}H_{17}F_2NS$ = 437.51) |
| P1-43 | m/z = 461.19($C_{33}H_{23}N_3$ = 461.57) |
| P1-44 | m/z = 551.19($C_{40}H_{25}NO_2$ = 551.65) |
| P1-45 | m/z = 567.20($C_{41}H_{29}NS$ = 567.75) |
| P1-46 | m/z = 593.22($C_{43}H_{31}NS$ = 593.79) |
| P1-47 | m/z = 601.20($C_{44}H_{27}NO_2$ = 601.71) |
| P1-48 | m/z = 659.17($C_{46}H_{29}NS_2$ = 659.87) |
| P1-49 | m/z = 749.27($C_{57}H_{35}NO$ = 749.91) |
| P1-50 | m/z = 643.20($C_{46}H_{29}NOS$ = 643.80) |
| P1-51 | m/z = 537.21($C_{40}H_{27}NO$ = 537.66) |
| P1-52 | m/z = 567.17($C_{40}H_{25}NOS$ = 567.71) |
| P1-53 | m/z = 577.28($C_{44}H_{35}N$ = 577.77) |
| P1-54 | m/z = 623.23($C_{44}H_{33}NOS$ = 623.81) |
| P1-55 | m/z = 582.12($C_{39}H_{22}N_2S_2$ = 582.74) |
| P1-56 | m/z = 793.28($C_{59}H_{39}NS$ = 794.03) |
| P1-57 | m/z = 561.21($C_{42}H_{27}NO$ = 561.68) |
| P1-58 | m/z = 669.25($C_{49}H_{35}NS$ = 669.89) |
| P1-59 | m/z = 715.23($C_{53}H_{33}NS$ = 715.91) |
| P1-60 | m/z = 643.20($C_{53}H_{33}NS$ = 643.80) |
| P1-61 | m/z = 669.25($C_{49}H_{35}NS$ = 669.89) |
| P1-62 | m/z = 759.26($C_{55}H_{37}NOS$ = 759.97) |
| P1-63 | m/z = 643.20($C_{46}H_{29}NOS$ = 643.80) |
| P1-64 | m/z = 659.17($C_{46}H_{29}NS_2$ = 659.87) |
| P1-65 | m/z = 807.26($C_{59}H_{37}NOS$ = 808.01) |
| P1-66 | m/z = 501.21($C_{37}H_{27}NO$ = 501.63) |
| P1-67 | m/z = 553.19($C_{40}H_{27}NS$ = 553.72) |
| P1-68 | m/z = 593.22($C_{43}H_{31}NS$ = 593.79) |
| P1-69 | m/z = 485.18($C_{36}H_{23}NO$ = 485.59) |
| P1-70 | m/z = 567.17($C_{40}H_{25}NOS$ = 567.71) |
| P1-71 | m/z = 809.31($C_{60}H_{43}NS$ = 810.07) |
| P1-72 | m/z = 593.27($C_{44}H_{35}NO$ = 593.77) |
| P1-73 | m/z = 583.14($C_{40}H_{25}NS_2$ = 583.77) |
| PI-74 | m/z = 593.27($C_{44}H_{35}NO$ = 593.77) |
| P1-75 | m/z = 659.23($C_{47}H_{33}NOS$ = 659.85) |
| P1-76 | m/z = 759.26($C_{55}H_{37}NOS$ = 759.97) |
| P1-77 | m/z = 593.22($C_{43}H_{31}NS$ = 593.79) |
| P1-78 | m/z = 567.17($C_{40}H_{25}NOS$ = 567.71) |
| P1-79 | m/z = 667.20($C_{48}H_{29}NOS$ = 667.83) |
| P1-80 | m/z = 698.27($C_{53}H_{34}N_2$ = 698.87) |
| P1-81 | m/z = 567.17($C_{40}H_{25}NOS$ = 567.71) |
| P1-82 | m/z = 501.16($C_{36}H_{23}NS$ = 501.65) |
| P1-83 | m/z = 593.22($C_{43}H_{31}NS$ = 593.79) |
| P1-84 | m/z = 537.21($C_{40}H_{27}NO$ = 537.66) |
| P1-85 | m/z = 553.19($C_{40}H_{27}NS$ = 553.72) |
| P1-86 | m/z = 593.22($C_{43}H_{31}NS$ = 593.79) |
| P1-87 | m/z = 537.21($C_{40}H_{27}NO$ = 537.66) |
| P1-88 | m/z = 642.21($C_{46}H_{30}N_2S$ = 642.82) |
| P1-89 | m/z = 725.31($C_{56}H_{39}N$ = 725.94) |
| P1-90 | m/z = 551.19($C_{40}H_{25}NO_2$ = 551.65) |
| P1-91 | m/z = 567.17($C_{40}H_{25}NOS$ = 567.71) |
| P1-92 | m/z = 593.22($C_{43}H_{31}NS$ = 593.79) |
| P1-93 | m/z = 577.24($C_{43}H_{31}NO$ = 577.73) |
| P1-94 | m/z = 583.14($C_{40}H_{25}NS_2$ = 583.77) |
| P1-95 | m/z = 701.27($C_{53}H_{35}NO$ = 701.87) |
| P1-96 | m/z = 525.17($C_{38}H_{23}NO_2$ = 525.61) |
| P1-97 | m/z = 527.17($C_{33}H_{25}NS$ = 527.69) |
| P1-98 | m/z = 567.20($C_{41}H_{29}NS$ = 567.75) |
| P1-99 | m/z = 541.15($C_{38}H_{23}NOS$ = 541.67) |
| P1-100 | m/z = 527.17($C_{33}H_{25}NS$ = 527.69) |
| P1-101 | m/z = 583.23($C_{45}H_{29}N$ = 583.73) |
| P1-102 | m/z = 551.22($C_{41}H_{29}NO$ = 551.69) |
| P1-103 | m/z = 603.20($C_{44}H_{29}NS$ = 603.78) |
| P1-104 | m/z = 585.25($C_{45}H_{31}N$ = 585.75) |

[Synthesis Example 2] Formula 2

The compound (Final product 2) represented by Formula 2 of the present invention may be prepared as in Reaction Scheme 4 below, but is not limited thereto.

<Reaction Scheme 4>

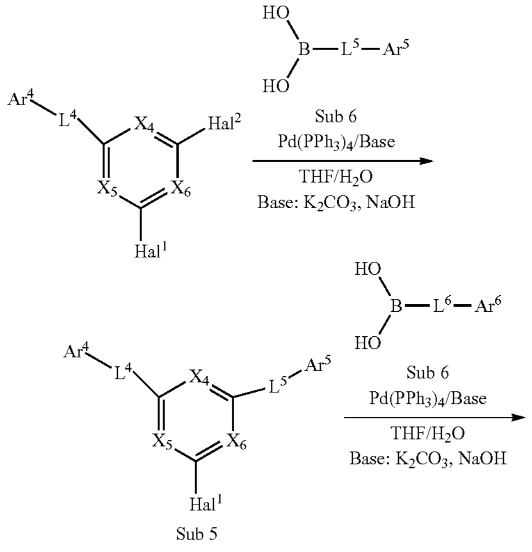

-continued

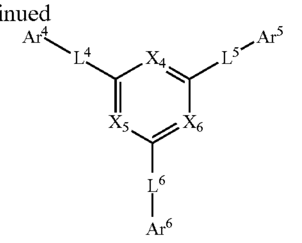

Final Product 2

(Hal[1] and Hal[2] are I, Br or Cl.)

I. Synthesis Example of Sub 5

1. Synthesis Example of Sub 5-1

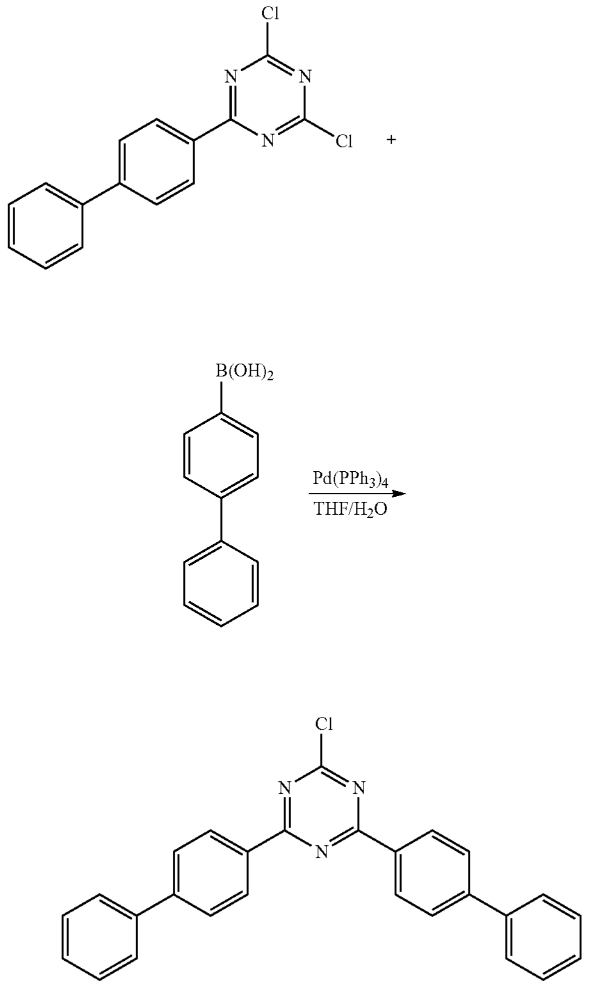

Sub 5-1

2-([1,1'-biphenyl]-4-yl)-4,6-dichloro-1,3,5-triazine (CAS Registry Number: 10202-45-6) (20 g, 66.19 mmol) and 4-biphenylboronic acid (CAS Registry Number: 5122-94-1) (13.1 g, 66.19 mmol) are placed in a round-bottom flask and the mixture was dissolved with THF (370 ml). Thereafter, $Pd(PPh_3)_4$ (3.8 g, 3.31 mmol), $K_2CO_3$ (27.4 g, 198.57 mmol) and water (165 ml) were added to the solution, stirred and refluxed. When the reaction was completed, the reaction product was extracted with ether and water and an organic layer was concentrated. The concentrated organic layer was dried over $MgSO_4$ and concentrated once more. Then, the concentrate was separated by a silica gel column and recrystallized to obtain 20.8 g (yield 75%) of the product.

2. Synthesis Example of Sub 5-8

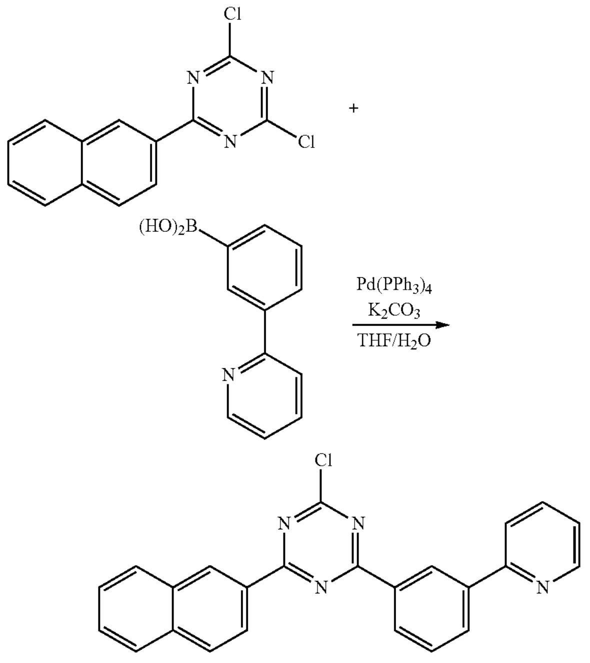

Sub 5-8

Synthesis was carried out in the same manner as for the synthesis of Sub 5-1 using 2,4-dichloro-6-(naphthalen-2-yl)-1,3,5-triazine (20 g, 72.43 mmol), (3-(pyridin-2-yl)phenyl) boronic acid (14.3 g, 72.43 mmol), $Pd(PPh_3)_4$ (0.05 eq.), $K_2CO_3$ (3 eq.), anhydrous THF and water to obtain 20.3 g (yield 71%) of the product.

3. Synthesis Example of Sub 5-19

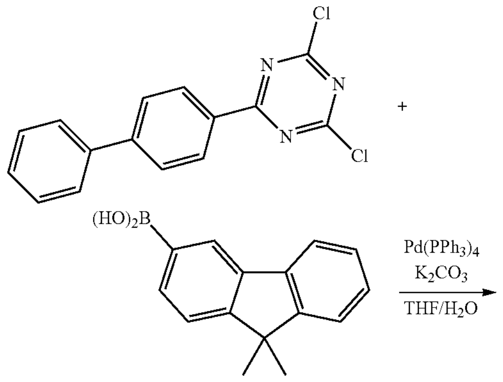

-continued

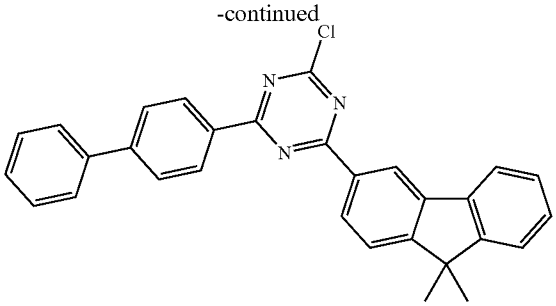

Sub 5-19

Synthesis was carried out in the same manner as for the synthesis of Sub 5-1 using 2-([1,1'-biphenyl]-4-yl)-4,6-dichloro-1,3,5-triazine (15 g, 49.64 mmol), (9,9-dimethyl-9H-fluoren-3-yl)boronic acid (11.8 g, 49.64 mmol), $Pd(PPh_3)_4$ (0.05 eq.), $K_2CO_3$ (3 eq.), anhydrous THF and water to obtain 15.7 g (yield 69%) of the product.

4. Synthesis Example of Sub 5-35

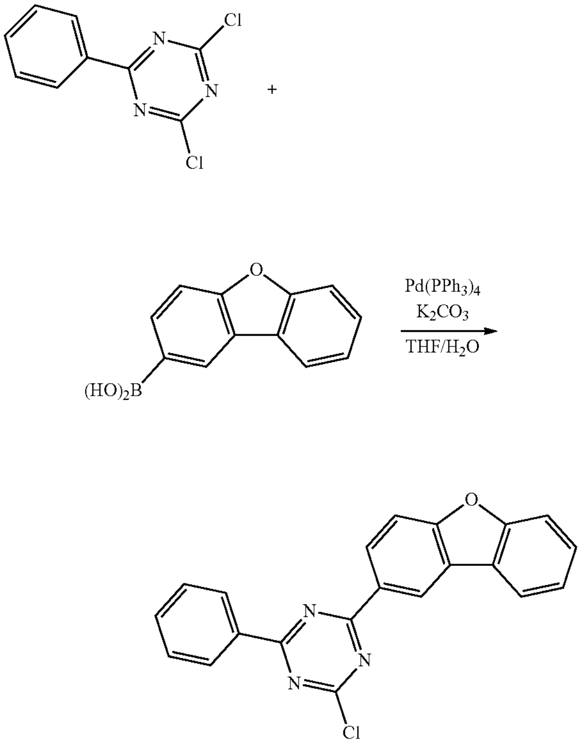

Sub 5-35

Synthesis was carried out in the same manner as for the synthesis of Sub 5-1 using 2,4-dichloro-6-phenyl-1,3,5-triazine (30 g, 132.71 mmol), dibenzo[b,d]furan-2-ylboronic acid (28.1 g, 132.71 mmol), $Pd(PPh_3)_4$ (0.05 eq.), $K_2CO_3$ (3 eq.), anhydrous THF and water to obtain 30.8 g (yield 65%) of the product.

The compound belonging to Sub 5 may be a compound as follows, but is not limited thereto, and Table 4 shows FD-MS values of the following compounds.

Sub 5-1

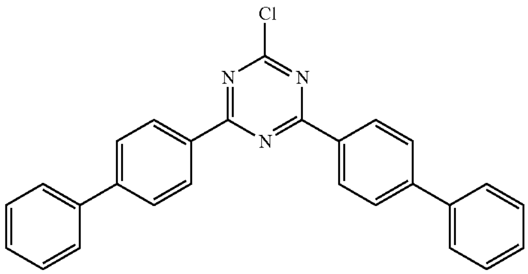

Sub 5-2

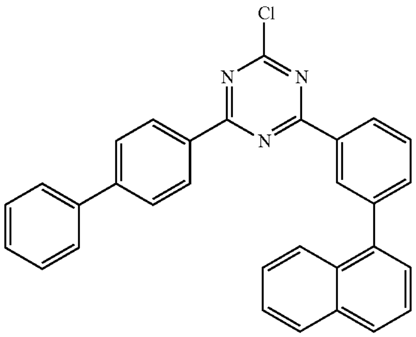

Sub 5-3

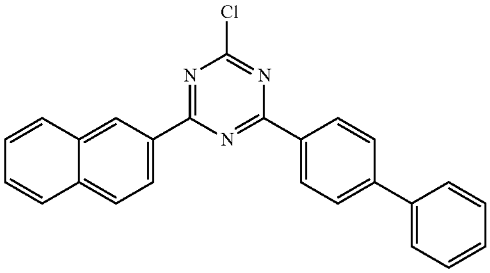

Sub 5-4

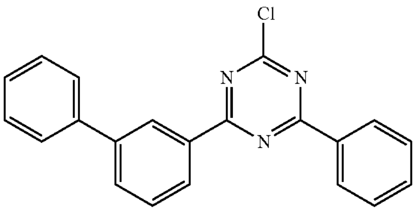

Sub 5-5

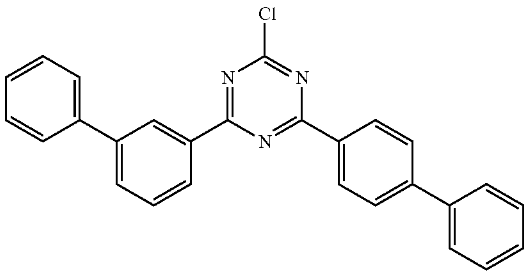

-continued
Sub 5-6
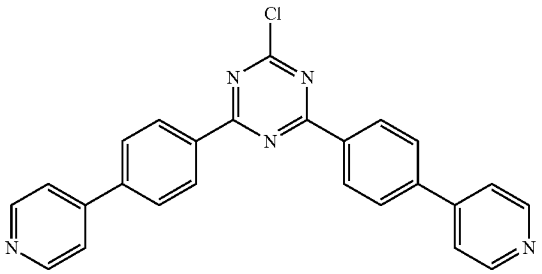
Sub 5-7
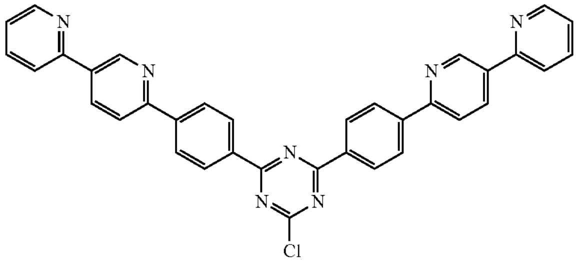
Sub 5-8
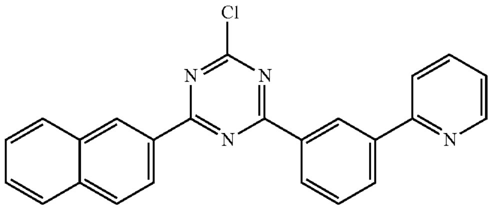
Sub 5-9
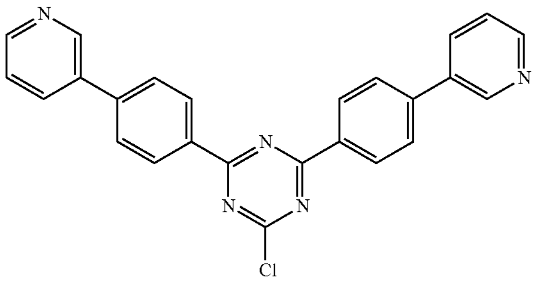
Sub 5-10
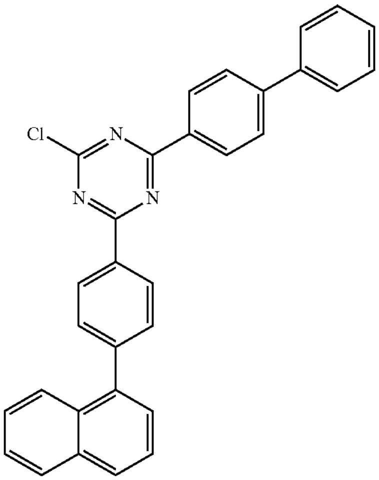
-continued
Sub 5-11
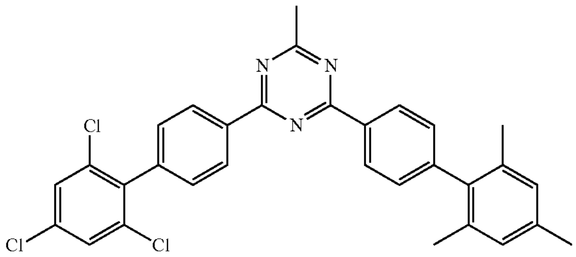
Sub 5-12
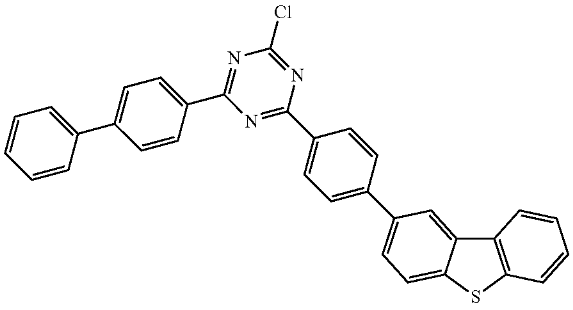
Sub 5-13
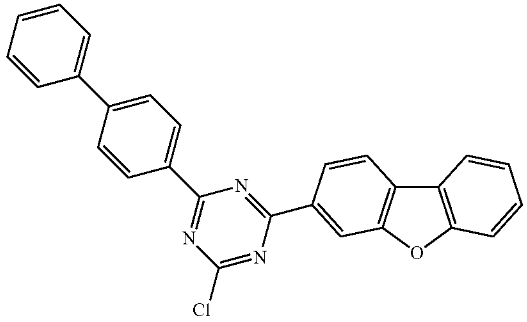
Sub 5-14
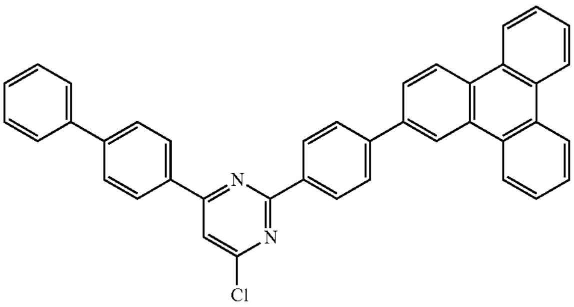
Sub 5-15
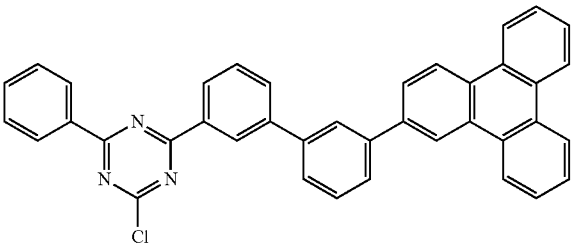

-continued
Sub 5-16
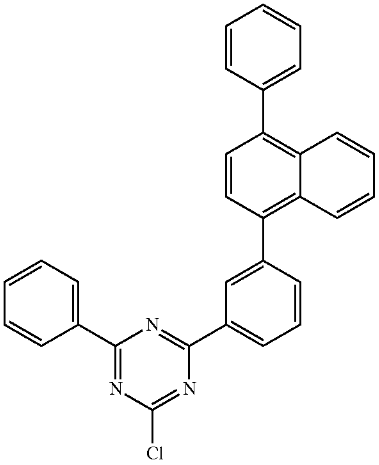
Sub 5-17
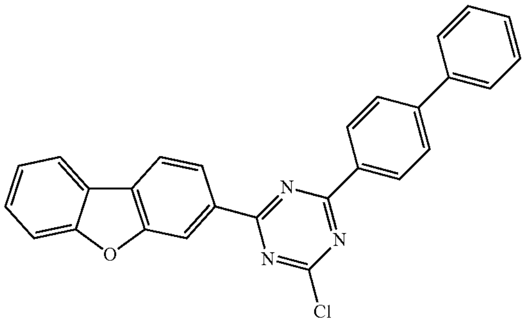
Sub 5-18
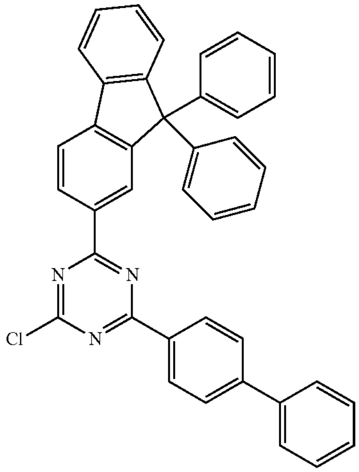
Sub 5-19
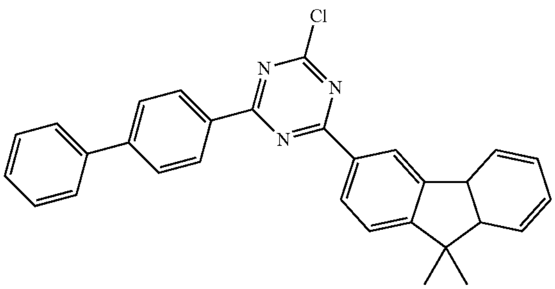
-continued
Sub 5-20
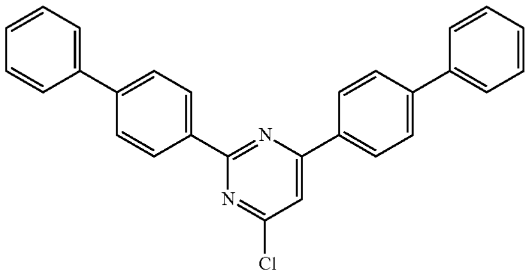
Sub 5-21
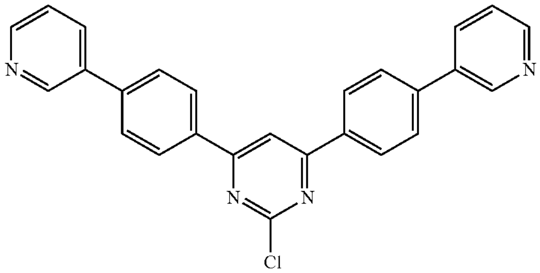
Sub 5-22
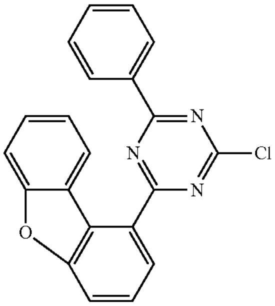
Sub 5-23
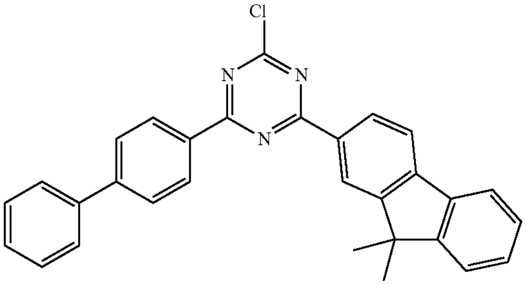
Sub 5-24
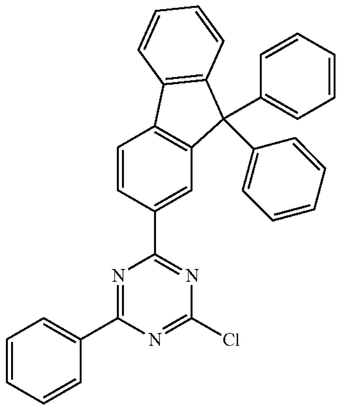

-continued
Sub 5-25
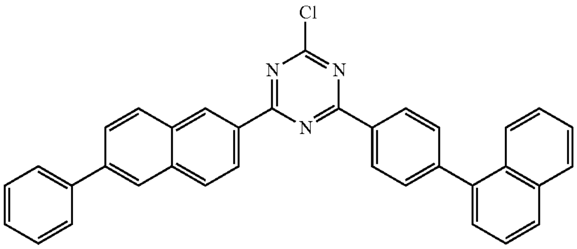
Sub 5-26
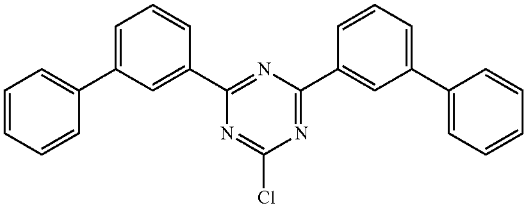
Sub 5-27
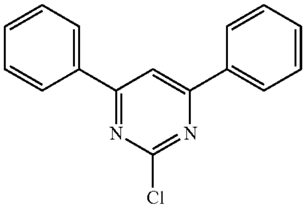
Sub 5-28
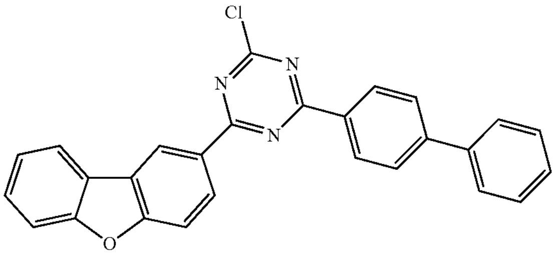
Sub 5-29
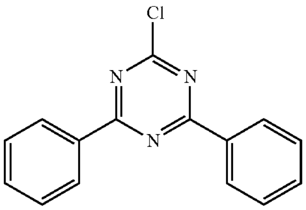
Sub 5-30
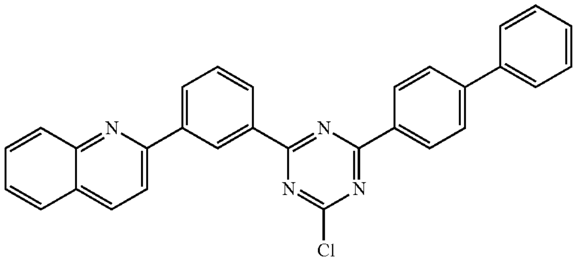
-continued
Sub 5-31
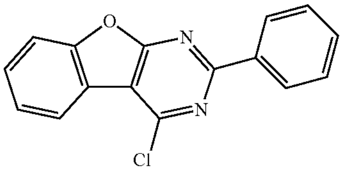
Sub 5-32
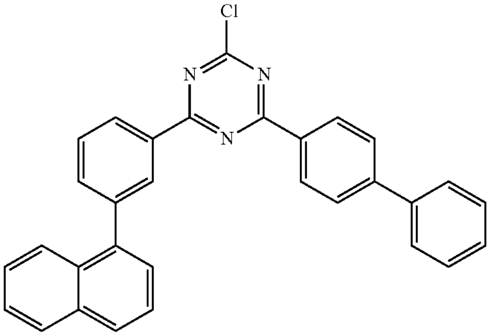
Sub 5-33
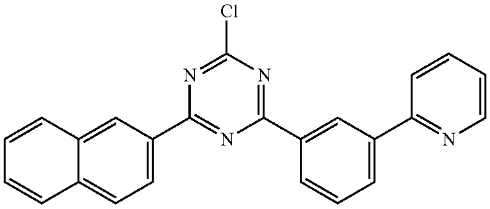
Sub 5-34
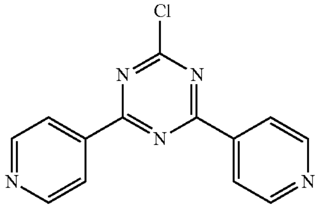
Sub 5-35
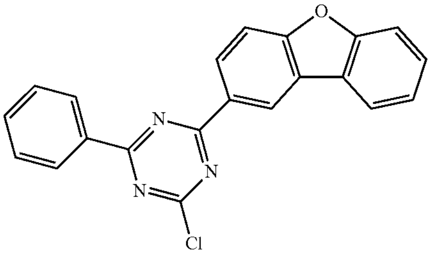
Sub 5-36
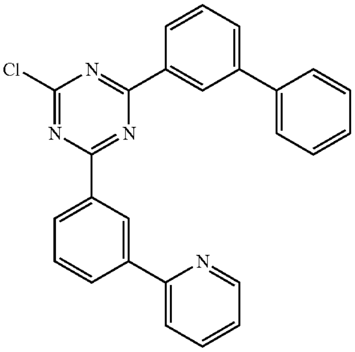

-continued
Sub 5-37
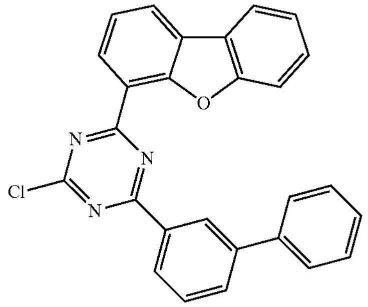
Sub 5-38
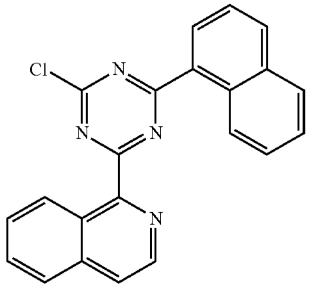
Sub 5-39
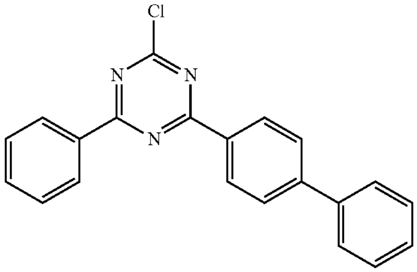
Sub 5-40
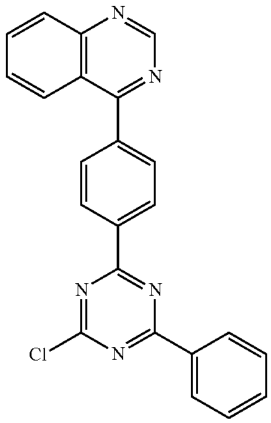
Sub 5-41
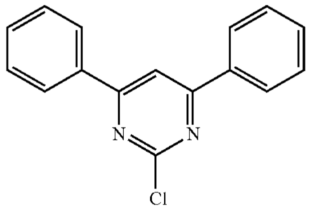
-continued
Sub 5-42
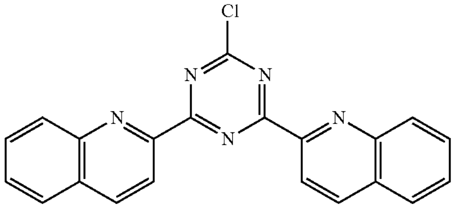
Sub 5-43
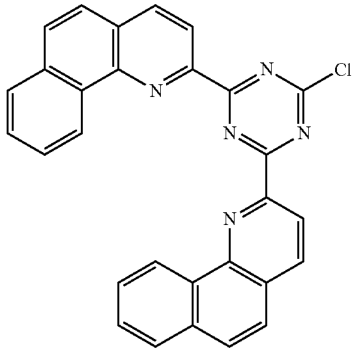
Sub 5-44
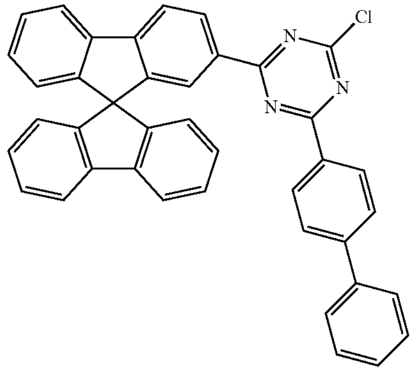
Sub 5-45
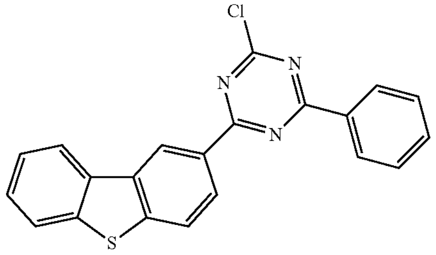
Sub 5-46
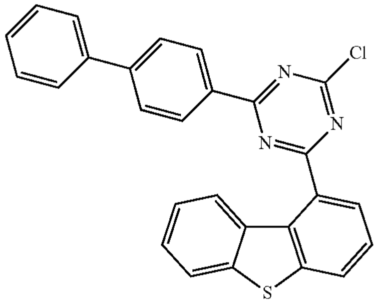

-continued

Sub 5-47

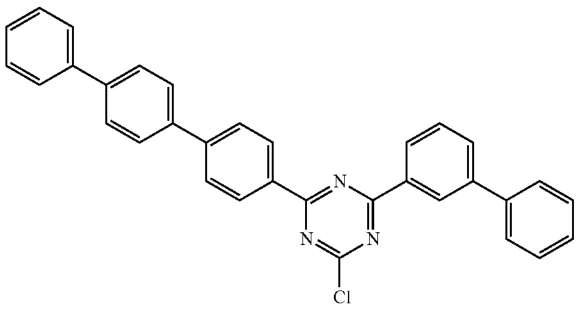

Sub 5-48

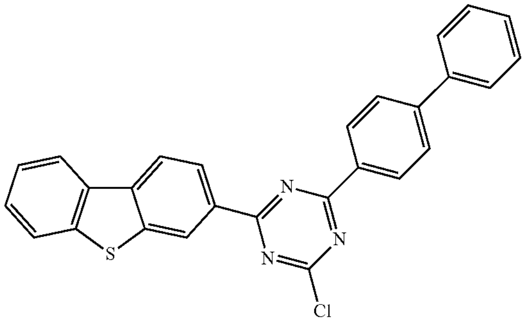

Sub 5-49

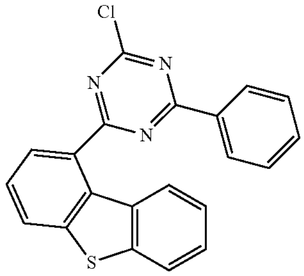

Sub 5-50

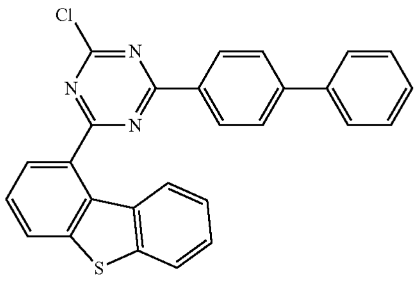

Sub 5-51

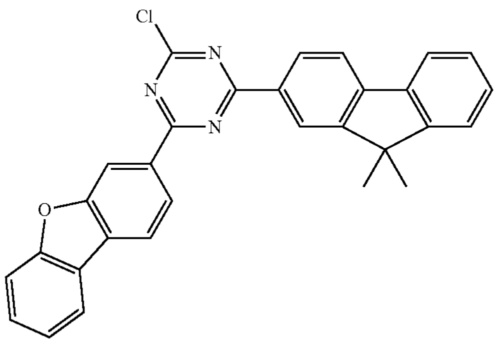

-continued

Sub 5-52

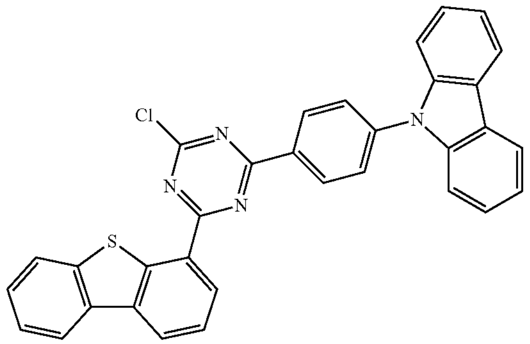

Sub 5-53

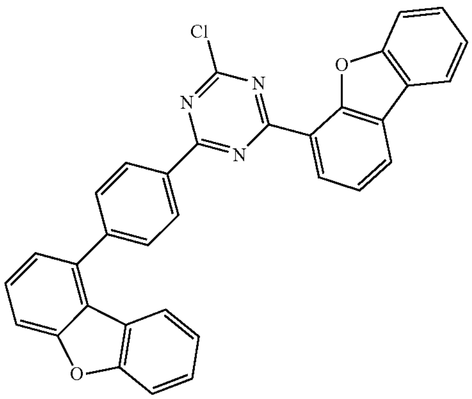

Sub 5-54

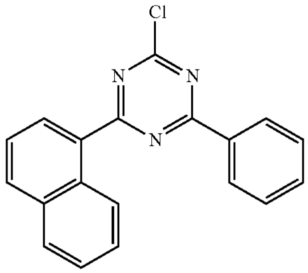

TABLE 4

| Compound | FD-MS |
|---|---|
| Sub 5-1 | m/z = 419.12($C_{27}H_{18}ClN_3$ = 419.91) |
| Sub 5-2 | m/z = 469.13($C_{31}H_{20}ClN_3$ = 469.97) |
| Sub 5-3 | m/z = 393.1($C_{25}H_{16}ClN_3$ = 393.87) |
| Sub 5-4 | m/z = 343.09($C_{21}H_{14}ClN_3$ = 343.81) |
| Sub 5-5 | m/z = 419.12($C_{27}H_{18}ClN_3$ = 419.91) |
| Sub 5-6 | m/z = 421.11($C_{25}H_{16}ClN_5$ = 421.89) |
| Sub 5-7 | m/z = 575.16($C_{35}H_{22}ClN_7$ = 576.06) |
| Sub 5-8 | m/z = 394.1($C_{24}H_{15}ClN_4$ = 394.86) |
| Sub 5-9 | m/z = 421.11($C_{25}H_{16}ClN_5$ = 421.89) |
| Sub 5-10 | m/z = 469.13($C_{31}H_{20}ClN_3$ = 469.97) |
| Sub 5-11 | m/z = 503.21($C_{33}H_{38}ClN_3$ = 504.07) |
| Sub 5-12 | m/z = 525.11($C_{33}H_{20}ClN_3S$ = 526.05) |
| Sub 5-13 | m/z = 433.1($C_{27}H_{16}ClN_3O$ = 433.9) |
| Sub 5-14 | m/z = 568.17($C_{40}H_{25}ClN_2$ = 569.1) |
| Sub 5-15 | m/z = 569.17($C_{39}H_{24}ClN_3$ = 570.09) |
| Sub 5-16 | m/z = 469.13($C_{31}H_{20}ClN_3$ = 469.97) |
| Sub 5-17 | m/z = 433.1($C_{27}H_{16}ClN_3O$ = 433.9) |
| Sub 5-18 | m/z = 583.18($C_{40}H_{26}ClN_3$ = 584.12) |
| Sub 5-19 | m/z = 461.17($C_{30}H_{24}ClN_3$ = 461.99) |
| Sub 5-20 | m/z = 418.12($C_{28}H_{19}ClN_2$ = 418.92) |
| Sub 5-21 | m/z = 420.11($C_{26}H_{17}ClN_4$ = 420.9) |

TABLE 4-continued

| Compound | FD-MS |
|---|---|
| Sub 5-22 | m/z = 357.07($C_{21}H_{12}ClN_3O$ = 357.8) |
| Sub 5-23 | m/z = 459.15($C_{30}H_{22}ClN_3$ = 459.98) |
| Sub 5-24 | m/z = 507.15($C_{34}H_{22}ClN_3$ = 508.02) |
| Sub 5-25 | m/z = 519.15($C_{35}H_{22}ClN_3$ = 520.03) |
| Sub 5-26 | m/z = 419.12($C_{27}H_{18}ClN_3$ = 419.91) |
| Sub 5-27 | m/z = 266.06($C_{18}H_{11}ClN_2$ = 266.73) |
| Sub 5-28 | m/z = 433.1($C_{27}H_{16}ClN_3O$ = 433.9) |
| Sub 5-29 | m/z = 267.O6($C_{15}H_{10}ClN_3$ = 267.72) |
| Sub 5-30 | m/z = 470.13($C_{30}H_{19}ClN_4$ = 470.96) |
| Sub 5-31 | m/z = 280.04($C_{16}H_9ClN_2O$ = 280.71) |
| Sub 5-32 | m/z = 469.13($C_{31}H_{20}ClN_3$ = 469.97) |
| Sub 5-33 | m/z = 394.1($C_{24}H_{15}ClN_4$ = 394.86) |
| Sub 5-34 | m/z = 269.05($C_{13}H_8ClN_5$ = 269.69) |
| Sub 5-35 | m/z = 357.07($C_{21}H_{12}ClN_3O$ = 357.8) |
| Sub 5-36 | m/z = 420.11($C_{26}H_{17}ClN_4$ = 420.9) |
| Sub 5-37 | m/z = 433.1($C_{27}H_{16}ClN_3O$ = 433.9) |
| Sub 5-38 | m/z = 368.08($C_{22}H_{13}ClN_4$ = 368.82) |
| Sub 5-39 | m/z = 343.09($C_{21}H_{14}ClN_3$ = 343.81) |
| Sub 5-40 | m/z = 395.09($C_{23}H_{14}ClN_5$ = 395.85) |
| Sub 5-41 | m/z = 266.06($C_{16}H_{11}ClN_2$ = 266.73) |
| Sub 5-42 | m/z = 369.08($C_{21}H_{12}ClN_5$ = 369.81) |
| Sub 5-43 | m/z = 469.11($C_{29}H_{16}ClN_5$ = 469.93) |
| Sub 5-44 | m/z = 581.17($C_{40}H_{24}ClN_3$ = 582.1) |
| Sub 5-45 | m/z = 373.04($C_{21}H_{12}ClN_3S$ = 373.86) |
| Sub 5-46 | m/z = 449.08($C_{27}H_{16}ClN_3S$ = 449.96) |
| Sub 5-47 | m/z = 495.15($C_{33}H_{22}ClN_3$ = 496.01) |
| Sub 5-48 | m/z = 449.08($C_{27}H_{16}ClN_3S$ = 449.96) |
| Sub 5-49 | m/z = 373.04($C_{21}H_{12}ClN_3S$ = 373.86) |
| Sub 5-50 | m/z = 449.08($C_{27}H_{16}ClN_3S$ = 449.96) |
| Sub 5-51 | m/z = 473.13($C_{30}H_{20}ClN_3O$ = 473.96) |
| Sub 5-52 | m/z = 538.1($C_{33}H_{19}ClN_4S$ = 539.05) |
| Sub 5-53 | m/z = 523.11($C_{33}H_{18}ClN_3O_2$ = 523.98) |
| Sub 5-54 | m/z = 317.07(C19H12ClN3 = 317.78) |

II. Synthesis Example of Sub 6

Sub 6 of Reaction Scheme 3 may be synthesized by Reaction Scheme 5 below, but is not limited thereto.

<Reaction Scheme 5>

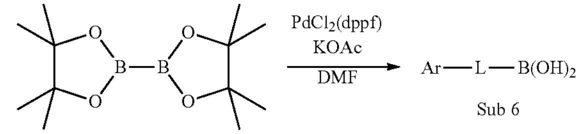

Sub 6

(Hal$^3$ is I, Br or Cl, L is L$^5$ or L$^6$, and Ar is Ar$^5$ or Ar$^6$.)

1. Synthesis Example of Sub 6-2

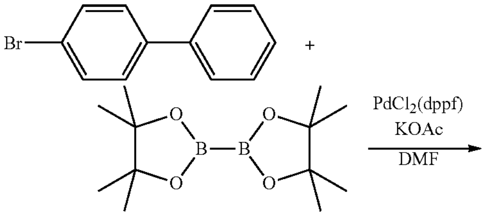

-continued

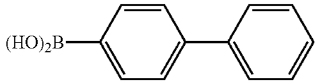

Sub 6-2

After 4-bromo-1,1'-biphenyl (5 g, 21.45 mmol) was dissolved in DMF (270 ml), bis(pinacolato)diboron (7.1 g, 27.89 mmol), $PdCl_2$(dppf), (0.78 g, 1.07 mmol), KOAc (6.3 g, 64.35 mmol) and DMF (270 ml) were added to the solution and the mixture was stirred and refluxed at 120° C. When the reaction is completed, the temperature of the reaction product is cooled to room temperature, extracted with MC, and wiped with 1N HCl. The organic layer was dried over $MgSO_4$ and concentrated. Then, the concentrate was separated by a silica gel column to obtain 3.4 g (80%) of the product.

2. Synthesis Example of Sub 6-37

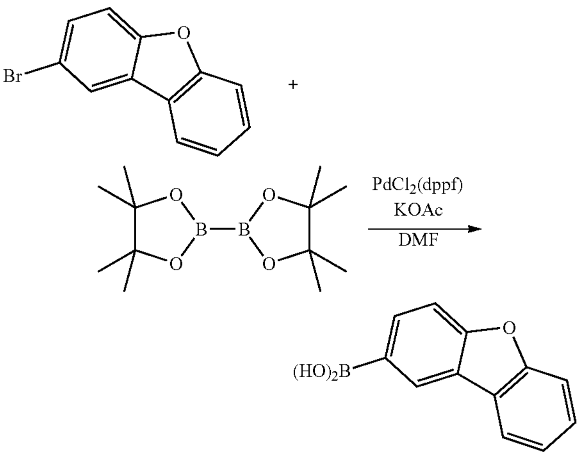

Sub 6-37

After 2-bromodibenzo[b,d]furan (10 g, 40.47 mmol) was dissolved in anhydrous DMF, bis(pinacolato)diboron (13.3 g, 52.61 mmol), $PdCl_2$(dppf), (0.05 eq.) and KOAc (3 eq.) were added to the solution and the mixture was stirred and refluxed at 120° C. When the reaction is completed, the temperature of the reaction product is cooled to room temperature, extracted with MC, and wiped with 1N HCl. The organic layer was dried over $MgSO_4$ and concentrated. Then, the concentrate was separated by a silica gel column to obtain 7 g (yield 82%) of the product.

The compound belonging to Sub 6 may be a compound as follows, but is not limited thereto, and Table 5 shows FD-MS values of the following compounds.

Sub 6-1

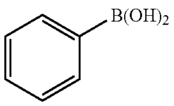

-continued
Sub 6-2
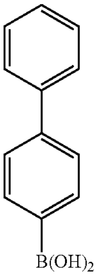
Sub 6-3
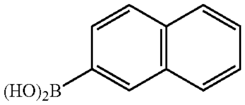
Sub 6-4
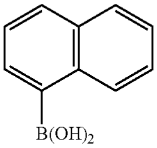
Sub 6-5
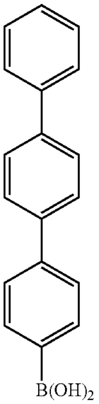
Sub 6-6
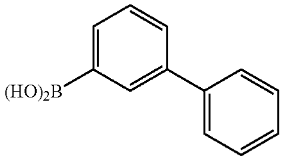
Sub 6-7
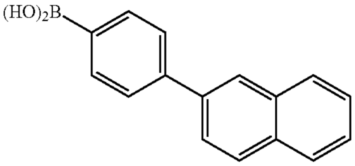
Sub 6-8
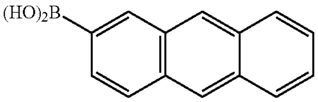
Sub 6-9
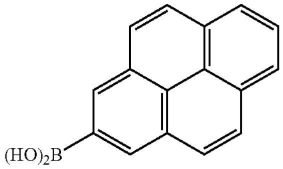
-continued
Sub 6-10
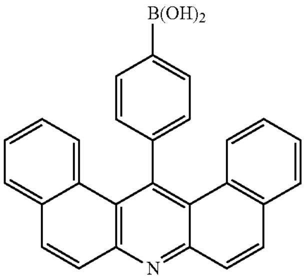
Sub 6-11
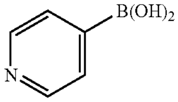
Sub 6-12
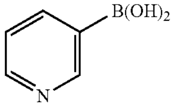
Sub 6-13
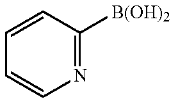
Sub 6-14
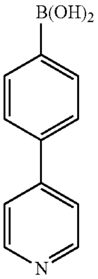
Sub 6-15
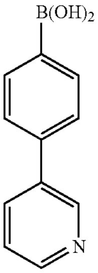
Sub 6-16
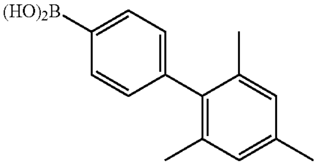
Sub 6-17
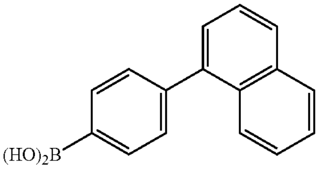

-continued
Sub 6-18
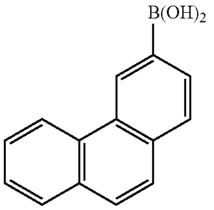
Sub 6-19
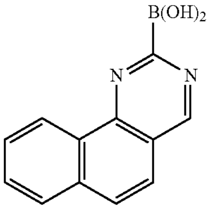
Sub 6-20
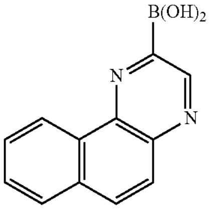
Sub 6-21
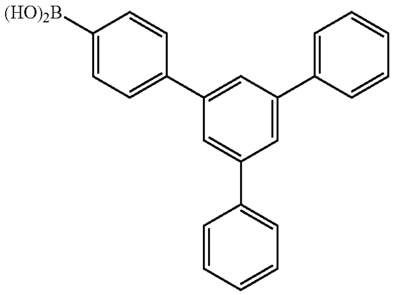
Sub 6-22
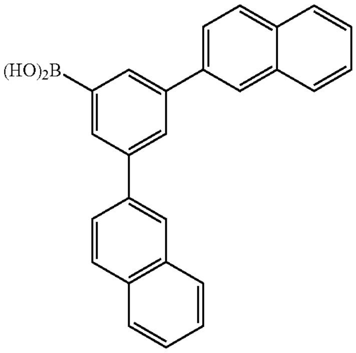
Sub 6-23
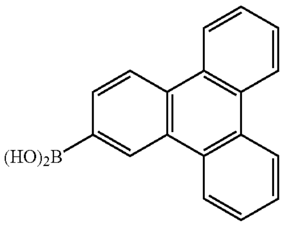
-continued
Sub 6-24
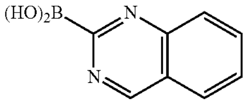
Sub 6-25
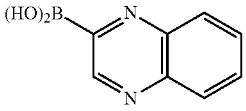
Sub 6-26
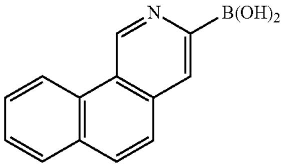
Sub 6-27
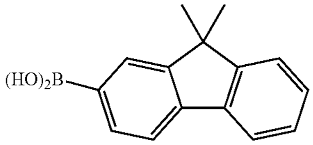
Sub 6-28
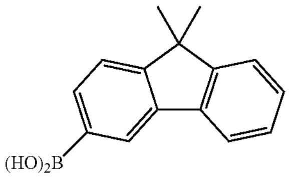
Sub 6-29
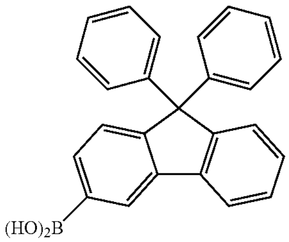
Sub 6-30
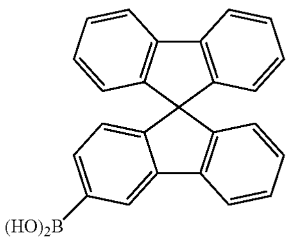
Sub 6-31
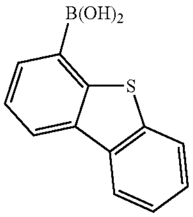

-continued
Sub 6-32
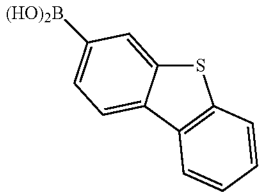
Sub 6-33
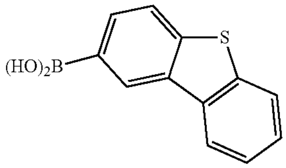
Sub 6-34
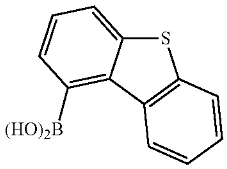
Sub 6-35
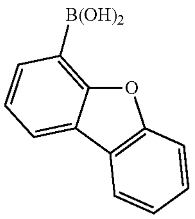
Sub 6-36
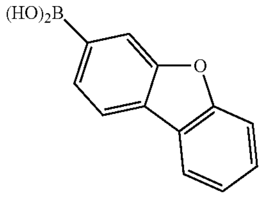
Sub 6-37
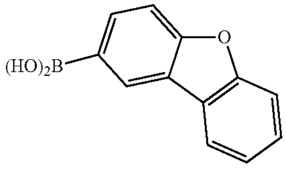
Sub 6-38
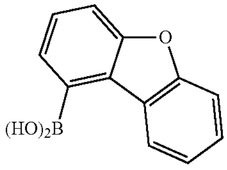
-continued
Sub 6-39
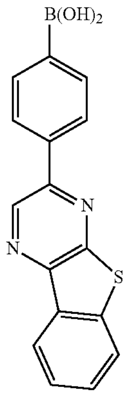
Sub 6-40
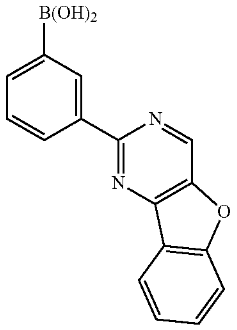
Sub 6-41
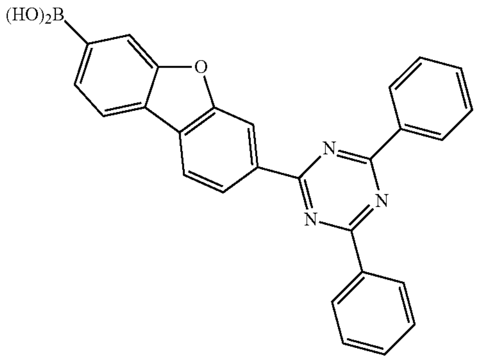
Sub 6-42
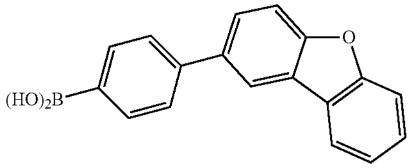
Sub 6-43
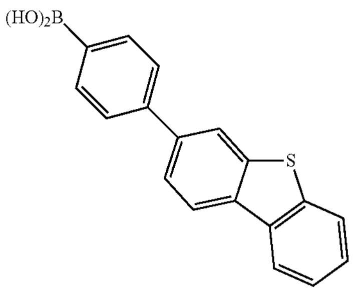

-continued
Sub 6-44
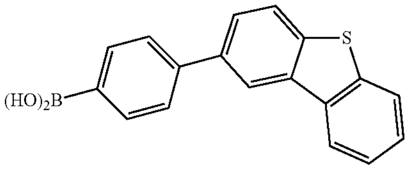
Sub 6-45
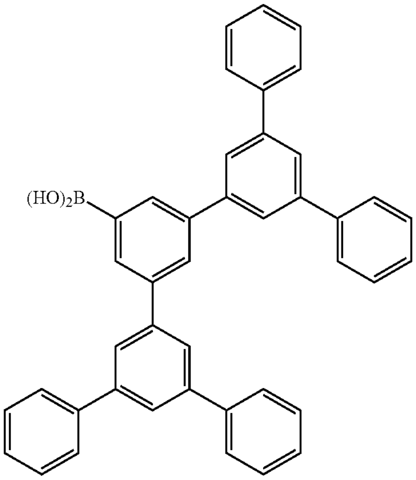
Sub 6-47
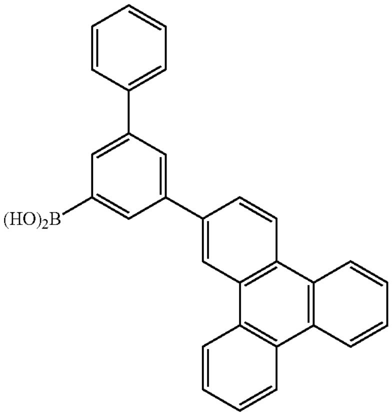
Sub 6-48
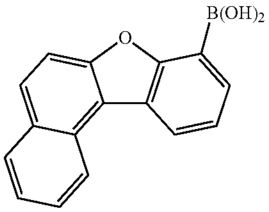
Sub 6-49
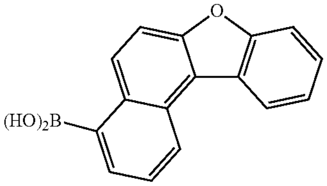
-continued
Sub 6-50
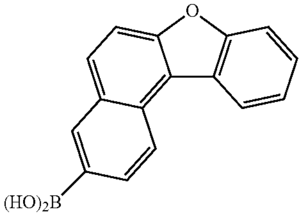
Sub 6-51
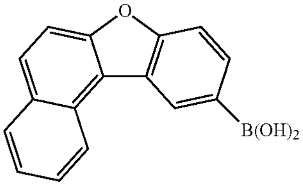
Sub 6-52
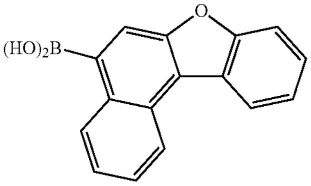
Sub 6-53
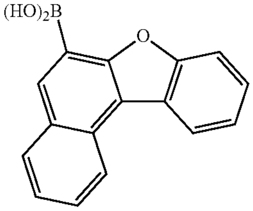
Sub 6-54
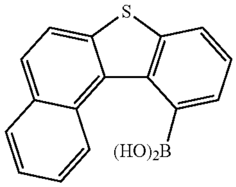
Sub 6-55
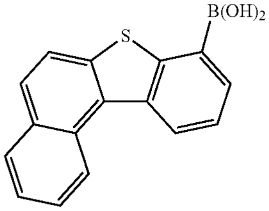
Sub 6-56
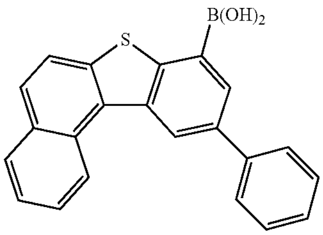

-continued

Sub 6-57

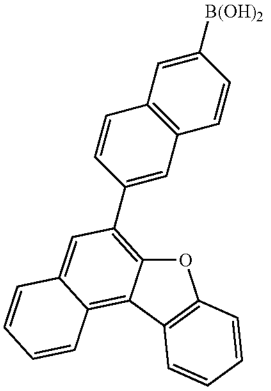

Sub 6-58

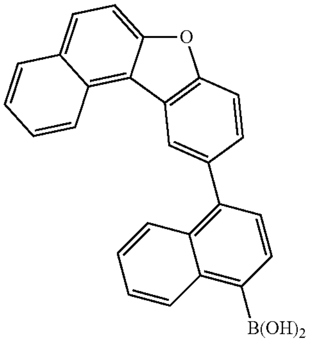

Sub 6-59

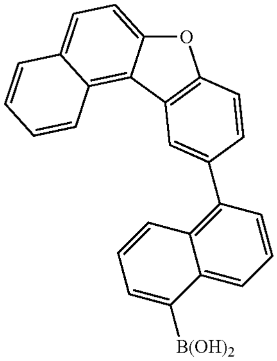

Sub 6-60

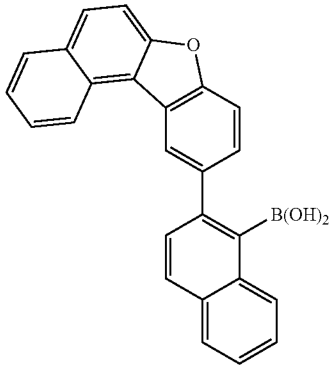

-continued

Sub 6-61

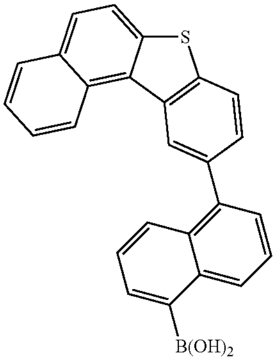

Sub 6-62

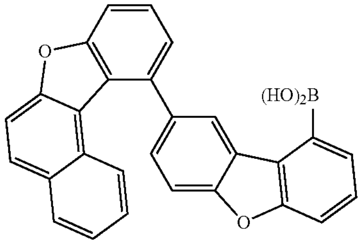

Sub 6-63

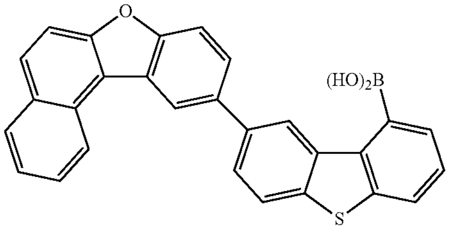

Sub 6-64

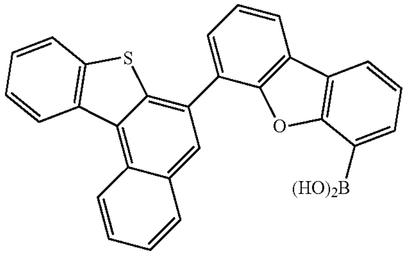

TABLE 5

| Compound | FD-MS |
|---|---|
| Sub 6-1 | m/z = 122.05($C_6H_7BO_2$ = 121.93) |
| Sub 6-2 | m/z = 198.09($C_{12}H_{11}BO_2$ = 198.03) |
| Sub 6-3 | m/z = 172.07($C_{10}H_9BO_2$ = 171.99) |
| Sub 6-4 | m/z = 172.07($C_{10}H_9BO_2$ = 171.99) |
| Sub 6-5 | m/z = 274.12($C_{18}H_{15}BO_2$ = 274.13) |
| Sub 6-6 | m/z = 198.09($C_{12}H_{11}BO_2$ = 198.03) |
| Sub 6-7 | m/z = 248.1($C_{16}H_{13}BO_2$ = 248.09) |
| Sub 6-8 | m/z = 222.09($C_{14}H_{11}BO_2$ = 222.05) |
| Sub 6-9 | m/z = 246.09($C_{16}H_{11}BO_2$ = 246.07) |
| Sub 6-10 | m/z = 399.14($C_{27}H_{18}BNO_2$ = 399.26) |
| Sub 6-11 | m/z = 123.05($C_5H_6BNO_2$ = 122.92) |
| Sub 6-12 | m/z = 123.05($C_5H_6BNO_2$ = 122.92) |
| Sub 6-13 | m/z = 123.05($C_5H_6BNO_2$ = 122.92) |
| Sub 6-14 | m/z = 199.08($C_{11}H_{10}BNO_2$ = 199.02) |
| Sub 6-15 | m/z = 199.08($C_{11}H_{10}BNO_2$ = 199.02) |
| Sub 6-16 | m/z = 240.13($C_{15}H_{17}BO_2$ = 240.11) |
| Sub 6-17 | m/z = 248.1($C_{16}H_{13}BO_2$ = 248.09) |

TABLE 5-continued

| Compound | FD-MS |
|---|---|
| Sub 6-18 | m/z = 222.09($C_{14}H_{11}BO_2$ = 222.05) |
| Sub 6-19 | m/z = 224.08($C_{12}H_9BN_2O_2$ = 224.03) |
| Sub 6-20 | m/z = 224.08($C_{12}H_9BN_2O_2$ = 224.03) |
| Sub 6-21 | m/z = 350.15($C_{24}H_{19}BO_2$ = 350.22) |
| Sub 6-22 | m/z = 374.15($C_{26}H_{19}BO_2$ = 374.25) |
| Sub 6-23 | m/z = 272.1($C_{18}H_{13}BO_2$ = 272.11) |
| Sub 6-24 | m/z = 174.06($C_8H_7BN_2O_2$ = 173.97) |
| Sub 6-25 | m/z = 174.06($C_8H_7BN_2O_2$ = 173.97) |
| Sub 6-26 | m/z = 223.08($C_{13}H_{15}BNO_2$ = 223.04) |
| Sub 6-27 | m/z = 238.12($C_{15}H_{15}BO_2$ = 238.09) |
| Sub 6-28 | m/z = 238.12($C_{15}H_{15}BO_2$ = 238.09) |
| Sub 6-29 | m/z = 362.15($C_{25}H_{19}BO_2$ = 362.24) |
| Sub 6-30 | m/z = 360.13($C_{25}H_{17}BO_2$ = 360.22) |
| Sub 6-31 | m/z = 228.04($C_{12}H_9BO_2S$ = 228.07) |
| Sub 6-32 | m/z = 228.04($C_{12}H_9BO_2S$ = 228.07) |
| Sub 6-33 | m/z = 228.04($C_{12}H_9BO_2S$ = 228.07) |
| Sub 6-34 | m/z = 228.04($C_{12}H_9BO_2S$ = 228.07) |
| Sub 6-35 | m/z = 212.06($C_{12}H_9BO_3$ = 212.01) |
| Sub 6-36 | m/z = 212.06($C_{12}H_9BO_3$ = 212.01) |
| Sub 6-37 | m/z = 212.06($C_{12}H_9BO_3$ = 212.01) |
| Sub 6-38 | m/z = 212.06($C_{12}H_9BO_3$ = 212.01) |
| Sub 6-39 | m/z = 306.06($C_{16}H_{11}BN_2O_2S$ = 306.15) |
| Sub 6-40 | m/z = 290.09($C_{16}H_{11}BN_2O_3$ = 290.09) |
| Sub 6-41 | m/z = 443.14($C_{27}H_{18}BN_3O_3$ = 443.27) |
| Sub 6-42 | m/z = 288.1 ($C_{18}H_{13}BO_3$ = 288.11) |
| Sub 6-43 | m/z = 304.07($C_{18}H_{13}BO_2S$ = 304.17) |
| Sub 6-44 | m/z = 304.07($C_{18}H_{13}BO_2S$ = 304.17) |
| Sub 6-45 | m/z = 578.24($C_{42}H_{31}BO_2$ = 578.52) |
| Sub 6-46 | m/z = 424.16($C_{30}H_{21}BO_2$ = 424.31) |
| Sub 6-47 | m/z = 424.16($C_{30}H_{21}BO_2$ = 424.31) |
| Sub 6-48 | m/z = 262.08($C_{16}H_{11}BO_3$ = 262.07) |
| Sub 6-54 | m/z = 278.06($C_{16}H_{11}BO_2S$ = 278.13) |
| Sub 6-57 | m/z = 354.09($C_{22}H_{15}BO_2S$ = 354.23) |
| Sub 6-56 | m/z = 388.13($C_{26}H_{17}BO_3$ = 388.23) |
| Sub 6-61 | m/z = 404.1($C_{26}H_{17}BO_2S$ = 404.29) |
| Sub 6-62 | m/z = 428.12($C_{28}H_{17}BO_4$ = 428.25) |
| Sub 6-63 | m/z = 444.1($C_{28}H_{17}BO_3S$ = 444.31) |

III. Synthesis of Compound of Formula 2

1. Synthesis Example of 3-15

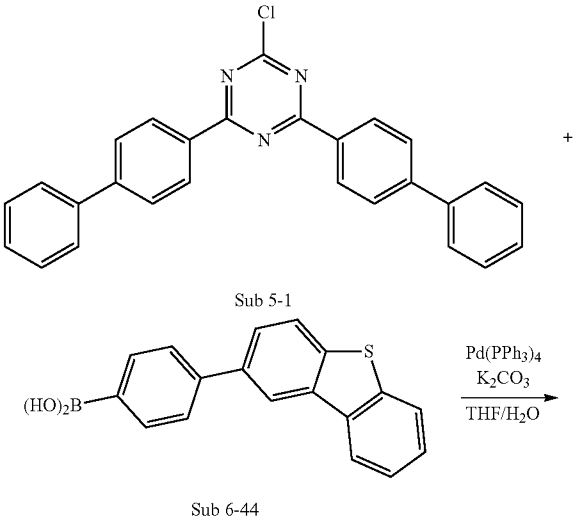

Sub 5-1

Sub 6-44

-continued

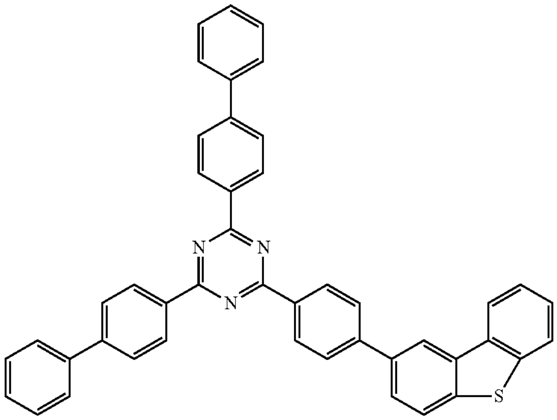

3-15

Sub 5-1 (5 g, 11.91 mmol) and Sub 6-44 (4 g, 13.1 mmol) was dissolved in THF (70 ml) in a round-bottom flask. Then, $Pd(PPh_3)_4$ (0.7 g, 0.6 mmol), $K_2CO_3$ (5 g, 35.73 mmol) and water (30 ml) were added to the solution and the mixture was stirred and refluxed. When the reaction is completed, the reaction product was extracted with ether and water and an organic layer was concentrated. The concentrated organic layer was dried over $MgSO_4$ and concentrated once more. Then, the concentrate was separated by a silica gel column and recrystallized to obtain 5.4 g (yield 71%) of the product.

2. Synthesis Example of 3-55

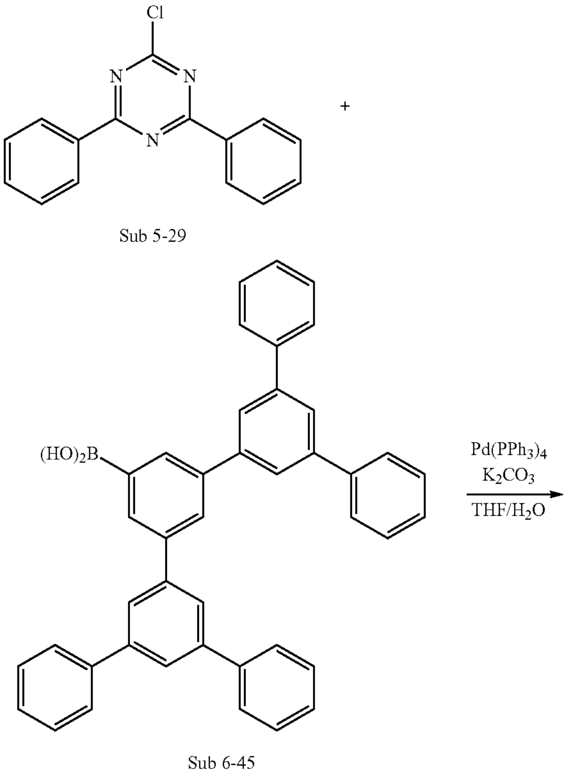

Sub 5-29

Sub 6-45

-continued

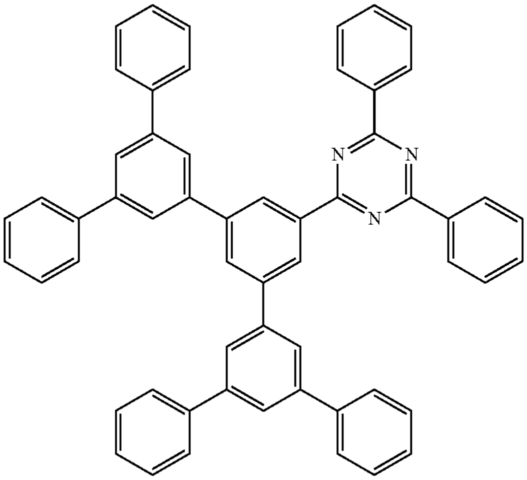

3-55

Synthesis was carried out in the same manner as for the synthesis of 3-15 using Sub 5-29 (4 g, 14.94 mmol), Sub 6-45 (9.5 g, 16.43 mmol), $Pd(PPh_3)_4$ (0.05 eq.), $K_2CO_3$ (3 eq.), anhydrous THF and water to obtain 8.8 g (yield 77%) of the product.

3. Synthesis Example of 3-96

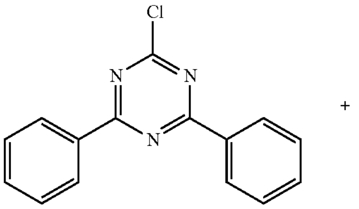

Sub 5-29

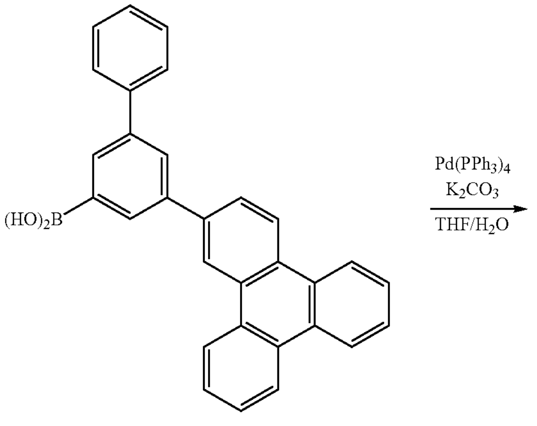

Sub 6-47

-continued

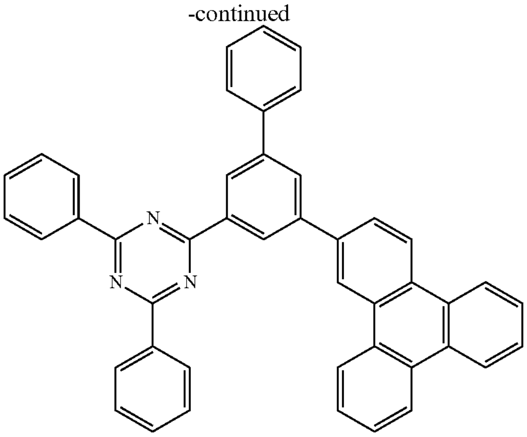

3-96

Synthesis was carried out in the same manner as for the synthesis of 3-15 using Sub 5-29 (4 g, 14.94 mmol), Sub 6-47 (7 g, 16.43 mmol), $Pd(PPh_3)_4$ (0.05 eq.), $K_2CO_3$ (3 eq.), anhydrous THF and water to obtain 6 g (yield 66%) of the product.

4. Synthesis Example of 3-106

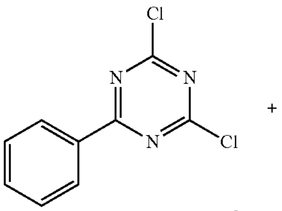

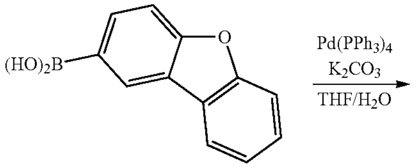

Sub 6-37

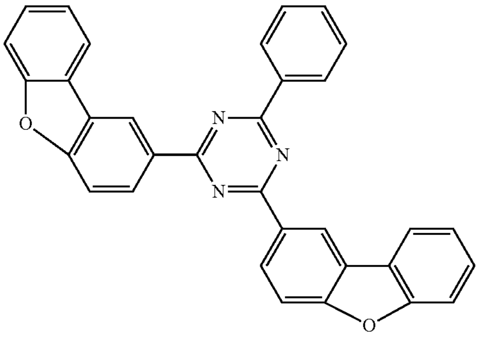

3-106

Synthesis was carried out in the same manner as for the synthesis of 3-15 using 2,4-dichloro-6-phenyl-1,3,5-triazine (7 g, 30.97 mmol), Sub 6-47 (13.1 g, 61.94 mmol), $Pd(PPh_3)_4$ (0.1 eq.), $K_2CO_3$ (6 eq.), anhydrous THF and water to obtain 9.7 g (yield 64%) of the product.

5. Synthesis Example of 3-111

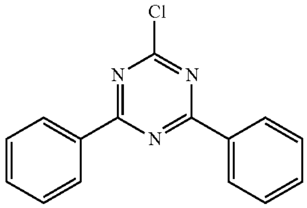

Sub 5-29

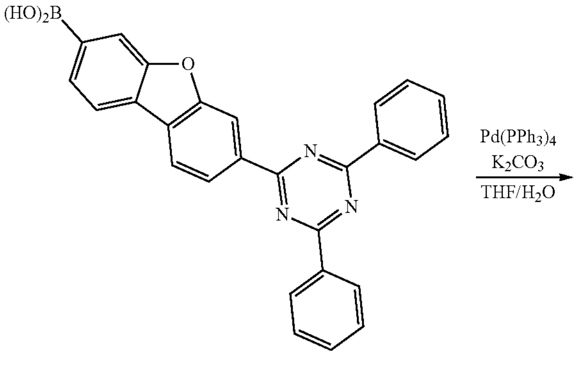

Sub 6-41

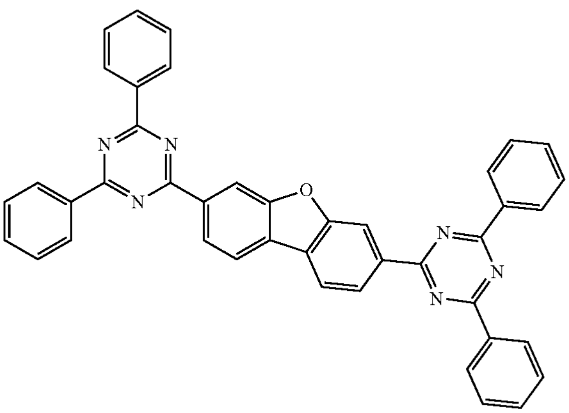

3-111

Synthesis was carried out in the same manner as for the synthesis of 3-15 using Sub 5-29 (4 g, 14.94 mmol), Sub 6-41 (7.3 g, 16.43 mmol), $Pd(PPh_3)_4$ (0.05 eq.), $K_2CO_3$ (3 eq.), anhydrous THF and water to obtain 7 g (yield 75%) of the product.

6. Synthesis Example of 3-138

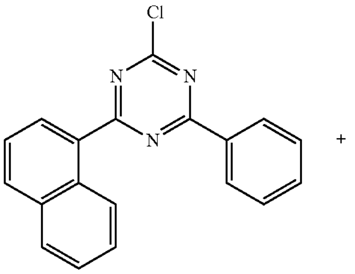

Sub 5-54

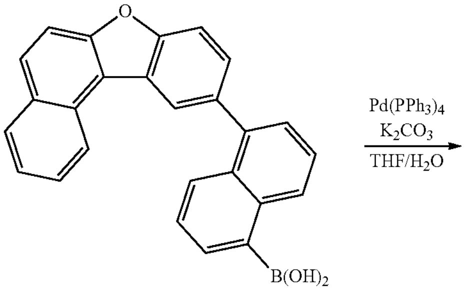

Sub 6-59

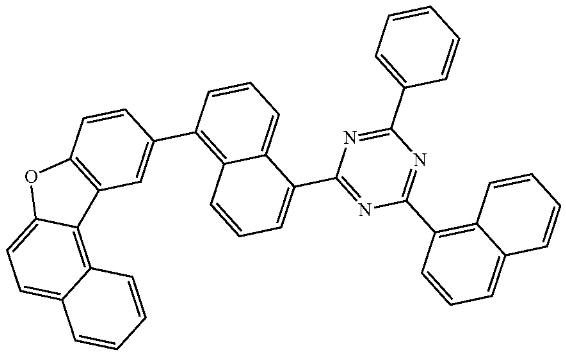

3-138

Synthesis was carried out in the same manner as for the synthesis of 3-15 using Sub 5-54 (4 g, 12.59 mmol), Sub 6-59 (5.86 g, 15.10 mmol), $Pd(PPh_3)_4$ (0.05 eq.), $K_2CO_3$ (3 eq.), anhydrous THF and water to obtain 6 g (yield 77%) of the product.

FD-MS values of compounds 3-1 to 3-141 synthesized by the above synthesis method are shown in Table 6 below.

TABLE 6

| Compound | FD-MS |
|---|---|
| 3-1 | m/z = 537.22($C_{39}H_{27}N_3$ = 537.67) |
| 3-2 | m/z = 587.24($C_{43}H_{29}N_3$ = 587.73) |
| 3-3 | m/z = 561.22($C_{41}H_{27}N_3$ = 561.69) |
| 3-4 | m/z = 637.25($C_{47}H_{31}N_3$ = 637.79) |
| 3-5 | m/z = 738.28($C_{54}H_{34}N_4$ = 738.89) |
| 3-6 | m/z = 537.22($C_{39}H_{27}N_3$ = 537.67) |
| 3-7 | m/z = 738.28($C_{54}H_{34}N_4$ = 738.89) |
| 3-8 | m/z = 814.31($C_{60}H_{38}N_4$ = 814.99) |
| 3-9 | m/z = 540.21($C_{36}H_{24}N_6$ = 540.63) |
| 3-10 | m/z = 771.29($C_{51}H_{33}N_9$ = 771.89) |
| 3-11 | m/z = 512.2($C_{36}H_{24}N_4$ = 512.62) |
| 3-12 | m/z = 639.24($C_{45}H_{29}N_5$ = 639.76) |
| 3-13 | m/z = 688.26($C_{50}H_{32}N_4$ = 688.83) |

TABLE 6-continued

| Compound | FD-MS |
|---|---|
| 3-14 | m/z = 663.36($C_{48}H_{45}N_3$ = 663.91) |
| 3-15 | m/z = 643.21($C_{45}H_{29}N_3S$ = 643.81) |
| 3-16 | m/z = 551.2($C_{39}H_{25}N_3O$ = 551.65) |
| 3-17 | m/z = 699.27($C_{52}H_{33}N_3$ = 699.86) |
| 3-18 | m/z = 879.34($C_{64}H_{41}N_5$ = 880.07) |
| 3-19 | m/z = 637.29($C_{45}H_{36}FN_3$ = 637.8) |
| 3-20 | m/z = 536.23($C_{40}H_{28}N_2$ = 536.68) |
| 3-21 | m/z = 539.21($C_{37}H_{25}N_5$ = 539.64) |
| 3-22 | m/z = 736.29($C_{56}H_{36}N_2$ = 736.92) |
| 3-23 | m/z = 611.24($C_{45}H_{29}N_3$ = 611.75) |
| 3-24 | m/z = 536.2($C_{38}H_{24}N_4$ = 536.64) |
| 3-25 | m/z = 789.31($C_{59}H_{39}N_3$ = 789.98) |
| 3-26 | m/z = 687.27($C_{51}H_{33}N_3$ = 687.85) |
| 3-27 | m/z = 543.25($C_{38}H_{21}D_5N_4$ = 543.68) |
| 3-28 | m/z = 665.26($C_{47}H_{31}N_5$ = 665.8) |
| 3-29 | m/z = 637.25($C_{47}H_{31}N_3$ = 637.79) |
| 3-30 | m/z = 501.22($C_{36}H_{27}N_3$ = 501.63) |
| 3-31 | m/z = 487.18($C_{33}H_{21}N_5$ = 487.57) |
| 3-32 | m/z = 865.35($C_{65}H_{43}N_3$ = 866.08) |
| 3-33 | m/z = 638.25($C_{46}H_{30}N_4$ = 638.77) |
| 3-34 | m/z = 560.23($C_{42}H_{28}N_2$ = 560.7) |
| 3-35 | m/z = 561.22($C_{41}H_{27}N_3$ = 561.69) |
| 3-36 | m/z = 635.26($C_{49}H_{33}N$ = 635.81) |
| 3-37 | m/z = 611.24($C_{45}H_{29}N_3$ = 611.75) |
| 3-38 | m/z = 610.24($C_{46}H_{30}N_2$ = 610.76) |
| 3-39 | m/z = 562.22($C_{40}H_{26}N_4$ = 562.68) |
| 3-40 | m/z = 637.25($C_{47}H_{31}N_3$ = 637.79) |
| 3-41 | m/z = 565.18($C_{39}H_{23}N_3O_2$ = 565.63) |
| 3-42 | m/z = 597.13($C_{39}H_{23}N_3S_2$ = 597.75) |
| 3-43 | m/z = 639.24($C_{45}H_{29}N_5$ = 639.76) |
| 3-44 | m/z = 679.27($C_{48}H_{33}N_5$ = 679.83) |
| 3-46 | m/z = 569.17($C_{37}H_{23}N_5S$ = 569.69) |
| 3-47 | m/z = 588.23($C_{42}H_{28}N_4$ = 588.71) |
| 3-48 | m/z = 636.21($C_{42}H_{29}N_4OP$ = 636.69) |
| 3-49 | m/z = 689.28($C_{51}H_{35}N_3$ = 689.86) |
| 3-50 | m/z = 615.24($C_{43}H_{29}N_5$ = 615.74) |
| 3-51 | m/z = 613.25($C_{45}H_{31}N_3$ = 613.76) |
| 3-52 | m/z = 765.31($C_{57}H_{39}N_3$ = 765.96) |
| 3-53 | m/z = 689.28($C_{51}H_{35}N_3$ = 689.86) |
| 3-54 | m/z = 613.25($C_{45}H_{31}N_3$ = 613.76) |
| 3-55 | m/z = 765.31($C_{57}H_{39}N_3$ = 765.96) |
| 3-56 | m/z = 779.29($C_{57}H_{37}N_3O$ = 779.94) |
| 3-57 | m/z = 703.26($C_{51}H_{33}N_3O$ = 703.85) |
| 3-58 | m/z = 627.23($C_{45}H_{29}N_3O$ = 627.75) |
| 3-59 | m/z = 643.21($C_{45}H_{29}N_3S$ = 643.81) |
| 3-60 | m/z = 637.25($C_{47}H_{31}N_3$ = 637.79) |
| 3-61 | m/z = 715.27($C_{51}H_{33}N_5$ = 715.86) |
| 3-62 | m/z = 613.25($C_{45}H_{31}N_3$ = 613.76) |
| 3-63 | m/z = 689.28($C_{51}H_{35}N_3$ = 689.86) |
| 3-64 | m/z = 489.15($C_{33}H_{19}N_3O_2$ = 489.53) |
| 3-65 | m/z = 689.28($C_{51}H_{35}N_3$ = 689.86) |
| 3-66 | m/z = 765.31($C_{57}H_{39}N_3$ = 765.96) |
| 3-67 | m/z = 765.31($C_{67}H_{39}N_3$ = 765.96) |
| 3-68 | m/z = 841.35($C_{63}H_{43}N_3$ = 842.06) |
| 3-69 | m/z = 614.25($C_{44}H_{30}N_4$ = 614.75) |
| 3-70 | m/z = 699.27($C_{52}H_{33}N_3$ = 699.86) |
| 3-71 | m/z = 577.25($C_{42}H_{31}N_3$ = 577.73) |
| 3-72 | m/z = 577.25($C_{42}H_{31}N_3$ = 577.73) |
| 3-73 | m/z = 591.23($C_{42}H_{29}N_3O$ = 591.71) |
| 3-74 | m/z = 577.25($C_{42}H_{31}N_3$ = 577.73) |
| 3-75 | m/z = 729.31($C_{54}H_{39}N_3$ = 729.93) |
| 3-76 | m/z = 654.28($C_{47}H_{34}N_4$ = 654.82) |
| 3-77 | m/z = 731.3($C_{52}H_{37}N_5$ = 731.9) |
| 3-78 | m/z = 867.32($C_{64}H_{41}N_3O$ = 868.05) |
| 3-79 | m/z = 769.3($C_{53}H_{35}N_7$ = 769.91) |
| 3-80 | m/z = 778.27($C_{56}H_{34}N_4O$ = 778.92) |
| 3-81 | m/z = 461.19($C_{33}H_{23}N_3$ = 461.57) |
| 3-82 | m/z = 615.24($C_{43}H_{29}N_5$ = 615.74) |
| 3-83 | m/z = 511.2($C_{37}H_{25}N_3$ = 511.63) |
| 3-84 | m/z = 563.21($C_{39}H_{25}N_5$ = 563.66) |
| 3-85 | m/z = 511.2($C_{37}H_{25}N_3$ = 511.63) |
| 3-86 | m/z = 589.23($C_{41}H_{27}N_5$ = 589.7) |
| 3-87 | m/z = 513.2($C_{35}H_{23}N_5$ = 513.6) |
| 3-88 | m/z = 562.22($C_{40}H_{26}N_4$ = 562.68) |
| 3-89 | m/z = 462.16($C_{30}H_{18}N_6$ = 462.52) |
| 3-90 | m/z = 612.21($C_{42}H_{24}N_6$ = 612.7) |
| 3-91 | m/z = 793.27($C_{57}H_{35}N_3O_2$ = 793.93) |
| 3-92 | m/z = 458.18($C_{34}H_{22}N_2$ = 458.56) |

TABLE 6-continued

| Compound | FD-MS |
|---|---|
| 3-93 | m/z = 499.2($C_{36}H_{25}N_3$ = 499.62) |
| 3-94 | m/z = 569.17($C_{37}H_{23}N_5S$ = 569.69) |
| 3-95 | m/z = 629.22($C_{43}H_{27}N_5O$ = 629.72) |
| 3-96 | m/z = 611.24($C_{45}H_{29}N_3$ = 611.75) |
| 3-97 | m/z = 692.27($C_{48}H_{32}N_6$ = 692.83) |
| 3-98 | m/z = 628.23($C_{44}H_{28}N_4O$ = 628.74) |
| 3-99 | m/z = 611.24($C_{45}H_{29}N_3$ = 611.75) |
| 3-100 | m/z = 563.21($C_{39}H_{25}N_5$ = 563.66) |
| 3-101 | m/z = 612.23($C_{44}H_{28}N_4$ = 612.74) |
| 3-102 | m/z = 551.2($C_{39}H_{25}N_3O$ = 551.65) |
| 3-103 | m/z = 539.16($C_{37}H_{21}N_3O_2$ = 539.59) |
| 3-104 | m/z = 565.2($C_{37}H_{23}N_7$ = 565.64) |
| 3-105 | m/z = 757.22($C_{53}H_{31}N_3OS$ = 757.91) |
| 3-106 | m/z = 489.15($C_{33}H_{19}N_3O_2$ = 489.53) |
| 3-107 | m/z = 662.25($C_{48}H_{30}N_4$ = 662.8) |
| 3-108 | m/z = 486.18($C_{34}H_{22}N_4$ = 486.58) |
| 3-109 | m/z = 591.21($C_{40}H_{25}N_5O$ = 591.67) |
| 3-110 | m/z = 782.28($C_{54}H_{34}N_6O$ = 782.91) |
| 3-111 | m/z = 630.22($C_{42}H_{26}N_6O$ = 630.71) |
| 3-112 | m/z = 796.27($C_{56}H_{36}N_4S$ = 796.99) |
| 3-113 | m/z = 691.23($C_{49}H_{29}N_3O_2$ = 691.79) |
| 3-114 | m/z = 562.22($C_{40}H_{26}N_4$ = 562.68) |
| 3-115 | m/z = 436.17($C_{30}H_{20}N_4$ = 436.52) |
| 3-116 | m/z = 641.21($C_{45}H_{27}N_3O_2$ = 641.73) |
| 3-117 | m/z = 449.15($C_{31}H_{19}N_3O$ = 449.51) |
| 3-118 | m/z = 575.2($C_{41}H_{25}N_3O$ = 575.67) |
| 3-119 | m/z = 525.18($C_{37}H_{23}N_3O$ = 525.61) |
| 3-120 | m/z = 499.17($C_{35}H_{21}N_3O$ = 499.57) |
| 3-121 | m/z = 555.14($C_{37}H_{21}N_3OS$ = 555.66) |
| 3-122 | m/z = 631.17($C_{43}H_{25}N_3OS$ = 631.75) |
| 3-123 | m/z = 707.2($C_{49}H_{29}N_3OS$ = 707.85) |
| 3-124 | m/z = 655.23($C_{46}H_{29}N_3O_2$ = 655.76) |
| 3-125 | m/z = 720.2($C_{49}H_{28}N_4OS$ = 720.85) |
| 3-126 | m/z = 705.21($C_{49}H_{27}N_3O_3$ = 705.77) |
| 3-127 | m/z = 691.23($C_{49}H_{29}N_3O_2$ = 691.79) |
| 3-128 | m/z = 707.2($C_{49}H_{29}N_3OS$ = 707.85) |
| 3-129 | m/z = 681.19($C_{47}H_{27}N_3OS$ = 681.81) |
| 3-130 | m/z = 581.19($C_{40}H_{27}N_3S$ = 581.74) |
| 3-131 | m/z = 518.16($C_{34}H_{22}N_4S$ = 518.64) |
| 3-132 | m/z = 591.18($C_{41}H_{25}N_3S$ = 591.73) |
| 3-133 | m/z = 665.21($C_{47}H_{27}N_3O_2$ = 665.75) |
| 3-134 | m/z = 681.19($C_{47}H_{27}N_3OS$ = 681.81) |
| 3-135 | m/z = 632.26($C_{45}H_{20}D_7N_3O$ = 632.77) |
| 3-136 | m/z = 641.19($C_{45}H_{27}N_3S$ = 641.79) |
| 3-137 | m/z = 625.22($C_{45}H_{27}N_3O$ = 625.73) |
| 3-138 | m/z = 625.22($C_{45}H_{27}N_3O$ = 625.73) |
| 3-139 | m/z = 707.2($C_{49}H_{23}N_30S$ = 707.85) |
| 3-141 | m/z = 535.20($C_{39}H_{25}N_3$ = 535.65) |

Manufacturing and Evaluation of Organic Electric Element

[Test Example 1] to [Test Example 18] Red Organic Light Emitting Element (Mixed Phosphorescent Host of the Light Emitting Layer)

After vacuum-depositing 4,4',4"-tris[2-naphthyl(phenyl)amino]triphenylamine (hereinafter, abbreviated as 2-TNATA) on an ITO layer (anode) formed on a glass substrate to form a hole injection layer with a thickness of 60 nm, a hole transport layer with a thickness of 60 nm was formed by vacuum-depositing 4,4'-bis[N-(1-naphthyl)-N-phenylamino]biphenyl (hereinafter, abbreviated as "NPB") on the hole injection layer.

Subsequently, a light emitting layer having a thickness of 30 nm was deposited on the hole transport layer. Here, as shown in Table 5 below, a mixture of the compound (first host) of Formula 1 and the compound (second host) of Formula 2 of the present invention in a weight ratio of 4:6 was used as a host and bis-(1-phenylisoquinolyl)iridium(III) acetylacetonate (hereinafter, abbreviated as "$(piq)_2Ir(acac)$") was used as a dopant material, wherein a dopant was doped into the host so that the weight ratio of the host and the dopant was 95:5.

Next, (1,1'-bisphenyl-4-olato)bis(2-methyl-8-quinolinolato)aluminum (hereinafter, abbreviated as "BAlq") was vacuum-deposited to a thickness of 10 nm on the light emitting layer to form a hole blocking layer. Subsequently, bis(10-hydroxybenzo[h]quinolinato)beryllium (hereinafter, abbreviated as "$BeBq_2$") was vacuum-deposited to a thickness of 40 nm on the hole blocking layer to form an electron transport layer. Thereafter, LiF was deposited to a thickness of 0.2 nm to form an electron injection layer on the electron transport layer, and then Al was deposited to a thickness of 150 nm to form a cathode on the electron injection layer. In this way, OLED was manufactured.

[Comparative Example 1] and [Comparative Example 2]

An organic electroluminescent element was manufactured in the same manner as in Example 1, except that Compound P1-27 or Compound 3-140 was used alone as the host material of the light emitting layer as shown in Table 7 below.

[Comparative Example 3] and [Comparative Example 4]

An organic electroluminescent element was manufactured in the same manner as in Example 1, except that a mixture of compound ref (first host) and compound 3-140 (second host) or 3-141 (second host) as described in Table 7 below was used as the host material of the light emitting layer.

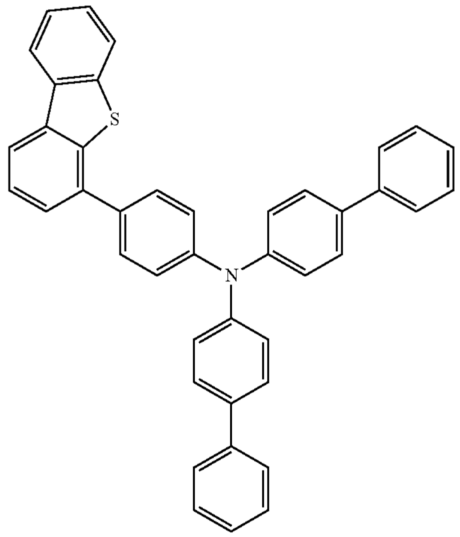

<ref>

Electroluminescence characteristics were measured with a PR-650 (Photo research) by applying a forward bias DC voltage to the organic electroluminescent elements prepared in Test Examples 1 to 18 of the present invention and Comparative Examples 1 to 4. T(95) life time was measured using a life time measuring apparatus manufactured by Mc science Inc. at reference brightness of 2500 cd/m$^2$. The measurement results are shown in the table 7 below.

TABLE 7

| | a first Compound | a second Compound | Voltage (V) | Current Density (mA/cm$^2$) | Brightness (cd/m$^2$) | Efficiency (cd/A) | Lifetime T(95) |
|---|---|---|---|---|---|---|---|
| comp.Ex1 | P1-27 | — | 6.2 | 15.8 | 2500 | 15.8 | 82.3 |
| comp.Ex2 | 3-140 | — | 5.7 | 13.7 | 2500 | 18.2 | 93.6 |
| comp.Ex3 | ref | 3-140 | 5.3 | 7.5 | 2500 | 33.3 | 119.9 |
| comp.Ex4 | ref | 3-141 | 5.4 | 7.8 | 2500 | 32.1 | 118.7 |
| Test Ex.1 | P1-3 | 3-90 | 4.9 | 6.7 | 2500 | 37.1 | 130.6 |
| Test Ex.2 | P1-27 | 3-90 | 4.6 | 7.1 | 2500 | 35.0 | 131.9 |
| Test Ex.3 | P1-81 | 3-90 | 4.8 | 6.9 | 2500 | 36.1 | 134.6 |
| Test Ex.4 | P1-3 | 3-96 | 5.1 | 6.2 | 2500 | 40.1 | 131.6 |
| Test Ex.5 | P1-27 | 3-96 | 4.8 | 6.6 | 2500 | 37.8 | 133.7 |
| Test Ex.6 | P1-81 | 3-96 | 5.0 | 6.4 | 2500 | 38.9 | 135.9 |
| Test Ex.7 | P1-3 | 3-103 | 5.0 | 6.0 | 2500 | 41.9 | 133.4 |
| Test Ex.8 | P1-27 | 3-103 | 4.7 | 6.3 | 2500 | 39.5 | 134.5 |
| Test Ex.9 | P1-81 | 3-103 | 4.9 | 6.2 | 2500 | 40.6 | 137.5 |
| Test Ex.10 | P1-3 | 3-134 | 5.0 | 6.5 | 2500 | 38.6 | 134.2 |
| Test Ex.11 | P1-27 | 3-134 | 4.8 | 6.9 | 2500 | 36.4 | 136.1 |
| Test Ex.12 | P1-81 | 3-134 | 4.9 | 6.7 | 2500 | 37.5 | 138.6 |
| Test Ex.13 | P1-3 | 3-140 | 5.0 | 6.0 | 2500 | 41.6 | 133.2 |
| Test Ex.14 | P1-27 | 3-140 | 4.7 | 6.4 | 2500 | 39.2 | 134.3 |
| Test Ex.15 | P1-81 | 3-140 | 4.9 | 6.2 | 2500 | 40.4 | 137.2 |
| Test Ex.16 | P1-3 | 3-141 | 5.1 | 6.3 | 2500 | 40.0 | 131.1 |
| Test Ex.17 | P1-27 | 3-141 | 4.8 | 6.6 | 2500 | 37.7 | 132.6 |
| Test Ex.18 | P1-81 | 3-141 | 5.0 | 6.5 | 2500 | 38.7 | 135.7 |

From the results of Table 7, it can be seen that the efficiency and lifespan of the organic electric element are remarkably improved when a mixture of the compound for an organic electroluminescent element of the present invention represented by Formula 1 and Formula 2 is used as a phosphorescent host (Test Examples 1 to 18), compared to the case where the compound represented by Formula 1 or Formula 2 was used alone (Comparative Examples 1 and 2) or when a mixture of the compound ref and the compound represented by Formula 2 of the present invention was used as a host (Comparative Examples 3 and 4).

In the case of Comparative Examples 3 and 4 using a mixture of two compounds as a host, the properties of the element were further improved, compared to Comparative Examples 1 and 2 in which the compound of the present invention represented by Formula 1 and Formula 2 was used as a single host, respectively, and the efficiency and lifespan of the organic electric element were most remarkably improved in the case of Test Examples 1 to 18 using a mixture of the compound of Formula 1 and the compound of Formula 2 of the present invention as a host, compared to Comparative Examples 3 and 4.

The ref compound includes a 3-condensed ring as a substituent of the amine group, whereas the substituent of the amine group in the compound represented by Formula 1 of the present invention comprises a 4-condensed ring group (at least one of A ring and the B ring is a $C_{10}$ or more aromatic ring group.). This compound of Formula 1 which has stability for holes and fast hole injection creates an electrochemical synergy with the compound of Formula 2 which has strong electron properties. Therefore, the host combination of the present invention is excellent because the efficiency and lifetime of the element are significantly improved.

[Test Example 19] to [Test Example 24] Red Organic Light Emitting Element According to the Mixing Ratio An organic electroluminescent element was manufactured in the same manner as in Example 1, except that the first host and the second host were mixed in a certain ratio as shown in Table 8 below.

Electroluminescence characteristics were measured with a PR-650 (Photo research) by applying a forward bias DC voltage to the organic electroluminescent elements prepared in Test Examples 19 to 24 of the present invention. T(95) life time was measured using a life time measuring apparatus manufactured by Mc science Inc. at reference brightness of 2500 cd/m$^2$. The measurement results are shown in the table 8 below.

TABLE 8

| | a first Compound | a second Compound | ratio | Voltage (V) | Current Density (mA/cm$^2$) | Brightness (cd/m$^2$) | Efficiency (cd/A) | Lifetime T(95) |
|---|---|---|---|---|---|---|---|---|
| Test Ex.19 | P1-81 | 3-96 | 7:3 | 5.4 | 6.7 | 2500 | 37.1 | 133.8 |
| Test Ex.20 | P1-81 | 3-96 | 5:5 | 5.1 | 6.5 | 2500 | 38.5 | 135.4 |
| Test Ex.21 | P1-81 | 3-96 | 3:7 | 4.9 | 6.4 | 2500 | 39.2 | 137.3 |
| Test Ex.22 | P1-27 | 3-103 | 7:3 | 5.0 | 6.6 | 2500 | 37.6 | 132.7 |
| Test Ex.23 | P1-27 | 3-103 | 5:5 | 4.8 | 6.4 | 2500 | 39.0 | 133.9 |
| Test Ex.24 | P1-27 | 3-103 | 3:7 | 4.6 | 6.3 | 2500 | 39.9 | 135.1 |

As shown in Table 8 above, the element was manufactured according to the mixing ratio (7:3, 5:5, 3:7) of the compounds of the present invention, and the characteristics of the element was measured. From Table 8, it can be seen that when the ratio of a first host to a second host is 3:7, the efficiency and lifespan are the best. That is, the higher the ratio of the second host in the mixture, the better the efficiency and lifespan.

These results suggest that it is important to derive a mixing ratio of a mixture that maximizes the charge balance in the light emitting layer because the amount of the mixing ratio affects the characteristics of the element.

Although the exemplary embodiments of the present invention have been described for illustrative purposes, those skilled in the art to which the present invention pertains will be capable of various modifications without departing from the essential characteristics of the present invention. Therefore, the embodiment disclosed herein is intended to illustrate the scope of the technical idea of the present invention, and the spirit and scope of the present invention are not limited by the embodiments. The scope of the present invention shall be construed on the basis of the accompanying claims, and it shall be construed that all of the technical ideas included within the scope equivalent to the claims belong to the present invention.

The invention claimed is:

1. An organic electric element comprising a first electrode, a second electrode, and an organic material layer formed between the first electrode and the second electrode, wherein the organic material layer comprises a phosphorescent light emitting layer, and host of the phosphorescent light emitting layer consists of a first host compound of Formula 1, and a second host compound of Formula 2-A, with the proviso that Formula 2-A has no carbazole moiety in the structure:

[Formula 1]

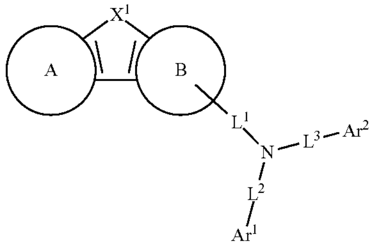

-continued

[Formula 2-A]

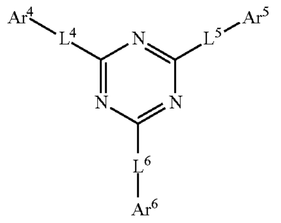

wherein:

A ring is a $C_6$-$C_{60}$ aromatic ring group or a $C_2$-$C_{60}$ heterocyclic group comprising at least one heteroatom selected from the group consisting of O, N, S, Si and P, and B ring is selected from the group consisting of Formulas a-6 to a-9

<Formula a-6>

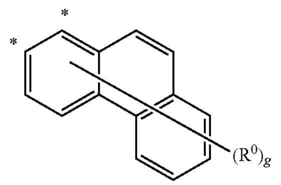

<Formula a-7>

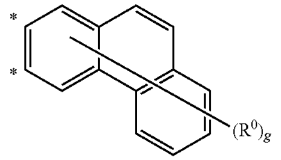

<Formula a-8>

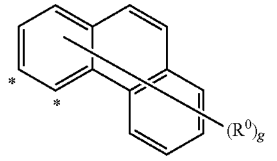

<Formula a-9>

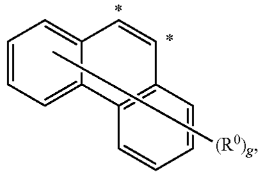

A ring may be substituted with one or more same or different $R^1$(s), B Ring may be substituted with one or more same or different $R^0$(s), wherein $R^1$ and $R^O$ are each independently selected from the group consisting of hydrogen, deuterium, halogen, a cyano group, a $C_6$-$C_{60}$ aryl group, a fluorenyl group, a $C_2$-$C_{60}$ heterocyclic group comprising at least one heteroatom of O, N, S, Si and P, a $C_3$-$C_{60}$ aliphatic ring, a $C_1$-$C_{30}$ alkyl group, a $C_2$-$C_{30}$ alkenyl group, a $C_2$-$C_{30}$ alkynyl group, a $C_1$-$C_{30}$ alkoxyl group and a $C_6$-$C_{30}$ aryloxy group,

* represents condensed position, g is an integer of 0 to 8, $X^1$ is O, or S, $L^1$ to $L^3$, $L^5$ and $L^6$ are each independently selected from the group consisting of a single bond, a $C_6$-$C_{60}$ arylene group, a fluorenylene group, and a $C_2$-$C_{60}$ heterocyclic group comprising at least one heteroatom selected from the group consisting of O, N, S, Si and P, and $L^4$ is a single bond, $Ar^1$, $Ar^2$, $Ar^5$ and $Ar^6$ are each independently selected from the group consisting of a $C_6$-$C_{60}$ aryl group, a fluorenyl group, and a $C_2$-$C_{60}$ heterocyclic group comprising at least one heteroatom selected from the group consisting of O, N, S, Si and P, with the proviso that either $Ar^1$-$L^2$ or $Ar^2$-$L^3$, or both $Ar^1$-$L^2$ and $Ar^2$-$L^3$ includes a $C_2$-$C_{60}$ heterocyclic group comprising at least one heteroatom selected from the group consisting of O, N, S, Si and P, $Ar^4$ is selected from the group consisting of dibenzofuran, dibenzothiophene, benzonaphthofuran, and benzonaphthothiophene, wherein $Ar^4$ may be substituted with deuterium, or phenyl or naphthyl that may be substituted with deuterium, at least one of $L^5$, $L^6$, $Ar^5$, and $Ar^6$ is naphthyl, and $L^1$ to $L^3$, $L^5$ and $L^6$, $Ar^1$, $Ar^2$, $Ar^5$ and $Ar^6$, $R^1$ and $R^0$may be each optionally substituted with one or more substituents selected from the group consisting of deuterium, halogen, a silane group unsubstituted or substituted with a $C_1$-$C_{20}$ alkyl group or a $C_6$-$C_{20}$ aryl group, a cyano group, a $C_1$-$C_{20}$ alkoxy group, a $C_1$-$C_{20}$ alkyl group, a $C_2$-$C_{20}$ alkenyl group, a $C_6$-$C_{20}$ aryl group, a fluorenyl group, a $C_2$-$C_{20}$ heterocyclic group containing at least one heteroatom of O, N, S, Si, and P, and a $C_3$-$C_{20}$ aliphatic ring group.

2. The organic electric element of claim 1, wherein Formula 1 is represented by one of Formula 1-A or Formula 1-B:

<Formula 1-A>

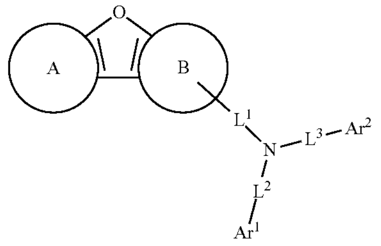

<Formula 1-B>

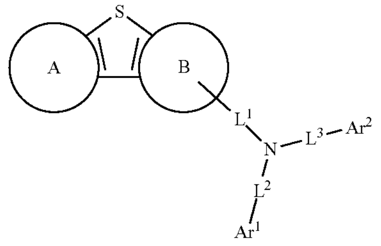

wherein A ring, B ring, $L^1$ to $L^3$, $Ar^1$, and $Ar^2$, are the same as defined in claim 1.

3. The organic electric element of claim 1, wherein A ring of Formula 1 is selected from the group consisting of Formulas a-1 to a-9

<Formula a-1>

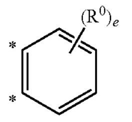

-continued

<Formula a-2>

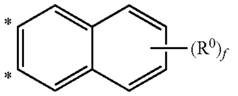

<Formula a-3>

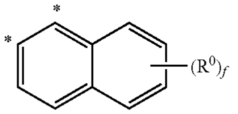

<Formula a-4>

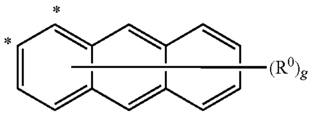

<Formula a-5>

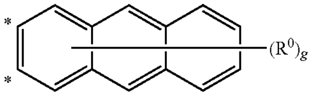

<Formula a-6>

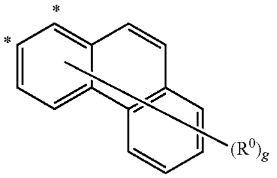

<Formula a-7>

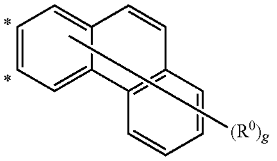

<Formula a-8>

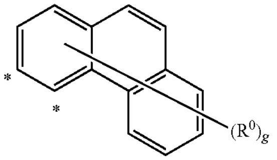

<Formula a-9>

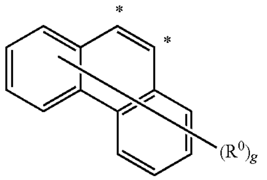

wherein * represents the condensed position, $R^0$ is defined the same as $R^{O}$ in claim 1, e is an integer of 0 to 4, f is an integer of 0 to 6, g is an integer of 0 to 8, when they are each an integer of 2 or more, $R^0$s are the same as or different from each other.

4. The organic electric element of claim 1, wherein the compound of Formula 2-A is one of the following compounds:

3-103

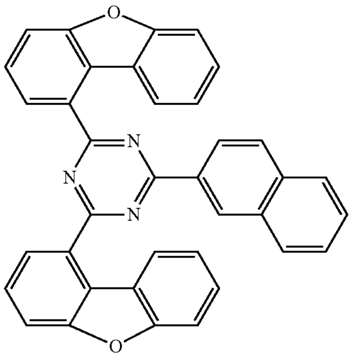

3-105

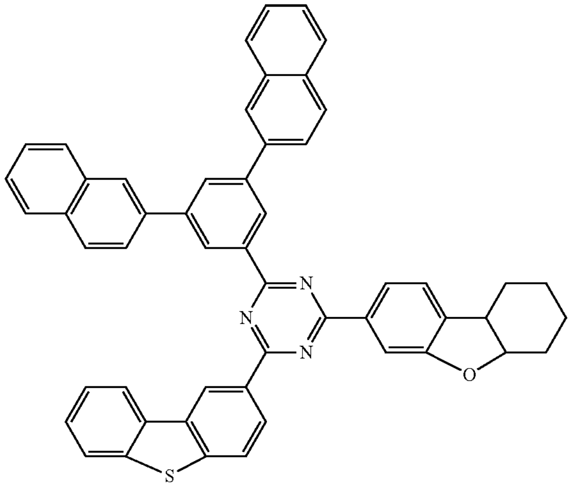

3-113

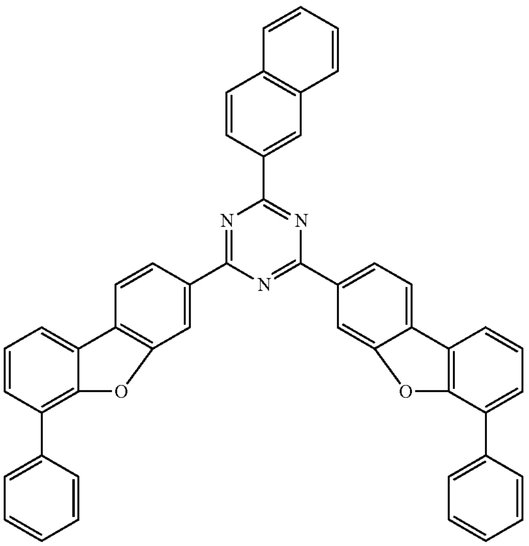

-continued 3-120

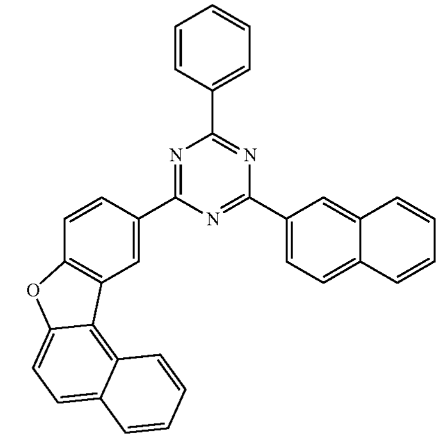

3-129

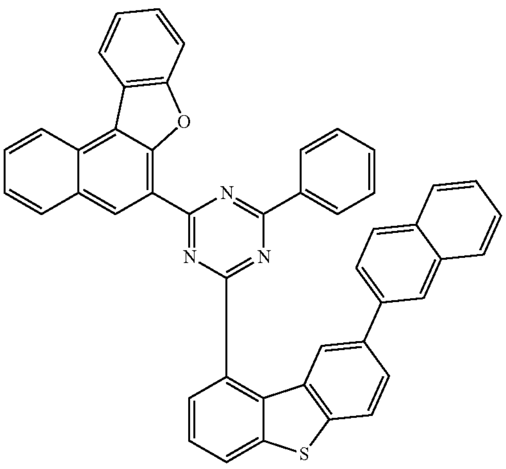

-continued 3-132

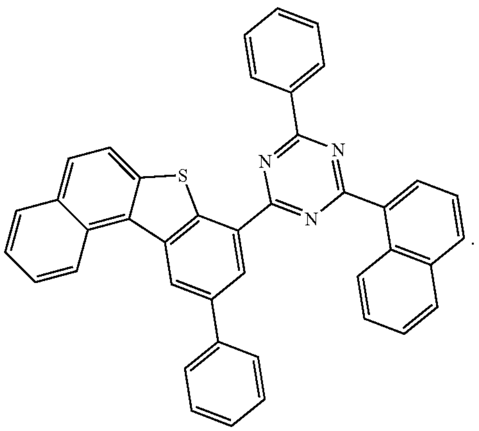

5. The organic electric element of claim 1, wherein the host is a mixture of the first compound and the second compound in a weight ratio of 2:8 to 8:2.

6. The organic electric element of claim 1, wherein the organic material layer comprises two or more stacks, and the stacks each comprise a hole transport layer, a light emitting layer, and an electron transport layer formed sequentially on the first electrode.

7. The organic electric element of claim 6, wherein the organic material layer further comprises a charge generation layer formed between the two or more stacks.

8. The organic electric element of claim 1, wherein the organic material layer comprises a hole transport band layer having one or more layers and formed between the light emitting layer and the first electrode, the hole transport band layer comprises at least one of a hole transport layer and an emission-auxiliary layer, and comprises the compound represented by Formula 1.

9. The organic electric element of claim 1, further comprising a layer for improving luminous efficiency on one side of the first electrode and/or the second electrode, wherein the one side is not facing the organic material layer.

10. An electronic device comprising a display device and a control unit for driving the display device, wherein the display device comprises the organic electric element of claim 1.

11. The electronic device of claim 10, wherein the organic electric element is selected from the group consisting of an organic electroluminescent element, an organic solar cell, an organic photo conductor, an organic transistor, an element for monochromatic illumination and a quantum dot display.

* * * * *